United States Patent
Chen et al.

(10) Patent No.: US 9,493,429 B2
(45) Date of Patent: Nov. 15, 2016

(54) SUBSTITUTED BENZOXAZOLES AND METHODS OF USE THEREOF

(71) Applicants: GENENTECH, INC., South San Francisco, CA (US); XENON PHARMACEUTICALS INC., Burnaby (CA)

(72) Inventors: Chien-An Chen, South San Francisco, CA (US); Sultan Chowdhury, Burnaby (CA); Christoph Martin Dehnhardt, Burnaby (CA); Shaoyi Sun, Burnaby (CA)

(73) Assignees: GENENTECH, INC., South San Francisco, CA (US); XENON PHARMACEUTICALS INC., Burnaby, BC (CA)

( * ) Notice: Subject to any disclaimer, the term of this patent is extended or adjusted under 35 U.S.C. 154(b) by 0 days.

(21) Appl. No.: 14/772,726

(22) PCT Filed: Mar. 14, 2014

(86) PCT No.: PCT/US2014/029004
§ 371 (c)(1),
(2) Date: Sep. 3, 2015

(87) PCT Pub. No.: WO2014/144545
PCT Pub. Date: Sep. 18, 2014

(65) Prior Publication Data
US 2016/0009667 A1    Jan. 14, 2016

(30) Foreign Application Priority Data

Mar. 15, 2013  (WO) ............... PCT/CN2013/072689

(51) Int. Cl.
| | | |
|---|---|---|
| *C07D 261/20* | (2006.01) | |
| *C07D 413/12* | (2006.01) | |
| *A61K 31/423* | (2006.01) | |
| *A61K 31/4439* | (2006.01) | |
| *A61P 9/00* | (2006.01) | |
| *A61P 25/24* | (2006.01) | |
| *A61P 25/18* | (2006.01) | |
| *A61P 11/00* | (2006.01) | |

(52) U.S. Cl.
CPC .......... *C07D 261/20* (2013.01); *C07D 413/12* (2013.01)

(58) Field of Classification Search
CPC . C07D 261/20; C07D 413/12; A61K 31/423
See application file for complete search history.

(56) References Cited

U.S. PATENT DOCUMENTS

| | | |
|---|---|---|
| 3,705,185 A | 12/1972 | Moore et al. |
| 5,171,748 A | 12/1992 | Roberts et al. |
| 5,573,653 A | 11/1996 | Bandlish |
| 5,580,982 A | 12/1996 | O'Malley et al. |
| 5,753,653 A | 5/1998 | Bender et al. |
| 6,096,771 A | 8/2000 | Kojima et al. |
| 7,262,304 B2 | 8/2007 | Ueno et al. |
| 7,291,638 B2 | 11/2007 | Lee et al. |
| 7,858,639 B2 | 12/2010 | Sun et al. |
| 8,153,814 B2 | 4/2012 | Beaudoin et al. |
| 8,193,194 B2 | 6/2012 | Martinborough et al. |
| 8,642,660 B2 | 2/2014 | Goldfarb |
| 8,889,741 B2 | 11/2014 | Shinozuka et al. |
| 8,933,236 B2 | 1/2015 | Chowdhury et al. |
| 8,952,169 B2 | 2/2015 | Andrez et al. |
| 9,102,621 B2 | 8/2015 | Brown et al. |
| 2006/0069093 A1 | 3/2006 | Scarborough et al. |
| 2007/0088015 A1 | 4/2007 | Silva et al. |
| 2008/0161303 A1 | 7/2008 | Zhang et al. |

(Continued)

FOREIGN PATENT DOCUMENTS

| | | |
|---|---|---|
| CN | 101466665 A | 6/2009 |
| CN | 101643458 A | 2/2010 |

(Continued)

OTHER PUBLICATIONS

Chemical Abstract Service STN Registry Database No. 891026-77-0 [entered STN: Jul. 9, 2006].*

(Continued)

*Primary Examiner* — Nyeemah A Grazier
*Assistant Examiner* — Amanda L Aguirre
(74) *Attorney, Agent, or Firm* — Viksnins Harris & Padys PLLP

(57) ABSTRACT

The invention provides compounds having the general formula (I): and pharmaceutically acceptable salts thereof, wherein the variables RA, subscript n, ring A, $X^2$, L, subscript m, $X^1$, $R^1$, $R^2$, $R^3$, $R^4$, and $R^N$ have the meaning as described herein, and compositions containing such compounds and methods for using such compounds and compositions.

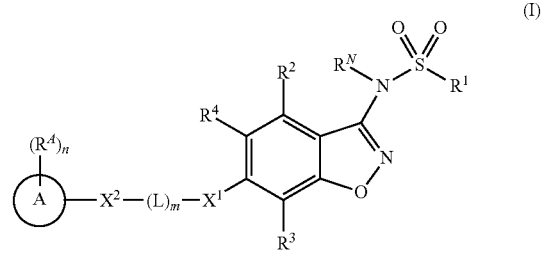

24 Claims, No Drawings

(56) References Cited

U.S. PATENT DOCUMENTS

| | | |
|---|---|---|
| 2008/0312286 A1 | 12/2008 | Pinkerton et al. |
| 2009/0012103 A1 | 1/2009 | Abelman et al. |
| 2010/0179137 A1 | 7/2010 | Kamikubo et al. |
| 2010/0197655 A1 | 8/2010 | Beaudoin et al. |
| 2010/0286110 A1 | 11/2010 | Fyfe et al. |
| 2011/0092703 A1 | 4/2011 | Sakuma et al. |
| 2012/0004714 A1 | 1/2012 | Kleve et al. |
| 2012/0010182 A1 | 1/2012 | Brown et al. |
| 2012/0010183 A1 | 1/2012 | Bell et al. |
| 2012/0010207 A1 | 1/2012 | Bell et al. |
| 2012/0196869 A1 | 8/2012 | Hadida Ruah et al. |
| 2013/0109667 A1 | 5/2013 | Markworth et al. |
| 2013/0109696 A1 | 5/2013 | Greener et al. |
| 2013/0109701 A1 | 5/2013 | Brown et al. |
| 2013/0109708 A1 | 5/2013 | Brown et al. |
| 2013/0150339 A1 | 6/2013 | Boezio et al. |
| 2013/0317000 A1* | 11/2013 | Chowdhury ......... C07D 413/12 514/210.19 |
| 2013/0324525 A1 | 12/2013 | Abelman et al. |
| 2013/0338111 A1 | 12/2013 | Beaudoin et al. |
| 2014/0045862 A1 | 2/2014 | Shinozuka et al. |
| 2014/0213616 A1 | 7/2014 | Hadida-Ruah et al. |
| 2014/0296266 A1 | 10/2014 | Hu et al. |
| 2015/0057271 A1 | 2/2015 | Boezio et al. |
| 2015/0224071 A1* | 8/2015 | Chowdhury ......... C07D 413/12 514/210.01 |
| 2015/0291514 A1 | 10/2015 | Brown et al. |

FOREIGN PATENT DOCUMENTS

| | | |
|---|---|---|
| EP | 0179619 B1 | 9/1990 |
| EP | 0516392 A2 | 12/1992 |
| EP | 2184278 A1 | 5/2010 |
| WO | 9008128 A1 | 7/1990 |
| WO | 0039077 A2 | 7/2000 |
| WO | 03059882 A1 | 7/2003 |
| WO | 2004014913 A2 | 2/2004 |
| WO | 2004052869 A1 | 6/2004 |
| WO | 2004092145 A1 | 10/2004 |
| WO | 2005013914 A2 | 2/2005 |
| WO | 2005032488 A2 | 4/2005 |
| WO | 2006015158 A1 | 2/2006 |
| WO | 2006020830 A3 | 2/2006 |
| WO | 2006039212 A2 | 4/2006 |
| WO | 2006121097 A1 | 11/2006 |
| WO | 2006122800 A1 | 11/2006 |
| WO | 2007030582 A3 | 3/2007 |
| WO | 2007045572 A1 | 4/2007 |
| WO | 2007062078 A2 | 5/2007 |
| WO | 2007067994 A1 | 6/2007 |
| WO | 2007120647 A2 | 10/2007 |
| WO | 2008094602 A2 | 8/2008 |
| WO | 2008097991 A1 | 8/2008 |
| WO | 2008118758 A1 | 10/2008 |
| WO | 2009010784 A1 | 1/2009 |
| WO | 2009012242 A3 | 1/2009 |
| WO | 2009157399 A1 | 12/2009 |
| WO | 2010022055 A2 | 2/2010 |
| WO | 2010079443 A1 | 7/2010 |
| WO | 2011014462 A1 | 2/2011 |
| WO | 2011016234 A1 | 2/2011 |
| WO | 2011037192 A1 | 2/2011 |
| WO | 2011059042 A1 | 5/2011 |
| WO | 2011063001 A1 | 5/2011 |
| WO | 2011088201 A1 | 7/2011 |
| WO | 2011100433 A1 | 8/2011 |
| WO | 2011153588 A1 | 12/2011 |
| WO | 2012004664 A2 | 1/2012 |
| WO | 2012004706 A3 | 1/2012 |
| WO | 2012004714 A2 | 1/2012 |
| WO | 2012004743 A1 | 1/2012 |
| WO | 2012007836 A1 | 1/2012 |
| WO | 2012007861 A1 | 1/2012 |
| WO | 2012007868 A2 | 1/2012 |
| WO | 2012007869 A2 | 1/2012 |
| WO | 2012007877 A2 | 1/2012 |
| WO | 2012007883 A1 | 1/2012 |
| WO | 2012035023 A1 | 3/2012 |
| WO | 2012039657 A1 | 3/2012 |
| WO | 2012085650 A1 | 6/2012 |
| WO | 2012095781 A1 | 7/2012 |
| WO | 2013025883 A1 | 2/2013 |
| WO | 2013056232 A2 | 4/2013 |
| WO | 2013063459 A1 | 5/2013 |
| WO | 2013064983 A1 | 5/2013 |
| WO | 2013064984 A1 | 5/2013 |
| WO | 2013072758 A1 | 5/2013 |
| WO | 2013086229 A1 | 6/2013 |
| WO | 2013088315 A1 | 6/2013 |
| WO | 2013102826 A1 | 7/2013 |
| WO | 2013118805 A1 | 8/2013 |
| WO | 2013118854 A1 | 8/2013 |
| WO | 2013122897 A1 | 8/2013 |
| WO | 2013134518 A1 | 9/2013 |
| WO | 2013146969 A1 | 10/2013 |
| WO | 2013177224 A1 | 11/2013 |
| WO | 2014008458 A2 | 1/2014 |
| WO | 2014014050 A1 | 1/2014 |
| WO | 2014066490 A1 | 5/2014 |
| WO | 2014066491 A1 | 5/2014 |
| WO | 2014096941 A1 | 6/2014 |
| WO | 2014144545 A2 | 9/2014 |
| WO | 2014151472 A1 | 9/2014 |
| WO | 2014153037 A1 | 9/2014 |
| WO | 2015051043 A1 | 4/2015 |
| WO | 2015078374 A1 | 6/2015 |

OTHER PUBLICATIONS

Chemical Abstract Service STN Registry Database No. 892698-09-8 [entered STN: Jul. 14, 2006].*

Goldin, et al., "Nomenclature of Voltage-Gated Sodium Channels", Neuron vol. 28, 365-368 (2000).

Gould, et al., "Development of inflammatory hypersensitivity and augmentation of sodium channels in rat dorsal root ganglia", Brain Res. 824 (2), 296-299 (1999).

Hains, et al., "Upregulation of sodium channel Nav1.3 and functional involvement in neuronal hyperexcitability associated with central neuropathic pain after spinal cord injury", J. Neurosci. 23 (26), 8881-8892 (2003).

Hayes, et al., "Na(V)1.7 Paint Control: A Novel Target", Neurosurgery 73, N16 (2013).

Ikoma, et al., "Neuronal sensitization for histamine-induced itch in lesional skin of patients with atopic dermatitis", Arch. Dermatol. 139, 1445-1458 (2003).

Ikoma, et al., "The neurobiology of itch", Nature Reviews Neuroscience 7, 535-547 (2006).

Ikuma, et al., "Preparation of 3-substituted proline derivatives as FXIa inhibitors", CA159:371450 (2013).

Improper Markush, Fed Reg V. 76(27), 7162-7175, Slide 1, 64-67 (2011).

Kis-Toth, et al., "Voltage-gated sodium channel NaV1.7 maintains the membrane potential and regulates the 45 activation and chemokine-induced migration of a monocyte-derived dendritic cell subset", J. Immunology 187, 1273-1280 (2011).

Klugbauer, et al., "Structure and functional expression of a new member of the tetrodotoxin-sensitive voltage-activated sodium channel family from human neuroendocrine cells", EMBO J. 14 (6), 1084-1090 (1995).

Kutt, et al., "A Comprehensive Self-Consistent Spectrophotometric Acidity Scale of Neutral Bronsted Acids in Acetonitrile", J. Org. Chem. 71, 2829-2838 (2006).

Lai, et al., "Inhibition of neuropathic pain by decreased expression of the tetrodotoxin-resistant sodium channel, NAV1.8", Pain 95 (1-2), 143-152 (2002).

Lai, et al., "The role of voltage-gated sodium channels in neuropathic pain", Current Opinion in Neurobiology 13, 291-297 (2003).

(56) References Cited

OTHER PUBLICATIONS

Leeman, et al., "Preparation of 4-benzimidazolylmethoxy-3-halophenylmethoxybenzoates and analogs as tRNA synthetase inhibitors", CA 133:35021 (2000).
Li, et al., "Recent advances in the structure-activity relationship study of small-molecule sodium channel blockers with analgesic effects", Acta Pharmaceutica Sinica, vol. 44, (2), 101-108 (2009). [English Translation.].
Liu, et al., "Mutations in cardiac sodium channels: clinical implications", Am. J. Pharmacogenomics 3(3), 173-179 (2003).
Mao, et al., "Systemic lidocaine for neuropathic pain relief", Pain 87, 7-17 (2000).
Massah, et al., "Synthesis. in vitro antibacterial and carbonic anyydrase II inhibitory activities of N-acylsulfonamides 2 using silica sulfuric acid as an efficient catalyst under both solvent-free and heterogeneous conditions", Bioorganic & Medicinal Chemistry 16, 5465-5472 (2008).
Meisler, et al., "Sodium channel gene family: epilepsy mutations, gene interactions and modifier effects", The Journal of Physiology 588.11, 1841-1848 (2010).
Morinville, et al., "Distribution of the voltage-gated sodium channel NaV1.7 in the rat: expression in the autonomic and endocrine systems", J. Comparative Neurology 504, 680-689 (2007).
Oaklander, et al., "Intractable post-herpetic itch and cutaneous deafferentation after facial singles", Pain 96,9-12 (2002).
Patani, et al., "Bioisosterism: A Rational Approach in Drug Design", Chem Rev 96, 3147-3176 (1996).
Patent Cooperation Treaty, International Searching Authority, Search Report and Written Opinion for PCT/CN2013/072689, 14 pages, Dec. 26, 2013.
Patent Cooperation Treaty, International Searching Authority, Search Report and Written Opinion for PCT/US2014/029004, 11 pages, Oct. 7, 2014.
Priest, et al., "Contribution of the tetrodotoxin-resistant voltage-gated sodium channel NaV1.9 to sensory transmission and nociceptive behavior", Proc Nail Acad Sci 102 (26) 9382-9387 (2005).
Priest, "Future potential and status of selective sodium channel blockers for the treatment of pain", Current Opinion in Drug Discovery and Development, 12(5), 682-692 (2009).
Prodrug, Dictionary 1-2, Internet (2002).
Pubchem, Compound Summary for CID 14280666, N-(1,2-benzoxazol-3-y1) methanesulfonamide, https://pubchem.ncbi.nim.nih.gov/summary/summary.cgi?cid=14280666, 3 pages (2007).
Raymond, et al., "Expression of alternatively spliced sodium channel alpha-subunit genes. Unique splicing patterns are observed in dorsal root ganglia", J. Bioi. Chern. 279(44), 46234-46241 (2004).
Reimann, et al., "Pain perception is altered by a nucleotide polymorphism in SCN9A", Proc. Nail. Acad. Sci. 107, 5148-5153 (2010).
Roberts, et al., "Molybdenum-Mediated Carbonylaiton of Aryl Halides with Nucleophiles Using Microwave Irradiation", Organic Letters, vol. 12 (19), 4280-4283 (2010).
Roberts, et al., "Novel Aryl and Heteroaryl Acyl Sulfamide Synthesis via Microwave-Assisted Palladium-Catalyzed Carbonylation", Organic Letters, vol. 12 (6), 1264-1267 (2010).
Ruan, et al., "Sodium channel mutations and arrhythmias", Nature Reviews Cardiology, 6, 337-348 (2009).
Rugiero, et al., "Selective Expression of a Persistent Tetrodotoxin-Resistant Na+ Current and NaV1.9 Subunit in Myenteric Sensory Neurons", J. Neurosci 23 (7), 2715-2725 (2003).
Sakuma, et al., "Preparation of piperazine", CA150:260220 (2009).
Sangameswaran, et al., "A novel tetrodotoxin-sensitive, voltage-gated sodium channel expressed in rat and human dorsal root ganglia", J. Bioi. Chem, 272 (23), 14805-14809 (1997).
Sato, et al., "The voltage-sensitive sodium channel is a bell-shaped molecule with several cavities", Nature 409, 1047-1051 (2001).
Schmelz, et al., "Itch and pain", Neuroscience and Biobehaviorial Reviews, 34, 171-176 (2010).
Seddon, "Pseudopolymorph: A Polemic", Crystal Growth and Design vol. 4(6), 1087 (2004).
Silos-Santiago, "Drugs in Clinical Development for Neuropathic Pain", presented at First World Conference Abdominal and Pelvic Pain, Amsterdam, pp. 1-23 (Jun. 6, 2013).
Smith, et al., "Sodium channel protein expression enhances the invasiveness of rat and human prostate cancer cells", FEBS Letters, 423, 19-24 (1998).
Tamaoka, "Paramyotonia congenita and skeletal sodium channelopathy", Intern. Med. 42 (9), 769-770 (2003).
Tanelian, et al., "Neuropathic pain can be relieved by drugs that are use-dependent sodium channel blockers: lidocaine, carbamazepine and mexileline", Anesthesiology, 74(5), 949-951 (1991).
Termin, et al., "Recent Advances in Voltage-Gated Sodium Channel Blockers: Therapeutic Potential as Drug Targets in the CNS", Annual Reports in Medicinal Chemistry 43, 43-60 (2008).
Toledo-Aral, et al., "Identification of PN1, a predominant voltage-dependent sodium channel expressed principally in peripheral neurons", Proc. Nail. Acad. Sci. 94 (4), 1527-1532 (1997).
Villamil, et al., "Efficacy of lidocaine in the treatment of pruritus in patients with chronic chlolestatic liver disease", Am. J. Med, 118, 1160-1163 (2005).
Vippagunta, et al., "Crystal Solids", Adv Drug Del Rev vol. 48, 3-26 (2001).
Wallace, et al., "Efficacy of oral mexileline for neuropathic pain with allodynia: a double-blind, placebo-controlled, crossover study", Reg. Anesth. Pain Med. 25 (5), 459-467 (2000).
Wolff, "Burger's Medicinal Chemistry and Drug Discovery", Fifth Edition, vol. 1: Principles and Practice, 975-977 (1995).
Wood, et al., "Voltage-gated sodium channels and pain pathways", J. Neurobiol. 61(1 ), 55-71 (2004).
Xiao, et al., "C-fiber spontaneous discharge evoked by chronic inftammation is suppressed by a long-term infusion of lidocaine yielding nanogram per milliliter plasma levels", Pain, 137,218-228 (2008).
Yang, et al., "Mutations in SCN9A, encoding a sodium channel alpha subunit, in patients with primary erythermalgia", J. Med. Genet. 41 (3), 171-174 (2004).
Yu, et al., "Reduced sodium current in GABAergic interneurons in a mouse model of severe myoclonic epilepsy in infancy", Nat Neurosci 9, 1142-1149 (2006).
Yu, et al., "Sodium Channel β4. a New Disulfide-Linked Auxiliary Subunit with Similarity to β2", J. Neurosci. 23(20), 7577-7585 (2003).
Yu, et al., "The VGL-chanome: a protein superfamily specialized for electrical signaling and ionic homeostasis", Sci. STKE 253, re15, 17 pages (2004).
Zhao, et al., "Voltage-gated sodium channel expression in rat and human epidermal keratinocytes: evidence for a role in pain", Pain, 139, 90-105 (2008).
Zuliani, et al., "Expert Opinion Ther Patents", 25(3), 279-290 (2015).
File CAPLUS, Registry No. 1333872-40-4, entered STN: Sep. 29, 2011.
Amaya, et al., "The voltage-gated sodium channel Na(v)1.9 is an effector of peripheral inflammatory pain hypersensitivity", J. Neurosci 26 (50), 12852-12860 (2006).
Arcangeli, et al., "Targeting Ion Channels in Cancer: A Novel Frontier in AntineoplasticTherapy", Current Medicinal Chemistry 16, 66-93 (2009).
Bach, et al., "A novel series of piperazinyl-pyridine ureas as antagonists of the purinergic P2712 receptor", Bioorganic & Medicinal Chemistry Letters 21, 2877-2881 (2011).
Banks, et al., "The Reaction of N-Aikylhydroxamic Acids with Sulphinyl Chlorides", J. Chem. Soc. Perkin Trans. II, 1211-1216 (1986).
Bean, et al., "Lidocaine Block of Cardiac Sodium Channels", J. Gen. Physiol. 81, 613-642 (1983).
Binder, et al., "Disease Mechanisms in Neuropathic Itch", Nature Clinical Practice Neurology 4(6), 329-337 (2008).
Black, et al., "Changes in the expression of tetrodotoxin-sensitive sodium channels within dorsal root ganglia neurons in inflammatory pain", Pain 108 (3), 237-247 (2004).

(56) References Cited

OTHER PUBLICATIONS

Blair, et al., "Roles of tetrodotoxin (TIX)-sensitive Na+ current, TIX-resistant Na+ current, and Ca2+ current in the action potentials of nociceptive sensory neurons", J. Neurosci 22, 10277-10290 (2002).
Brackenbury, et al., "Activity-dependent regulation of voltage-gated Na+ channel expression in Mat-LyLu rat prostate cancer cell line", J. Physiol 573.2, 343-356 (2006).
Braga, et al., "Making crystals from crystals: a green route to crystal engineering and polymorphism", Chern Commun J Roy Soc Chern, 3635-3645 (2005).
Caldwell, et al., "Sodium channel Na(v)1.6 is localized at nodes of ranvier, dendrites, and synapses", Proc. Nail. Acad. Sci. 97(10), 5616-5620 (2000).
CAS Registry, Nos. 1027529-26-5, 1027209-51-3 and 1026292-79-4, 1 page (2015).
Catron, et al., "Preparation of 4-[4-[2-phenylcclohexen-1-en-1-yl)methyl]piperazin-1-ui]-N-(phenylsulfonyl) 13 benzamides and 4-[4-[(2-phenylcyclohexen-1-en-1-yl)methyl]ipiperazin-1-71]-N-(3-pyridylsulfonlyl) benzamides", CAPLUS 2012:637301, 156:638098, 2 pages (2012).
Catterall, "From ionic currents to molecular mechanisms: the structure and function of voltage-gated sodium channels", Neuron 26(1), 13-25 (2000).
Catterall, "Molecular mechanisms of gating and drug block of sodium channels", Novartis Foundation Symposium 241, 206-225 (2002).
Catterall, "Structural biology: A 3D view of sodium channels", Nature, vol. 409, 988-990 (2001).
Cestele, et al., "Molecular mechanisms of neurotoxin action on voltage-gated sodium channels", Biochimie vol. 82 (9-1 0), 883-892 (2000).
Chan, et al., "Rh(II)-Catalyzed Intermolecular Oxidative Sulfamidalion of Aldehydes: A Mild Efficient Synthesis of N-Sulfonylcarboxamides", J. Am. Chern. Soc., 129, 14106-14107 (2007).
Chemical Abstracts_4, XP002744146, Database accession No. 1294599-14-6 Abstract, (May 15, 2011).
Chemical Abstracts_1, XP002744143, Database accession No. 1321299-48-2 Abstract (Aug. 22, 2011).
Chemical Abstracts_10, XP002744152, Database accession No. 1288553-28-5 Abstract (May 1, 2011).
Chemical Abstracts_11, XP002744153, Database accession No. 1278399-39-5 Abstract (Apr. 11, 2011).
Chemical Abstracts_12, XP002744154, Database accession No. 1297052-59-5 Abstract (May 19, 2011).
Chemical Abstracts_13, XP002744155, Database accession No. 1277490-84-2 Abstract (Apr. 10, 2011).
Chemical Abstracts_2, XP002744144, Database accession No. 1320435-32-2 Abstract (Aug. 22, 2011).
Chemical Abstracts_3, XP002744145, Database accession No. 1319619-74-3 Abstract (Aug. 18, 2011).
Chemical Abstracts_5, XP002744147, Database accession No. 1051238-85-7 Abstract (Sep. 21, 2008).
Chemical Abstracts_6, XP002744148, Database accession No. 1051172-94-1 Abstract (Sep. 21, 2008).
Chemical Abstracts_7, XP002744149, Database accession No. 1301192-24-4 (May 26, 2011).
Chemical Abstracts_8, XP002744150, Database accession No. 1299653-84-3 Abstract (May 24, 2011).
Chemical Abstracts_9, XP002744151, Database accession No. 299214-10-0 (May 24, 2011).
Chioni, et al., "A novel adhesion molecule in human breast cancer cell lines: Voltage-gated Na+ channel β1 subunit", Int'l J. Biochem. Cell Biol. 41, 1216-1227 (2009).

Chung, et al., "Sodium channels and neuropathic pain", Novartis Foundation Symposium 261, 19-31 (2004).
Clare, et al., "Voltage-gated sodium channels as therapeutic targets", Drug Discovery Today 5(11), 506-520 (2000).
Cox, et al., "An SCN9A channelopathy causes congenital inability to experience pain", Nature 444, 894-898 (2006).
Daeniker, et al., "234. Uber bicyclische Sulfonamide", Helvetica Chimica ACTA, vol. 45 (6), 1972-1981 (1962). [English Translation.].
Database Reaxys, XP002692384, Accession No. XRN: 6729065, 6731122, 1 page, (D. Bertoia et al., Base 24 promoted ring-opening reactions of 2-p-lolyl-5,6-dihydro-1, 4,3-oxathiazine 4,4-dioxides, Gazella Chimica Ilaliana, vol. 118 (6), 435-440 (1988).
Devor, et al., "Na+ ChannelImmunolocalization in Peripheral Mammalian Axons and Changes following Nerve Injury and Neuroma Formation", J. Neurosci. 13 (5), 1976-1992 (1993).
Dib-Hajj, et al., "Genetics and Molecular Pathophysiology of NaV1.7-related Pain Syndromes", Advances in Genetics 63,85-110 (2008).
Dib-Hajj, et al., "NaN, a novel voltage-gated Na channel, is expressed preferentially in peripheral sensory neurons and down-regulated after axotomy", Proc. Natl. Acad. Sci. 95 (15), 8963-8968 (1998).
Dickore, "Synthese und reaktionen von 1.3.4-oxathiazolin-3-dioxyden", Justus Liebigs Annalen Der Chemie, vol. 671, 135-146, XP055053742, Compounds IVa, IVb, IVd, V, VI (1964). [English Translation.].
Diss, et al., "A potential novel marker for human prostate cancer: voltage-gated sodium channel expression in vivo", Prostate Cancer and Prostatic Diseases 8, 266-273 (2005).
Diss, et al., "Expression profiles of voltage-gated sodium channel a-subunit genes in rat and human prostate cancer cell lines", The Prostate 48, 165-178 (2001).
Diss, et al., "Identification and characterization of the promoter region of the NaV1.7 voltage-gated sodium channel gene (SCN9A)", Mol. Cell. Neurosci. 37, 537-547 (2008).
Dong, et al., "Small interfering RNA-mediated selective knock-down of Na(V)1.8 tetrodotoxin-resistant sodium channel reverses mechanical allodynia in neuropathic rats", Neuroscience 146, 812-821 (2007).
England, et al., "Isoform-selective voltage-gated Na(+) channel modulators as next-generation analgesics", Future Med Chem 2 (5), 775-790 (2010).
Estacion, et al., "A sodium channel gene SCN9A polymorphism that increases nociceptor excitability", Ann Neurol 66 (6), 862-866 (2009).
Fishman, et al., "Intravenous lidocaine for treatment-resistant pruritus", American J. of Medicine 102, 584-585 (1997).
Fraser, et al., "Voltage-gated sodium channel expression and potentiation of human breast cancer metastasis", Clin. Cancer Res. 11(15), 5381-5389 (2005).
Goldberg, et al., "Loss-of-function mutations in the Nav1.7 gene underlie congenital indifference to pain in multiple human populations", Clin. Genet. 71, 311-319 (2007).
Lamoureux, et al., "Use of the adamantane structure in medicinal chemistry", Curr Med Chem 17(26), 2967-2978 (2010).
Deng, et al., "Dynamic 1-15 Receptor-Based Pharmacophore Model Development and Its Application in Designing Novel HIV-1 Integrase Inhibitors", Journal of Medicinal Chemistry. vol. 48. No. 5, 1496-1505 (2005), Supporting Information, S1-S14. XP055285519. DOI: 10.1021jjm049410e (2005).
Kuo, et al., "Application of CoMFA and CoMSIA 3D-QSAR and Docking Studies in Optimization of Mercaptobenzenesulfonamides as HIV-1 Integrase Inhibitors", Journal of Medicinal Chemistry. American Chemical Society. US. vol. 47. No. 2, 385-399 (2003).

* cited by examiner

SUBSTITUTED BENZOXAZOLES AND METHODS OF USE THEREOF

FIELD OF THE INVENTION

The present invention relates to organic compounds useful for therapy and/or prophylaxis in a mammal, and in particular to inhibitors of sodium channel (e.g., NAV1.7) that are useful for treating sodium channel-mediated diseases or conditions, such as pain, as well as other diseases and conditions associated with the mediation of sodium channels.

Voltage-gated sodium channels, transmembrane proteins that initiate action potentials in nerve, muscle and other electrically excitable cells, are a necessary component of normal sensation, emotions, thoughts and movements (Catterall, W. A., Nature (2001), Vol. 409, pp. 988-990). These channels consist of a highly processed alpha subunit that is associated with auxiliary beta subunits. The pore-forming alpha subunit is sufficient for channel function, but the kinetics and voltage dependence of channel gating are in part modified by the beta subunits (Goldin et al., Neuron (2000), Vol. 28, pp. 365-368). Electrophysiological recording, biochemical purification, and molecular cloning have identified ten different sodium channel alpha subunits and four beta subunits (Yu, F. H., et al., Sci. STKE (2004), 253; and Yu, F. H., et al., Neurosci. (2003), 20:7577-85).

The hallmarks of sodium channels include rapid activation and inactivation when the voltage across the plasma membrane of an excitable cell is depolarized (voltage-dependent gating), and efficient and selective conduction of sodium ions through conducting pores intrinsic to the structure of the protein (Sato, C., et al., Nature (2001), 409:1047-1051). At negative or hyperpolarized membrane potentials, sodium channels are closed. Following membrane depolarization, sodium channels open rapidly and then inactivate. Channels only conduct currents in the open state and, once inactivated, have to return to the resting state, favoured by membrane hyperpolarization, before they can reopen. Different sodium channel subtypes vary in the voltage range over which they activate and inactivate as well as their activation and inactivation kinetics.

The sodium channel family of proteins has been extensively studied and shown to be involved in a number of vital body functions. Research in this area has identified variants of the alpha subunits that result in major changes in channel function and activities, which can ultimately lead to major pathophysiological conditions. The members of this family of proteins are denoted NaV1.x, where x=1 to 9. NaV1.1 and NaV1.2 are highly expressed in the brain (Raymond, C. K., et al., J. Biol. Chem. (2004), 279(44):46234-41) and are vital to normal brain function. Some loss of function mutations in NaV1.1 in humans result in epilepsy, apparently because many of these channels are expressed in inhibitory neurons (Yu, F. H., et al., Nat Neurosci (2006), 9 (9), 1142-9). Thus, block of NaV1.1 in the CNS may be counter-productive because it can produce hyperexcitability. However, NaV1.1 is also expressed in the peripheral nervous system and block may afford analgesic activity.

NaV1.3 is expressed primarily in the fetal central nervous system. It is expressed at very low levels or not at all in the peripheral nervous system, but expression is upregulated in the dorsal horn sensory neurons of rats after nervous system injury (Hains, B. D., et al., J. Neurosci. (2003), 23(26):8881-92). Thus, it is an inducible target for treatment of pain following nerve injury.

NaV1.4 is expressed primarily in skeletal muscle (Raymond, C. K., et al., op. cit.). Mutations in this gene have been shown to have profound effects on muscle function including paralysis, (Tamaoka A., Intern. Med. (2003), (9): 769-70).

NaV1.5, is expressed mainly in cardiac myocytes (Raymond, C. K., et al., op. cit.), including atria, ventricles, the sino-atrial node, atrio-ventricular node and cardiac Purkinje fibers. The rapid upstroke of the cardiac action potential and the rapid impulse conduction through cardiac tissue is due to the opening of NaV1.5. Abnormalities in the function of NaV1.5 can result in the genesis of a variety of cardiac arrhythmias. Mutations in human NaV1.5 result in multiple arrhythmic syndromes, including, for example, long QT3 (LQT3), Brugada syndrome (BS), an inherited cardiac conduction defect, sudden unexpected nocturnal death syndrome (SUNDS) and sudden infant death syndrome (SIDS) (Liu, H., et al., Am. J. Pharmacogenomics (2003), 3(3):173-9). Sodium channel blocker therapy has been used extensively in treating cardiac arrhythmias.

NaV1.6 is a widely distributed voltage-gated sodium channel found throughout the central and peripheral nervous systems. It is expressed at high density in the nodes of Ranvier of myelinated neurons (Caldwell, J. H., et al., Proc. Natl. Acad. Sci. USA (2000), 97(10): 5616-20).

NaV1.7 is a tetrodotoxin-sensitive voltage-gated sodium channel encoded by the gene SCN9A. Human NaV1.7 was first cloned from neuroendocrine cells (Klugbauer, N., et al., 1995 EMBO J., 14 (6): 1084-90.) and rat NaV1.7 was cloned from a pheochromocytoma PC12 cell line (Toledo-Aral, J. J., et al., Proc. Natl. Acad. Sci. USA (1997), 94:1527-1532) and from rat dorsal root ganglia (Sangameswaran, L., et al., (1997), J. Biol. Chem., 272 (23): 14805-9). NaV1.7 is expressed primarily in the peripheral nervous system, especially nociceptors and olfactory neurons and sympathetic neurons. The inhibition, or blocking, of NaV1.7 has been shown to result in analgesic activity. Knockout of NaV1.7 expression in a subset of sensory neurons that are predominantly nociceptive results in resistance to inflammatory pain (Nassar, et al., op. cit.). Likewise, loss of function mutations in humans results in congenital indifference to pain (CIP), in which the individuals are resistant to both inflammatory and neuropathic pain (Cox, J. J., et al., Nature (2006); 444:894-898; Goldberg, Y. P., et al., Clin. Genet. (2007); 71:311-319). Conversely, gain of function mutations in NaV1.7 have been established in two human heritable pain conditions, primary erythromelalgia and familial rectal pain, (Yang, Y., et al., J. Med. Genet. (2004), 41(3):171-4). In addition, a single nucleotide polymorphism (R1150W) that has very subtle effects on the time- and voltage-dependence of channel gating has large effects on pain perception (Estacion, M., et al., 2009. Ann Neurol 66: 862-6; Reimann, F., et al., Proc Natl Acad Sci USA (2010), 107: 5148-53). About 10% of the patients with a variety of pain conditions have the allele conferring greater sensitivity to pain and thus might be more likely to respond to block of NaV1.7. Because NaV1.7 is expressed in both sensory and sympathetic neurons, one might expect that enhanced pain perception would be accompanied by cardiovascular abnormalities such as hypertension, but no correlation has been reported. Thus, both the CLP mutations and SNP analysis suggest that human pain responses are more sensitive to changes in NaV1.7 currents than are perturbations of autonomic function.

NaV1.8 is expressed primarily in sensory ganglia of the peripheral nervous system, such as the dorsal root ganglia (Raymond, C. K., et al., op. cit.). There are no identified human mutations for NaV1.8 that produce altered pain responses. NaV1.8 differs from most neuronal NaV's in that it is insensitive to block by tetrodotoxin. Thus, one can isolate the current carried by this channel with tetrodotoxin. These studies have shown that a substantial portion of total sodium current is NaV1.8 in some dorsal root ganglion neurons (Blair, N. T., et al., J Neurosci (2002), 22: 10277-90). Knock-down of NaV1.8 in rats has been achieved by using antisense DNA or small interfering RNAs and virtually complete reversal of neuropathic pain was achieved in the spinal nerve ligation and chronic constriction injury models (Dong, X. W., et al., Neuroscience (2007), 146: 812-21; Lai J., et al. Pain (2002), 95: 143-52). Thus, NaV1.8 is considered a promising target for analgesic agents based upon the limited tissue distribution of this NaV isoform and the analgesic activity produced by knock-down of channel expression.

NaV1.9 is also a tetrodotoxin insensitive, sodium channel expressed primarily in dorsal root ganglia neurons (Dib-Hajj, S. D., et al. (see Dib-Hajj, S. D., et al., Proc. Natl. Acad. Sci. USA (1998), 95(15):8963-8). It is also expressed in enteric neurons, especially the myenteric plexus (Rugiero, F., et al., J Neurosci (2003), 23: 2715-25). The limited tissue distribution of this NaV isoform suggests that it may be a useful target for analgesic agents (Lai, J., et al., op. cit.; Wood, J. N., et al., op. cit.; Chung, J. M., et al., op. cit.). Knock-out of NaV1.9 results in resistance to some forms of inflammatory pain (Amaya, F., et al., J Neurosci (2006), 26: 12852-60; Priest, B. T., et al., Proc Natl Acad Sci USA (2005), 102: 9382-7).

This closely related family of proteins has long been recognized as targets for therapeutic intervention. Sodium channels are targeted by a diverse array of pharmacological agents. These include neurotoxins, antiarrhythmics, anticonvulsants and local anesthetics (England, S., et al., Future Med Chem (2010), 2: 775-90; Termin, A., et al., Annual Reports in Medicinal Chemistry (2008), 43: 43-60). All of the current pharmacological agents that act on sodium channels have receptor sites on the alpha subunits. At least six distinct receptor sites for neurotoxins and one receptor site for local anesthetics and related drugs have been identified (Cestèle, S., et al., Biochimie (2000), Vol. 82, pp. 883-892).

The small molecule sodium channel blockers or the local anesthetics and related antiepileptic and antiarrhythmic drugs interact with overlapping receptor sites located in the inner cavity of the pore of the sodium channel (Catterall, W. A., Neuron (2000), 26:13-25). Amino acid residues in the S6 segments from at least three of the four domains contribute to this complex drug receptor site, with the IVS6 segment playing the dominant role. These regions are highly conserved and as such most sodium channel blockers known to date interact with similar potency with all channel subtypes. Nevertheless, it has been possible to produce sodium channel blockers with therapeutic selectivity and a sufficient therapeutic window for the treatment of epilepsy (e.g., lamotrignine, phenytoin and carbamazepine) and certain cardiac arrhythmias (e.g., lignocaine, tocainide and mexiletine). However, the potency and therapeutic index of these blockers is not optimal and have limited the usefulness of these compounds in a variety of therapeutic areas where a sodium channel blocker would be ideally suited.

Sodium channel blockers have been shown to be useful in the treatment of pain, including acute, chronic, inflammatory and/or neuropathic pain (see, e.g., Wood, J. N., et al., J. Neurobiol. (2004), 61(1), 55-71. Preclinical evidence demonstrates that sodium channel blockers can suppress neuronal firing in peripheral and central sensory neurons, and it is via this mechanism that they are considered to be useful for relieving pain. In some instances, abnormal or ectopic firing can original from injured or otherwise sensitized neurons. For example, it has been shown that sodium channels can accumulate in peripheral nerves at sites of axonal injury and may function as generators of ectopic firing (Devor et al., J. Neurosci. (1993), 132: 1976). Changes in sodium channel expression and excitability have also been shown in animal models of inflammatory pain where treatment with proinflammatory materials (CFA, Carrageenan) promoted pain-related behaviors and correlated with increased expression of sodium channel subunits (Gould et al., Brain Res., (1999), 824(2): 296-99; Black et al., Pain (2004), 108(3): 237-47). Alterations in either the level of exprssion or distribution of sodium channels, therefore, may have a major influence on neuronal excitability and pain-related behaviors.

Controlled infusions of lidocaine, a known sodium channel blocker, indicate that the drug is efficacious against neuropathic pain, but has a narrow therapeutic index. Likewise, the orally available local anesthetic, mexiletine, has dose-limiting side effects (Wallace, M. S., et al., Reg. Anesth. Pain Med. (2000), 25: 459-67). A major focus of drug discovery targeting voltage-gated sodium channels has been on strategies for improving the therapeutic index. One of the leading strategies is to identify selective sodium channel blockers designed to preferentially block NaV1.7, NaV1.8, NaV1.9 and/or NaV1.3. These are the sodium channel isoforms preferentially expressed in sensory neurons and unlikely to be involved in generating any dose-limiting side effects. For example, there is concern that blocking of NaV1.5 would be arrhythmogenic, so that selectivity of a sodium channel blocker against NaV1.5 is viewed as highly desirable. Furthermore, nearly 700 mutations of the SCN1A gene that codes for NaV1.1 have been identified in patients with Severe Myoclonic Epilepsy of Infancy (SMEI), making this the most commonly mutated gene in human epilepsy. Half of these mutations result in protein truncation (Meisler, M. H., et al., The Journal of Physiology (2010), 588: 1841-8). Thus, selectivity of a sodium channel blocker against NaV1.1 is also desirable.

In addition to the strategies of identifying selective sodium channel blockers, there is the continuing strategy of identifying therapeutic agents for the treatment of neuropathic pain. There has been some degree of success in treating neuropathic pain symptoms by using medications originally approved as anticonvulsants, such as gabapentin, and more recently pregabalin. However, pharmacotherapy for neuropathic pain has generally had limited success for a variety of reasons: sedation, especially by drugs first developed as anticonvulsants or anti-depressants, addiction or tachyphylaxis, especially by opiates, or lack of efficacy, especially by NSAIDs and anti-inflammatory agents. Consequently, there is still a considerable need to explore novel treatment modalities for neuropathic pain, which includes, but is not limited to, post-herpetic neuralgia, trigeminal neuralgia, diabetic neuropathy, chronic lower back pain, phantom limb pain, and pain resulting from cancer and chemotherapy, chronic pelvic pain, complex regional pain syndrome and related neuralgias.

There are a limited number of effective sodium channel blockers for the treatment of pain with a minimum of adverse side effects which are currently in the clinic. There is also an unmet medical need to treat neuropathic pain and other sodium channel associated pathological states effectively and without adverse side effects due to the blocking of sodium channels not involved in nociception. The present invention provides methods to meet these critical needs.

SUMMARY OF THE INVENTION

In one aspect the present invention provides for novel compounds. In a first embodiment of such compounds (Embodiment 1; abbreviated as "E1") the invention provides for a compound of Formula I:

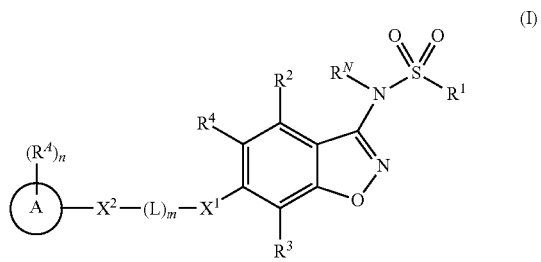

(I)

or a pharmaceutically acceptable salt thereof, wherein:

$R^1$ is $C_{1-8}$ alkyl, $C_{1-8}$ haloalkyl, $C_{1-8}$ alkoxy, $C_{3-12}$ carbocycle, C-linked $C_{2-11}$ heterocycle or $NR^{1A}R^{1B}$, wherein $R^{1A}$ and $R^{1B}$ are each independently selected from the group consisting of hydrogen, $C_{1-8}$ alkyl, $C_{1-8}$ alkoxy, (6-10 membered aryl)-$(X^{R1})_{0-1}$—, (5-10 membered heteroaryl)-$(X^{R1})_{0-1}$—, and wherein $R^{1A}$ and $R^{1B}$ are optionally combined to form a 3 to 8 membered heterocyclic ring optionally comprising 1 additional heteroatoms selected from N, O and S as ring vertex and optionally fused thereto is a benzene or pyridine ring; $X^{R1}$ is selected from the group consisting of $C_{1-4}$ alkylene, $C_{1-4}$ heteroalkylene, $C_{2-4}$ alkenylene, $C_{2-4}$ alkynylene; and wherein the aliphatic and aromatic portions of $R^1$ are optionally substituted with from 1 to 5 $R^{R1}$ substituents selected from the group consisting of $C_{1-8}$ alkyl, $C_{1-8}$ haloalkyl, oxo (=O), F, Cl, Br, I, —OH, —CN, —NO$_2$, —$(X^{1R})_{0-1}NR^{R1a}R^{R1b}$, —$(X^{1R})_{0-1}OR^{R1a}$, —$(X^{1R})_{0-1}SR^{R1a}$, —$(X^{1R})_{0-1}N(R^{R1a})C(=O)OR^{R1c}$, —$(X^{1R})_{0-1}OC(=O)N(R^{R1a})(R^{R1b})$, —$(X^{1R})_{0-1}N(R^{R1a})C(=O)N(R^{R1a})(R^{R1b})$, —$(X^{1R})_{0-1}C(=O)N(R^{R1a})(R^{R1b})$, —$(X^{1R})_{0-1}N(R^{R1a})C(=O)R^{R1b}$, —$(X^{1R})_{0-1}C(=O)OR^{R1a}$, —$(X^{1R})_{0-1}OC(=O)R^{R1a}$, —$(X^{1R})_{0-1}P(=O)(OR^{R1a})(OR^{R1b})$, —$(X^{1R})_{0-1}S(O)_{1-2}R^{R1c}$, —$(X^{1R})_{0-1}S(O)_{1-2}N(R^{R1a})(R^{R1b})$, —$(X^{1R})_{0-1}N(R^{R1a})S(O)_{1-2}N(R^{R1a})(R^{R1b})$ and —$(X^{1R})_{0-1}N(R^{R1a})S(O)_{1-2}(R^{R1c})$, wherein $X^{1R}$ is selected from the group consisting of $C_{1-4}$ alkylene, $C_{1-4}$ heteroalkylene, $C_{2-4}$ alkenylene and $C_{2-4}$ alkynylene; wherein $R^{R1a}$ and $R^{R1b}$ are independently selected from the group consisting of hydrogen, $C_{1-8}$ alkyl, $C_{1-8}$ haloalkyl, $C_{3-8}$ carbocycle, phenyl, benzyl, $C_{5-6}$ heteroaryl and $C_{2-7}$ heterocycle; $R^{R1c}$ is selected from the group consisting of $C_{1-8}$ alkyl, $C_{1-8}$ haloalkyl, $C_{3-8}$ carbocycle, phenyl, benzyl, $C_{5-6}$ heteroaryl and $C_{2-7}$ heterocycle;

$R^N$ is hydrogen, $C_{1-4}$ alkyl or $C_{1-4}$ haloalkyl;

$R^2$ and $R^3$ are each independently selected from the group consisting of H, F, Cl, Br, I, —CN, $C_{1-8}$ alkyl, $C_{1-8}$ haloalkyl and $C_{1-8}$ alkoxy;

$R^4$ is selected from the group consisting of H, F, Cl, Br, I, —CN, $C_{1-8}$ alkyl, $C_{1-8}$ haloalkyl, $C_{1-8}$ alkoxy, $C_{3-8}$ carbocycle, $C_{2-7}$ heterocycle, phenyl and 5-6 membered heteroaryl comprising 1 to 3 heteroatoms selected from N, O and S, wherein said 5-6 membered heteroaryl is further optionally substituted with from 1 to 3 $R^5$ substituents selected from F, Cl, Br, I, —CN, $C_{1-4}$ alkyl, $C_{1-4}$ haloalkyl and $C_{1-4}$ alkoxy;

L is a linker selected from the group consisting of $C_{1-4}$ alkylene, $C_{2-4}$ alkenylene, $C_{2-4}$ alkynylene, and $C_{1-4}$ heteroalkylene, wherein L is optionally substituted with from 1 to 3 $R^L$ substituents selected from the group consisting of =O, $C_{1-4}$ alkyl, $C_{1-4}$ haloalkyl and $C_{1-4}$ acyl;

the subscript m represents the integer 0 or 1;

$X^1$ and $X^2$ are each independently selected from the group consisting of absent, —O—, —S(O)—, —S(O)$_2$— and —N($R^X$)— wherein Rx is H, $C_{1-8}$ alkyl, $C_{1-8}$ acyl or —S(O)$_2$($C_{1-8}$ alkyl), and wherein if the subscript m is 0 then one of $X^1$ or $X^2$ is absent;

the subscript n is an integer from 0 to 5;

A is selected from the group consisting of hydrogen, $C_3$-$C_{20}$carbocycle, $C_3$-$C_{20}$heterocycle, aryl, and heteroaryl, wherein if A is hydrogen then the subscript n is 0; and $R^A$ is selected from the group consisting of $C_{1-8}$ alkyl, $C_{1-8}$ haloalkyl, F, Cl, Br, I, —OH, —CN, —NO$_2$, carbocycle, heterocycle, heteroaryl, —$(X^{RA})_{0-1}NR^{A1}R^{A2}$, —$(X^{RA})_{0-1}OR^{A1}$, —$(X^{RA})_{0-1}SR^{A1}$, —$(X^{RA})_{0-1}N(R^{A1})C(=O)OR^{A3}$, —$(X^{RA})_{0-1}OC(=O)N(R^{A1})(R^{A2})$, —$(X^{RA})_{0-1}N(R^{A1})C(=O)N(R^{A1})(R^{A2})$, —$(X^{RA})_{0-1}C(=O)N(R^{A1})(R^{A2})$, —$(X^{RA})_{0-1}N(R^{A1})C(=O)R^{A2}$, —$(X^{RA})_{0-1}C(=O)OR^{A1}$, —$(X^{RA})_{0-1}OC(=O)R^{A1}$, —P(=O)(OR^{A1})(OR^{A2})$, —$(X^{RA})_{0-1}S(O)_{1-2}R^{A3}$, —$(X^{RA})_{0-1}S(O)_{1-2}N(R^{A1})(R^{A2})$, —$(X^{RA})_{0-1}N(R^{A1})S(O)_{1-2}N(R^{A1})(R^{A2})$ and —$(X^{RA})_{0-1}N(R^{A1})S(O)_{1-2}(R^{A3})$, wherein $X^{RA}$ is selected from the group consisting of $C_{1-4}$ alkylene, $C_{1-4}$ heteroalkylene, $C_{2-4}$ alkenylene and $C_{2-4}$ alkynylene; wherein $R^{A1}$ and $R^{A2}$ are independently selected from the group consisting of hydrogen, $C_{1-8}$ alkyl, $C_{1-8}$ haloalkyl, $C_{3-8}$ carbocycle, tetrahydronapthalene, phenyl, benzyl, $C_{5-6}$ heteroaryl and $C_{2-7}$ heterocycle; $R^{A3}$ is selected from the group consisting of $C_{1-8}$ alkyl, $C_{1-8}$ haloalkyl, $C_{3-8}$ carbocycle, tetrahydronapthalene, phenyl, benzyl, $C_{5-6}$ heteroaryl and $C_{2-7}$ heterocycle; and wherein the aliphatic and aromatic portions of a $R^A$ substitutent is optionally substituted with from 1 to 5 $R^{RA}$ substitutents selected from, F, Cl, Br, I, —NH$_2$, —OH, —CN, —NO$_2$, =O, $C_{1-4}$ alkyl, $C_{1-4}$ haloalkyl, $C_{1-4}$ alkoxy, $C_{1-4}$ (halo)alkyl-C(=O)—, $C_{1-4}$ (halo)alkyl-S(O)$_{0-2}$—, $C_{1-4}$ (halo)alkyl-C(=O)N(H)—, $C_{1-4}$ (halo)alkyl-N(H)—C(=O)—, ((halo)alkyl)$_2$N—C(=O)—, $C_{1-4}$ (halo)alkyl-OC(=O)N(H)—, $C_{1-4}$ (halo)alkyl-OC(=O)N(H)—, (halo)alkyl-N(H)—C(=O)O—, ((halo)alkyl)$_2$N—C(=O)O—, $C_{1-4}$ alkylamino, $C_{1-4}$ dialkylamino, $C_{3-6}$ carbocycle, $C_{3-6}$ cycloalkoxy, $C_{2-5}$ heterocycloalkoxy and tetrahydronaphthalene.

Further embodiments (E2-E30) of the first embodiment of compounds of the invention, are described below.

E2 A compound of E1, wherein the compound has the formula

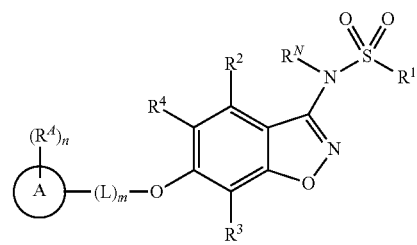

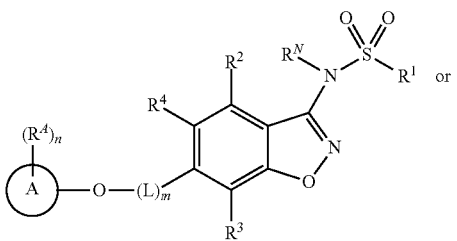

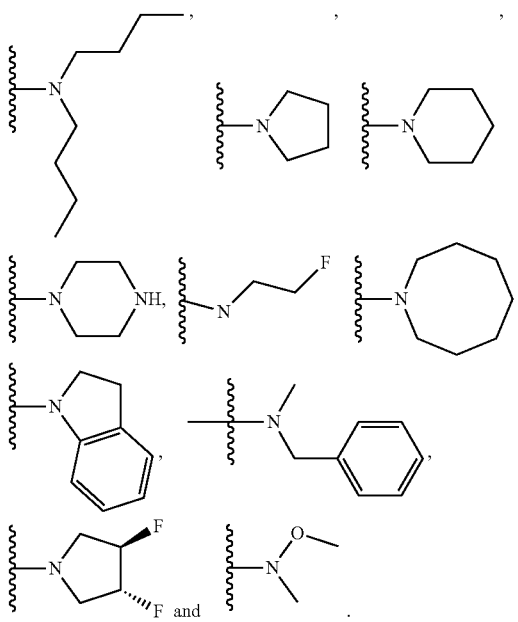

E3 The compound of E1 or E2 wherein $R^2$ and $R^3$ are each H.

E4 The compound of E1, E2, or E3 wherein $R^4$ is F, Cl, Br, I, —CN, $C_{1-8}$ alkyl, $C_{1-8}$ haloalkyl, $C_{1-8}$ alkoxy, or $C_{3-8}$ carbocycle.

E5 The compound of E1, E2, or E3 wherein $R^4$ is Cl or $C_{3-8}$ carbocycle.

E6 The compound of E1, E2, or E3 wherein $R^4$ is Cl or $C_{3-8}$ cyclopropyl.

E7 The compound of E1, E2, E3, E4, E5, or E6, wherein $R^1$ is $C_{1-8}$ alkyl or $C_{3-12}$ carbocycle, wherein the aliphatic portions of $R^1$ are optionally substituted with from 1 to 5 $R^{R1}$ substituents.

E8 The compound of E7 wherein the aliphatic portions of $R^1$ are optionally substituted with —$(X^{1R})_{0-1}OR^{R1a}$.

E9 The compound of E7 wherein $R^1$ is methyl, cyclopropyl, or 2-methoxyethyl.

E10 The compound of E1, E2, E3, E4, E5, or E6, wherein $R^1$ is selected from the group consisting of: —NH(CH$_3$), —N(CH$_3$)$_2$,

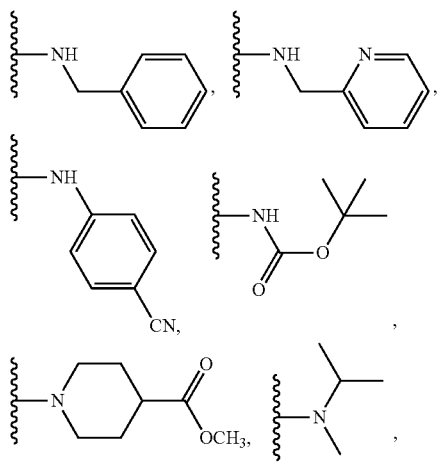

E11 A compound of E1, E2, E3, E4, E5, E6, E7, E8, E9, or E10 wherein $X^1$ is —O— or —N(H)—; $X^2$ is absent; the subscript m is 1; and -(L)- is an optionally substituted group selected from the group consisting of $C_{1-4}$ alkylene, $C_{2-4}$ alkenylene or $C_{2-4}$ alkynylene.

E12 A compound of E1, E2, E3, E4, E5, E6, E7, E8, E9 or E10, wherein $X^1$ is —O— or —N(H)—; $X^2$ is absent; the subscript m is 1; and -(L)- is selected from the group consisting of —CH$_2$—, —C(=O)—, —C(H)(CH$_3$)—, —CH$_2$—CH$_2$—, —CH$_2$—C(H)(CH$_3$)—, —C(H)(CH$_3$)—C(H$_2$)—, —CH$_2$CH$_2$CH$_2$—, —CH$_2$—C(H)(CH$_3$)—CH$_2$— or —CH$_2$CH$_2$CH$_2$CH$_2$—.

E13 A compound of E12, wherein $X^1$ is —O—; the subscript m is 1 and -(L)- is —CH$_2$— or —CH$_2$—CH$_2$—.

E14 The compound of E1, E2, E3, E4, E5, E6, E7, E8, E9, or E10 wherein $X^1$ is absent; $X^2$ is —O— or —N(H)—; the subscript m is 1; and -(L)- is selected from the group consisting of —C(H)$_2$—, —C(=O)—, —C(H)(CH$_3$)—, —CH$_2$—CH$_2$—, —CH$_2$—C(H)(CH$_3$)—, —C(H)(CH$_3$)—C(H$_2$)—, —CH$_2$CH$_2$CH$_2$—, —CH$_2$—C(H)(CH$_3$)—CH$_2$— or —CH$_2$CH$_2$CH$_2$CH$_2$—.

E15 A compound of E1, E2, E3, E4, E5, E6, E7, E8, E9, or E10 wherein $X^1$ and $X^2$ is absent; the subscript m is 1; and -(L)- is selected from the group consisting of —C(H)$_2$—, —C(=O)—, —C(H)(CH$_3$)—, —CH$_2$—CH$_2$—, —CH$_2$—C(H)(CH$_3$)—, —C(H)(CH$_3$)—C(H$_2$)—, —CH$_2$CH$_2$CH$_2$—, —CH$_2$—C(H)(CH$_3$)—CH$_2$— or —CH$_2$CH$_2$CH$_2$CH$_2$—.

E16 A compound of E1, E2, E3, E4, E5, E6, E7, E8, E9, or E10 wherein $X^1$ and $X^2$ is absent; the subscript m is 1; and -(L)- is an optionally substituted $C_{1-4}$ heteroalkylene.

E17 A compound of E1, E2, E3, E4, E5, E6, E7, E8, E9, or E10 wherein m is 0; $X^1$ is selected from —O—, and —N(H)—; and $X^2$ is absent.

E18 A compound of E1, E2, E3, E4, E5, E6, E7, E8, E9, E10, E11, E12, E13, E14, E15, E16, or E17 wherein A is an optionally substituted ring selected from the group consisting of cyclopropane, cyclobutane, cyclopentane, cyclohexane, cycloheptane, adamantane, bicyclo[2.1.1]hexane, bicyclo[2.2.2]octane, bicyclo[2.2.1]heptane, bicyclo[3.1.1]heptane, bicyclo[3.2.1]octane, bicyclo[4.1.1]octane, bicyclo

[3.3.1]nonane and 1,2,3,4-tetrahydro-1,4-methanonaphthalene, 1,2,3,4-tetrahydroisoquinoline and chroman.

E19 A compound of E18, wherein ring A is an optionally substituted ring selected from the group consisting of cyclopropane, cyclobutane, cyclopentane, cyclohexane, adamantane, cubane, bicyclo[2.2.2]octane, bicyclo[3.1.1]heptane, bicyclo[2.2.1]heptane, spiro[2,5]octane, tetrahydronaphthalene and chroman.

E20 A compound of E1, E2, E3, E4, E5, E6, E7, E8, E9, E10, E11, E12, E13, E14, E15, E16, or E17 wherein ring A is selected from the group consisting of

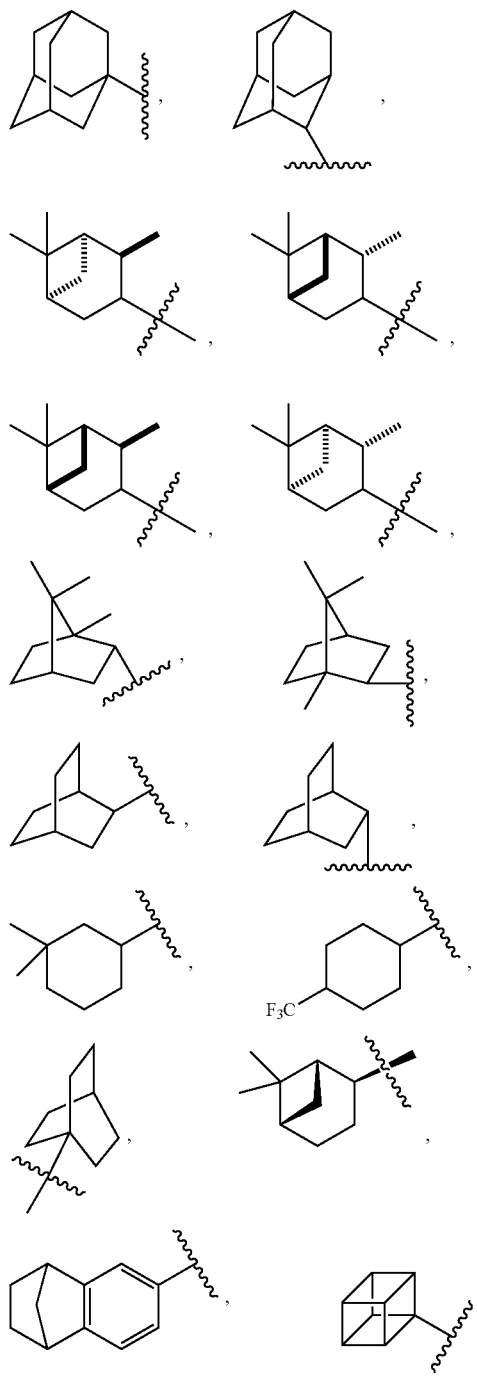

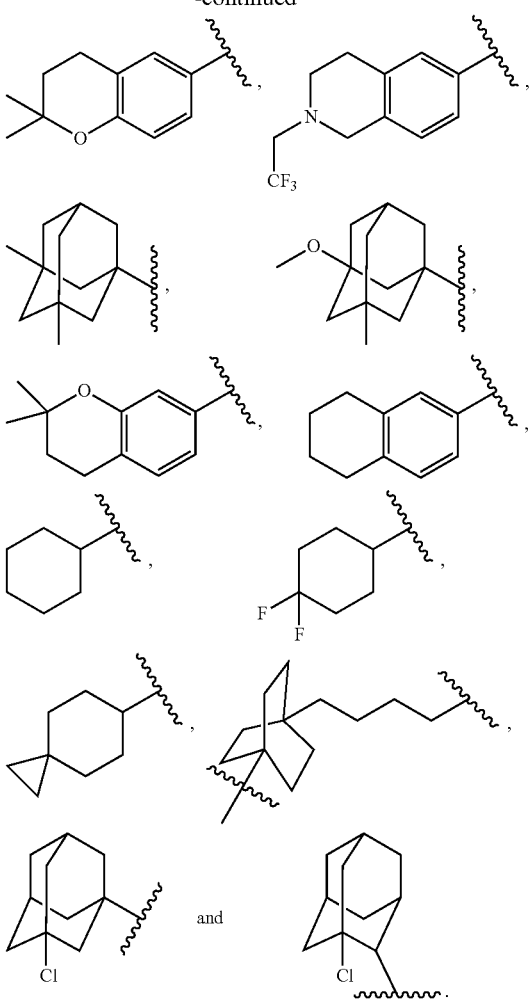

E21 A compound of E1, E2, E3, E4, E5, E6, E7, E8, E9, E10, E11, E12, E13, E14, E15, E16, or E17 wherein ring A is an optionally substituted ring selected from the group consisting of azetidine, pyrrolidine, piperidine, homopiperidine, (1R,5S)-8-azabicyclo[3.2.1]octane, 3-oxa-9-azabicyclo[3.3.1]-nonane, (1s,4s)-7-azabicyclo[2.2.1]heptane, (1R,4S)-5-azabicyclo[2.1.1]hexane, 7-(trifluoromethyl)-1,2,3,4-tetrahydropyrrolo[1,2-a]pyrazine and quinuclidine.

E22 A compound of E17, wherein A is selected from the group consisting of

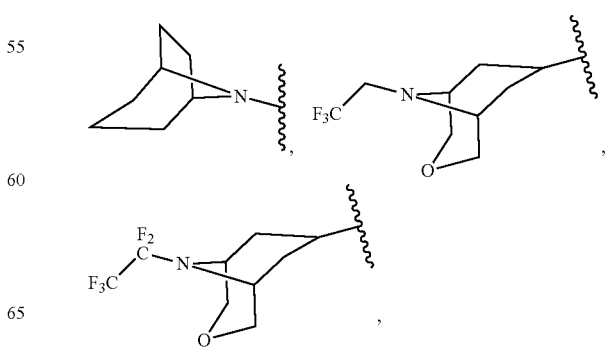

-continued

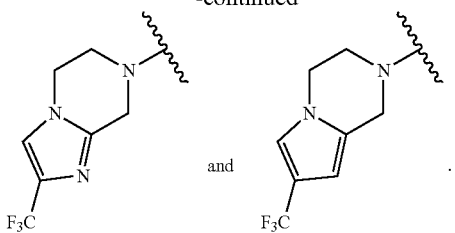

and

E23 A compound of E1, E2, E3, E4, E5, E6, E7, E8, E9, E10, E11, E12, E13, E14, E15, E16, E17, E18, E20 or E21, wherein $R^A$ is selected from the group consisting of $C_{1-4}$ alkyl, $C_{1-4}$ haloalkyl, $C_{3-5}$ carbocycle, $C_{2-4}$ heterocycle, F, Cl, Br, I, —OH, —NH$_2$, —CN, —NO$_2$, $C_{1-4}$ alkoxy, —C(=O)—N($R^{A1}$)($R^{A2}$) and —N($R^{A1}$)($R^{A2}$).

E24 A compound of E23, wherein $R^A$ is methyl, trifluromethyl, difluoromethyl, monofluoromethyl, ethyl, pentafluoroethyl, cyclopropyl, —F, Cl, —OH, —NH$_2$ or CN.

E25 The compound of E1, E2, E3, E4, E5, E6, E7, E8, E9, E10, E11, E12, E13, E14, E15, E16, or E17 wherein A is selected from the group consisting of benzene, pyridine, pyrimidine, pyrazine, pyridazine, benzothiazole, indole, quinoline, isoquinoline, quinazoline, benzoxazalole, benzimidazole, pyrrolopyridine, dihydrobenzofuran, dihydroindene, and indoline.

E26 The compound of E26 wherein $R^A$ is selected from the group consisting of $C_{1-4}$ alkyl, $C_{1-4}$ haloalkyl, $C_{3-5}$ carbocycle, 3-5 membered heterocycle, $C_{1-4}$ haloalkoxy, F, Cl, Br, I, —OH, —NH$_2$, —CN, —NO$_2$, $C_{1-4}$ alkoxy, —($X^{RA}$)$_{0-1}$O$R^{A1}$, —C(=O)—N($R^{A1}$)($R^{A2}$) and —N($R^{A1}$)($R^{A2}$), wherein the aliphatic portions of a $R^A$ are optionally substituted with from 1 to 5 $R^{RA}$ substitutents selected from, F, Cl, Br, and I.

E27 The compound of E26 wherein $R^A$ is methyl, trifluromethyl, difluoromethyl, monofluoromethyl, ethyl, pentafluoroethyl, cyclopropyl, n-propoxy, isopropoxy, sec-butyloxy, n-butyloxy, tert-butyloxy, —F, Cl, —OH, —NH$_2$ or —CN.

E28 A compound of E1, E2, E3, E4, E5, E6, E7, E8, E9, E10, E11, E12, E13, E14, E15, E16, or E17 wherein

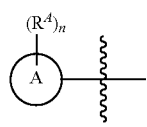

is selected from:

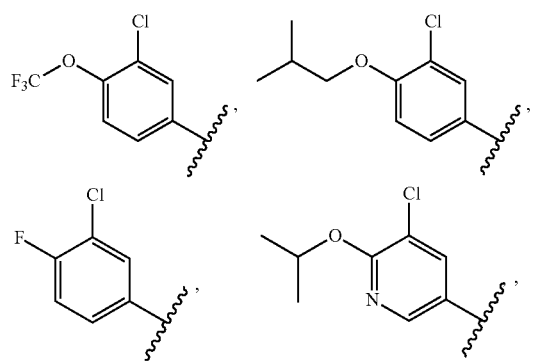

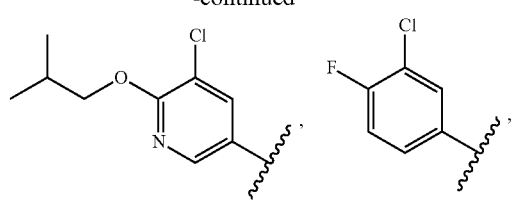

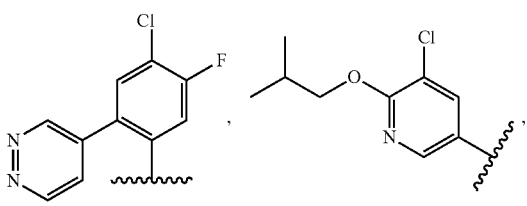

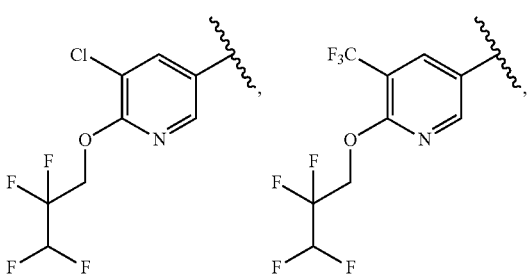

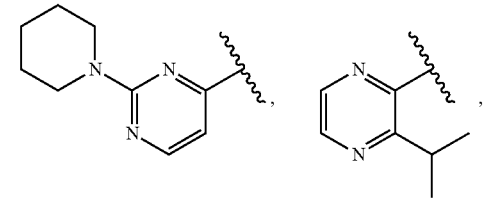

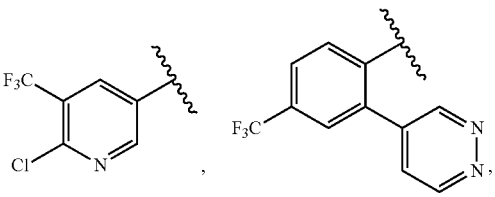

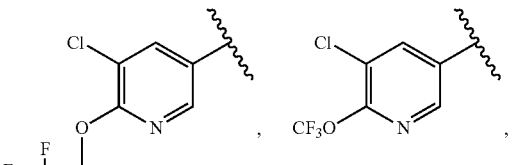

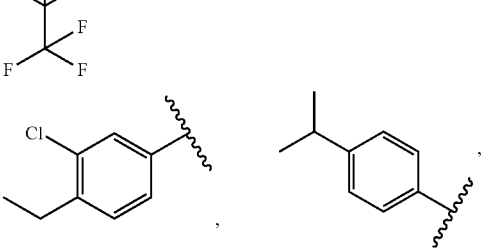

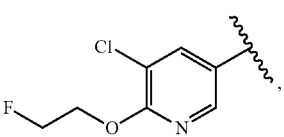

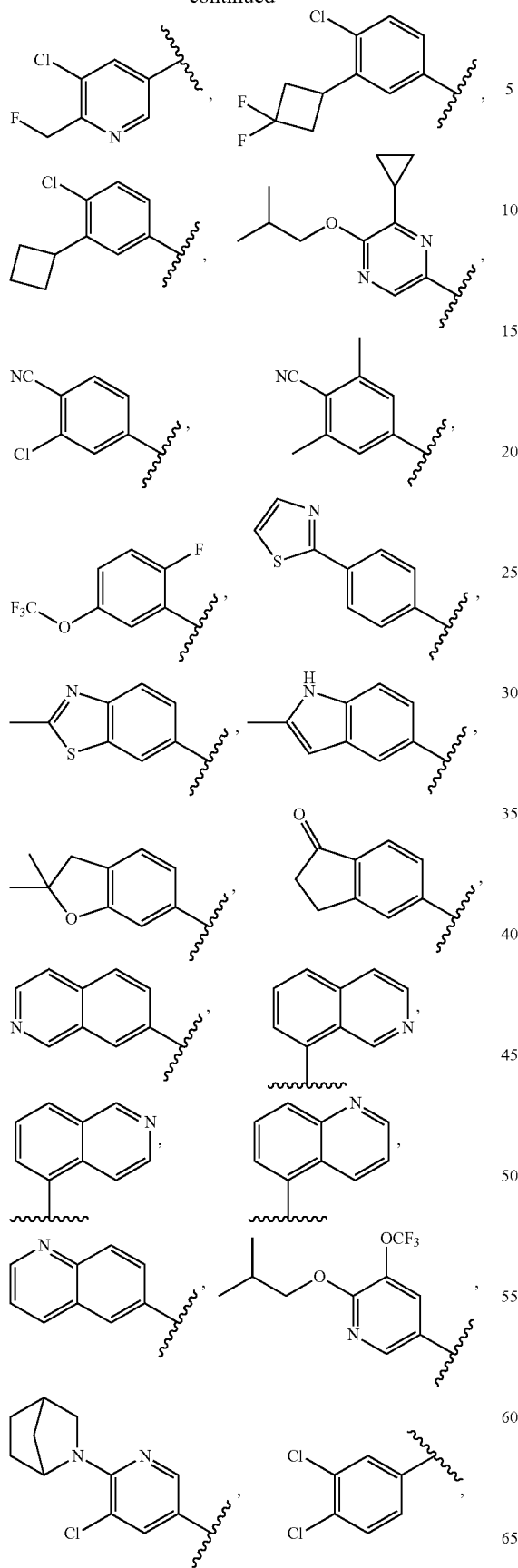
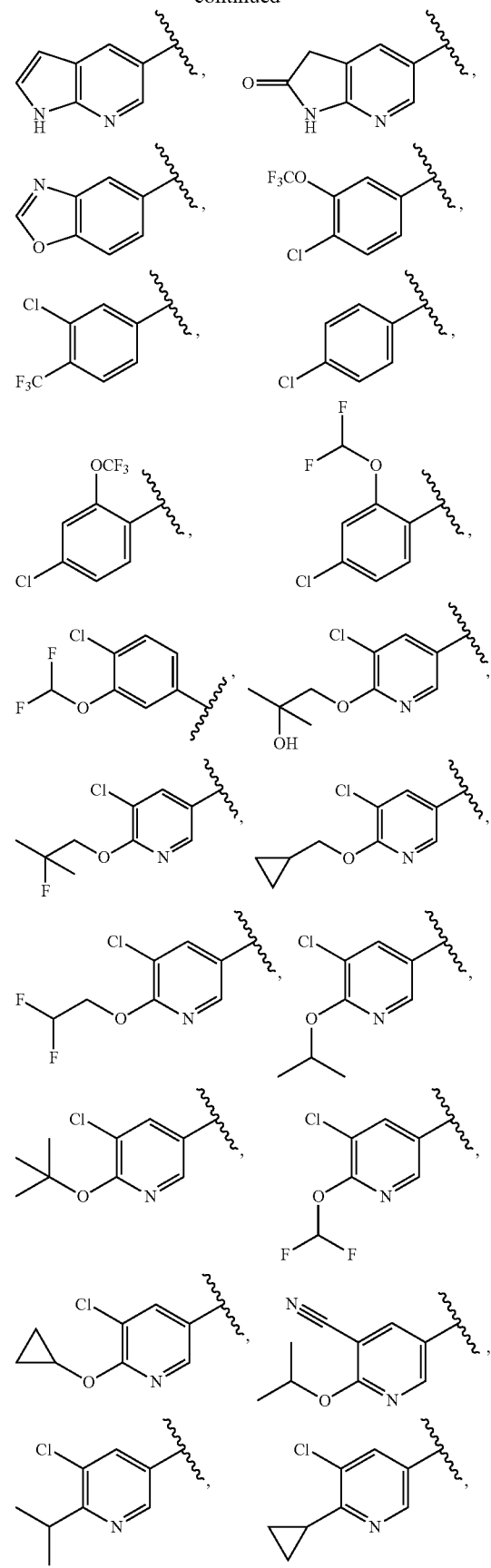

-continued
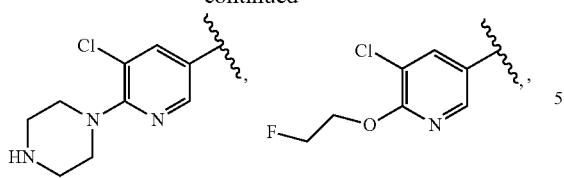
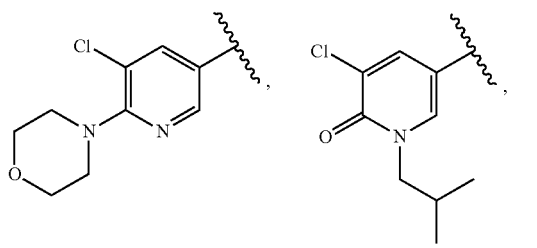
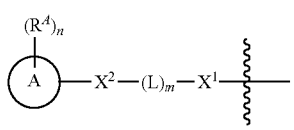
E29 A compound of E1, E2, E3, E4, E5, E6, E7, E8, E9, or E10 wherein
is selected from:
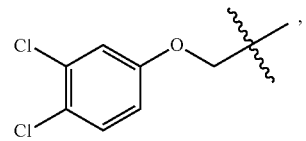
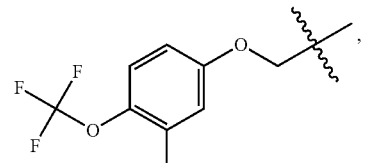
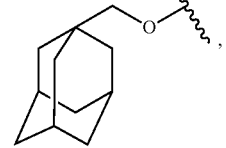
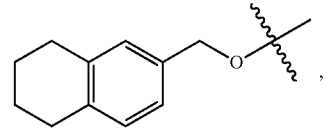
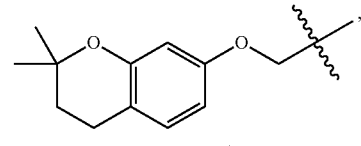
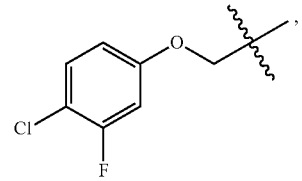
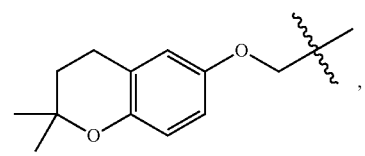
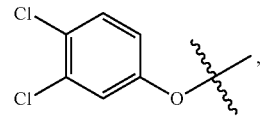
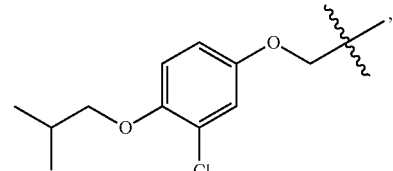
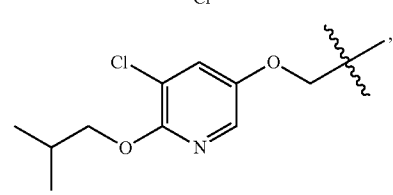

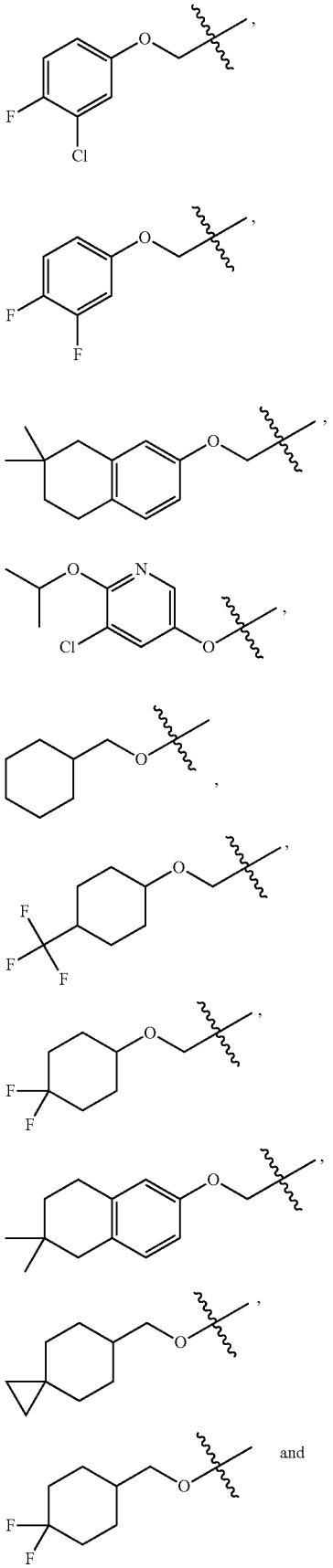

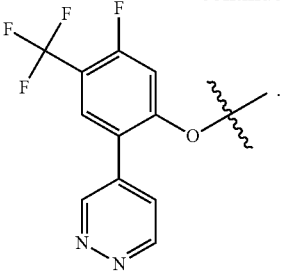

E30 A compound of E1, selected from the compounds prepared in the Examples herein.

In another aspect the present invention provides for a pharmaceutical composition comprising compounds of formula I or any embodiment thereof, and a pharmaceutically acceptable excipient.

In another aspect of the invention, the present invention provides for a method of treating a disease or condition in a mammal selected from the group consisting of pain, depression, cardiovascular diseases, respiratory diseases, and psychiatric diseases, and combinations thereof, Such disesase or conditions can include neuropathic pain, inflammatory pain, visceral pain, cancer pain, chemotherapy pain, trauma pain, surgical pain, post-surgical pain, childbirth pain, labor pain, neurogenic bladder, ulcerative colitis, chronic pain, persistent pain, peripherally mediated pain, centrally mediated pain, chronic headache, migraine headache, sinus headache, tension headache, phantom limb pain, dental pain, peripheral nerve injury or a combination thereof. Such disease or condition can include pain associated with HIV, HIV treatment induced neuropathy, trigeminal neuralgia, post-herpetic neuralgia, eudynia, heat sensitivity, tosarcoidosis, irritable bowel syndrome, Crohns disease, pain associated with multiple sclerosis (MS), amyotrophic lateral sclerosis (ALS), diabetic neuropathy, peripheral neuropathy, arthritis, rheumatoid arthritis, osteoarthritis, atherosclerosis, paroxysmal dystonia, myasthenia syndromes, myotonia, malignant hyperthermia, cystic fibrosis, pseudoaldosteronism, rhabdomyolysis, hypothyroidism, bipolar depression, anxiety, schizophrenia, sodium channel toxi related illnesses, familial erythromelalgia, primary erythromelalgia, familial rectal pain, cancer, epilepsy, partial and general tonic seizures, restless leg syndrome, arrhythmias, fibromyalgia, neuroprotection under ischaemic conditions cause by stroke or neural trauma, tach-arrhythmias, atrial fibrillation and ventricular fibrillation.

In another aspect of the invention, the present invention provides for a method of treating pain in a mammal by the inhibition of ion flux through a voltage-dependent sodium channel in the mammal, wherein the method comprises administering to the mammal in need thereof a therapeutically effective amount of a compound of Formula I or any embodiment thereof.

In another aspect of the invention, the present invention provides for a method of decreasing ion flux through a voltage-dependent sodium channel in a cell in a mammal, wherein the method comprises contacting the cell with a compound of Formula I or any embodiment thereof.

In another aspect of the invention, the present invention provides for a method of treating pruritus in a mammal, wherein the method comprises administering to the mammal in need thereof a therapeutically effective amount of a compound of Formula I or any embodiment thereof.

In another aspect of the invention, the present invention provides for a method of treating cancer in a mammal, wherein the method comprises administering to the mammal in need thereof a therapeutically effective amount of a compound of Formula I or any embodiment thereof.

In another aspect of the invention, the present invention provides for a method of treating, but not preventing, pain in a mammal, wherein the method comprises administering to the mammal in need thereof a therapeutically effective amount of a compound of Formula I or any embodiment thereof. In such method, pain can include of neuropathic pain, inflammatory pain, visceral pain, cancer pain, chemotherapy pain, trauma pain, surgical pain, post-surgical pain, childbirth pain, labor pain, neurogenic bladder, ulcerative colitis, chronic pain, persistent pain, peripherally mediated pain, centrally mediated pain, chronic headache, migraine headache, sinus headache, tension headache, phantom limb pain, dental pain, peripheral nerve injury or a combination thereof. In such methods, pain can include pain is associated with a disease or condition selected from the group consisting of HIV, HIV treatment induced neuropathy, trigeminal neuralgia, post-herpetic neuralgia, eudynia, heat sensitivity, tosarcoidosis, irritable bowel syndrome, Crohns disease, pain associated with multiple sclerosis (MS), amyotrophic lateral sclerosis (ALS), diabetic neuropathy, peripheral neuropathy, arthritis, rheumatoid arthritis, osteoarthritis, atherosclerosis, paroxysmal dystonia, myasthenia syndromes, myotonia, malignant hyperthermia, cystic fibrosis, pseudoaldosteronism, rhabdomyolysis, hypothyroidism, bipolar depression, anxiety, schizophrenia, sodium channel toxi related illnesses, familial erythromelalgia, primary erythromelalgia, familial rectal pain, cancer, epilepsy, partial and general tonic seizures, restless leg syndrome, arrhythmias, fibromyalgia, neuroprotection under ischaemic conditions cause by stroke or neural trauma, tach-arrhythmias, atrial fibrillation and ventricular fibrillation.

In another aspect of the invention, the present invention provides for a method for the treatment or prophylaxis of pain, depression, cardiovascular diseases, respiratory diseases, and psychiatric diseases, and combinations thereof, which method comprises administering an effective amount of a compound of the invention.

In another aspect of the invention, the present invention provides for a compound of formula I or any embodiment thereof or the use as a medicament for the treatment of diseases and disorders selected from the group consisting of pain, depression, cardiovascular diseases, respiratory diseases, and psychiatric diseases, or a combination thereof.

In another aspect of the invention, the present invention provides for a the use of a compound of any of formula I or an embodiment thereof for the manufacture of a medicament for the treatment of diseases and disorders selected from the group consisting of pain, depression, cardiovascular diseases, respiratory diseases, and psychiatric diseases, or a combination thereof

DETAILED DESCRIPTION OF THE INVENTION

Definitions

As used herein, the term "alkyl", by itself or as part of another substituent, means, unless otherwise stated, a straight or branched chain hydrocarbon radical, having the number of carbon atoms designated (i.e., $C_{1-8}$ means one to eight carbons). Examples of alkyl groups include methyl, ethyl, n-propyl, iso-propyl, n-butyl, t-butyl, iso-butyl, sec-butyl, n-pentyl, n-hexyl, n-heptyl, n-octyl, and the like. The term "alkenyl" refers to an unsaturated alkyl radical having one or more double bonds. Similarly, the term "alkynyl" refers to an unsaturated alkyl radical having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "heteroalkyl," by itself or in combination with another term, means, unless otherwise stated, a stable straight or branched chain hydrocarbon radical, consisting of the stated number of carbon atoms and from one to three heteroatoms selected from the group consisting of O, N, Si and S, and wherein the nitrogen and sulfur atoms can optionally be oxidized and the nitrogen heteroatom can optionally be quaternized. The heteroatom(s) O, N and S can be placed at any interior position of the heteroalkyl group. The heteroatom Si can be placed at any position of the heteroalkyl group, including the position at which the alkyl group is attached to the remainder of the molecule. A "heteroalkyl" can contain up to three units of unsaturation, and also include mono- and poly-halogenated variants, or combinations thereof. Examples include —$CH_2$—$CH_2$—O—$CH_3$, —$CH_2$—$CH_2$—O—$CF_3$, —$CH_2$—$CH_2$—NH—$CH_3$, —$CH_2$—$CH_2$—N($CH_3$)—$CH_3$, —$CH_2$—S—$CH_2$—$CH_3$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH=N($CH_3$)—$CH_3$. Up to two heteroatoms can be consecutive, such as, for example, —$CH_2$—NH—O$CH_3$ and —$CH_2$—O—Si($CH_3$)$_3$.

The term "alkylene" by itself or as part of another substituent means a divalent radical derived from an alkane (including branched alkane), as exemplified by —$CH_2CH_2CH_2CH_2$— and —CH($CH_2$)$CH_2CH_2$—. Typically, an alkyl (or alkylene) group will have from 1 to 24 carbon atoms, with those groups having 10 or fewer carbon atoms being preferred in the present invention. "Alkenylene" and "alkynylene" refer to the unsaturated forms of "alkylene" having double or triple bonds, respectively. "Alkylene", "alkenylene" and "alkynylene" are also meant to include mono and poly-halogenated variants.

The term "heteroalkylene" by itself or as part of another substituent means a divalent radical, saturated or unsaturated or polyunsaturated, derived from heteroalkyl, as exemplified by —$CH_2$—$CH_2$—S—$CH_2CH_2$— and —$CH_2$—S—$CH_2$—$CH_2$—NH—$CH_2$—, —O—$CH_2$—CH=CH—, —$CH_2$—CH=C(H)$CH_2$—O—$CH_2$— and S—$CH_2$—C≡C—. For heteroalkylene groups, heteroatoms can also occupy either or both of the chain termini (e.g., alkyleneoxy, alkylenedioxy, alkyleneamino, alkylenediamino, and the like). The term "heteroalkylene" is also meant to include mono and poly-halogenated variants.

The terms "alkoxy," "alkylamino" and "alkylthio", are used in their conventional sense, and refer to those alkyl groups attached to the remainder of the molecule via an oxygen atom ("oxy"), an amino group ("amino") or thio group, and further include mono- and poly-halogenated variants thereof. Additionally, for dialkylamino groups, the alkyl portions can be the same or different.

The terms "halo" or "halogen," by themselves or as part of another substituent, mean, unless otherwise stated, a fluorine, chlorine, bromine, or iodine atom. The term "(halo)alkyl" is meant to include both a "alkyl" and "haloalkyl" substituent. Additionally, the term "haloalkyl," is meant to include monohaloalkyl and polyhaloalkyl. For example, the term "C$_{1-4}$ haloalkyl" is mean to include trifluoromethyl, 2,2,2-trifluoroethyl, 4-chlorobutyl, 3-bromopropyl, difluoromethyl, and the like.

The term "aryl" as used herein refers to a single all carbon aromatic ring or a multiple condensed all carbon ring system wherein at least one of the rings is aromatic. For example, in certain embodiments, an aryl group has 6 to 20 carbon atoms, 6 to 14 carbon atoms, or 6 to 12 carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Non-limiting examples of aryl groups include, but are not limited to, phenyl, indenyl, naphthyl, 1,2,3,4-tetrahydronaphthyl, anthracenyl, and the like.

The term "carbocycle" or "carbocyclyl" refers to a single saturated (i.e., cycloalkyl) or a single partially unsaturated (e.g., cycloalkenyl, cycloalkadienyl, etc.) all carbon ring having 3 to 7 carbon atoms (i.e., (C$_3$-C$_7$)carbocycle). The term "carbocycle" or "carbocyclyl" also includes multiple condensed, saturated and partially unsaturated all carbon ring systems (e.g., ring systems comprising 2, 3 or 4 carbocyclic rings). Accordingly, carbocycle includes multicyclic carbocyles such as a bicyclic carbocycles (e.g., bicyclic carbocycles having about 6 to 12 carbon atoms such as bicyclo[3.1.0]hexane and bicyclo[2.1.1]hexane), and polycyclic carbocycles (e.g tricyclic and tetracyclic carbocycles with up to about 20 carbon atoms). The rings of the multiple condensed ring system can be connected to each other via fused, spiro and bridged bonds when allowed by valency requirements. For example, multicyclic carbocyles can be connected to each other via a single carbon atom to form a spiro connection (e.g., spiropentane, spiro[4,5]decane, etc), via two adjacent carbon atoms to form a fused connection (e.g., carbocycles such as decahydronaphthalene, norsabinane, norcarane) or via two non-adjacent carbon atoms to form a bridged connection (e.g., norbornane, bicyclo[2.2.2] octane, etc). The "carbocycle" or "carbocyclyl" can also be optionally substituted with one or more (e.g., 1, 2 or 3) oxo groups. Non-limiting examples of carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, bicyclo[2.2.1]heptane, pinane, adamantane, norborene, spirocyclic C$_{5-12}$ alkane, and 1-cyclohex-3-enyl.

The term "heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from heteroaryls (to form for example a naphthyridinyl such as 1,8-naphthyridinyl), heterocycles, (to form for example a 1,2,3,4-tetrahydronaphthyridinyl such as 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has about 1-20 carbon atoms and about 1-6 heteroatoms within the heteroaryl ring. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heteroaryl) can be at any position of the multiple condensed ring system including a heteroaryl, heterocycle, aryl or carbocycle portion of the multiple condensed ring system. It is also to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thianaphthenyl, pyrrolo[2,3-b]pyridinyl, quinazolinyl-4(3H)-one, triazolyl, 4,5, 6,7-tetrahydro-1H-indazole and 3b,4,4a,5-tetrahydro-1H-cyclopropa[3,4]cyclo-penta[1,2-c]pyrazole.

The term "heterocyclyl" or "heterocycle" as used herein refers to a single saturated or partially unsaturated ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems are further described below. Thus, the term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The ring may be substituted with one or more (e.g., 1, 2 or 3) oxo groups and the sulfur and nitrogen atoms may also be present in their oxidized forms. Exemplary heterocycles include but are not limited to azetidinyl, tetrahydrofuranyl and piperidinyl. The term "heterocycle" also includes multiple condensed ring systems (e.g., ring systems comprising 2, 3 or 4 rings) wherein a single heterocycle ring (as defined above) can be condensed with one or more groups selected from heterocycles (to form for example a 1,8-decahydronapthyridinyl), carbocycles (to form for example a decahydroquinolyl) and aryls to form the multiple condensed ring system. Thus, a heterocycle (a single saturated or single partially unsaturated ring or multiple condensed ring system) has about 2-20 carbon atoms and 1-6 heteroatoms within the heterocycle ring. Such multiple condensed ring systems may be optionally substituted with one or more (e.g., 1, 2, 3 or 4) oxo groups on the carbocycle or heterocycle portions of the multiple condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heterocycle) can be at any position of the multiple condensed ring system including a heterocycle, aryl and carbocycle portion of the ring. It is also to be understood that the point of attachment for a heterocycle or heterocycle multiple condensed ring system can be at any suitable atom of the heterocycle or heterocycle multiple condensed ring system including a carbon atom and a heteroatom (e.g., a nitrogen). Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, spiro[cyclopropane-1,1'-isoindolinyl]-3'-one, isoindolinyl-1-one, 2-oxa-6-azaspiro[3.3]heptanyl, imidazolidin-2-one N-methylpiperidine, imidazolidine, pyrazolidine, butyrolactam, valerolactam, imidazolidinone, hydantoin, dioxolane, phthalimide, 1,4-dioxane, thiomorpholine, thiomorpholine-S-oxide, thiomorpholine-S,S-oxide, pyran, 3-pyrroline, thiopyran, pyrone, tetrhydrothiophene, quinuclidine, tropane, 2-azaspiro[3.3]heptane, (1R,5S)-3-azabicyclo[3.2.1]octane, (1s,4s)-2-azabicyclo[2.2.2]octane, (1R,4R)-2-oxa-5-azabicyclo[2.2.2]octane, and pyrrolidin-2-one.

The above terms (e.g., "alkyl," "aryl" and "heteroaryl"), in some embodiments, will include both substituted and unsubstituted forms of the indicated radical. Preferred substituents for each type of radical are provided below.

Substituents for the alkyl radicals (including those groups often referred to as alkylene, alkenyl, alkynyl, heteroalkyl, carbocycle and heterocycle) can be a variety of groups including, but not limited to, -halogen, —OR', —NR'R", —SR', —SiR'R"R'", —OC(O)R', —C(O)R', —CO$_2$R', —CONR'R", —OC(O)NR'R", —NR"C(O)R', —NR"C(O) NR'R", —NR"C(O)$_2$R', —NHC(NH$_2$)=NH, —NR'C(NH$_2$)=NH, —NHC(NH$_2$)=NR', —NR'"C(NR'R")=N—CN, —NR'"C(NR'R")=NOR', —NHC(NH$_2$)=NR', —S(O)R', —S(O)$_2$R', —S(O)$_2$NR'R", —NR'S(O)$_2$R", —NR'"S(O)$_2$NR'R", —CN, —NO$_2$, —(CH$_2$)$_{1-4}$—OR', —(CH$_2$)$_{1-4}$—NR'R", —(CH$_2$)$_{1-4}$—SR', —(CH$_2$)$_{1-4}$—SiR'R"R'", —(CH$_2$)$_{1-4}$—OC(O)R', —(CH$_2$)$_{1-4}$—C(O)R', —(CH$_2$)$_{1-4}$—CO$_2$R', —(CH$_2$)$_{1-4}$CONR'R", in a number ranging from zero to (2m'+1), where m' is the total number of carbon atoms in such radical. R', R" and R'" each independently refer groups including, for example, hydrogen, unsubstituted C$_{1-6}$ alkyl, unsubstituted heteroalkyl, unsubstituted aryl, aryl substituted with 1-3 halogens, unsubstituted C$_{1-6}$ alkyl, C$_{1-6}$ alkoxy or C$_{1-6}$ thioalkoxy groups, or unsubstituted aryl-C$_{1-4}$ alkyl groups, unsubstituted heteroaryl, substituted heteroaryl, among others. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl. Other substitutents for alkyl radicals, including heteroalkyl, alkylene, include for example, =O, =NR', =N—OR', =N—CN, =NH, wherein R' include substituents as described above.

Similarly, substituents for the aryl and heteroaryl groups are varied and are generally selected from the group including, but not limited to, halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR$^1$C(O)NR'"R'", —NHC(NH$_2$)=NH, —NR'C(NH$_2$)=NH, —NHC(NH$_2$)=NR', —S(O) R', —S(O)$_2$R', —S(O)$_2$NR'R", —NR'S(O)$_2$R", —N$_3$, perfluoro-C$_{1-4}$ alkoxy, and perfluoro-C$_{1-4}$ alkyl, —(CH$_2$)$_{1-4}$—OR', —(CH$_2$)$_{1-4}$—NR'R", —(CH$_2$)$_{1-4}$—SR', —(CH$_2$)$_{1-4}$—SiR'R"R'", —(CH$_2$)$_{1-4}$—OC(O)R', —(CH$_2$)$_{1-4}$—C(O)R', —(CH$_2$)$_{1-4}$—CO$_2$R', —(CH$_2$)$_{1-4}$CONR'R", in a number ranging from zero to the total number of open valences on the aromatic ring system; and where R', R" and R'" are independently selected from hydrogen, C$_{1-6}$ alkyl, C$_{3-6}$ carbocycle, C$_{2-6}$ alkenyl, C$_{2-6}$ alkynyl, unsubstituted aryl and heteroaryl, (unsubstituted aryl)-C$_{1-4}$ alkyl, and unsubstituted aryloxy-C$_{1-4}$ alkyl. Other suitable substituents include each of the above aryl substituents attached to a ring atom by an alkylene tether of from 1-4 carbon atoms. When a substituent for the aryl or heteroaryl group contains an alkylene linker (e.g., —(CH$_2$)$_{1-4}$—NR'R"), the alkylene linker includes halo variants as well. For example, the linker "—(CH$_2$)$_{1-4}$—" when used as part of a substituent is meant to include difluoromethylene, 1,2-difluoroethylene, etc.

As used herein, the term "heteroatom" is meant to include oxygen (O), nitrogen (N), sulfur (S) and silicon (Si).

As used herein, the term "chiral" refers to molecules which have the property of non-superimposability of the mirror image partner, while the term "achiral" refers to molecules which are superimposable on their mirror image partner.

As used herein, the term "stereoisomers" refers to compounds which have identical chemical constitution, but differ with regard to the arrangement of the atoms or groups in space.

As used herein a wavy line "⌇" that intersects a bond in a chemical structure indicates the point of attachment of the bond that the wavy bond intersects in the chemical structure to the remainder of a molecule.

As used herein, the term "C-linked" means that the group that the term describes is attached the remainder of the molecule through a ring carbon atom.

As used herein, the term "N-linked" means that the group that the term describes is attached to the remainder of the molecule through a ring nitrogen atom.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers can separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

As used herein, the term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

As used herein, the term "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

As used herein, the term "protecting group" refers to a substituent that is commonly employed to block or protect a particular functional group on a compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl) ethyl, 2-(trimethylsilyl)ethoxymethyl, 2-(p-toluenesulfonyl) ethyl, 2-(p-nitrophenylsulfenyl)ethyl, 2-(diphenylphosphino)-ethyl, nitroethyl and the like. For a general description of protecting groups and their use, see P. G. M. Wuts and T. W. Greene, Greene's Protective Groups in Organic Synthesis 4$^{th}$ edition, Wiley-Interscience, New York, 2006.

As used herein, the term "mammal" includes, but is not limited to, humans, mice, rats, guinea pigs, monkeys, dogs, cats, horses, cows, pigs, and sheep As used herein, the term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. As used herein the term "prodrug" refers to those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of the invention include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of the invention can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as ($C_{1-6}$)alkanoyloxymethyl, 1-(($C_{1-6}$)alkanoyloxy)ethyl, 1-methyl-1-(($C_{1-6}$)alkanoyloxy)ethyl, ($C_{1-6}$)alkoxycarbonyloxymethyl, N—($C_{1-6}$)alkoxycarbonylaminomethyl, succinoyl, ($C_{1-6}$)alkanoyl, alpha-amino($C_{1-4}$)alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_{1-6})alkyl)_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present invention provides for metabolites of compounds of the invention. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention can exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention.

The compounds of the present invention can also contain unnatural proportions of atomic isotopes at one or more of the atoms that constitute such compounds. For example, the present invention also embraces isotopically-labeled variants of the present invention which are identical to those recited herein, bur the for the fact that one or more atoms are replace by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated in to compounds of the invention include istopes of hydrogen, carbon, nitrogen, oxygen, phosphorous, sulfur, fluorine, chlorine and iodine, such as $^{2}H$ ("D"), $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically labeled compounds of the present invention (e.g., those labeled with $^{3}H$ or $^{14}C$) are useful in compound and/or substrate tissue distribution assays. Tritiated ($^{3}H$) and carbon-14 ($^{14}C$) isotopes are useful for their ease of preparation and detectability. Further substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$, and $^{18}F$ are useful for positron emission tomography (PET) studies to examine substrate receptor occupancy. Isotopically labeled compounds of the present inventions can generally be prepared by following procedures analogous to those disclosed in the Schemes and/or in the Examples herein below, by substituting an isotopically labeled reagent for a non-isotopically labeled reagent.

The terms "treat" and "treatment" refer to both therapeutic treatment and/or prophylactic treatment or preventative measures, wherein the object is to prevent or slow down (lessen) an undesired physiological change or disorder, such as, for example, the development or spread of cancer. For purposes of this invention, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treatment" can also mean prolonging survival as compared to expected survival if not receiving treatment. Those in need of treatment include those already with the disease or disorder as well as those prone to have the disease or disorder or those in which the disease or disorder is to be prevented.

The phrase "therapeutically effective amount" or "effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. For cancer therapy, efficacy can, for example, be measured by assessing the time to disease progression (TTP) and/or determining the response rate (RR).

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

A. Compounds

In another embodiment, the compound is selected from compounds of formula I as described in the Examples herein and salts thereof.

Synthesis of Compounds

Compounds of formula (I) may be prepared by the process illustrated in Scheme 1.

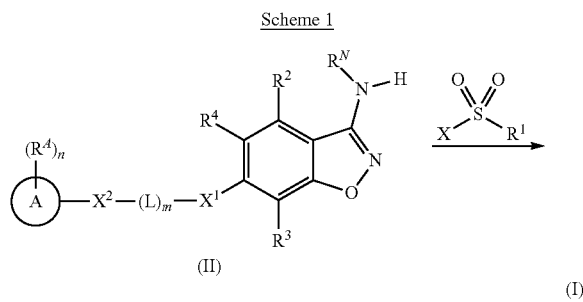

A compound of Formula I can be prepared by treating an amine of Formula II with a sulfonylating reagent, e.g., a reagent of formula X—SO$_2$—R$^1$ wherein X is a suitable leaving group, such as chloro, to provide the compound of Formula I. Accordingly, the invention also provides novel amines of Formula II, which are useful intermediates for preparing the corresponding sulfonamides of Formula I. The invention also provides a method for preparing a compound of Formula I comprising treating a corresponding amine of Formula II with corresponding sulfonylating reagent to provide the compound of Formula I.

An intermediate amine of Formula II wherein R$^N$ is H can be prepared by treating a cyano fluoride of Formula III with N-hydroxyacetamide as illustrated in Scheme 2.

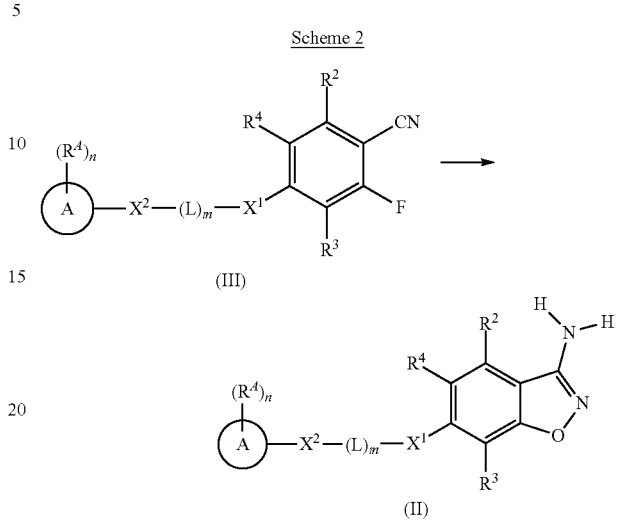

Amines of Formula II wherein R$^N$ is H are general intermediates that can be converted to
compounds of formula I using standard techniques. Accordingly, the invention also provides novel amines of Formula II wherein R$^N$ is H as well as novel compounds of Formula III, which are useful intermediates for preparing the corresponding sulfonamides of Formula I. The invention also provides a method for preparing a compound of Formula II, wherein R$^N$ is H comprising treating a corresponding amine of Formula III with N-hydroxyacetamide to provide the compound of Formula II.

B. Pharmaceutical Compositions and Administration

In addition to one or more of the compounds provided above (or stereoisomers, geometric isomers, tautomers, solvates, metabolites, isotopes, pharmaceutically acceptable salts, or prodrugs thereof), the invention also provides for compositions and medicaments comprising a compound of Formula I or and embodiment thereof and at least one pharmaceutically acceptable carrier, diluent or excipient. The compositions of the invention can be used to selectively inhibit NaV1.7 in patients (e.g, humans).

The term "composition," as used herein, is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

In one embodiment, the invention provides for pharmaceutical compositions (or medicaments) comprising a compound of Formula I or an embodiment thereof, and its stereoisomers, geometric isomers, tautomers, solvates, metabolites, isotopes, pharmaceutically acceptable salts, or prodrugs thereof) and a pharmaceutically acceptable carrier, diluent or excipient. In another embodiment, the invention provides for preparing compositions (or medicaments) comprising compounds of the invention. In another embodiment, the invention provides for administering compounds of Formula I or its embodiments and compositions comprising compounds of Formula I or an embodiment thereof to a patient (e.g., a human patient) in need thereof.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The effective amount of the compound to be administered will be governed by such considerations, and is the minimum amount necessary to inhibit NaV1.7 activity as required to prevent or treat the undesired disease or disorder, such as for example, pain. For example, such amount may be below the amount that is toxic to normal cells, or the mammal as a whole.

In one example, the therapeutically effective amount of the compound of the invention administered parenterally per dose will be in the range of about 0.01-100 mg/kg, alternatively about e.g., 0.1 to 20 mg/kg of patient body weight per day, with the typical initial range of compound used being 0.3 to 15 mg/kg/day. The daily does is, in certain embodiments, given as a single daily dose or in divided doses two to six times a day, or in sustained release form. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, intracerebral, intraocular, intralesional or subcutaneous administration.

The compositions comprising compounds of Formula I or an embodiment thereof are normally formulated in accordance with standard pharmaceutical practice as a pharmaceutical composition. A typical formulation is prepared by mixing a compound of the present invention and a diluent, carrier or excipient. Suitable diluents, carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which a compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). A active pharmaceutical ingredient of the invention (e.g., compound of Formula I or an embodiment thereof) can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy: Remington the Science and Practice of Pharmacy (2005) $21^{st}$ Edition, Lippincott Williams & Wilkins, Philidelphia, Pa.

Sustained-release preparations of a compound of the invention (e.g., compound of Formula I or an embodiment thereof) can be prepared. Suitable examples of sustained-release preparations include semipermeable matrices of solid hydrophobic polymers containing a compound of Formula I or an embodiment thereof, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate (Sidman et al., Biopolymers 22:547, 1983), non-degradable ethylene-vinyl acetate (Langer et al., J. Biomed. Mater. Res. 15:167, 1981), degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid (EP 133,988A). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy.

The formulations include those suitable for the administration routes detailed herein. The formulations can conveniently be presented in unit dosage form and can be prepared by any of the methods well known in the art of pharmacy. Techniques and formulations generally are found in Remington: The Science and Practice of Pharmacy: Remington the Science and Practice of Pharmacy (2005) $21^{st}$ Edition, Lippincott Williams & Wilkins, Philidelphia, Pa. Such methods include the step of bringing into association the active ingredient with the carrier which constitutes one or more accessory ingredients.

In general the formulations are prepared by uniformly and intimately bringing into association the active ingredient with liquid carriers, diluents or excipients or finely divided solid carriers, diluents or excipients, or both, and then, if necessary, shaping the product. A typical formulation is prepared by mixing a compound of the present invention and a carrier, diluent or excipient. The formulations can be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. A compound of the present invention is typically formulated into pharmaceutical dosage forms to provide an easily controllable dosage of the drug and to enable patient compliance with the prescribed regimen.

In one example, compounds of Formula I or an embodiment thereof may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of Formula I (or an embodiment thereof) is formulated in an acetate buffer, at pH 5. In another embodiment, the compounds of Formula I or an embodiment thereof are sterile. The compound may be stored, for example, as a solid or amorphous composition, as a lyophilized formulation or as an aqueous solution.

Formulations of a compound of the invention (e.g., compound of Formula I or an embodiment thereof) suitable for oral administration can be prepared as discrete units such as pills, capsules, cachets or tablets each containing a predetermined amount of a compound of the invention.

Compressed tablets can be prepared by compressing in a suitable machine the active ingredient in a free-flowing form such as a powder or granules, optionally mixed with a binder, lubricant, inert diluent, preservative, surface active or dispersing agent. Molded tablets can be made by molding in a suitable machine a mixture of the powdered active ingredient moistened with an inert liquid diluent. The tablets can optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs can be prepared for oral use. Formulations of a compound of the invention (e.g., compound of Formula I or an embodiment thereof) intended for oral use can be prepared according to any method known to the art for the manufacture of pharmaceutical compositions and such compositions can contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

An example of a suitable oral administration form is a tablet containing about 1 mg, 5 mg, 10 mg, 25 mg, 30 mg, 50 mg, 80 mg, 100 mg, 150 mg, 250 mg, 300 mg and 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredient can be employed with either a paraffinic or a water-miscible ointment base. Alternatively, the active ingredients can be formulated in a cream with an oil-in-water cream base. If desired, the aqueous phase of the cream base can include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations can desirably include a compound which enhances absorption or penetration of the active ingredient through the skin or other affected areas. Examples of such dermal penetration enhancers include dimethyl sulfoxide and related analogs.

The oily phase of the emulsions of this invention can be constituted from known ingredients in a known manner. While the phase can comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

In one aspect of topical applications, it is desired to administer an effective amount of a pharmaceutical composition according to the invention to target area, e.g., skin surfaces, mucous membranes, and the like, which are adjacent to peripheral neurons which are to be treated. This amount will generally range from about 0.0001 mg to about 1 g of a compound of the invention per application, depending upon the area to be treated, whether the use is diagnostic, prophylactic or therapeutic, the severity of the symptoms, and the nature of the topical vehicle employed. A preferred topical preparation is an ointment, wherein about 0.001 to about 50 mg of active ingredient is used per cc of ointment base. The pharmaceutical composition can be formulated as transdermal compositions or transdermal delivery devices ("patches"). Such compositions include, for example, a backing, active compound reservoir, a control membrane, liner and contact adhesive. Such transdermal patches may be used to provide continuous pulsatile, or on demand delivery of the compounds of the present invention as desired.

Aqueous suspensions of a compound of the invention (e.g., compound of Formula I or an embodiment thereof) contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose or saccharin.

Formulations of a compound of the invention (e.g., compound of Formula I or an embodiment thereof) can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a non-toxic parenterally acceptable diluent or solvent, such as a solution in 1,3-butanediol or prepared as a lyophilized powder. Among the acceptable vehicles and solvents that can be employed are water, Ringer's solution and isotonic sodium chloride solution. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The amount of active ingredient that can be combined with the carrier material to produce a single dosage form will vary depending upon the host treated and the particular mode of administration. For example, a time-release formulation intended for oral administration to humans can contain approximately 1 to 1000 mg of active material compounded with an appropriate and convenient amount of carrier material which can vary from about 5 to about 95% of the total compositions (weight:weight). The pharmaceutical composition can be prepared to provide easily measurable amounts for administration. For example, an aqueous solution intended for intravenous infusion can contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration can be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration can be prepared according to conventional methods and can be delivered with other therapeutic agents such as compounds heretofore used in the treatment of disorders as described below.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

When the binding target is located in the brain, certain embodiments of the invention provide for a compound of formula I (or an embodiment thereof) to traverse the blood-brain barrier. Certain neurodegenerative diseases are associated with an increase in permeability of the blood-brain barrier, such that a compound of formula I (or an embodiment thereof) can be readily introduced to the brain. When the blood-brain barrier remains intact, several art-known approaches exist for transporting molecules across it, including, but not limited to, physical methods, lipid-based methods, and receptor and channel-based methods.

Physical methods of transporting a compound of formula I (or an embodiment thereof) across the blood-brain barrier include, but are not limited to, circumventing the blood-brain barrier entirely, or by creating openings in the blood-brain barrier.

Circumvention methods include, but are not limited to, direct injection into the brain (see, e.g., Papanastassiou et al., Gene Therapy 9:398-406, 2002), interstitial infusion/convection-enhanced delivery (see, e.g., Bobo et al., Proc. Natl. Acad. Sci. U.S.A. 91:2076-2080, 1994), and implanting a delivery device in the brain (see, e.g., Gill et al., Nature Med. 9:589-595, 2003; and Gliadel Wafers™, Guildford. Pharmaceutical). Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Volumes 1 and 2, Plenum Press, N.Y., 1989)), and permeabilization by, e.g., bradykinin or permeabilizer A-7 (see, e.g., U.S. Pat. Nos. 5,112,596, 5,268,164, 5,506,206, and 5,686,416).

Lipid-based methods of transporting a compound of formula I (or an embodiment thereof) across the blood-brain barrier include, but are not limited to, encapsulating the a compound of formula I (or an embodiment thereof) in liposomes that are coupled to antibody binding fragments that bind to receptors on the vascular endothelium of the blood-brain barrier (see, e.g., U.S. Patent Application Publication No. 2002/0025313), and coating a compound of formula I (or an embodiment thereof) in low-density lipoprotein particles (see, e.g., U.S. Patent Application Publication No. 2004/0204354) or apolipoprotein E (see, e.g., U.S. Patent Application Publication No. 2004/0131692).

Receptor and channel-based methods of transporting a compound of formula I (or an embodiment thereof) across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating a compound of formula I (or an embodiment thereof) with a transferrin and modulating activity of the one or more transferrin receptors (see, e.g., U.S. Patent Application Publication No. 2003/0129186), and cationizing the antibodies (see, e.g., U.S. Pat. No. 5,004,697).

For intracerebral use, in certain embodiments, the compounds can be administered continuously by infusion into the fluid reservoirs of the CNS, although bolus injection may be acceptable. The inhibitors can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the inhibitors can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

A compound of formula I (or an embodiment thereof) used in the invention are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. A compound of formula I (or an embodiment thereof) need not be, but is optionally formulated with one or more agent currently used to prevent or treat the disorder in question. The effective amount of such other agents depends on the amount of a compound of the invention present in the formulation, the type of disorder or treatment, and other factors discussed above.

These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a compound of formula I (or an embodiment thereof) (when used alone or in combination with other agents) will depend on the type of disease to be treated, the properties of the compound, the severity and course of the disease, whether the compound is administered for preventive or therapeutic purposes, previous therapy, the patient's clinical history and response to the compound, and the discretion of the attending physician. The compound is suitably administered to the patient at one time or over a series of treatments. Depending on the type and severity of the disease, about 1 μg/kg to 15 mg/kg (e.g., 0.1 mg/kg-10 mg/kg) of compound can be an initial candidate dosage for administration to the patient, whether, for example, by one or more separate administrations, or by continuous infusion. One typical daily dosage might range from about 1 μg kg to 100 mg/kg or more, depending on the factors mentioned above. For repeated administrations over several days or longer, depending on the condition, the treatment would generally be sustained until a desired suppression of disease symptoms occurs. One exemplary dosage of a compound of formula I (or an embodiment thereof) would be in the range from about 0.05 mg/kg to about 10 mg/kg. Thus, one or more doses of about 0.5 mg/kg, 2.0 mg/kg, 4.0 mg/kg, or 10 mg/kg (or any combination thereof) may be administered to the patient. Such doses may be administered intermittently, e.g., every week or every three weeks (e.g., such that the patient receives from about two to about twenty, or, e.g., about six doses of the antibody). An initial higher loading dose, followed by one or more lower doses may be administered. An exemplary dosing regimen comprises administering an initial loading dose of about 4 mg/kg, followed by a weekly maintenance dose of about 2 mg kg of the compound. However, other dosage regimens may be useful. The progress of this therapy is easily monitored by conventional techniques and assays.

Other typical daily dosages might range from, for example, about 1 g/kg to up to 100 mg/kg or more (e.g., about 1 µg kg to 1 mg/kg, about 1 µg/kg to about 5 mg/kg, about 1 mg kg to 10 mg/kg, about 5 mg/kg to about 200 mg/kg, about 50 mg/kg to about 150 mg/mg, about 100 mg/kg to about 500 mg/kg, about 100 mg/kg to about 400 mg/kg, and about 200 mg/kg to about 400 mg/kg), depending on the factors mentioned above. Typically, the clinician will administer a compound until a dosage is reached that results in improvement in or, optimally, elimination of, one or more symptoms of the treated disease or condition. The progress of this therapy is easily monitored by conventional assays. One or more agent provided herein may be administered together or at different times (e.g., one agent is administered prior to the administration of a second agent). One or more agent may be administered to a subject using different techniques (e.g., one agent may be administered orally, while a second agent is administered via intramuscular injection or intranasally). One or more agent may be administered such that the one or more agent has a pharmacologic effect in a subject at the same time. Alternatively, one or more agent may be administered, such that the pharmacological activity of the first administered agent is expired prior the administration of one or more secondarily administered agents (e.g., 1, 2, 3, or 4 secondarily administered agents).

C. Indications and Methods of Treatment

The compounds of the invention modulate, preferably inhibit, ion flux through a voltage-dependent sodium channel in a mammal, (e.g, a human). Any such modulation, whether it be partial or complete inhibition or prevention of ion flux, is sometimes referred to herein as "blocking" and corresponding compounds as "blockers" or "inhibitors". In general, the compounds of the invention modulate the activity of a sodium channel downwards by inhibiting the voltage-dependent activity of the sodium channel, and/or reduce or prevent sodium ion flux across a cell membrane by preventing sodium channel activity such as ion flux.

The compounds of the invention inhibit the ion flux through a voltage-dependent sodium channel. In one aspect, the compounds are state or frequency dependent modifiers of the sodium channels, having a low affinity for the rested/closed state and a high affinity for the inactivated state. Without being bound by any particular theory, it is thought that these compounds are likely to interact with overlapping sites located in the inner cavity of the sodium conducting pore of the channel similar to that described for other state-dependent sodium channel blockers (Cestèle, S., et al., op. cit.). These compounds may also be likely to interact with sites outside of the inner cavity and have allosteric effects on sodium ion conduction through the channel pore.

Any of these consequences may ultimately be responsible for the overall therapeutic benefit provided by these compounds.

Accordingly, the compounds of the invention are sodium channel blockers and are therefore useful for treating diseases and conditions in mammals, for example humans, and other organisms, including all those diseases and conditions which are the result of aberrant voltage-dependent sodium channel biological activity or which may be ameliorated by modulation of voltage-dependent sodium channel biological activity. In particular, the compounds of the invention, i.e., the compounds of formula (I) and embodiments and (or stereoisomers, geometric isomers, tautomers, solvates, metabolites, isotopes, pharmaceutically acceptable salts, or prodrugs thereof), are useful for treating diseases and conditions in mammals, for example humans, which are the result of aberrant voltage-dependent NaV1.7 biological activity or which may be ameliorated by the modulation, preferably the inhibition, of NaV1.7 biological activity. In certain aspects, the compounds of the invention selectively inhibit NaV1.7 over NaV1.5.

As defined herein, a sodium channel-mediated disease or condition refers to a disease or condition in a mammal, preferably a human, which is ameliorated upon modulation of the sodium channel and includes, but is not limited to, pain, central nervous conditions such as epilepsy, anxiety, depression and bipolar disease; cardiovascular conditions such as arrhythmias, atrial fibrillation and ventricular fibrillation; neuromuscular conditions such as restless leg syndrome and muscle paralysis or tetanus; neuroprotection against stroke, neural trauma and multiple sclerosis; and channelopathies such as erythromyalgia and familial rectal pain syndrome.

In one aspect, the present invention relates to compounds, pharmaceutical compositions and methods of using the compounds and pharmaceutical compositions for the treatment of sodium channel-mediated diseases in mammals, preferably humans and preferably diseases and conditions related to pain, central nervous conditions such as epilepsy, anxiety, depression and bipolar disease; cardiovascular conditions such as arrhythmias, atrial/fibrillation and ventricular fibrillation; neuromuscular conditions such as restless leg syndrome and muscle paralysis or tetanus; neuroprotection against stroke, neural trauma and multiple sclerosis; and channelopathies such as erythromyalgia and familial rectal pain syndrome, by administering to a mammal, for example a human, in need of such treatment an effective amount of a sodium channel blocker modulating, especially inhibiting, agent.

A sodium channel-mediated disease or condition also includes pain associated with HIV, HIV treatment induced neuropathy, trigeminal neuralgia, glossopharyngeal neuralgia, neuropathy secondary to metastatic infiltration, adiposis dolorosa, thalamic lesions, hypertension, autoimmune disease, asthma, drug addiction (e.g., opiate, benzodiazepine, amphetamine, cocaine, alcohol, butane inhalation), Alzheimer, dementia, age-related memory impairment, Korsakoff syndrome, restenosis, urinary dysfunction, incontinence, Parkinson's disease, cerebrovascular ischemia, neurosis, gastrointestinal disease, sickle cell anemia, transplant rejection, heart failure, myocardial infarction, reperfusion injury, intermittant claudication, angina, convulsion, respiratory disorders, cerebral or myocardial ischemias, long-QT syndrome, Catecholeminergic polymorphic ventricular tachycardia, ophthalmic diseases, spasticity, spastic paraplegia, myopathies, myasthenia gravis, paramyotonia congentia, hyperkalemic periodic paralysis, hypokalemic periodic paralysis, alopecia, anxiety disorders, psychotic disorders, mania, paranoia, seasonal affective disorder, panic disorder, obsessive compulsive disorder (OCD), phobias, autism, Aspergers Syndrome, Retts syndrome, disintegrative disorder, attention deficit disorder, aggressivity, impulse control disorders, thrombosis, pre clampsia, congestive cardiac failure, cardiac arrest, Freidrich's ataxia, Spinocerebellear ataxia, myelopathy, radiculopathy, systemic lupus erythamatosis, granulomatous disease, olivo-ponto-cerebellar atrophy, spinocerebellar ataxia, episodic ataxia, myokymia, progressive pallidal atrophy, progressive supranuclear palsy and spasticity, traumatic brain injury, cerebral oedema, hydrocephalus injury, spinal cord injury, anorexia nervosa, bulimia, Prader-Willi syndrome, obesity, optic neuritis, cataract, retinal haemorrhage, ischaemic retinopathy, retinitis pigmentosa, acute and chronic glaucoma, macular degeneration, retinal artery occlusion, Chorea, Huntington's chorea, cerebral edema, proctitis, post-herpetic neuralgia, eudynia, heat sensitivity, sarcoidosis, irritable bowel syndrome, Tourette syndrome, Lesch-Nyhan Syndrome, Brugado syndrome, Liddle syndrome, Crohns disease, multiple sclerosis and the pain associated with multiple sclerosis (MS), amyotrophic lateral sclerosis (ALS), disseminated sclerosis, diabetic neuropathy, peripheral neuropathy, charcot marie tooth syndrome, arthritic, rheumatoid arthritis, osteoarthritis, chondrocalcinosis, atherosclerosis, paroxysmal dystonia, myasthenia syndromes, myotonia, myotonic dystrophy, muscular dystrophy, malignant hyperthermia, cystic fibrosis, pseudoaldosteronism, rhabdomyolysis, mental handicap, hypothyroidism, bipolar depression, anxiety, schizophrenia, sodium channel toxin related illnesses, familial erythromelalgia, primary erythromelalgia, rectal pain, cancer, epilepsy, partial and general tonic seizures, febrile seizures, absence seizures (petit mal), myoclonic seizures, atonic seizures, clonic seizures, Lennox Gastaut, West Syndome (infantile spasms), multiresistant seizures, seizure prophylaxis (anti-epileptogenic), familial Mediterranean fever syndrome, gout, restless leg syndrome, arrhythmias, fibromyalgia, neuroprotection under ischaemic conditions caused by stroke or neural trauma, tachy-arrhythmias, atrial fibrillation and ventricular fibrillation and as a general or local anaesthetic.

As used herein, the term "pain" refers to all categories of pain and is recognized to include, but is not limited to, neuropathic pain, inflammatory pain, nociceptive pain, idiopathic pain, neuralgic pain, orofacial pain, burn pain, burning mouth syndrome, somatic pain, visceral pain, myofacial pain, dental pain, cancer pain, chemotherapy pain, trauma pain, surgical pain, post-surgical pain, childbirth pain, labor pain, chronic regional pain syndrome (CRPS), reflex sympathetic dystrophy, brachial plexus avulsion, neurogenic bladder, acute pain (e.g., musculoskeletal and post-operative pain), chronic pain, persistent pain, peripherally mediated pain, centrally mediated pain, chronic headache, migraine headache, familial hemiplegic migraine, conditions associated with cephalic pain, sinus headache, tension headache, phantom limb pain, peripheral nerve injury, pain following stroke, thalamic lesions, radiculopathy, HIV pain, post-herpetic pain, non-cardiac chest pain, irritable bowel syndrome and pain associated with bowel disorders and dyspepsia, and combinations thereof.

Furthermore, sodium channel blockers have clinical uses in addition to pain. The present invention therefore also relates to compounds, pharmaceutical compositions and methods of using the compounds and pharmaceutical compositions for the treatment of diseases or conditions such as cancer and pruritus (itch).

Pruritus, commonly known as itch, is a common dermatological condition. While the exact causes of pruritus are complex and incompletely understood, there has long been evidence that itch involves sensory neurons, especially C fibers, similar to those that mediate pain (Schmelz, M., et al., J. Neurosci. (1997), 17: 8003-8). In particular, it is believed that sodium influx through voltage-gated sodium channels is essential for the propagation of itch sensation from the skin. Transmission of the itch impulses results in the unpleasant sensation that elicits the desire or reflex to scratch.

Multiple causes and electrical pathways for eliciting itch are known. In humans, pruritis can be elicited by histamine or PAR-2 agonists such as mucunain that activate distinct populations of C fibers (Namer, B., et al., J. Neurophysiol. (2008), 100: 2062-9). A variety of neurotrophic peptides are known to mediate itch in animal models (Wang, H., and Yosipovitch, G., International Journal of Dermatology (2010), 49: 1-11). Itch can also be elicited by opioids, evidence of distinct pharmacology from that of pain responses.

There exists a complex interaction between itch and pain responses that arises in part from the overlapping sensory input from the skin (Ikoma, A., et al., Arch. Dermatol. (2003), 139: 1475-8) and also from the diverse etiology of both pain and pruritis. Pain responses can exacerbate itching by enhancing central sensitization or lead to inhibition of painful scratching. Particularly severe forms of chronic itch occur when pain responses are absent, as in the case of post-herpetic itch (Oaklander, A. L., et al., Pain (2002), 96: 9-12).

The compounds of the invention can also be useful for treating pruritus. The rationale for treating itch with inhibitors of voltage-gated sodium channels, especially NaV1.7, is as follows:

1) The propagation of electrical activity in the C fibers that sense pruritinergic stimulants requires sodium entry through voltage-gated sodium channels.

2) NaV1.7 is expressed in the C fibers and kerotinocytes in human skin (Zhao, P., et al., Pain (2008), 139: 90-105).

3) A gain of function mutation of NaV1.7 (L858F) that causes erythromelalgia also causes chronic itch (Li, Y., et al., Clinical and Experimental Dermatology (2009), 34: e313-e4).

4) Chronic itch can be alleviated with treatment by sodium channel blockers, such as the local anesthetic lidocaine (Oaklander, A. L., et al., Pain (2002), 96: 9-12; Villamil, A. G., et al., The American Journal of Medicine (2005), 118: 1160-3). In these reports, lidocaine was effective when administered either intravenously or topically (a Lidoderm patch). Lidocaine can have multiple activities at the plasma concentrations achieved when administered systemically, but when administered topically, the plasma concentrations are only about 1 µM (Center for Drug Evaluation and Research NDA 20-612). At these concentrations, lidocaine is selective for sodium channel block and inhibits spontaneous electrical activity in C fibers and pain responses in animal models (Xiao, W. H., and Bennett, G. J. Pain (2008), 137: 218-28). The types of itch or skin irritation, include, but are not limited to:

a) psoriatic pruritus, itch due to hemodyalisis, aguagenic pruritus, and itching caused by skin disorders (e.g., contact dermatitis), systemic disorders, neuropathy, psychogenic factors or a mixture thereof;

b) itch caused by allergic reactions, insect bites, hypersensitivity (e.g., dry skin, acne, eczema, psoriasis), inflammatory conditions or injury;

c) itch associated with vulvar vestibulitis; and d) skin irritation or inflammatory effect from administration of another therapeutic such as, for example, antibiotics, antivirals and antihistamines.

The compounds of the invention are also useful in treating certain cancers, such as hormone sensitive cancers, such as prostate cancer (adenocarcinoma), breast cancer, ovarian cancer, testicular cancer and thyroid neoplasia, in a mammal, preferably a human. The voltage gated sodium channels have been demonstrated to be expressed in prostate and breast cancer cells. Up-regulation of neonatal NaV1.5 occurs as an integral part of the metastatic process in human breast cancer and could serve both as a novel marker of the metastatic phenotype and a therapeutic target (Clin. Cancer Res. (2005), August 1; 11(15): 5381-9). Functional expression of voltage-gated sodium channel alpha-subunits, specifically NaV1.7, is associated with strong metastatic potential in prostate cancer (CaP) in vitro. Voltage-gated sodium channel alpha-subunits immunostaining, using antibodies specific to the sodium channel alpha subunit was evident in prostatic tissues and markedly stronger in CaP vs non-CaP patients (Prostate Cancer Prostatic Dis., 2005; 8(3):266-73). See also Diss, J. K. J., et al., Mol. Cell. Neurosci. (2008), 37:537-547 and Kis-Toth, K., et al., The Journal of Immunology (2011), 187:1273-1280.

In consideration of the above, in one embodiment, the present invention provides a method for treating a mammal for, or protecting a mammal from developing, a sodium channel-mediated disease, especially pain, comprising administering to the mammal, especially a human, in need thereof, a therapeutically effective amount of a compound of the invention or a pharmaceutical composition comprising a therapeutically effective amount of a compound of the invention wherein the compound modulates the activity of one or more voltage-dependent sodium channels.

In another embodiment of the invention is a method of treating a disease or a condition in a mammal, preferably a human, wherein the disease or condition is selected from the group consisting of pain, depression, cardiovascular diseases, respiratory diseases, and psychiatric diseases, and combinations thereof, and wherein the method comprises administering to the mammal in need thereof a therapeutically effective amount of an embodiment of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

One embodiment of this embodiment is wherein the disease or condition is selected from the group consisting of neuropathic pain, inflammatory pain, visceral pain, cancer pain, chemotherapy pain, trauma pain, surgical pain, post surgical pain, childbirth pain, labor pain, neurogenic bladder, ulcerative colitis, chronic pain, persistent pain, peripherally mediated pain, centrally mediated pain, chronic headache, migraine headache, sinus headache, tension headache, phantom limb pain, peripheral nerve injury, and combinations thereof.

Another embodiment of this embodiment is wherein the disease or condition is selected from the group consisting of pain associated with DIV, HIV treatment induced neuropathy, trigeminal neuralgia, post herpetic neuralgia, eudynia, heat sensitivity, tosarcoidosis, irritable bowel syndrome, Crohns disease, pain associated with multiple sclerosis (MS), amyotrophic lateral sclerosis (ALS), diabetic neuropathy, peripheral neuropathy, arthritic, rheumatoid arthritis, osteoarthritis, atherosclerosis, paroxysmal dystonia, myasthenia syndromes, myotonia, malignant hyperthermia, cystic fibrosis, pseudoaldosteronism, rhabdomyolysis, hypothyroidism, bipolar depression, anxiety, schizophrenia, sodium channel toxin related illnesses, familial erythromelalgia, primary erythromelalgia, familial rectal pain, cancer, epilepsy, partial and general tonic seizures, restless leg syndrome, arrhythmias, fibromyalgia, neuroprotection under ischaemic conditions caused by stroke or neural trauma, tachy arrhythmias, atrial fibrillation and ventricular fibrillation.

Another embodiment of the invention is a method of treating, but not preventing, pain in a mammal, wherein the method comprises administering to the mammal in need thereof a therapeutically effective amount of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

One embodiment of this embodiment is a method wherein the pain is selected from the group consisting of neuropathic pain, inflammatory pain, visceral pain, cancer pain, chemotherapy pain, trauma pain, surgical pain, post surgical pain, childbirth pain, labor pain, dental pain, chronic pain, persistent pain, peripherally mediated pain, centrally mediated pain, chronic headache, migraine headache, sinus headache, tension headache, phantom limb pain, peripheral nerve injury, trigeminal neuralgia, post herpetic neuralgia, eudynia, familial erythromelalgia, primary erythromelalgia, familial rectal pain or fibromyalgia, and combinations thereof.

Another embodiment of this embodiment is a method wherein the pain is associated with a disease or condition selected from HIV, HIV treatment induced neuropathy, heat sensitivity, tosarcoidosis, irritable bowel syndrome, Crohns disease, multiple sclerosis, amyotrophic lateral sclerosis, diabetic neuropathy, peripheral neuropathy, rheumatoid arthritis, osteoarthritis, atherosclerosis, paroxysmal dystonia, myasthenia syndromes, myotonia, malignant hyperthermia, cystic fibrosis, pseudoaldosteronism, rhabdomyolysis, hypothyroidism, bipolar depression, anxiety, schizophrenia, sodium channel toxin related illnesses, neurogenic bladder, ulcerative colitis, cancer, epilepsy, partial and general tonic seizures, restless leg syndrome, arrhythmias, ischaemic conditions caused by stroke or neural trauma, tachy arrhythmias, atrial fibrillation and ventricular fibrillation.

Another embodiment of the invention is the method of treating pain in a mammal, preferably a human, by the inhibition of ion flux through a voltage dependent sodium channel in the mammal, wherein the method comprises administering to the mammal in need thereof a therapeutically effective amount of an embodiment of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

Another embodiment of the invention is the method of treating pruritus in a mammal, preferably a human, wherein the method comprises administering to the mammal in need thereof a therapeutically effective amount of an embodiment of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

Another embodiment of the invention is the method of treating cancer in a mammal, preferably a human, wherein the method comprises administering to the mammal in need thereof a therapeutically effective amount of an embodiment of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

Another embodiment of the invention is the method of decreasing ion flux through a voltage dependent sodium channel in a cell in a mammal, wherein the method comprises contacting the cell with an embodiment of a compound of the invention, as set forth above, as a stereoisomer, enantiomer or tautomer thereof or mixtures thereof, or a pharmaceutically acceptable salt, solvate or prodrug thereof.

Another embodiment of the invention is the method of selectively inhibiting a first voltage-gated sodium channel over a second voltage-gated sodium channel in a mammal, wherein the method comprises administering to the mammal an inhibitory amount of a compound of formula (I), or an embodiment of a compound of formula (I).

Another embodiment of the invention is the method of selectively inhibiting NaV1.7 in a mammal or a mammalian cell as compared to NaV1.5, wherein the method comprises administering to the mammal in need thereof an inhibitory amount of a compound of formula (I) or an embodiment of an embodiment thereof.

For each of the above embodiments described related to treating diseases and conditions in a mammal, the present invention also contemplates relatedly a compound of formula I or an embodiment thereof for the use as a medicament in the treatment of such diseases and conditions.

For each of the above embodiments described related to treating diseases and conditions in a mammal, the present invention also contemplates relatedly the use of a compound of formula I or an embodiment thereof for the manufacture of a medicament for the treatment of such diseases and conditions.

Another embodiment of the invention is a method of using the compounds of formula (I) as standards or controls in in vitro or in vivo assays in determining the efficacy of test compounds in modulating voltage-dependent sodium channels.

In another embodiment of the invention, the compounds of formula (I) are isotopically-labeled by having one or more atoms therein replaced by an atom having a different atomic mass or mass number. Such isotopically-labeled (i.e., radio-labelled) compounds of formula (I) are considered to be within the scope of this invention. Examples of isotopes that can be incorporated into the compounds of formula (I) include isotopes of hydrogen, carbon, nitrogen, oxygen, phosphorous, sulfur, fluorine, chlorine, and iodine, such as but not limited to $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively.

These isotopically-labeled compounds would be useful to help determine or measure the effectiveness of the compounds, by characterizing, for example, the site or mode of action on the sodium channels, or binding affinity to pharmacologically important site of action on the sodium channels, particularly NaV1.7. Certain isotopically-labeled compounds of formula (I), for example, those incorporating a radioactive isotope, are useful in drug and/or substrate tissue distribution studies. The radioactive isotopes tritium, i.e. $^{3}H$, and carbon-14, i.e., $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of formula (I) can generally be prepared by conventional techniques known to those skilled in the art or by processes analogous to those described in the Examples as set out below using an appropriate isotopically-labeled reagent in place of the non-labeled reagent previously employed.

Testing Compounds

The assessment of the compounds of the invention in mediating, especially inhibiting, the sodium channel ion flux can be determined using the assays described hereinbelow. Alternatively, the assessment of the compounds in treating conditions and diseases in humans may be established in industry standard animal models for demonstrating the efficacy of compounds in treating pain. Animal models of human neuropathic pain conditions have been developed that result in reproducible sensory deficits (allodynia, hyperalgesia, and spontaneous pain) over a sustained period of time that can be evaluated by sensory testing. By establishing the degree of mechanical, chemical, and temperature induced allodynia and hyperalgesia present, several physio-pathological conditions observed in humans can be modeled allowing the evaluation of pharmacotherapies.

In rat models of peripheral nerve injury, ectopic activity in the injured nerve corresponds to the behavioural signs of pain. In these models, intravenous application of the sodium channel blocker and local anesthetic lidocaine can suppress the ectopic activity and reverse the tactile allodynia at concentrations that do not affect general behaviour and motor function (Mao, J. and Chen, L. L, Pain (2000), 87:7-17). Allometric scaling of the doses effective in these rat models, translates into doses similar to those shown to be efficacious in humans (Tanelian, D. L. and Brose, W. G., Anesthesiology (1991), 74(5):949-951). Furthermore, Lidoderm®, lidocaine applied in the form of a dermal patch, is currently an FDA approved treatment for post-herpetic neuralgia (Devers, A. and Glaler, B. S., Clin. J. Pain (2000), 16(3):205-8).

The present invention readily affords many different means for identification of sodium channel modulating agents that are useful as therapeutic agents. Identification of modulators of sodium channel can be assessed using a variety of in vitro and in vivo assays, e.g., measuring current, measuring membrane potential, measuring ion flux, (e.g., sodium or guanidinium), measuring sodium concentration, measuring second messengers and transcription levels, and using e.g., voltage-sensitive dyes, radioactive tracers, and patch-clamp electrophysiology.

One such protocol involves the screening of chemical agents for ability to modulate the activity of a sodium channel thereby identifying it as a modulating agent.

A typical assay described in Bean et al., J. General Physiology (1983), 83:613-642, and Leuwer, M., et al., Br. J. Pharmacol (2004), 141(1):47-54, uses patch-clamp techniques to study the behaviour of channels. Such techniques are known to those skilled in the art, and may be developed, using current technologies, into low or medium throughput assays for evaluating compounds for their ability to modulate sodium channel behaviour.

Throughput of test compounds is an important consideration in the choice of screening assay to be used. In some strategies, where hundreds of thousands of compounds are to be tested, it is not desirable to use low throughput means. In other cases, however, low throughput is satisfactory to identify important differences between a limited number of compounds. Often it will be necessary to combine assay types to identify specific sodium channel modulating compounds.

Electrophysiological assays using patch clamp techniques is accepted as a gold standard for detailed characterization of sodium channel compound interactions, and as described in Bean et al., op. cit. and Leuwer, M., et al., op. cit. There is a manual low-throughput screening (LTS) method which can compare 2-10 compounds per day; a recently developed system for automated medium-throughput screening (MTS) at 20-50 patches (i.e. compounds) per day; and a technology from Molecular Devices Corporation (Sunnyvale, Calif.) which permits automated high-throughput screening (HTS) at 1000-3000 patches (i.e. compounds) per day.

One automated patch-clamp system utilizes planar electrode technology to accelerate the rate of drug discovery. Planar electrodes are capable of achieving high-resistance, cells-attached seals followed by stable, low-noise whole-cell recordings that are comparable to conventional recordings. A suitable instrument is the PatchXpress 7000A (Axon Instruments Inc, Union City, Calif.). A variety of cell lines and culture techniques, which include adherent cells as well as cells growing spontaneously in suspension are ranked for seal success rate and stability. Immortalized cells (e.g. HEK and CHO) stably expressing high levels of the relevant sodium ion channel can be adapted into high-density suspension cultures.

Other assays can be selected which allow the investigator to identify compounds which block specific states of the channel, such as the open state, closed state or the resting state, or which block transition from open to closed, closed to resting or resting to open. Those skilled in the art are generally familiar with such assays.

Binding assays are also available. Designs include traditional radioactive filter based binding assays or the confocal based fluorescent system available from Evotec OAI group of companies (Hamburg, Germany), both of which are HTS.

Radioactive flux assays can also be used. In this assay, channels are stimulated to open with veratridine or aconitine and held in a stabilized open state with a toxin, and channel blockers are identified by their ability to prevent ion influx. The assay can use radioactive 22[Na] and 14[C] guanidinium ions as tracers. FlashPlate & Cytostar-T plates in living cells avoids separation steps and are suitable for HTS. Scintillation plate technology has also advanced this method to HTS suitability. Because of the functional aspects of the assay, the information content is reasonably good.

Yet another format measures the redistribution of membrane potential using the FLIPR system membrane potential kit (HTS) available from Molecular Dynamics (a division of Amersham Biosciences, Piscataway, N.J.). This method is limited to slow membrane potential changes. Some problems may result from the fluorescent background of compounds. Test compounds may also directly influence the fluidity of the cell membrane and lead to an increase in intracellular dye concentrations. Still, because of the functional aspects of the assay, the information content is reasonably good.

Sodium dyes can be used to measure the rate or amount of sodium ion influx through a channel. This type of assay provides a very high information content regarding potential channel blockers. The assay is functional and would measure Na+ influx directly. CoroNa Red, SBFI and/or sodium green (Molecular Probes, Inc. Eugene Oreg.) can be used to measure Na influx; all are Na responsive dyes. They can be used in combination with the FLIPR instrument. The use of these dyes in a screen has not been previously described in the literature. Calcium dyes may also have potential in this format.

In another assay, FRET based voltage sensors are used to measure the ability of a test compound to directly block Na influx. Commercially available HTS systems include the VIPR™ II FRET system (Life Technologies, or Aurora Biosciences Corporation, San Diego, Calif., a division of Vertex Pharmaceuticals, Inc.) which may be used in conjunction with FRET dyes, also available from Aurora Biosciences. This assay measures sub-second responses to voltage changes. There is no requirement for a modifier of channel function. The assay measures depolarization and hyperpolarizations, and provides ratiometric outputs for quantification. A somewhat less expensive MTS version of this assay employs the FLEXstation™ (Molecular Devices Corporation) in conjunction with FRET dyes from Aurora Biosciences. Other methods of testing the compounds disclosed herein are also readily known and available to those skilled in the art.

Modulating agents so identified are then tested in a variety of in vivo models so as to determine if they alleviate pain, especially chronic pain or other conditions such as cancer and pruritus (itch) with minimal adverse events. The assays described below in the Biological Assays Section are useful in assessing the biological activity of the instant compounds.

Typically, the efficacy of a compound of the invention is expressed by its IC50 value ("Inhibitory Concentration—50%"), which is the measure of the amount of compound required to achieve 50% inhibition of the activity of the target sodium channel over a specific time period. For example, representative compounds of the present invention have demonstrated IC50's ranging from less than 100 nanomolar to less than 10 micromolar in the patch voltage clamp NaV1.7 electrophysiology assay described herein.

In another aspect of the invention, the compounds of the invention can be used in in vitro or in vivo studies as exemplary agents for comparative purposes to find other compounds also useful in treatment of, or protection from, the various diseases disclosed herein.

Another aspect of the invention relates to inhibiting NaV1.1, NaV1.2, NaV1.3, NaV1.4, NaV1.5, NaV1.6, NaV1.7, NaV1.8, or NaV1.9 activity, preferably NaV1.7 activity, in a biological sample or a mammal, preferably a human, which method comprises administering to the mammal, preferably a human, or contacting said biological sample with a compound of formula (I) or a pharmaceutical composition comprising a compound of formula (I). The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of NaV1.1, NaV1.2, NaV1.3, NaV1.4, NaV1.5, NaV1.6, NaV1.7, NaV1.8, or NaV1.9 activity in a biological sample is useful for a variety of purposes that are known to one of skill in the art. Examples of such purposes include, but are not limited to, the study of sodium ion channels in biological and pathological phenomena; and the comparative evaluation of new sodium ion channel inhibitors.

The compounds of the invention (or stereoisomers, geometric isomers, tautomers, solvates, metabolites, isotopes, pharmaceutically acceptable salts, or prodrugs thereof) and/or the pharmaceutical compositions described herein which comprise a pharmaceutically acceptable excipient and one or more compounds of the invention, can be used in the preparation of a medicament for the treatment of sodium channel-mediated disease or condition in a mammal.

D. Combination Therapy

The compounds of the invention may be usefully combined with one or more other compounds of the invention or one or more other therapeutic agent or as any combination thereof, in the treatment of sodium channel-mediated diseases and conditions. For example, a compound of the invention may be administered simultaneously, sequentially or separately in combination with other therapeutic agents, including, but not limited to:

- opiates analgesics, e.g., morphine, heroin, cocaine, oxymorphine, levorphanol, levallorphan, oxycodone, codeine, dihydrocodeine, propoxyphene, nalmefene, fentanyl, hydrocodone, hydromorphone, meripidine, methadone, nalorphine, naloxone, naltrexone, buprenorphine, butorphanol, nalbuphine and pentazocine;
- non-opiate analgesics, e.g., acetomeniphen, salicylates (e.g., aspirin);
- nonsteroidal antiinflammatory drugs (NSAIDs), e.g., ibuprofen, naproxen, fenoprofen, ketoprofen, celecoxib, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac;
- anticonvulsants, e.g., carbamazepine, oxcarbazepine, lamotrigine, valproate, topiramate, gabapentin and pregabalin;
- antidepressants such as tricyclic antidepressants, e.g., amitriptyline, clomipramine, despramine, imipramine and nortriptyline;
- COX-2 selective inhibitors, e.g., celecoxib, rofecoxib, parecoxib, valdecoxib, deracoxib, etoricoxib, and lumiracoxib;
- alpha-adrenergics, e.g., doxazosin, tamsulosin, clonidine, guanfacine, dexmetatomidine, modafinil, and 4-amino-6,7-dimethoxy-2-(5-methane sulfonamido-1,2,3,4-tetrahydroisoquinol-2-yl)-5-(2-pyridyl) quinazoline;
- barbiturate sedatives, e.g., amobarbital, aprobarbital, butabarbital, butabital, mephobarbital, metharbital, methohexital, pentobarbital, phenobartital, secobarbital, talbutal, theamylal and thiopental;
- tachykinin (NK) antagonist, particularly an NK-3, NK-2 or NK-1 antagonist, e.g., (αR, 9R)-7-[3,5-bis(tiifluoromethyDbenzyl)]-8,9,10,11-tetrahydro-9-methyl-5-(4-methylphenyl)-7H-[1,4]diaz ocino[2,1-g][1,7]-naphthyridine-6-13-dione (TAK-637), 5-[[2R,3 S)-2-[(1R)-1-[3,5-bis(trifluoromethylphenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy5-(trifluoromethoxy)phenyl]-methylamino]-2-phenylpiperidine (2S,3S);
- coal-tar analgesics, in particular paracetamol;
- serotonin reuptake inhibitors, e.g., paroxetine, sertraline, norfluoxetine (fluoxetine desmethyl metabolite), metabolite demethylsertraline, '3 fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine, trazodone and fluoxetine;
- noradrenaline (norepinephrine) reuptake inhibitors, e.g., maprotiline, lofepramine, mirtazepine, oxaprotiline, fezolamine, tomoxetine, mianserin, buprorion, buprorion metabolite hydroxybuproprion, nomifensine and viloxazine (Vivalan®)), especially a selective noradrenaline reuptake inhibitor such as reboxetine, in particular (S,S)-reboxetine, and venlafaxine duloxetine neuroleptics sedative/anxiolytics;
- dual serotonin-noradrenaline reuptake inhibitors, such as venlafaxine, venlafaxine metabolite O-desmethylvenlafaxine, clomipramine, clomipramine metabolite desmethylclomipramine, duloxetine, milnacipran and imipramine;
- acetylcholinesterase inhibitors such as donepezil;
- 5-HT3 antagonists such as ondansetron;
- metabotropic glutamate receptor (mGluR) antagonists;
- local anaesthetic such as mexiletine and lidocaine;
- corticosteroid such as dexamethasone;
- antiarrhythimics, e.g., mexiletine and phenytoin;
- muscarinic antagonists, e.g., tolterodine, propiverine, tropsium t chloride, darifenacin, solifenacin, temiverine and ipratropium;
- cannabinoids;
- vanilloid receptor agonists (e.g., resinferatoxin) or antagonists (e.g., capsazepine);
- sedatives, e.g., glutethimide, meprobamate, methaqualone, and dichloralphenazone;
- anxiolytics such as benzodiazepines,
- antidepressants such as mirtazapine,
- topical agents (e.g., lidocaine, capsacin and resiniferotoxin);
- muscle relaxants such as benzodiazepines, baclofen, carisoprodol, chlorzoxazone, cyclobenzaprine, methocarbamol and orphrenadine;
- anti-histamines or H1 antagonists;
- NMDA receptor antagonists;
- 5-HT receptor agonists/antagonists;
- PDEV inhibitors;
- Tramadol®,
- cholinergic (nicotine) analgesics;
- alpha-2-delta ligands;
- prostaglandin E2 subtype antagonists;
- leukotriene B4 antagonists;
- 5-lipoxygenase inhibitors; and
- 5-HT3 antagonists.

Sodium channel-mediated diseases and conditions that may be treated and/or prevented using such combinations include but not limited to, pain, central and peripherally mediated, acute, chronic, neuropathic as well as other diseases with associated pain and other central nervous disorders such as epilepsy, anxiety, depression and bipolar disease; or cardiovascular disorders such as arrhythmias, atrial fibrillation and ventricular fibrillation; neuromuscular disorders such as restless leg syndrome and muscle paralysis or tetanus; neuroprotection against stroke, neural trauma and multiple sclerosis; and channelopathies such as erythromyalgia and familial rectal pain syndrome.

As used herein "combination" refers to any mixture or permutation of one or more compounds of the invention and one or more other compounds of the invention or one or more additional therapeutic agent. Unless the context makes clear otherwise, "combination" may include simultaneous or sequentially delivery of a compound of the invention with one or more therapeutic agents. Unless the context makes clear otherwise, "combination" may include dosage forms of a compound of the invention with another therapeutic agent. Unless the context makes clear otherwise, "combination" may include routes of administration of a compound of the invention with another therapeutic agent. Unless the context makes clear otherwise, "combination" may include formulations of a compound of the invention with another therapeutic agent. Dosage forms, routes of administration and pharmaceutical compositions include, but are not limited to, those described herein.

The invention will be more fully understood by reference to the following examples. They should not, however, be construed as limiting the scope of the invention.

EXAMPLES

These examples serve to provide guidance to a skilled artisan to prepare and use the compounds, compositions and methods of the invention. While particular embodiments of the present invention are described, the skilled artisan will appreciate that various changes and modifications can be made without departing from the spirit and scope of the inventions.

The chemical reactions in the examples described can be readily adapted to prepare a number of other compounds of the invention, and alternative methods for preparing the compounds of this invention are deemed to be within the scope of this invention. For example, the synthesis of non-exemplified compounds according to the invention can be successfully performed by modifications apparent to those skilled in the art, for example, by appropriately protecting interfering group, by utilizing other suitable reagents known in the art, for example, by appropriately protecting interfering groups by utilizing other suitable reagents known in the art other than those described, and/or by making routine modifications of reaction conditions.

In the examples below, unless otherwise indicated all temperatures are set forth in degrees Celcius. Commerically available reagents were purchased from suppliers such as Aldrich Chemical Company, Lancaster, TCI or Maybridge and were used without further purification unless otherwise indicated. The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. $^1$H NMR spectra were obtained in deuterated CDCl$_3$, d$_6$-DMSO, CH$_3$OD or d$_6$-acetone solvent solutions (reported in ppm) using or trimethylsilane (TMS) or residual non-deuterated solvent peaks as the reference standard. When peak multiplicities are reported, the following abbreviates are used: s (singlet), d (doublet), t (triplet), q (quartet), m (multiplet, br (broadened), dd (doublet of doublets), dt (doublet of triplets). Coupling constants, when given, ar reported in Hz (Hertz).

All abbreviations used to describe reagents, reaction conditions or equipment are intended to be consistent with the definitions set forth in the "List of standard abbreviates and acronyms". The chemical names of discrete compounds of the invention were obtained using the structure naming feature of ChemDraw naming program.

Analytic Conditions

LCMS Analytical Methods

Final compounds were analyzed using a couple of LC/MS conditions, with UV detector monitoring at 214 nm and 254 nm, and mass spectrometry scanning 110-800 amu in ESI+ ionization mode.

LC/MS Method A: column: XBridge C18, 4.6×50 mm, 3.5 um; mobile phase: A water (10 mM ammonium hydrogen carbonate), B CH$_3$CN; gradient: 5%-95% B in 8.0 min; flow rate: 1.2 mL/min; oven temperature 40° C.

LC/MS Method B: column: XBridge C18, 4.6×50 mm, 3.5 um; mobile phase: A water (0.1% ammonia), B CH$_3$CN; gradient: 5%-95% B in 8.0 min; flow rate: 1.2 mL/min; oven temperature 40° C.

LC/MS Method C: column: XBridge C18, 4.6×50 mm, 3.5 um; mobile phase: A water (0.1% TFA), B CH$_3$CN; gradient: 5%-95% B in 8.0 min; flow rate. 1.2 mL/min; oven temperature 40° C.

ABBREVIATIONS

MeCN Acetonitrile
EtOAc Ethyl acetate
DCE Dichloroethane
DCM Dichloromethane
DIPEA Diisopropylethylamine
DME Ethyleneglycol dimethyl ether
DMF N,N-Dimethylformamide
DMSO Dimethylsulfoxide
HCl Hydrochloric acid
HPLC High Pressure Liquid Chromatography
LCMS Liquid Chromatography Mass Spectrometry
MeOH Methanol
NMP N-methyl-2-pyrrolidone
RPHPLC Reverse phase high pressure liquid chromatography
RT Retention time
sat. Saturated
SGC Silica gel column chromatography
SCX-2 Isolute® silica-based sorbent with a chemically bonded propylsulfonic acid functional group
NH$_2$ cartridge Isolute® silica-based sorbent with a chemically bonded Aminopropyl functional group
THF Tetrahydrofuran Example 1

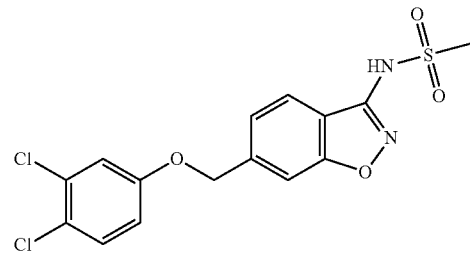 [SMILES: CS(=O)(=O)Nc1noc2cc(COc3ccc(Cl)c(Cl)c3)ccc12]

N-(6-((3,4-dichlorophenoxy)methyl)benzo[d]isoxazol-3-yl)methanesulfonamide

Synthetic scheme

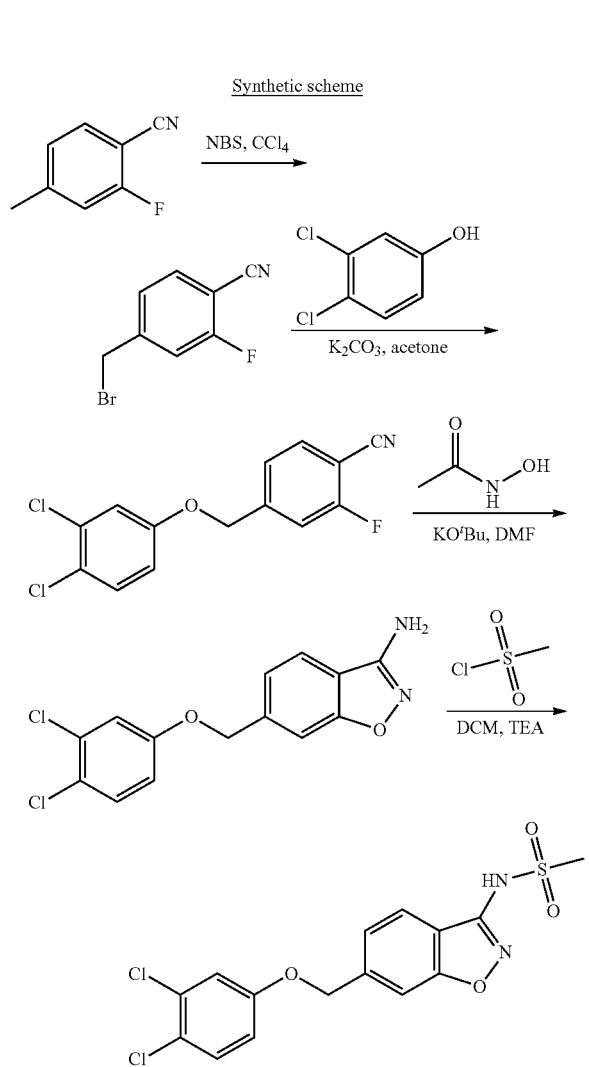

Step 1

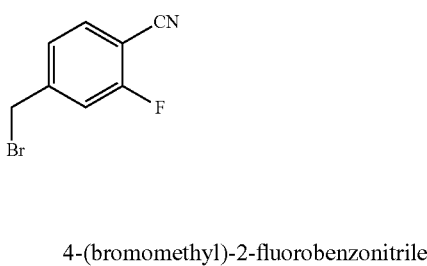

4-(bromomethyl)-2-fluorobenzonitrile

A mixture of 2-fluoro-4-methylbenzonitrile (0.500 g, 3.7 mmol), N-bromosuccinimide (0.725 g, 4.1 mmol) and benzoyl peroxide (0.05 g) in $CCl_4$ (20 mL) was stirred at 90° C. for 18 hrs. The mixture was diluted with DCM (20 ml) and water (20 ml). The organic layer was separated, dried over $Na_2SO_4$, filtered and evaporated to provide crude product as yellow solid (0.6 g, 76%). The crude product was used in the next step without further purification.

Step 2

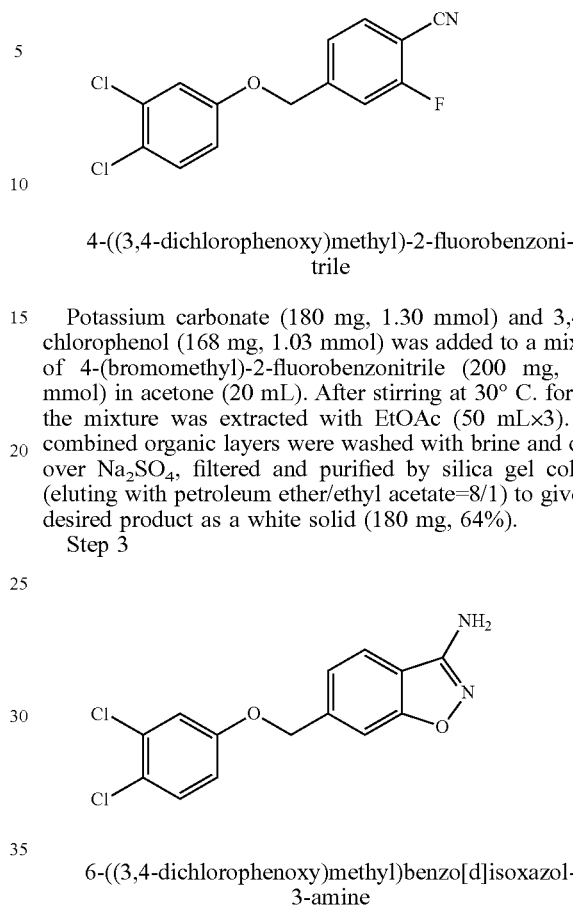

4-((3,4-dichlorophenoxy)methyl)-2-fluorobenzonitrile

Potassium carbonate (180 mg, 1.30 mmol) and 3,4-dichlorophenol (168 mg, 1.03 mmol) was added to a mixture of 4-(bromomethyl)-2-fluorobenzonitrile (200 mg, 0.94 mmol) in acetone (20 mL). After stirring at 30° C. for 4 h, the mixture was extracted with EtOAc (50 mL×3). The combined organic layers were washed with brine and dried over $Na_2SO_4$, filtered and purified by silica gel column (eluting with petroleum ether/ethyl acetate=8/1) to give the desired product as a white solid (180 mg, 64%).

Step 3

6-((3,4-dichlorophenoxy)methyl)benzo[d]isoxazol-3-amine

A mixture of N-hydroxyacetamide (51 mg, 0.68 mmol) and potassium tert-butoxide (76 mg, 0.68 mmol) in DMF (10 mL) was stirred at room temperature for 1 h then 4-((3,4-dichlorophenoxy)methyl)-2-fluorobenzonitrile (100 mg, 0.34 mmol) was added. After stirring at room temperature for 3 h, the mixture was extracted with EtOAc (20 mL×3). The combined organic layers were washed with brine and dried over $Na_2SO_4$, filtered and evaporated to give crude product as a yellow solid (45 mg, 85%). LCMS (ESI) m/z: 309.1 [M+H]⁺.

Step 4

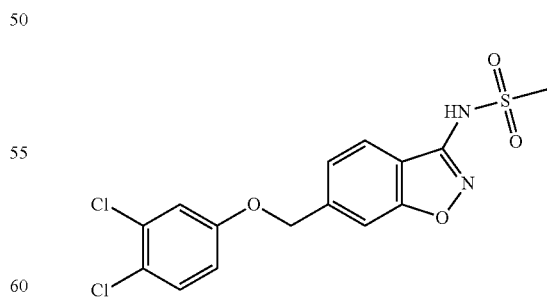

N-(6-((3,4-dichlorophenoxy)methyl)benzo[d]isoxazol-3-yl)methanesulfonamide

A mixture of 6-((3,4-dichlorophenoxy)methyl)benzo[d]isoxazol-3-amine (45 mg, 0.15 mmol), triethylamine (5.0 mL) and methanesulfonyl chloride (25 mg, 0.22 mmol) in DCM (15 mL) was stirred at room temperature for 3 h. The reaction was quenched with sat. NaHCO₃ (150 mL) and the mixture was extracted with EtOAc (20 mL×3). The combined organic layers were washed with brine, dried over Na₂SO₄, filtered, evaporated to give the crude product. The residue was purified by reverse phase combiflash (20%-50% MeCN in 0.1% NH₄HCO₃) to afford the target compound as a white solid (22 mg, 39%). LCMS (ESI) Method A: RT=5.08 min, m/z: 386.7 [M+H]⁺. ¹H-NMR (500 MHz, MeOH-d₄): δ 7.75 (d, J=8.5 Hz, 1H), 7.53 (s, 1H), 7.31 (d, J=9.0 Hz, 2H), 7.13 (d, J=2.5 Hz, 1H), 6.90-6.88 (m, 1H), 5.16 (s, 2H), 3.17 (s, 3H).

Example 2

N-(5-chloro-6-((3,4-dichlorophenoxy)methyl)benzo[d]isoxazol-3-yl)methanesulfonamide Synthetic scheme

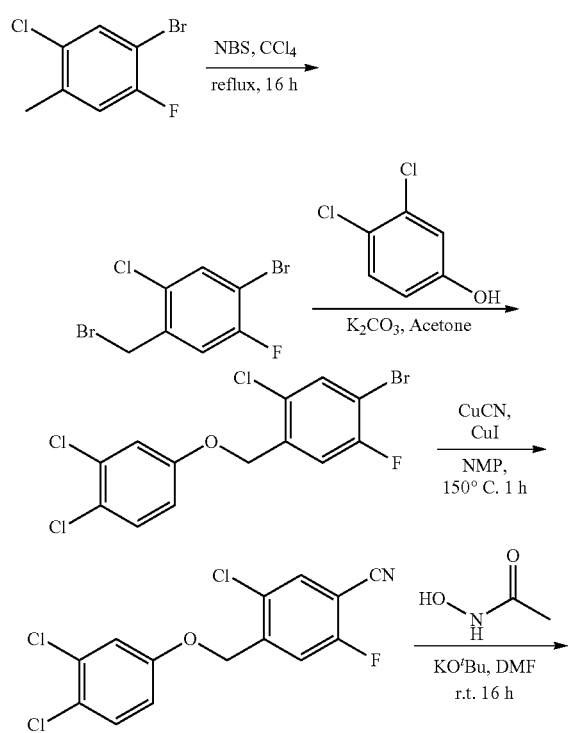

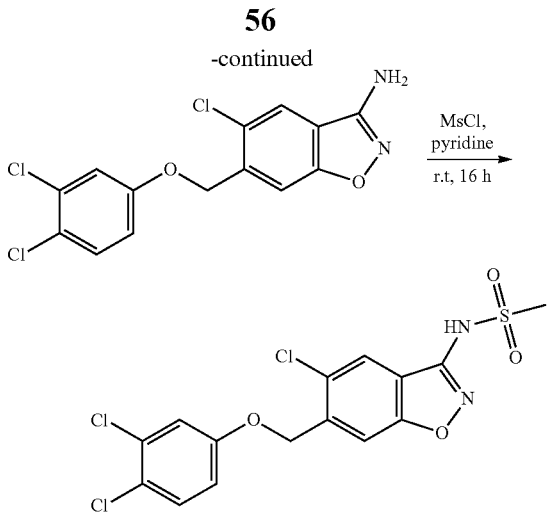

Step 1

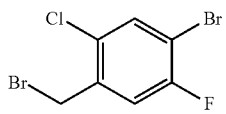

1-bromo-4-(bromomethyl)-5-chloro-2-fluorobenzene

A mixture of 1-bromo-5-chloro-2-fluoro-4-methylbenzene (500 mg, 2.3 mmol), N-bromosuccinimide (481 mg, 2.7 mmol) and azobisisobutyronitrile (38 mg, 0.23 mmol) in CCl₄ (10 mL) was stirred at 90° C. for 16 h. The mixture was diluted with DCM (20 ml) and water (20 ml). The organic layer was separated, dried over Na₂SO₄, filtered and evaporated to get crude product. The residue was purified by silica column chromatography (eluting with petroleum ether/ethyl acetate=50/1) to give 1-bromo-4-(bromomethyl)-5-chloro-2-fluorobenzene as a solid (324 mg, 47%).

Step 2

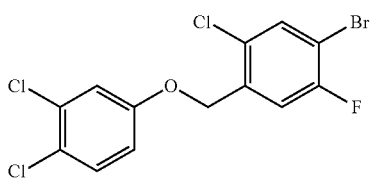 [SMILES: Fc1cc(COc2ccc(Cl)c(Cl)c2)c(Cl)cc1Br]

1-bromo-5-chloro-4-((3,4-dichlorophenoxy)methyl)-2-fluorobenzene

Potassium carbonate (414 mg, 3.0 mmol) and 3,4-dichlorophenol (194 mg, 1.2 mmol) were added to a mixture of 1-bromo-4-(bromomethyl)-5-chloro-2-fluorobenzene (300 mg, 1.0 mmol) in acetone (10 mL). After stirring at 50° C. for 4 h, the reaction mixture was filtered and concentrated. The residue was purified by silica gel column (eluting with petroleum ether/ethyl acetate=10/1) to give 1-bromo-5-chloro-4-((3,4-dichlorophenoxy)methyl)-2-fluorobenzene as a white solid (240 mg, 64%).

Step 3

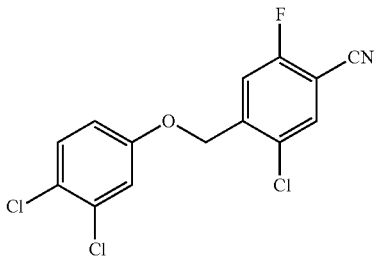 [SMILES: N#Cc1cc(Cl)c(COc2ccc(Cl)c(Cl)c2)cc1F]

5-chloro-4-((3,4-dichlorophenoxy)methyl)-2-fluorobenzonitrile

A 10 ml of microwave vial was charged with 1-bromo-5-chloro-4-((3,4-dichlorophenoxy)methyl)-2-fluorobenzene (384 mg, 0.58 mmol), copper(I) cyanide (104 mg, 1.16 mmol), copper(I) iodide (11 mg, 0.058 mmol) and NMP (3 mL). After irradiated with microwave at 150° C. for 4 h, the mixture was concentrated and purified by reverse phase combiflash (40%-80% MeCN in 0.1% NH$_4$HCO$_3$) to get target compound (90 mg, 52%) as an off-white solid.

Step 4

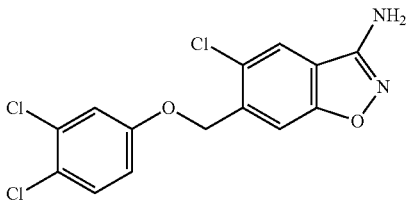 [SMILES: Nc1noc2cc(COc3ccc(Cl)c(Cl)c3)c(Cl)cc12]

5-chloro-6-((3,4-dichlorophenoxy)methyl)benzo[d]isoxazol-3-amine

To a mixture of N-hydroxyacetamide (35 mg, 0.45 mmol) in dry DMF (2 mL) was added potassium t-butoxide (50 mg, 0.45 mmol). The mixture was stirred at room temperature for 30 min then 5-chloro-4-((3,4-dichlorophenoxy)methyl)-2-fluorobenzonitrile (50 mg, 0.15 mmol) was added. After stirring at room temperature for additional 16 h, the mixture was concentrated and purified by reverse phase combiflash (20%-60% MeCN in 0.1% NH$_4$HCO$_3$) to get 5-chloro-6-(3,4-dichlorophenoxy)methyl)benzo[d]isoxazol-3-amine (42 mg, 81% yield) as a white solid. LCMS(ESI) m/z: 343.0 [M+H]$^+$.

Step 5

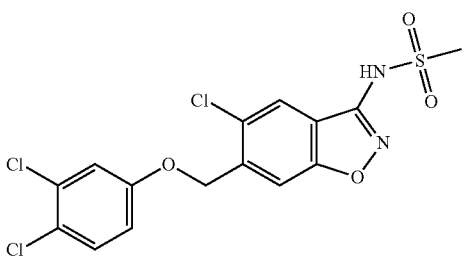 [SMILES: CS(=O)(=O)Nc1noc2cc(COc3ccc(Cl)c(Cl)c3)c(Cl)cc12]

N-(5-chloro-6-((3,4-dichlorophenoxy)methyl)benzo[d]isoxazol-3-yl) methanesulfonamide Methanesulfonyl chloride (0.14 mmol, 16 mg) was added dropwise to a mixture of 5-chloro-6-((3,4-dichlorophenoxy)methyl)benzo[d]isoxazol-3-amine (42 mg, 0.12 mmol) in dry pyridine (2 mL) at 0° C. After stirring at room temperature for 16 h, the mixture was concentrated and purified by reverse phase combiflash (20%-50% MeCN in 0.1% NH$_4$HCO$_3$) to get target compound (14.1 mg, 20% yield) as a white solid. LCMS(ESI) Method A: RT=5.58 min, m/z: 420.9 [M+H]$^+$; $^1$H-NMR (500 MHz, MeOD-d$_4$): δ 7.85 (s, 1H), 7.60 (s, 1H), 7.46 (d, J=9.0 Hz, 1H), 7.27 (d, J=3.0 Hz, 1H), 7.05-7.02 (m, 1H), 5.27 (s, 2H), 3.10 (s, 3H).

Example 3

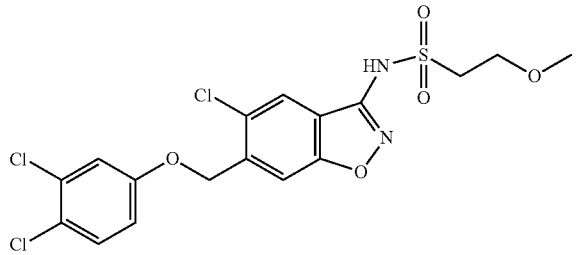 [SMILES: COCCS(=O)(=O)Nc1noc2cc(COc3ccc(Cl)c(Cl)c3)c(Cl)cc12]

N-(5-chloro-6-((3,4-dichlorophenoxy)methyl)benzo[d]isoxazol-3-yl)-2-methoxyethanesulfonamide Synthetic scheme

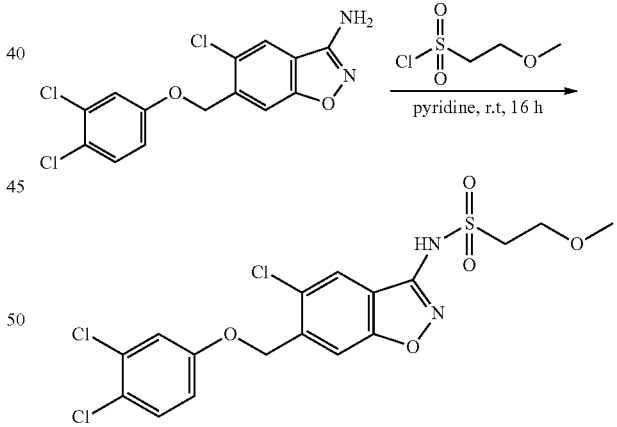

2-Methoxyethanesulfonyl chloride (0.14 mmol, 22 mg) was added dropwise to a mixture of 5-chloro-6-((3,4-dichlorophenoxy)methyl)benzo[d]isoxazol-3-amine (42 mg, 0.12 mmol) in dry pyridine (2 mL) at 0° C. After stirring at room temperature for 16 h, the mixture was concentrated and purified by reverse phase combiflash (20%-50% MeCN in 0.1% NH$_4$HCO$_3$) to get target compound (17.5 mg, 32%) as a white solid. LCMS(ESI) Method A: RT=5.60 min, m/z: 465.0 [M+H]$^+$; $^1$H-NMR (500 MHz, MeOD-d$_4$): δ 7.87 (s, 1H), 7.61 (s, 1H), 7.47 (d, J=8.5 Hz, 1H), 7.28 (d, J=3.0 Hz, 1H), 7.05-7.03 (m, 1H), 5.28 (s, 2H), 3.82 (t, J=14 Hz, 2H), 3.59 (t, J=14 Hz, 2H), 3.33 (s, 3H).

Example 4

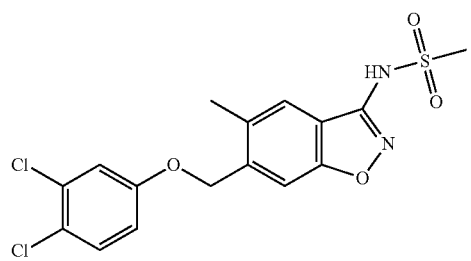 [SMILES: Cc1cc2c(NS(C)(=O)=O)noc2cc1COc1ccc(Cl)c(Cl)c1]

N-(6-((3,4-dichlorophenoxy)methyl)-5-methylbenzo[d]isoxazol-3-yl)-methanesulfonamide Synthetic scheme

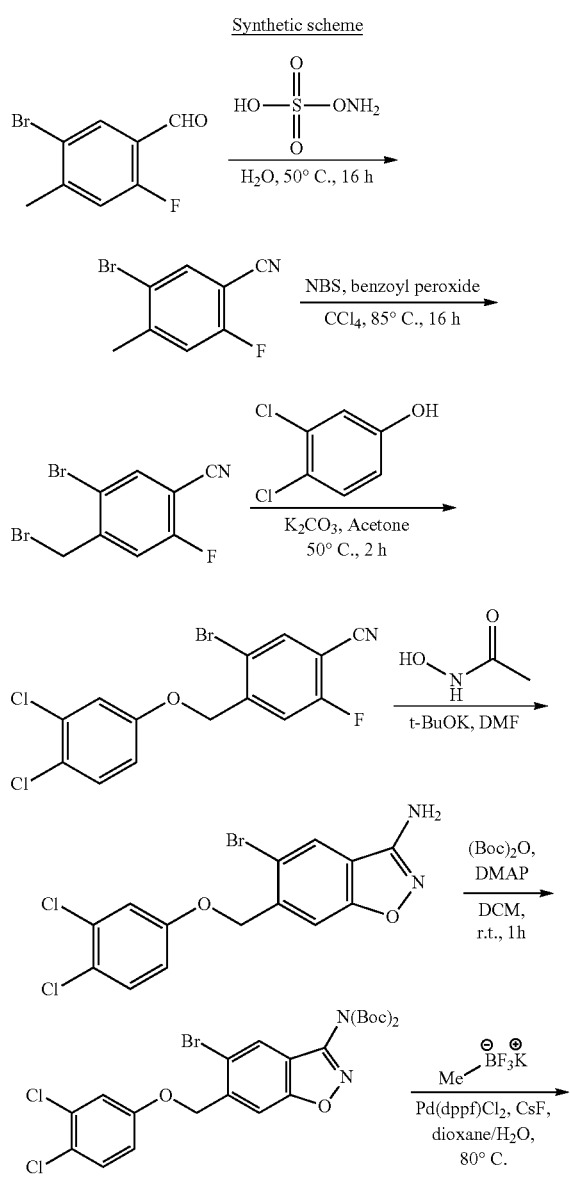

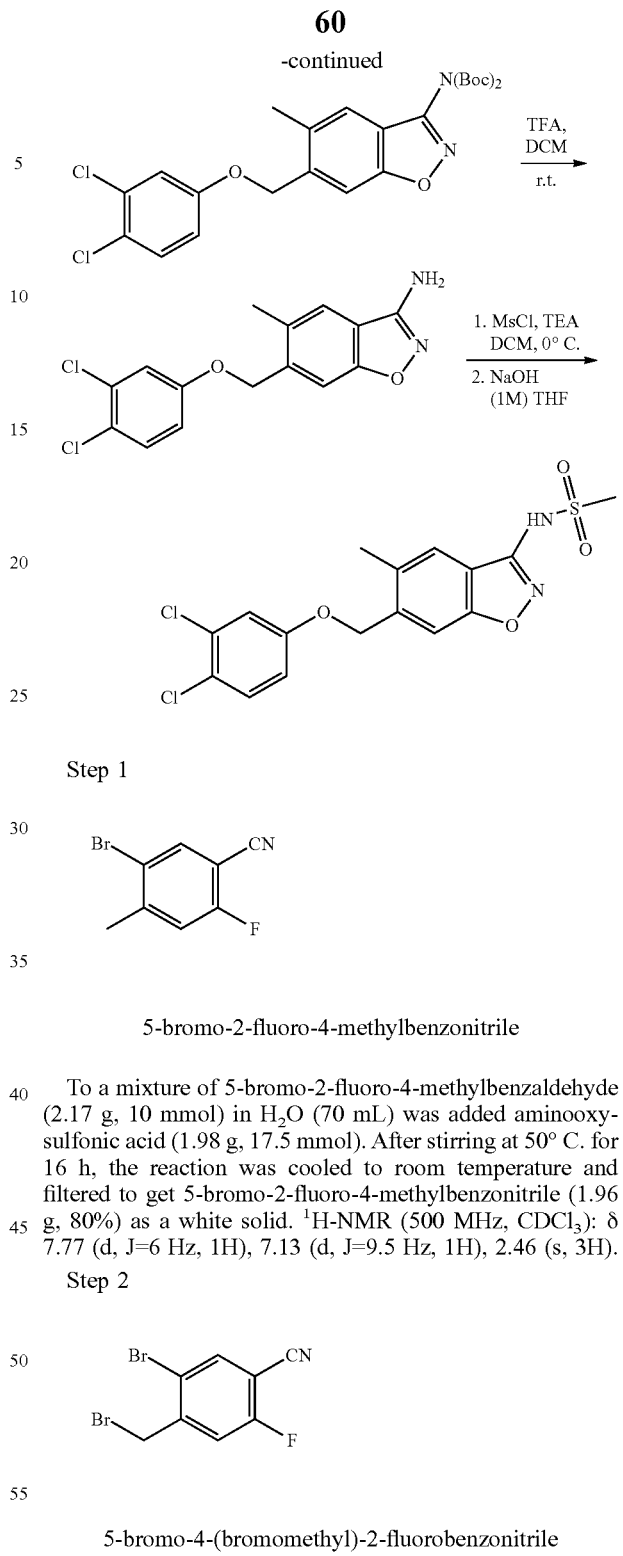

Step 1

5-bromo-2-fluoro-4-methylbenzonitrile

To a mixture of 5-bromo-2-fluoro-4-methylbenzaldehyde (2.17 g, 10 mmol) in H₂O (70 mL) was added aminooxysulfonic acid (1.98 g, 17.5 mmol). After stirring at 50° C. for 16 h, the reaction was cooled to room temperature and filtered to get 5-bromo-2-fluoro-4-methylbenzonitrile (1.96 g, 80%) as a white solid. $^1$H-NMR (500 MHz, CDCl₃): δ 7.77 (d, J=6 Hz, 1H), 7.13 (d, J=9.5 Hz, 1H), 2.46 (s, 3H).

Step 2

5-bromo-4-(bromomethyl)-2-fluorobenzonitrile

A mixture of 5-bromo-2-fluoro-4-methylbenzonitrile (170 mg, 0.79 mmol), N-bromosuccinimide (148 mg, 0.83 mmol) and benzoyl peroxide (6 mg, 0.02 mmol) in CCl₄ (2 mL) was stirred at 85° C. for 16 h. The solvent was removed and the residue was purified by silica gel chromatography (eluting with petroleum ether/EtOAc=20/1) to afford 5-bromo-4-(bromomethyl)-2-fluorobenzonitrile (100 mg, 43%) as a white solid. $^1$H-NMR (500 MHz, CDCl₃): δ 7.84 (d, J=6 Hz, 1H), 7.38 (d, J=9 Hz, 1H), 4.53 (s, 2H).

Step 3

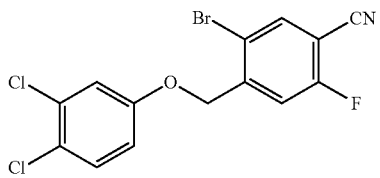 [SMILES: N#Cc1cc(Br)c(COc2ccc(Cl)c(Cl)c2)cc1F]

5-bromo-4-((3,4-dichlorophenoxy)methyl)-2-fluorobenzonitrile

A mixture of 5-bromo-4-(bromomethyl)-2-fluorobenzonitrile (306 mg, 1.9 mmol), 3,4-dichlorophenol (500 mg, 1.7 mmol) and potassium carbonate (706 mg, 5.1 mmol) in acetone (6 mL) was stirred at 50° C. for 2 h. The reaction was quenched with $H_2O$ (10 mL) and extracted with ethyl acetate (5 mL×4). The combined organic layers were dried over $Na_2SO_4$, filtered, and concentrated in vacuo to afford 5-bromo-4-((3,4-dichlorophenoxy)methyl)-2-fluorobenzonitrile (675 mg, 89% yield) as a white solid. $^1$H-NMR (500 MHz, $CDCl_3$): δ 7.84 (d, J=6 Hz, 1H), 7.49 (m, 1H), 7.39 (m, 1H), 7.10 (d, J=2.5 Hz, 1H), 6.86-6.83 (m, 1H), 5.07 (s, 2H).

Step 4

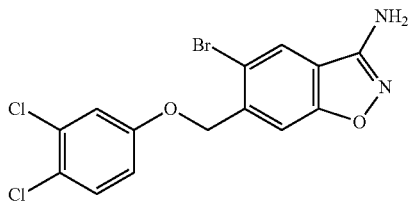 [SMILES: Nc1noc2cc(COc3ccc(Cl)c(Cl)c3)c(Br)cc12]

5-bromo-6-((3,4-dichlorophenoxy)methyl)benzo[d]isoxazol-3-amine

To a solution of N-hydroxyacetamide (60 mg, 0.8 mmol) in dry DMF (2 mL) was added potassium tert-butoxide (90 mg, 0.8 mmol) and the reaction mixture was stirred at 30° C. for 0.5 h. Then 5-bromo-4-((3,4-dichlorophenoxy)methyl)-2-fluorobenzonitrile (100 mg, 0.27 mmol) was added and the mixture was stirred at 30° C. for another 2 h. The resulting mixture was purified directly by reverse phase combiflash (20%-50% $CH_3CN/H_2O$ in 0.1% $NH_4HCO_3$) to get the target compound (66 mg, 63%) as a white solid. LCMS (ESI) m/z: 386.9 [M+H]$^+$; $^1$H-NMR (500 MHz, $CDCl_3$): δ 7.78 (s, 1H), 7.65 (s, 1H), 7.38 (d, J=9.0 Hz, 1H), 7.12 (d, J=3.0 Hz, 1H), 6.88-6.86 (m, 1H), 5.17 (s, 2H), 4.38 (br s, 2H).

Step 5

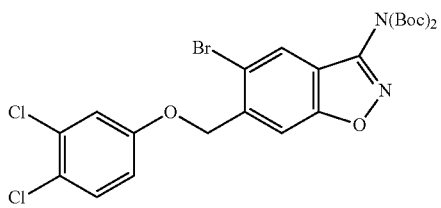

tert-butyl N-[5-bromo-6-(3,4-dichlorophenoxymethyl)-1,2-benzoxazol-3-yl]-N-[(tert-butoxy)-carbonyl]carbamate To a solution of 5-bromo-6-((3,4-dichlorophenoxy)methyl)benzo[d]isoxazol-3-amine (592 mg, 1.52 mmol) and di-tert-butyl dicarbonate (673 mg, 3.05 mmol) in DCM (10 mL) was added DMAP (36 mg, 0.305 mmol). The reaction mixture was stirred at room temperature for 16 h. The solvent was removed and the residue was purified by silica-gel column (eluting with petroleum ether/ethyl acetate=5/1) to afford the target product (641 mg, 72%) as an oil. $^1$H-NMR (500 MHz, $CDCl_3$): δ 7.83 (s, 1H), 7.80 (s, 1H), 7.38 (d, J=8.5 Hz, 1H), 7.14 (d, J=3.0 Hz, 1H), 6.91-6.88 (m, 1H), 5.19 (s, 2H), 1.44 (s, 18H).

Step 6

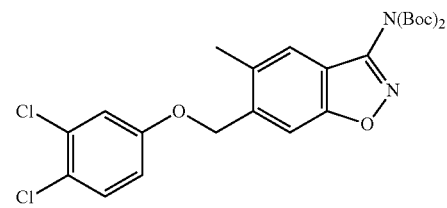

tert-butyl N-[(tert-butoxy)carbonyl]-N-[6-(3,4-dichlorophenoxymethyl)-5-methyl-1,2-benzoxazol-3-yl]carbamate To a mixture of tert-butyl N-[5-bromo-6-(3,4-dichlorophenoxymethyl)-1,2-benzoxazol-3-yl]-N-[(tert-butoxy)carbonyl]carbamate (300 mg, 0.51 mmol) and potassium methyltrifluoroborate (81 mg, 0.66 mmol) in dioxane (6 mL) and $H_2O$ (0.3 mL) was added [1,1'-Bis(diphenylphosphino)ferrocene]palladium(II) chloride (62 mg, 0.076 mmol) and cesium fluoride (271 mg, 1.78 mmol) and then stirred at 80° C. for 16 h. The reaction mixture was filtered through celite and diluted with ethyl acetate. The filtrate was concentrated and the residue was purified by reverse phase combiflash (20%-50% $CH_3CN/H_2O$ in 0.1% $NH_4HCO_3$) to afford the target compound (117 mg, 45%). LCMS (ESI) m/z: 367.0 [M-156+H]$^+$.

Step 7

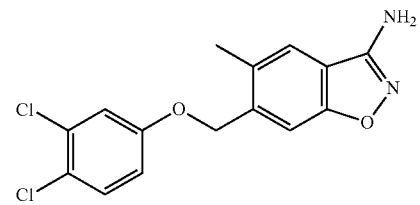 [SMILES: Cc1cc2c(N)noc2cc1COc1ccc(Cl)c(Cl)c1]

6-((3,4-dichlorophenoxy)methyl)-5-methylbenzo[d]isoxazol-3-amine

To a solution of tert-butyl N-[(tert-butoxy)carbonyl]-N-[6-(3,4-dichlorophenoxymethyl)-5-methyl-1,2-benzoxazol- 3-yl]carbamate (117 mg, 0.23 mmol) in DCM (4 mL) was added trifluoroacetic acid (2 mL). The reaction mixture was stirred at room temperature for 2 h then sat. Na$_2$CO$_3$ (5 mL) was added and extracted with DCM (4 mL×2). The combined organic layers were dried (Na$_2$SO$_4$), filtered and concentrated in vacuo to afford crude oil product (80 mg, 95%). The crude product was used in the next step without further purification. LCMS (ESI): m/z: 323.0 [M+H]$^+$.

Step 8

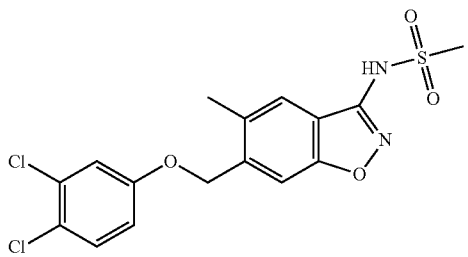 [SMILES: Cc1cc2c(NS(C)(=O)=O)noc2cc1COc1ccc(Cl)c(Cl)c1]

N-(6-((3,4-dichlorophenoxy)methyl)-5-methylbenzo[d]isoxazol-3-yl)methanesulfonamide Methanesulfonyl chloride (0.74 mmol, 85 mg) was added dropwise to a solution of 6-((3,4-dichlorophenoxy)methyl)-5-methylbenzo[d]isoxazol-3-amine (80 mg, 0.25 mmol, crude) and triethylamine (76 mg, 0.75 mmol) in DCM (2 mL) at 0° C. After stirring at room temperature for 2 h, the solvent was removed under vacuum. The residue was dissolved in THF (2 mL) and NaOH (1 M, 1.0 mL). After stirring at room temperature for 2 h, HCl (1M) was added to adjust pH to 6; the reaction mixture was diluted with ethyl acetate (15 mL) and washed with water (3 mL), brine (3 mL) and dried over Na$_2$SO$_4$. The solvent was removed and the residue was purified by reverse phase combiflash (20%-50% CH$_3$CN/H$_2$O in 0.1% NH$_4$HCO$_3$) to give the target compound (25 mg, 39%) as a white solid. LCMS (ESI) Method A: RT=5.36 min, m/z 401.0 [M+H]$^+$; $^1$H-NMR (500 MHz, MeOD-d$_4$): δ 7.47 (s, 1H), 7.33-7.31 (m, 2H), 7.14 (d, J=2.5 Hz, 1H), 6.92-6.89 (m, 1H), 5.07 (s, 2H), 2.98 (s, 3H), 2.32 (s, 3H).

Example 5

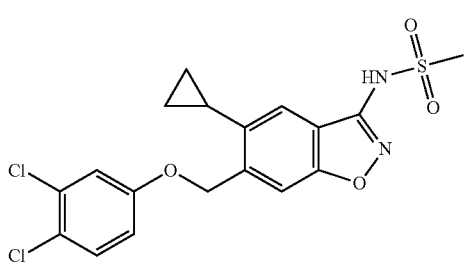 [SMILES: CS(=O)(=O)Nc1noc2cc(COc3ccc(Cl)c(Cl)c3)c(C3CC3)cc12]

N-(5-cyclopropyl-6-((3,4-dichlorophenoxy)methyl)benzo[d]isoxazol-3-yl)-methanesulfonamide Synthetic scheme

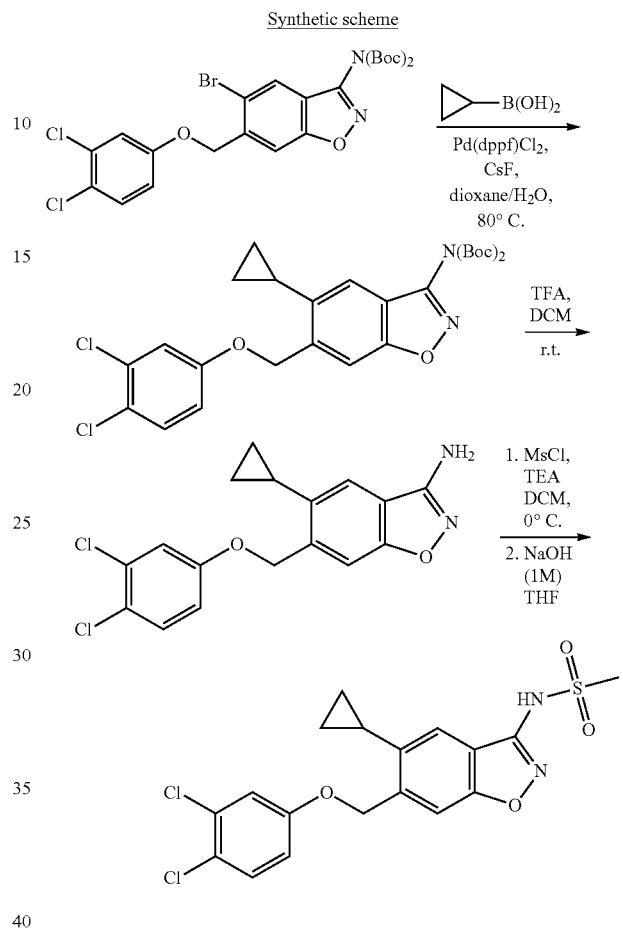

Step 1

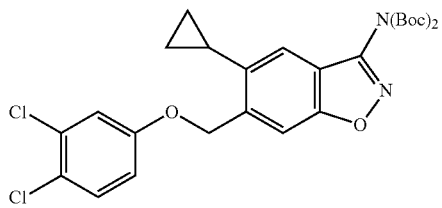

tert-butyl N-[(tert-butoxy)carbonyl]-N-[5-cyclopropyl-6-(3,4-dichlorophenoxymethyl)-1,2-benzoxazol-3-yl]carbamate To a mixture of tert-butyl N-[5-bromo-6-(3,4-dichlorophenoxymethyl)-1,2-benzoxazol-3-yl]-N-[(tert-butoxy)carbonyl]carbamate (200 mg, 0.34 mmol) and cyclopropylboronic acid (59 mg, 0.68 mmol) in dioxane (6 mL) and H$_2$O (0.3 mL) was added [1,1'-Bis(diphenyl-phosphino)ferrocene]palladium(II) chloride (42 mg, 0.05 mmol) and cesium fluoride (180 mg, 1.19 mmol). After stirring at 90° C. for 16 h, the mixture was filtered through celite and the filtrate was concentrated. The residue was purified by reverse phase combiflash (20%-50% CH$_3$CN/H$_2$O in 0.1% NH$_4$HCO$_3$) to afford target compound (170 mg, 91%). LCMS (ESI) m/z: 393.0 [M-156+H]$^+$.

Step 2

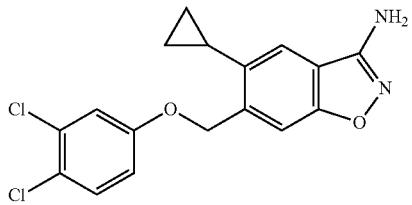 [SMILES: Nc1noc2cc(COc3ccc(Cl)c(Cl)c3)c(C3CC3)cc12]

5-cyclopropyl-6-((3,4-dichlorophenoxy)methyl)benzo[d]isoxazol-3-amine

To a solution of tert-butyl N-[(tert-butoxy)carbonyl]-N-[5-cyclopropyl-6-(3,4-dichloro-phenoxymethyl)-1,2-benzoxazol-3-yl]carbamate (170 mg, 0.31 mmol) in DCM (6 mL) was added trifluoroacetic acid (2 mL). After stirring at room temperature for 2 h, the reaction was quenched with sat. Na$_2$CO$_3$ (5 mL) and extracted with DCM (5 mL×2). The combined organic layers were dried over Na$_2$SO$_4$, filtered and concentrated in vacuo to afford target compound (102 mg, 95%). The crude product was used in the next step without further purification. LCMS (ESI): m/z: 349.0 [M+H]$^+$.

Step 3

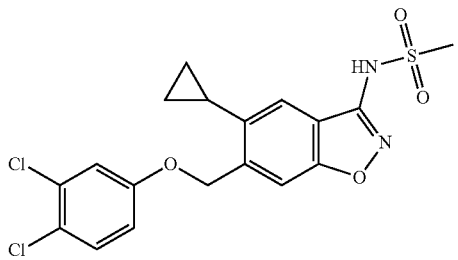 [SMILES: CS(=O)(=O)Nc1noc2cc(COc3ccc(Cl)c(Cl)c3)c(C3CC3)cc12]

N-(5-cyclopropyl-6-((3,4-dichlorophenoxy)methyl)benzo[d]isoxazol-3-yl)-methanesulfonamide Methanesulfonyl chloride (92 mg, 0.8 mmol) was added dropwise to a solution of 5-cyclopropyl-6-((3,4-dichlorophenoxy)methyl)benzo[d]isoxazol-3-amine (140 mg, 0.4 mmol, crude) and triethylamine (122 mg, 1.2 mmol) in DCM (3 mL) at 0° C. After stirring at room temperature for 2 h, the solvent was removed under vacuum. The residue was dissolved in THF (2 mL) and NaOH (1 M, 3 mL). After stirring at room temperature for 2 h, HCl (1M) was added to adjust pH to 6; the reaction mixture was diluted with ethyl acetate (15 mL) and washed with water (3 mL), brine (3 mL) and dried over Na$_2$SO$_4$. The solvent was removed and the residue was purified by reverse phase combiflash (20%-50% CH$_3$CN/H$_2$O in 0.1% NH$_4$HCO$_3$) to get the target compound (64 mg, 37%) as a white solid. LCMS(ESI) Method A: RT=5.59 min, m/z: 427.0 [M+H]$^+$; $^1$H-NMR (500 MHz, MeOD-d$_4$): δ 7.56 (d, J=9 Hz, 1H), 7.44-7.42 (m, 2H), 7.21 (s, 1H), 6.92-6.89 (m, 1H), 5.38 (s, 2H), 2.83 (s, 3H), 2.03 (m, 1H), 0.91 (m, 2H), 0.65 (m, 2H).

Example 6

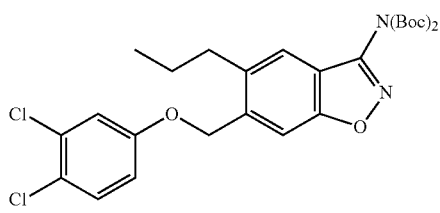

N-(6-((3,4-dichlorophenoxy)methyl)-5-propylbenzo[d]isoxazol-3-yl)methanesulfonamide Synthetic scheme

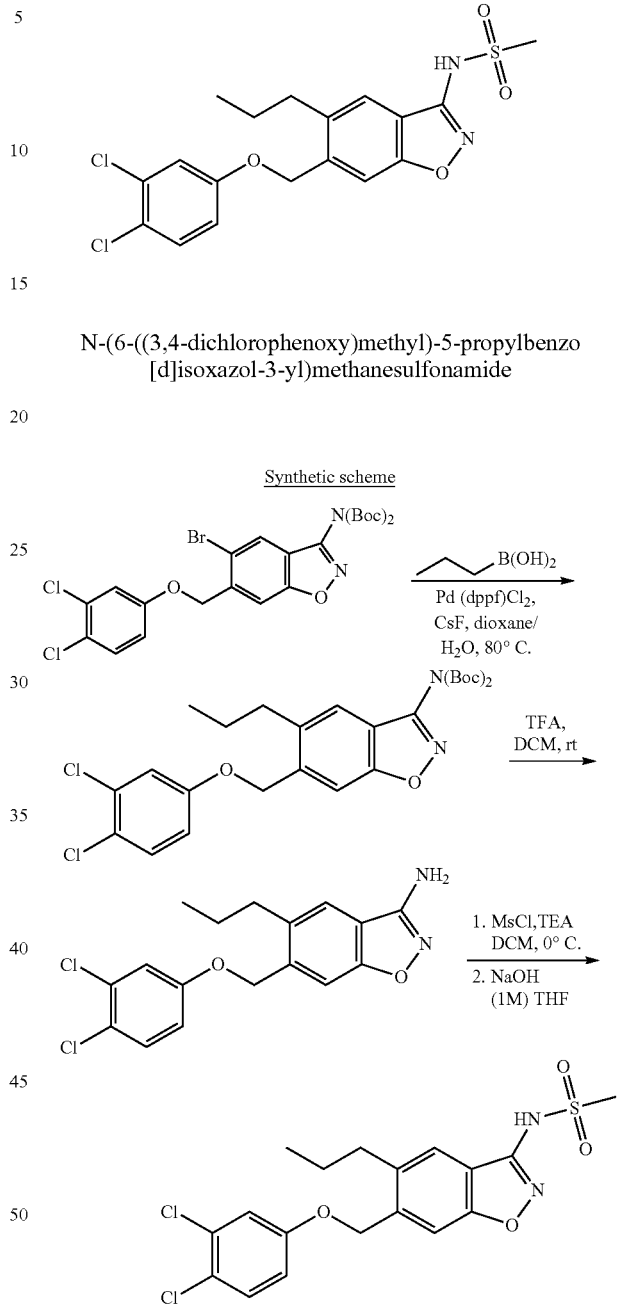

Step 1 tert-butyl N-[(tert-butoxy)carbonyl]-N-[6-(3,4-dichlorophenoxymethyl)-5-propyl-1,2-benzoxazol-3-yl]carbamate To the mixture of tert-butyl N-[5-bromo-6-(3,4-dichlorophenoxymethyl)-1,2-benzoxazol-3-yl]-N-[(tert-butoxy)carbonyl]carbamate (200 mg, 0.34 mmol) and propylboronic acid (60 mg, 0.68 mmol) in dioxane (6 mL) and H₂O (0.3 mL) was added [1,1'-Bis(diphenylphosphino)-ferrocene] palladium(II) chloride (42 mg, 0.05 mmol) and cesium fluoride (180 mg, 1.19 mmol). After stirring at 90° C. for 16 h, the mixture was filtered through celite and the filtrate was concentrated. The residue was purified by reverse phase combiflash (20%-50% CH₃CN/H₂O in 0.1% NH₄HCO₃) to give oil product (50 mg, 27%). LCMS (ESI) m/z: 395.0 [M-156+H]⁺.

Step 2

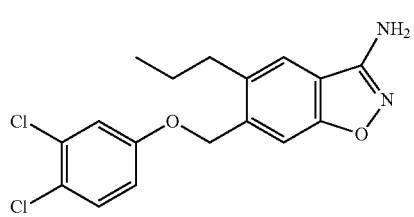 [SMILES: CCCc1cc2c(N)noc2cc1COc1ccc(Cl)c(Cl)c1]

6-((3,4-dichlorophenoxy)methyl)-5-propylbenzo[d]isoxazol-3-amine

To a solution of tert-butyl N-[(tert-butoxy)carbonyl]-N-[6-(3,4-dichlorophenoxymethyl)-5-propyl-1,2-benzoxazol-3-yl]carbamate (50 mg, 0.09 mmol) in DCM (2 mL) was added trifluoroacetic acid (1 mL). After stirring at room temperature for 2 h, the reaction was quenched by sat. Na₂CO₃ (3 mL) and extracted with DCM (2 mL×2). The combined organic layers were dried over Na₂SO₄, filtered and concentrated in vacuo to afford crude oil product (28 mg, 90%). The crude product was used in the next step without further purification. LCMS (ESI): m/z: 351.0 [M+H]⁺.

Step 3

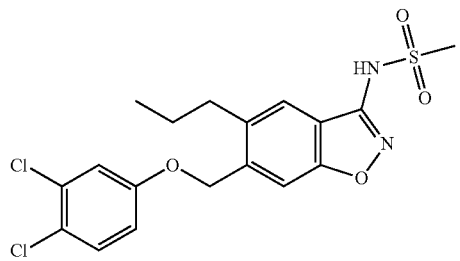 [SMILES: CCCc1cc2c(NS(C)(=O)=O)noc2cc1COc1ccc(Cl)c(Cl)c1]

N-(6-((3,4-dichlorophenoxy)methyl)-5-propylbenzo[d]isoxazol-3-yl) methanesulfonamide Methanesulfonyl chloride (19 mg, 0.16 mmol) was added dropwise to a solution of 6-((3,4-dichlorophenoxy)methyl)-5-propylbenzo[d]isoxazol-3-amine (28 mg, 0.08 mmol, crude) and triethylamine (24 mg, 0.24 mmol) in DCM (1 mL) at 0° C. After stirring at room temperature for 2 h, the solvent was removed under vacuum. The residue was dissolved in THF (1 mL) and NaOH (1 M, 2 mL). After stirring at room temperature for 2 h, HCl (1M) was added to adjust pH to 6; the reaction mixture was diluted with ethyl acetate (5 mL) and washed with water (3 mL), brine (3 mL) and dried over Na₂SO₄. The solvent was removed and the residue was purified by reverse phase combiflash (20%-50% CH₃CN/H₂O in 0.1% NH₄HCO₃) to get the target compound (10 mg, 29%) as a white solid. LCMS(ESI) Method A: RT=5.68 min, m/z: 428.9 [M+H]⁺; ¹H-NMR (500 MHz, MeOD-4): δ 7.57-7.55 (m, 3H), 7.44 (d, J=3 Hz, 1H), 7.12-7.10 (m, 1H), 5.25 (s, 2H), 3.04 (s, 3H), 2.70-2.67 (m, 2H), 1.65-1.63 (m, 2H), 0.94 (t, J=10 Hz, 3H).

Example 7

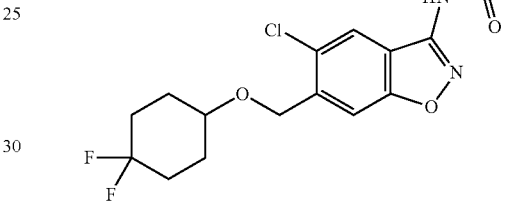

N-(5-chloro-6-((4,4-difluorocyclohexyloxy)methyl)benzo[d]isoxazol-3-yl)-methanesulfonamide Synthetic scheme

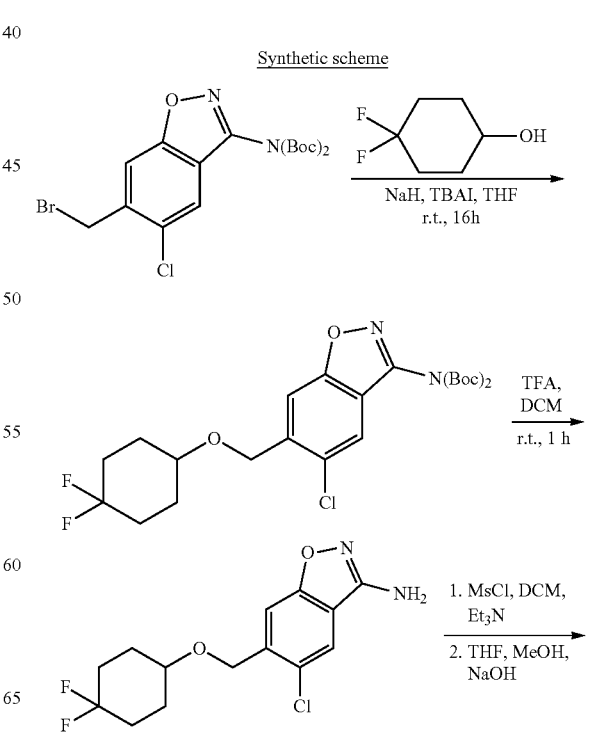

-continued

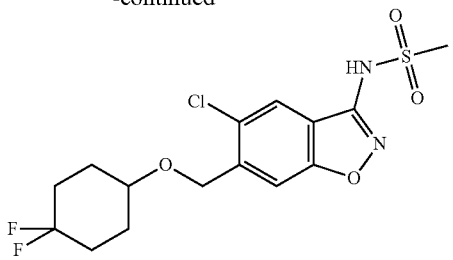

Step 1

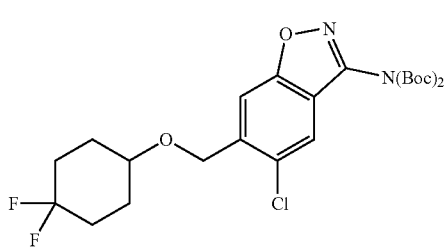

tert-butyl N-[(tert-butoxy)carbonyl]-N-(5-chloro-6-{[(4,4-difluorocyclohexyl)oxy]methyl}-1,2-benzoxazol-3-yl)carbamate A mixture of 4,4-difluorocyclohexanol (240 mg 1.6 mmol) in dry THF (10 mL) at 0° C. was added sodium hydride (64 mg, 1.6 mmol, 60%). After stirring at room temperature for 1 h, tert-butyl N-[6-(bromomethyl)-5-chloro-1,2-benzoxazol-3-yl]-N-[(tert-butoxy)carbonyl]carbamate (184 mg 0.40 mmol) in dry THF (3 mL) and TBAI (4 mg 0.01 mmol) were added. After stirring at room temperature for 16 h, the reaction was quenched by water, extracted with ethyl acetate (30 mL×3), dried over anhydrous Na$_2$SO$_4$, concentrated and purified by silica-gel column chromatography (eluting with petroleum ether/EtOAc, from 10/1 to 3/1) to give tert-butyl N-[(tert-butoxy)carbonyl]-N-(5-chloro-6-{[(4,4-difluorocyclohexyl)oxy]methyl}-1,2-benzoxazol-3-yl)carbamate (120 mg, 60%). LCMS (ESI) m/z: 361.0 [M−156+H]$^+$.

Step 2

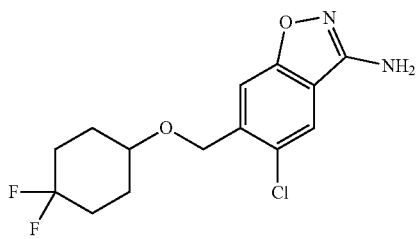 [SMILES: Nc1noc2cc(COC3CCC(F)(F)CC3)c(Cl)cc12]

5-chloro-6-((4,4-difluorocyclohexyloxy)methyl)benzo[d]isoxazol-3-amine

A solution of tert-butyl N-[(tert-butoxy)carbonyl]-N-(5-chloro-6-{[(4,4-difluoro-cyclohexyl)oxy]methyl}-1,2-benzoxazol-3-yl)carbamate (120 mg, 0.23 mmol) in TFA (5.0 mL) and DCM (5.0 mL) was stirred at room temperature for 1 h. The reaction was quenched by saturated aqueous NaHCO$_3$ and extracted with DCM (30 mL×2). The combined organic layers were dried over Na$_2$SO$_4$, filtered and concentrated to give 5-chloro-6-((4,4-difluoro-cyclohexyloxy)methyl)benzo[d]isoxazol-3-amine (90 mg, crude) as a solid which was used in the next step without purification. LCMS (ESI) m/z: 317.0 [M+H]$^+$.

Step 3

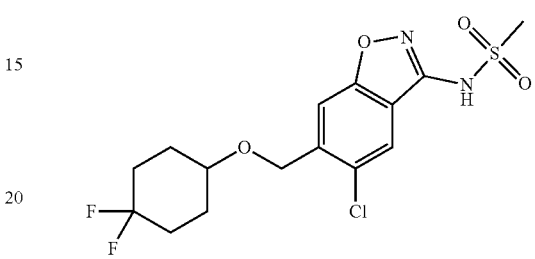

N-(5-chloro-6-((4,4-difluorocyclohexyloxy)methyl)benzo[d]isoxazol-3-yl)-methanesulfonamide To a solution of 5-chloro-6-((4,4-difluorocyclohexyloxy)methyl)benzo[d]isoxazol-3-amine (90 mg, crude) in DCM (6 mL) was added methanesulfonyl chloride (48 mg, 0.42 mmol) and triethylamine (84 mg, 0.84 mmol). After stirring at room temperature for 1 h, the solvent was removed in vacuo and the crude product was dissolved in THF/CH$_3$OH (4 mL/1 mL) then aqueous sodium hydroxide (2 mL, 1.0 M) was added. The mixture was stirred at rt for 1 h and extracted with EtOAc (20 mL×3). The combined organic layers were concentrated and purified by reverse phase prep-HPLC to afford N-(5-chloro-6-((4,4-difluorocyclohexyloxy)-methyl)benzo[d]isoxazol-3-yl) methanesulfonamide (42 mg, two steps yield: 47%) as a white solid. (LCMS (ESI) Method A: RT=4.81 min, m/z: 395.0 [M+H]$^+$. $^1$H NMR (500 MHz, MeOD-d$_4$): δ 7.81 (s, 1H), 7.60 (s, 1H), 4.72 (s, 2H), 3.78-3.77 (m, 1H), 3.16 (s, 3H) 2.15-2.09 (m, 2H), 1.96-1.90 (m, 6H).

Example 8

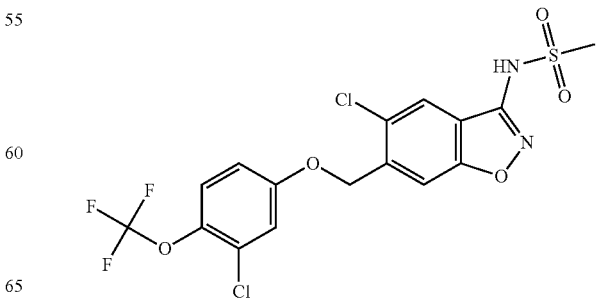

71

N-(5-chloro-6-((3-chloro-4-(trifluoromethoxy)phenoxy)methyl)benzo[d]isoxazol-3-yl)-methanesulfonamide Synthetic scheme

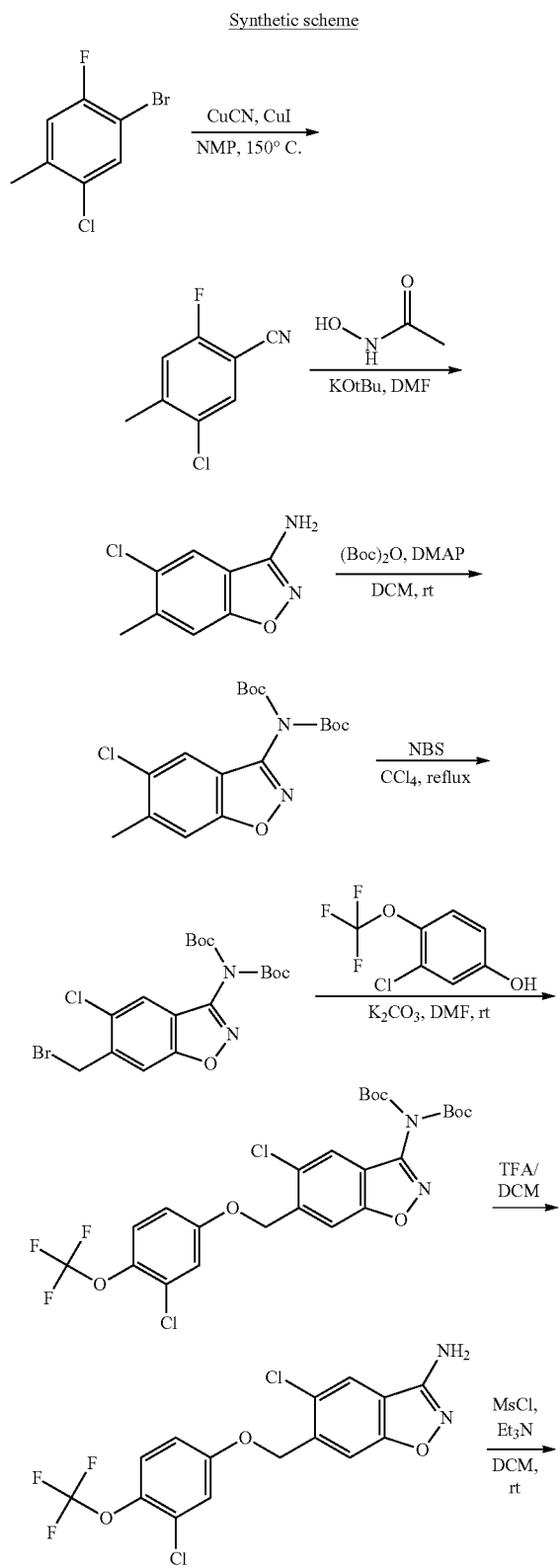

-continued

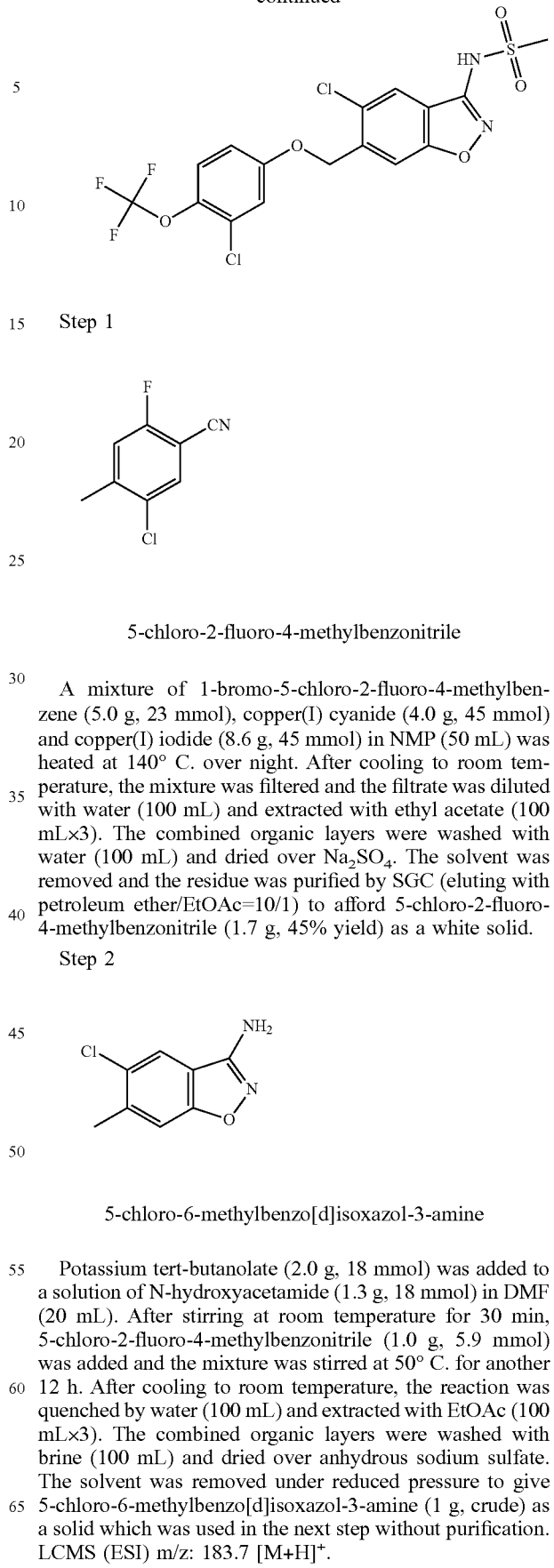

Step 1

5-chloro-2-fluoro-4-methylbenzonitrile

A mixture of 1-bromo-5-chloro-2-fluoro-4-methylbenzene (5.0 g, 23 mmol), copper(I) cyanide (4.0 g, 45 mmol) and copper(I) iodide (8.6 g, 45 mmol) in NMP (50 mL) was heated at 140° C. over night. After cooling to room temperature, the mixture was filtered and the filtrate was diluted with water (100 mL) and extracted with ethyl acetate (100 mL×3). The combined organic layers were washed with water (100 mL) and dried over $Na_2SO_4$. The solvent was removed and the residue was purified by SGC (eluting with petroleum ether/EtOAc=10/1) to afford 5-chloro-2-fluoro-4-methylbenzonitrile (1.7 g, 45% yield) as a white solid.

Step 2

5-chloro-6-methylbenzo[d]isoxazol-3-amine

Potassium tert-butanolate (2.0 g, 18 mmol) was added to a solution of N-hydroxyacetamide (1.3 g, 18 mmol) in DMF (20 mL). After stirring at room temperature for 30 min, 5-chloro-2-fluoro-4-methylbenzonitrile (1.0 g, 5.9 mmol) was added and the mixture was stirred at 50° C. for another 12 h. After cooling to room temperature, the reaction was quenched by water (100 mL) and extracted with EtOAc (100 mL×3). The combined organic layers were washed with brine (100 mL) and dried over anhydrous sodium sulfate. The solvent was removed under reduced pressure to give 5-chloro-6-methylbenzo[d]isoxazol-3-amine (1 g, crude) as a solid which was used in the next step without purification. LCMS (ESI) m/z: 183.7 $[M+H]^+$.

Step 3

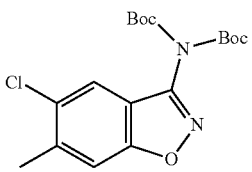 [SMILES: Cc1cc2onc(N(C(=O)OC(C)(C)C)C(=O)OC(C)(C)C)c2cc1Cl]

tert-butyl N-[(tert-butoxy)carbonyl]-N-(5-chloro-6-methyl-1,2-benzoxazol-3-yl)carbamate A solution of 5-chloro-6-methylbenzo[d]isoxazol-3-amine (1.0 g, 5.5 mmol) in DCM (20 mL) was added di-tert-butyl-dicarbonate (3.0 g, 14 mmo) and catalytic amount of N,N-dimethylpyridin-4-amine. After stirring at 25° C. for 16 h, the mixture was concentrated into about 5 mL, treated with hexanes and filtered to yield tert-butyl N-[(tert-butoxy)carbonyl]-N-(5-chloro-6-methyl-1,2-benzoxazol-3-yl)carbamate (1.6 g, 76%) as a white solid. LCMS (ESI) m/z: 227.1 [M-156+H]$^+$, $^1$H-NMR (500 MHz, CDCl$_3$): 7.53 (s, 1H), 7.48 (s, 1H), 2.54 (s, 3H), 1.42 (s, 18H).

Step 4

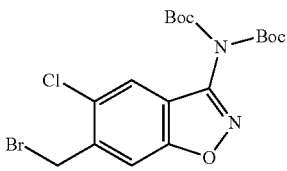 [SMILES: CC(C)(C)OC(=O)N(C(=O)OC(C)(C)C)c1noc2cc(CBr)c(Cl)cc12]

tert-butyl N-[6-(bromomethyl)-5-chloro-1,2-benzoxazol-3-yl]-N-[(tert-butoxy)carbonyl]carbamate A solution of tert-butyl N-[(tert-butoxy)carbonyl]-N-(5-chloro-6-methyl-1,2-benzoxazol-3-yl)carbamate (100 mg, 0.26 mmol) in CCl$_4$ (2 mL) was added N-bromosuccinimide (51 mg, 0.29 mmol) and 2,2-azobis(2-methylpropionitrile) (4 mg, 0.026 mmol). The reaction mixture was heated to reflux for 3 h then cooled to ambient temperature. The solvent was removed in vacuo and purified by SGC (eluting with petroleum ether/EtOAc=10/1) to afforded tert-butyl N-[6-(bromomethyl)-5-chloro-1,2-benzoxazol-3-yl]-N-[(tert-butoxy)carbonyl]carbamate (100 mg, 84%) as a white solid. LCMS (ESI) m/z: 305.0 [M-156+H]$^+$.

Step 5

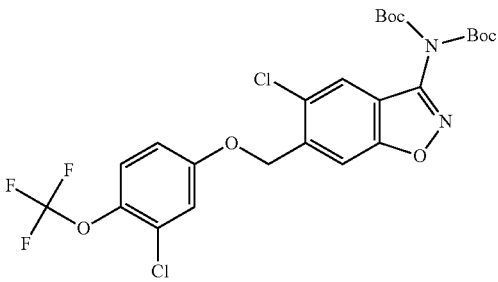 [SMILES: CC(C)(C)OC(=O)N(C(=O)OC(C)(C)C)c1noc2cc(COc3ccc(OC(F)(F)F)c(Cl)c3)c(Cl)cc12]

tert-butyl N-[(tert-butoxy)carbonyl]-N-{5-chloro-6-[3-chloro-4-(trifluoromethoxy)-phenoxymethyl]-1,2-benzoxazol-3-yl}carbamate A solution of tert-butyl N-[6-(bromomethyl)-5-chloro-1,2-benzoxazol-3-yl]-N-[(tert-butoxy)carbonyl]carbamate (100 mg, 0.22 mmol) in DMF (2 mL) was added 3-chloro-4-(trifluoromethoxy)phenol (55 mg, 0.26 mmol) and potassium carbonate (61 mg, 0.44 mmol). After stirring at 25° C. for 16 h, the mixture was diluted with water (10 mL) and extracted with EtOAc (10 mL×3). The combined organic layers were washed with brine (10 mL), dried over anhydrous sodium sulfate, filtered and concentrated to afford tert-butyl N-[(tert-butoxy)carbonyl]-N-{5-chloro-6-[3-chloro-4-(trifluoromethoxy)phenoxymethyl]-1,2-benzoxazol-3-yl}carbamate (100 mg, crude) as an oil which was used in the next step without further purification. LCMS (ESI) m/z: 437.0 [M-156+H]$^+$.

Step 6

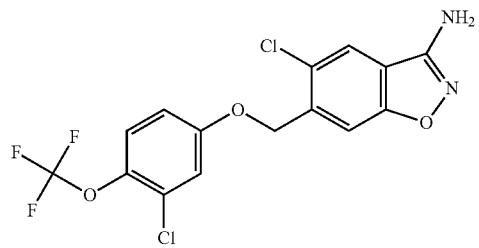 [SMILES: Nc1noc2cc(COc3ccc(OC(F)(F)F)c(Cl)c3)c(Cl)cc12]

5-chloro-6-[3-chloro-4-(trifluoromethoxy)phenoxymethyl]-1,2-benzoxazol-3-amine

A solution of tert-butyl N-[(tert-butoxy)carbonyl]-N-{5-chloro-6-[3-chloro-4-(trifluoromethoxy)phenoxymethyl]-1,2-benzoxazol-3-yl}carbamate (100 mg, 0.17 mmol) in DCM (2 mL) was added trifluoroacetic acid (1 mL). After stirring at room temperature for 2 h, the solvent was removed and the crude product was dissolved in EtOAc (10 mL). The organic layer was washed with aqueous sodium bicarbonate (10 mL) and brine (10 mL), dried over anhydrous sodium sulfate, filtered and concentrated. The residue was purified by CombiFlash (0-70% CH$_3$CN/H$_2$O in 0.1% NH$_4$HCO$_3$) to afford 5-chloro-6-[3-chloro-4-(trifluoromethoxy) phenoxymethyl]-1,2-benzoxazol-3-amine (20 mg, 30%) as a white solid. LCMS (ESI): m/z: 391.7 [M+H]$^+$. $^1$H-NMR (500 MHz, DMSO-d$_6$): 8.04 (s, 1H), 7.77 (s, 1H), 7.53 (d, J=9.5 Hz, 1H), 7.48 (d, J=2.5 Hz, 1H), 7.18 (dd, J=9.0 Hz, 3.0 Hz, 1H), 6.57 (s, 2H), 5.29 (s, 2H).

Step 7

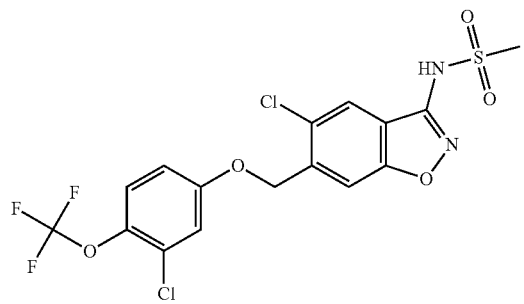 [SMILES: CS(=O)(=O)Nc1noc2cc(COc3ccc(OC(F)(F)F)c(Cl)c3)c(Cl)cc12]

N-{5-chloro-6-[3-chloro-4-(trifluoromethoxy)phenoxymethyl]-1,2-benzoxazol-3-yl}-methanesulfonamide To a stirred solution of 5-chloro-6-[3-chloro-4-(trifluoromethoxy)phenoxymethyl]-1,2-benzoxazol-3-amine (20 mg, 0.05 mmol) in DCM (2 mL) was added methanesulfonyl chloride (7 mg, 0.06 mmol) and triethylamine (10 mg, 0.10 mmol). After stirring at room temperature for 2 h, the solvent was removed in vacuo and the crude product was dissolved in THF/CH$_3$OH (2 mL/0.5 mL). Aqueous sodium hydroxide (0.5 mL, 1.0 M) was added and the mixture was stirred at 25° C. for 6 h then acidified with HCl. The solid was collected and further purified by CombiFlash (0-45% CH$_3$CN/H$_2$O in 0.1% NH$_4$HCO$_3$) to afford N-{5-chloro-6-[3-chloro-4-(trifluoromethoxy)phenoxymethyl]-1,2-benzoxazol-3-yl}methanesulfonamide (15 mg, 63%) as a white solid. LCMS (ESI) Method A: RT=5.79 min, m/z: 470.9 [M+H]$^+$. $^1$H-NMR (500 MHz, DMSO-d$_6$): δ 8.15 (s, 1H), 7.76 (s, 2H), 7.53 (d, J=9.0 Hz, 1H), 7.48 (d, J=3.0 Hz, 1H), 7.18 (dd, J=9.0 Hz, 3.0 Hz, 1H), 5.29 (s, 2H), 2.98 (s, 3H).

Example 9

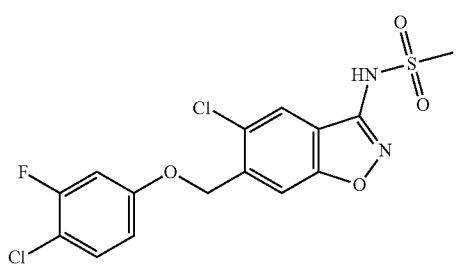 [SMILES: CS(=O)(=O)Nc1noc2cc(COc3ccc(Cl)c(F)c3)c(Cl)cc12]

N-(5-chloro-6-((4-chloro-3-fluorophenoxy)methyl)benzo[d]isoxazol-3-yl)-methanesulfonamide Synthetic scheme

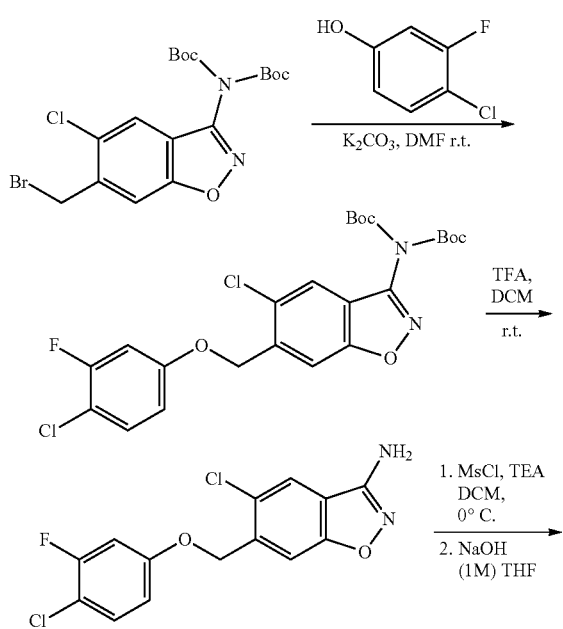

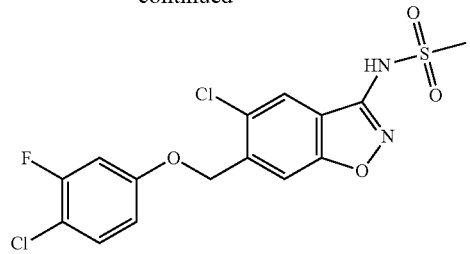

Step 1

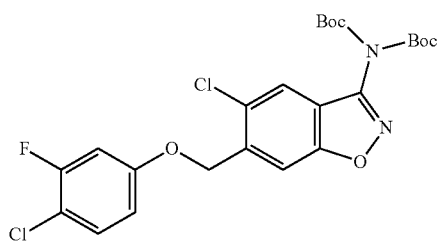 [SMILES: CC(C)(C)OC(=O)N(C(=O)OC(C)(C)C)c1noc2cc(COc3ccc(Cl)c(F)c3)c(Cl)cc12]

tert-butyl N-[(tert-butoxy)carbonyl]-N-[5-chloro-6-(4-chloro-3-fluorophenoxymethyl)-1,2-benzoxazol-3-yl]carbamate To a solution of tert-butyl N-[6-(bromomethyl)-5-chloro-1,2-benzoxazol-3-yl]-N-[(tert-butoxy)carbonyl]carbamate (200 mg, 0.43 mmol) in DMF (5 mL) was added 4-chloro-3-fluorophenol (70 mg, 0.48 mmol) and potassium carbonate (180 mg, 1.29 mmol). After stirring at 25° C. for 16 h, the reaction mixture was diluted with water (10 mL) and extracted with EtOAc (10 mL×3). The combined organic layers were washed with brine (10 mL), dried over anhydrous sodium sulfate, filtered and concentrated to afford target compound as oil which was used in the next step without further purification. LCMS (ESI) m/z: 370.8[M-156+H]$^+$.

Step 2

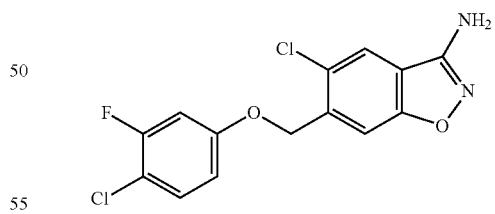

5-chloro-6-((4-chloro-3-fluorophenoxy)methyl)benzo[d]isoxazol-3-amine

To a solution of tert-butyl N-[(tert-butoxy)carbonyl]-N-[5-chloro-6-(4-chloro-3-fluoro-phenoxymethyl)-1,2-benzoxazol-3-yl]carbamate (crude) in DCM (2 mL) was added trifluoroacetic acid (1 mL). After stirring at room temperature for 1 h, the solvent was removed in vacuo and the crude product was dissolved in EtOAc (10 mL). The organic layer was washed with aqueous sodium bicarbonate (10 mL), brine (10 mL), dried over anhydrous sodium sulfate, filtered and concentrated. The residue was purified by CombiFlash (0-70% CH$_3$CN/H$_2$O in 0.1% NH$_4$HCO$_3$) to afford 5-chloro-6-((4-chloro-3-fluorophenoxy)methyl)-benzo[d]isoxazol-3-amine (130 mg, 91% for two steps) as a white solid. LCMS (ESI): m/z: 326.9 [M+H]$^+$.

Step 3

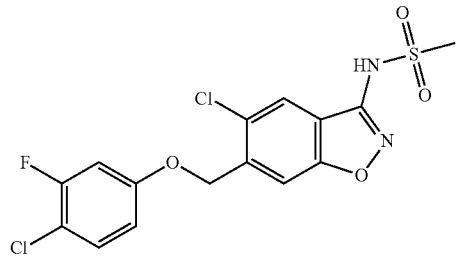 [SMILES: CS(=O)(=O)Nc1noc2cc(COc3ccc(Cl)c(F)c3)c(Cl)cc12]

N-(5-chloro-6-((4-chloro-3-fluorophenoxy)methyl)benzo[d]isoxazol-3-yl) methanesulfonamide Methanesulfonyl chloride (0.52 mmol, 59 mg) was added dropwise to a solution of 5-chloro-6-((4-chloro-3-fluorophenoxy)methyl)benzo[d]isoxazol-3-amine (85 mg, 0.26 mmol) and triethylamine (79 mg, 0.78 mmol) in DCM (2 mL) at 0° C. After stirring at room temperature for 2 h, the solvent was removed under vacuum and the residue was dissolved in THF (2 mL) and NaOH (1 M, 1.0 mL). After stirring at room temperature for 2 h, HCl (1M) was added to adjust pH to 6; the reaction mixture was diluted with ethyl acetate (15 mL), washed with water (3 mL), brine (3 mL), dried over Na$_2$SO$_4$, filtered and concentrated. The residue was purified by reverse phase combiflash (20%-50% CH$_3$CN/H$_2$O in 0.1% NH$_4$HCO$_3$) to get the target compound (52 mg, 50%) as a white solid. LCMS(ESI) Method A: RT=5.28 min, m/z: 405.0 [M+H]$^+$; $^1$H-NMR (500 MHz, DMSO-d$_6$) δ 7.63 (s, 1H), 7.60 (s, 1H), 7.51 (m, 1H), 7.26 (dd, J=11.4, 2.8 Hz, 1H), 6.98 (dd, J=8.8, 2.0 Hz, 1H), 5.24 (s, 2H), 2.80 (s, 3H).

Example 10

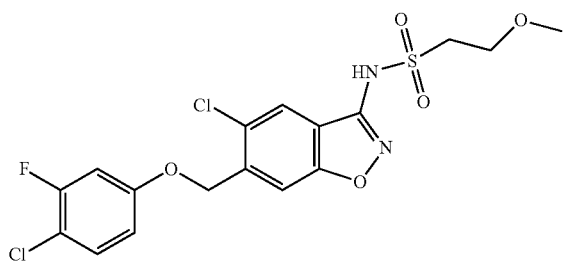 [SMILES: COCCS(=O)(=O)Nc1noc2cc(COc3ccc(Cl)c(F)c3)c(Cl)cc12]

N-(5-chloro-6-((4-chloro-3-fluorophenoxy)methyl)benzo[d]isoxazol-3-yl)-2-methoxyethanesulfonamide Synthetic scheme

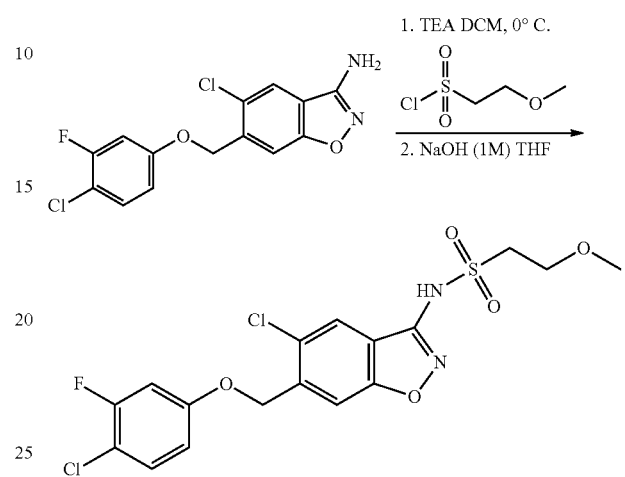

2-Methoxyethanesulfonyl chloride (0.52 mmol, 82 mg) was added dropwise to a solution of 5-chloro-6-((4-chloro-3-fluorophenoxy)methyl)benzo[d]isoxazol-3-amine (85 mg, 0.26 mmol) and triethylamine (79 mg, 0.78 mmol) in DCM (2 mL) at 0° C. After stirring at room temperature for 2 h, the solvent was removed under vacuum and the residue was dissolved in THF (2 mL) and NaOH (1 M, 1.0 mL). The mixture was stirred at room temperature for 2 h then HCl (1M) was added to adjust pH to 6. The reaction mixture was diluted with ethyl acetate (15 mL), washed with water (3 mL), brine (3 mL), dried over Na$_2$SO$_4$, filtered and concentrated. The residue was purified by reverse phase combiflash (20%-50% CH$_3$CN/H$_2$O in 0.1% NH$_4$HCO$_3$) to give the target compound (23 mg, 20%) as a white solid. LCMS(ESI) Method A: RT=5.40 min, m/z: 449.0 [M+H]$^+$; $^1$H-NMR (500 MHz, MeOD-d$_4$) δ 8.00 (s, 1H), 7.82 (s, 1H), 7.42 (m, 1H), 7.05 (d, J=11.0 Hz, 1H), 6.94 (dd, J=8.9, 1.7 Hz, 1H), 5.31 (s, 2H), 3.84 (t, J=5.8 Hz, 2H), 3.71 (t, J=5.8 Hz, 2H), 3.25 (s, 3H).

Example 11

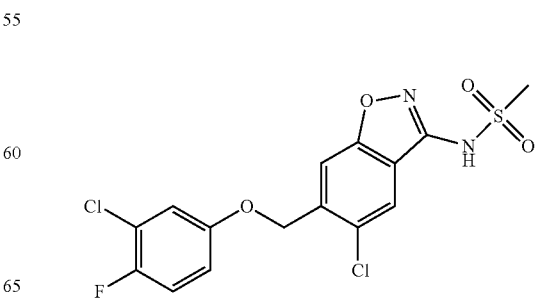

N-(5-chloro-6-((3-chloro-4-fluorophenoxy)methyl)benzo[d]isoxazol-3-yl)-methanesulfonamide

Synthetic scheme

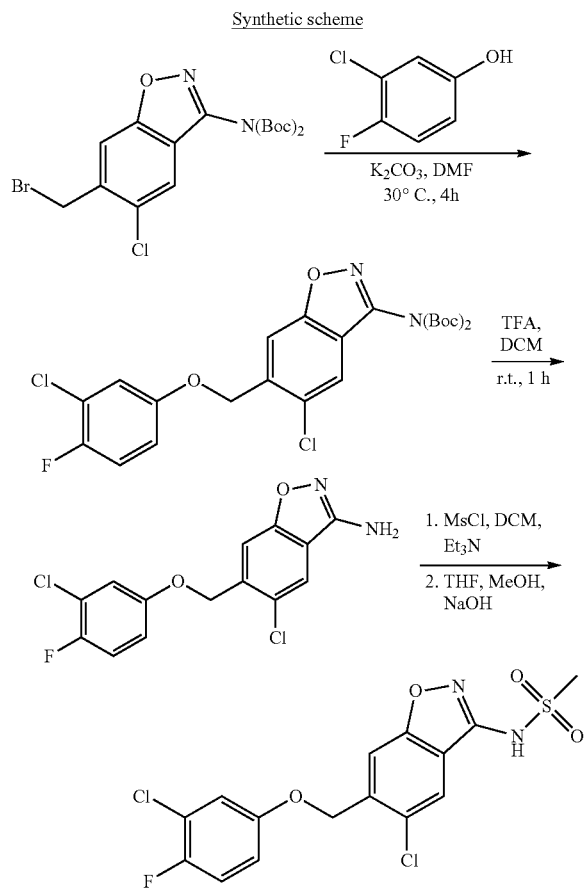

Step 1

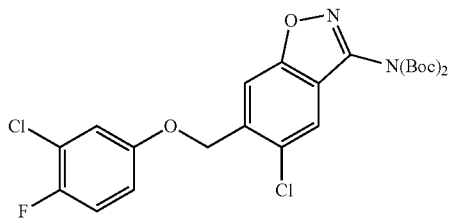

tert-butyl N-[(tert-butoxy)carbonyl]-N-[5-chloro-6-(3-chloro-4-fluorophenoxymethyl)-1,2-benzoxazol-3-yl]carbamate A mixture of tert-butyl N-[6-(bromomethyl)-5-chloro-1,2-benzoxazol-3-yl]-N-[(tert-butoxy)-carbonyl]carbamate (230 mg, 0.50 mmol), 3-chloro-4-fluorophenol (75 mg, 0.50 mmol) and potassium carbonate (210 mg, 1.5 mmol) in DMF (6 mL) was stirred at 30° C. for 4 h. The mixture was filtered and concentrated in vacuo. The resulting residue was purified by silica gel column chromatography (eluting with petroleum ether/ethyl acetate, from 20/1 to 3/1) to give tert-butyl N-[(tert-butoxy)carbonyl]-N-[5-chloro-6-(3-chloro-4-fluorophenoxy-methyl)-1,2-benzoxazol-3-yl]carbamate (190 mg, 73%) as a white solid. LCMS (ESI) m/z: 370.8 [M-156+H]$^+$.

Step 2

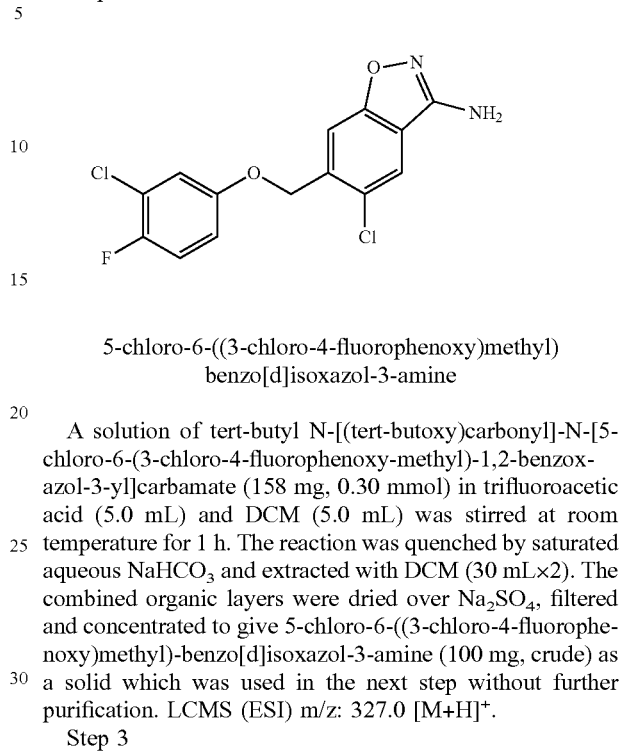

5-chloro-6-((3-chloro-4-fluorophenoxy)methyl)benzo[d]isoxazol-3-amine

A solution of tert-butyl N-[(tert-butoxy)carbonyl]-N-[5-chloro-6-(3-chloro-4-fluorophenoxy-methyl)-1,2-benzoxazol-3-yl]carbamate (158 mg, 0.30 mmol) in trifluoroacetic acid (5.0 mL) and DCM (5.0 mL) was stirred at room temperature for 1 h. The reaction was quenched by saturated aqueous NaHCO$_3$ and extracted with DCM (30 mL×2). The combined organic layers were dried over Na$_2$SO$_4$, filtered and concentrated to give 5-chloro-6-((3-chloro-4-fluorophenoxy)methyl)-benzo[d]isoxazol-3-amine (100 mg, crude) as a solid which was used in the next step without further purification. LCMS (ESI) m/z: 327.0 [M+H]$^+$.

Step 3

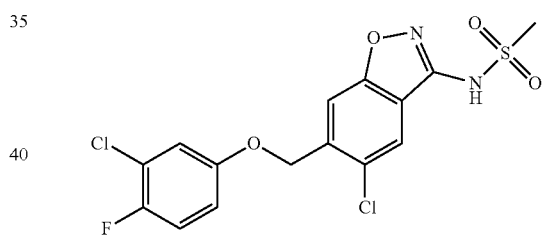

N-(5-chloro-6-((3-chloro-4-fluorophenoxy)methyl)benzo[d]isoxazol-3-yl)-methanesulfonamide To a solution of 5-chloro-6-((3-chloro-4-fluorophenoxy)methyl)benzo[d]isoxazol-3-amine (100 mg, 0.3 mmol) in DCM (6 mL) was added methanesulfonyl chloride (52 mg, 0.45 mmol) and triethylamine (90 mg, 0.90 mmol). After stirring at room temperature for 1 h, the solvent was removed in vacuo and the crude product was dissolved in THF/CH$_3$OH (4 mL/1 mL). The aqueous sodium hydroxide (2 mL, 1.0 M) was added and the reaction was stirred at room temperature for another 1 h. The reaction mixture was extracted with EtOAc (20 mL×3) and the combined organic layers were concentrated and purified by reverse-phase prep-HPLC to afford N-(5-chloro-6-((3-chloro-4-fluorophenoxy)methyl)benzo[d]isoxazol-3-yl)methanesulfonamide (70 mg, 59% for two steps) as white solid. LCMS (ESI) Method A: RT=5.26 min, m/z: 405.0 [M+H]$^+$. $^1$H-NMR (500 MHz, DMSO-d$_6$): δ 7.63 (s, 1H), 7.61 (s, 1H), 7.37-7.35 (m, 2H), 7.11-7.08 (m, 1H), 6.07 (br s, 1H), 5.22 (s, 2H), 2.81 (s, 3H).

Example 12

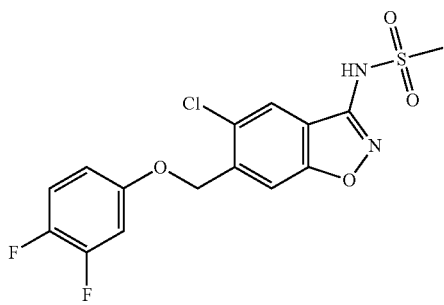 [SMILES: CS(=O)(=O)Nc1noc2cc(COc3ccc(F)c(F)c3)c(Cl)cc12]

N-(5-chloro-6-((3,4-difluorophenoxy)methyl)benzo[d]isoxazol-3-yl)methanesulfonamide The synthetic procedure was the same as Example 11. LCMS (ESI) Method A: RT=5.42 min, m/z: 388.8 [M+H]+. 1H-NMR (500 MHz, DMSO-d6): δ 11.64 (br s, 1H), 8.07 (s, 1H), 7.95 (s, 1H), 7.43-7.29 (m, 2H), 6.94 (m, 1H), 5.26 (s, 2H), 3.33 (s, 3H).

Example 13

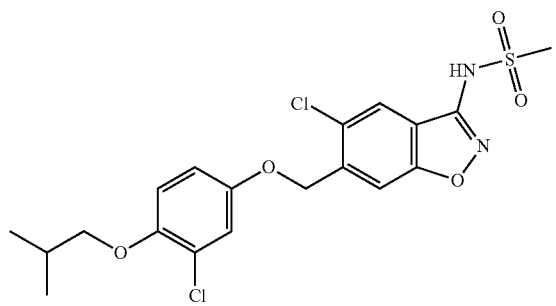 [SMILES: CC(C)COc1ccc(OCc2cc3onc(NS(C)(=O)=O)c3cc2Cl)cc1Cl]

N-(5-chloro-6-((3-chloro-4-isobutoxyphenoxy)methyl)benzo[d]isoxazol-3-yl)-methanesulfonamide The synthetic procedure was the same as Example 11. LCMS (ESI) Method A: RT=6.13 min, in/z: 458.6 [M+H]+. 1H-NMR (500 MHz, MeOD-d4): δ 7.85 (s, 1H), 7.61 (s, 1H), 7.13 (d, J=2.5 Hz, 1H), 7.02 (d, J=9.0 Hz, 1H), 6.97-6.94 (m, 1H), 5.21 (s, 2H), 3.78 (d, J=6.5 Hz, 2H), 3.12 (s, 3H), 2.12-2.08 (m, 1H), 1.08 (d, J=7.0 Hz, 6H).

Example 14

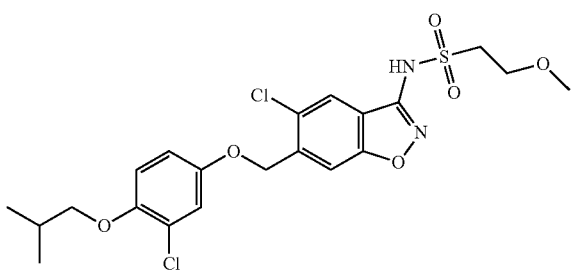 [SMILES: COCCS(=O)(=O)Nc1noc2cc(COc3ccc(OCC(C)C)c(Cl)c3)c(Cl)cc12]

N-(5-chloro-6-((3-chloro-4-isobutoxyphenoxy)methyl)benzo[d]isoxazol-3-yl)-2-methoxyethanesulfonamide The synthetic procedure was the same as Examples 10 and 11. LCMS (ESI) Method A: RT=6.19 min, m/z: 503.1 [M+H]+. 1H-NMR (500 MHz, MeOD-d4): δ 7.87 (s, 1H), 7.62 (s, 1H), 7.13 (d, J=2.5 Hz, 1H), 7.01 (d, J=9.5 Hz, 1H), 6.96-6.94 (m, 1H), 5.21 (s, 2H), 3.84-3.77 (m, 4H), 3.60 (d, J=13.5 Hz, 2H), 3.32 (s, 3H), 2.12-2.08 (m, 1H), 1.07 (d, J=7.0 Hz, 6H).

Example 15

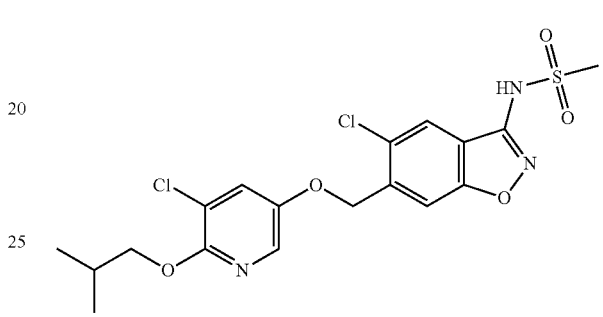

N-(5-chloro-6-((5-chloro-6-isobutoxypyridin-3-yloxy)methyl)benzo[d]isoxazol-3-yl)-methanesulfonamide The synthetic procedure was the same as Example 11. LCMS (ESI) Method A: RT=5.88 min, m/z: 460.0 [M+H]+. 1H-NMR (500 MHz, MeOD-d4): δ 7.90 (s, 1H), 7.87 (d, J=2.5 Hz, 1H), 7.71 (s, 1H), 7.64 (d, J=3.0 Hz, 1H), 5.28 (s, 2H), 4.09 (d, J=6.5 Hz, 2H), 3.19 (s, 3H), 2.11-2.08 (m, 1H), 1.05 (d, J=6.5 Hz, 6H).

Example 16

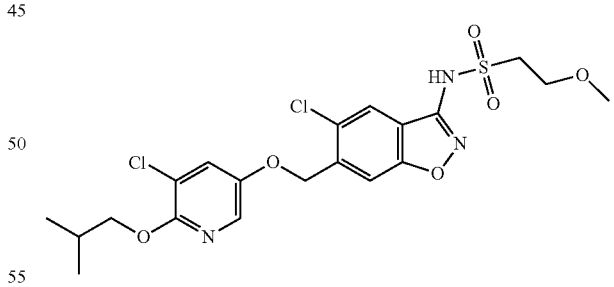

N-(5-chloro-6-((5-chloro-6-isobutoxypyridin-3-yloxy)methyl)benzo[d]isoxazol-3-yl)-2-methoxyethanesulfonamide The synthetic procedure was the same as Examples and 11. LCMS (ESI) Method A: RT=6.04 min, m/z: 504.0 [M+H]+. 1H-NMR (500 MHz, MeOD-d4): δ 7.94 (s, 1H), 7.88 (s, 1H), 7.74 (s, 1H), 7.65 (s, 1H), 5.29 (s, 2H), 4.10-4.09 (m, 2H), 3.83 (br s, 2H), 3.65 (br s, 2H), 3.28 (s, 3H), 2.11-2.08 (m, 1H), 1.05 (d, J=6.5 Hz, 6H).

Example 17

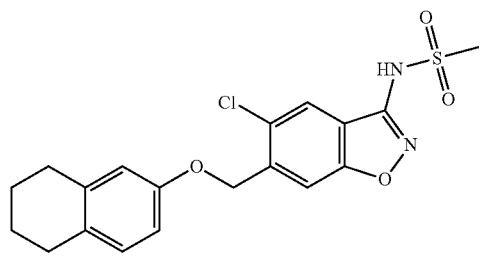 [SMILES: CS(=O)(=O)Nc1noc2cc(COc3ccc4c(c3)CCCC4)c(Cl)cc12]

N-(5-chloro-6-((5,6,7,8-tetrahydronaphthalen-2-yloxy)methyl)benzo[d]isoxazol-3-yl)-methanesulfonamide

Synthetic scheme

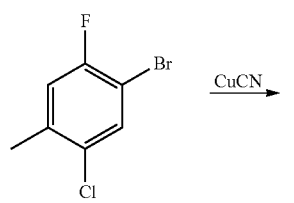

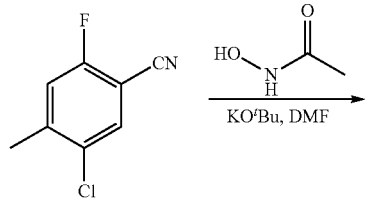

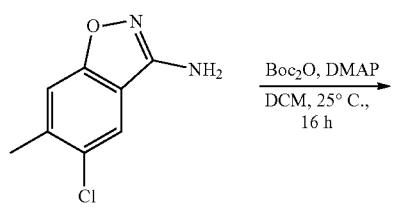

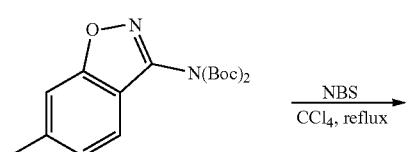

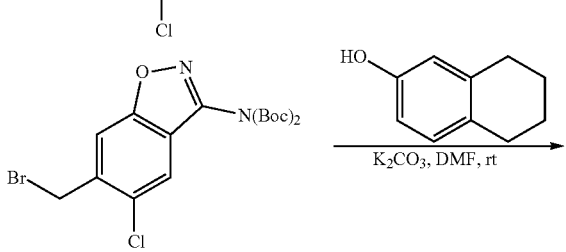

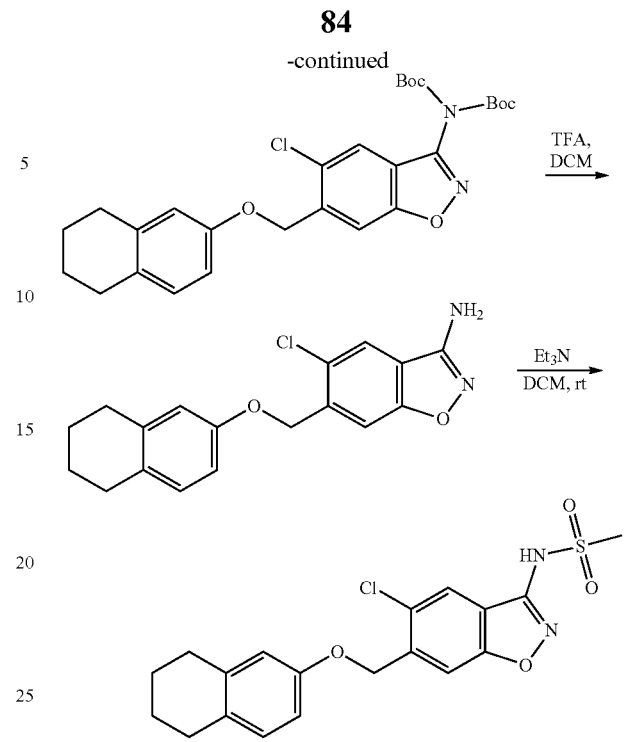

Step 1

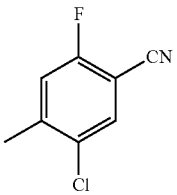

5-chloro-2-fluoro-4-methylbenzonitrile

A mixture of 1-bromo-5-chloro-2-fluoro-4-methylbenzene (5.0 g, 23 mmol), copper(I) cyanide (4.0 g, 45 mmol) and copper(I) iodide (8.6 g, 45 mmol) in NMP (50 mL) was heated at 140° C. over night. After cooling to room temperature, the mixture filtered and the filtrate was diluted with water (100 mL) and extracted with ethyl acetate (100 mL×3). The combined organic layers were washed with brine (100 mL), dried over Na₂SO₄, filtered and concentrated. The residue was purified by SGC (eluting with petroleum ether/ethyl acetate=10/1) to afford 5-chloro-2-fluoro-4-methylbenzonitrile (1.7 g, 45%) as a white solid.

Step 2

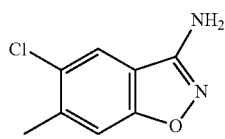

5-chloro-6-methylbenzo[d]isoxazol-3-amine

Potassium tert-butanolate (2.0 g, 18 mmol) was added to a solution of N-hydroxyacetamide (1.3 g, 18 mmol) in DMF (20 mL). The resulting white suspension was stirred at room temperature for 30 min then 5-chloro-2-fluoro-4-methylbenzonitrile (1.0 g, 5.9 mmol) was added and the mixture was stirred at 50° C. for 12 h. After cooling to room temperature, water (100 mL) was added and extracted with EtOAc (100 mL×3). The combined organic layers were washed with brine (100 mL), dried over anhydrous sodium sulfate, filtered and concentrated to give 5-chloro-6-methylbenzo[d]isoxazol-3-amine (1 g, crude) as a solid which was used in the next step without further purification. LCMS (ESI) m/z: 183.7 [M+H]$^+$.

Step 3

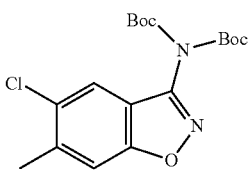 [SMILES: Cc1cc2onc(N(C(=O)OC(C)(C)C)C(=O)OC(C)(C)C)c2cc1Cl]

tert-butyl N-[(tert-butoxy)carbonyl]-N-(5-chloro-6-methyl-1,2-benzoxazol-3-yl)carbamate A solution of 5-chloro-6-methylbenzo[d]isoxazol-3-amine (1.0 g, 5.5 mmol) in DCM (20 mL) was added di-tert-butyl-dicarbonate (3.0 g, 14 mmo) and a catalytic amount of N,N-dimethylpyridin-4-amine. After stirring at 25° C. for 16 h, the mixture was concentrated in vacuo to about 5 mL volumn, treated with hexanes and filtered to yield tert-butyl N-[(tert-butoxy)carbonyl]-N-(5-chloro-6-methyl-1,2-benzoxazol-3-yl)carbamate (1.6 g, 76%) as a white solid. LCMS (ESI) m/z: 227.1 [M-156+H]$^+$, $^1$H-NMR (500 MHz, CDCl$_3$): δ 7.53 (s, 1H), 7.48 (s, 1H), 2.54 (s, 3H), 1.42 (s, 18H).

Step 4

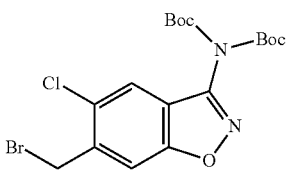 [SMILES: CC(C)(C)OC(=O)N(C(=O)OC(C)(C)C)c1noc2cc(CBr)c(Cl)cc12]

tert-butyl N-[6-(bromomethyl)-5-chloro-1,2-benzoxazol-3-yl]-N-[(tert-butoxy)carbonyl]carbamate To a solution of tert-butyl N-[(tert-butoxy)carbonyl]-N-(5-chloro-6-methyl-1,2-benzoxazol-3-yl)carbamate (100 mg, 0.26 mmol) in CCl$_4$ (2 mL) was added N-bromosuccinimide (51 mg, 0.29 mmol) and 2,2-azobis(2-methylpropionitrile) (4 mg, 0.026 mmol). The reaction mixture was heated to reflux for 3 hours then cooled to ambient temperature. The solvent was removed in vacuo and the residue was purified by SGC (eluting with petroleum ether/EtOAc=10/1) to afford tert-butyl N-[6-(bromomethyl)-5-chloro-1,2-benzoxazol-3-yl]-N-[(tert-butoxy)carbonyl]carbamate (100 mg, 84%) as a white solid. LCMS (ESI) m/z: 305.0 [M-156+H]$^+$.

Step 5

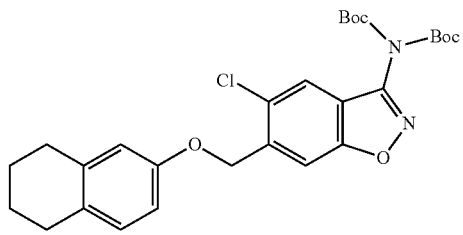 [SMILES: CC(C)(C)OC(=O)N(C(=O)OC(C)(C)C)c1noc2cc(COc3ccc4c(c3)CCCC4)c(Cl)cc12]

tert-butyl N-[(tert-butoxy)carbonyl]-N-{5-chloro-6-[(5,6,7,8-tetrahydronaphthalen-2-yloxy)methyl]-1,2-benzoxazol-3-yl}carbamate To a solution of tert-butyl N-[6-(bromomethyl)-5-chloro-1,2-benzoxazol-3-yl]-N-[(tert-butoxy)carbonyl]carbamate (300 mg, 0.65 mmol) in DMF (5 mL) was added 5,6,7,8-tetrahydronaphthalen-2-ol (115 mg, 0.78 mmol) and potassium carbonate (269 mg, 1.95 mmol). After stirring at 25° C. for 16 h, the mixture was diluted with water (10 mL) and extracted with EtOAc (10 mL×3). The combined organic layers were washed with brine (10 mL), dried over anhydrous sodium sulfate, filtered and concentrated to afford the target compound as an oil which was used in the next step without further purification. LCMS (ESI) m/z: 373.0 [M-156+H]$^+$.

Step 6

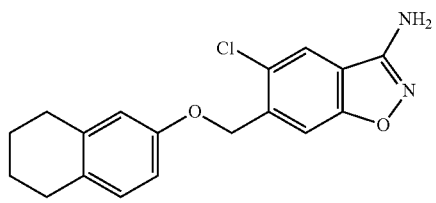 [SMILES: Nc1noc2cc(COc3ccc4c(c3)CCCC4)c(Cl)cc12]

5-chloro-6-((5,6,7,8-tetrahydronaphthalen-2-yloxy)methyl)benzo[d]isoxazol-3-amine To a solution of tert-butyl N-[(tert-butoxy)carbonyl]-N-{5-chloro-6-[(5,6,7,8-tetrahydro-naphthalen-2-yloxy)methyl]-1,2-benzoxazol-3-yl}carbamate (crude) in DCM (2 mL) was added trifluoroacetic acid (1 mL). After stirring at room temperature for 1 h, the solvent was removed in vacuo and the crude product was dissolved in EtOAc (10 mL). The organic layer was washed with aqueous sodium bicarbonate (10 mL) and brine (10 mL), dried over anhydrous sodium sulfate, filtered and concentrated. The residue was purified by CombiFlash (0-70% CH$_3$CN/H$_2$O in 0.1% NH$_4$HCO$_3$) to afford 5-chloro-6-((5,6,7,8-tetrahydronaphthalen-2-yloxy)methyl)benzo[d]isoxazol-3-amine (150 mg, 66% yield for two steps) as a white solid. LCMS (ESI): m/z: 329.1 [M+H]$^+$.

Step 7

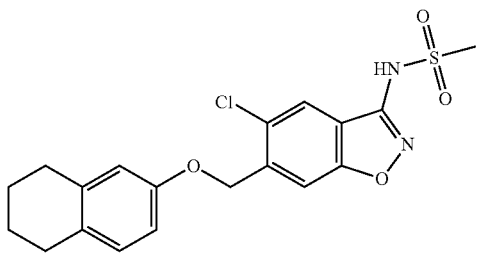 [SMILES: CS(=O)(=O)Nc1noc2cc(COc3ccc4c(c3)CCCC4)c(Cl)cc12]

N-(5-chloro-6-((5,6,7,8-tetrahydronaphthalen-2-yloxy)methyl)benzo[d]isoxazol-3-yl)-methanesulfonamide To a solution of 5-chloro-6-((5,6,7,8-tetrahydronaphthalen-2-yloxy)methyl)benzo[d]isoxazol-3-amine (50 mg, 0.15 mmol) in DCM (2 mL) was added methanesulfonyl chloride (21 mg, 0.18 mmol) and triethylamine (30 mg, 0.30 mmol). After stirring at room temperature for 2 h, the solvent was removed in vacuo and the crude product was dissolved in THF/CH$_3$OH (2 mL/0.5 mL). The aqueous sodium hydroxide (0.5 mL, 1.0 M) was added and the mixture was stirred at 25° C. for 16 h then acidified with HCl. The solid was collected and purified by CombiFlash (0-45% CH$_3$CN/H$_2$O in 0.1% NH$_4$HCO$_3$) to afford N-(5-chloro-6-((5,6,7,8-tetra-hydro-naphthalen-2-yloxy)methyl)benzo[d]isoxazol-3-yl) methanesulfonamide (7.2 mg, 12%) as a white solid. LCMS (ESI) Method A: RT=5.78 min, m/z: 406.8 [M+H]$^+$. $^1$H-NMR (500 MHz, MeOD-d$_4$): δ 7.73 (s, 1H), 7.49 (s, 1H), 6.87 (d, J=8.5 Hz, 1H), 6.65 (m, 1H), 6.61 (d, J=2.0 Hz, 1H), 5.09 (s, 2H), 3.01 (s, 3H), 2.64 (br s, 2H), 2.59 (br s, 2H), 1.69-1.67 (m, 4H).

Example 18

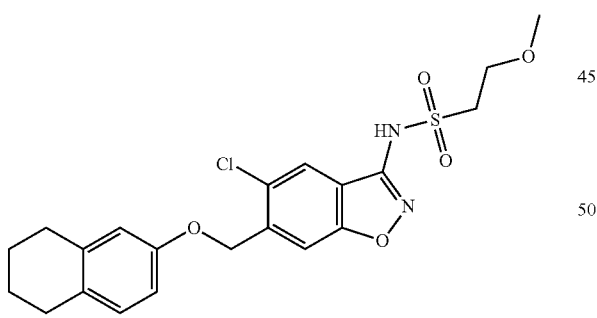

N-(5-chloro-6-((5,6,7,8-tetrahydronaphthalen-2-yloxy)methyl)benzo[d]isoxazol-3-yl)-2-methoxyethanesulfonamide The synthetic procedure was the same as Example 17. LCMS (ESI) Method A: RT=5.90 min, m/z: 450.9 [M+H]$^+$. $^1$H-NMR (500 MHz, MeOD-d$_4$): δ 7.84 (s, 1H), 7.57 (s, 1H), 6.99 (d, J=8.5 Hz, 1H), 6.77 (m, 1H), 6.73 (d, J=2.0 Hz, 1H), 5.21 (s, 2H), 3.82 (t, J=14 Hz, 2H), 3.58 (t, J=14 Hz, 2H), 3.33 (s, 3H), 2.76 (br s, 2H), 2.72 (br s, 2H), 1.81-1.79 (m, 4H).

Example 19

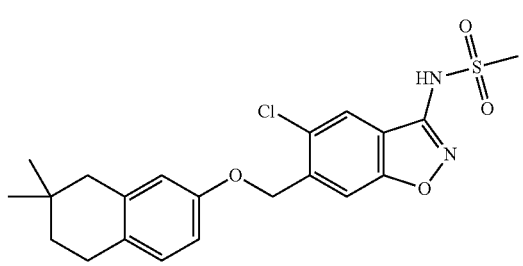

N-(5-chloro-6-((7,7-dimethyl-5,6,7,8-tetrahydronaphthalen-2-yloxy)methyl)benzo[d]-isoxazol-3-yl)methanesulfonamide The synthetic procedure was the same as Example 17. LCMS (ESI) Method A: RT=6.20 min, m/z: 435.0 [M+H]$^+$. $^1$H-NMR (500 MHz, MeOD-d$_4$): δ 7.83 (s, 1H), 7.58 (s, 1H), 7.02 (d, J=8.0 Hz, 1H), 6.80-6.77 (m, 1H), 6.71 (d, J=2.5 Hz, 1H), 5.21 (s, 2H), 3.10 (s, 3H), 2.77-2.74 (m, 2H), 2.52 (br s, 2H), 1.59-1.56 (m, 2H), 1.00 (s, 6H).

Example 20

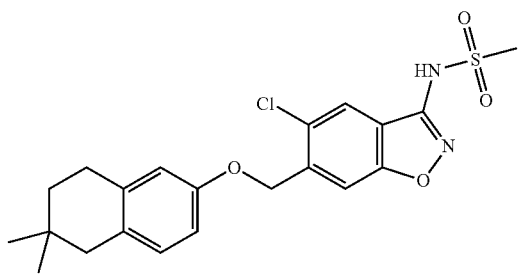

N-(5-chloro-6-((6,6-dimethyl-5,6,7,8-tetrahydronaphthalen-2-yloxy)methyl)benzo[d]-isoxazol-3-yl)methanesulfonamide Synthetic scheme

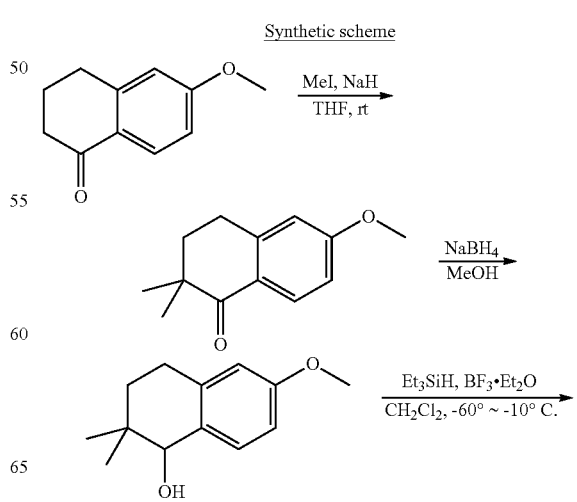

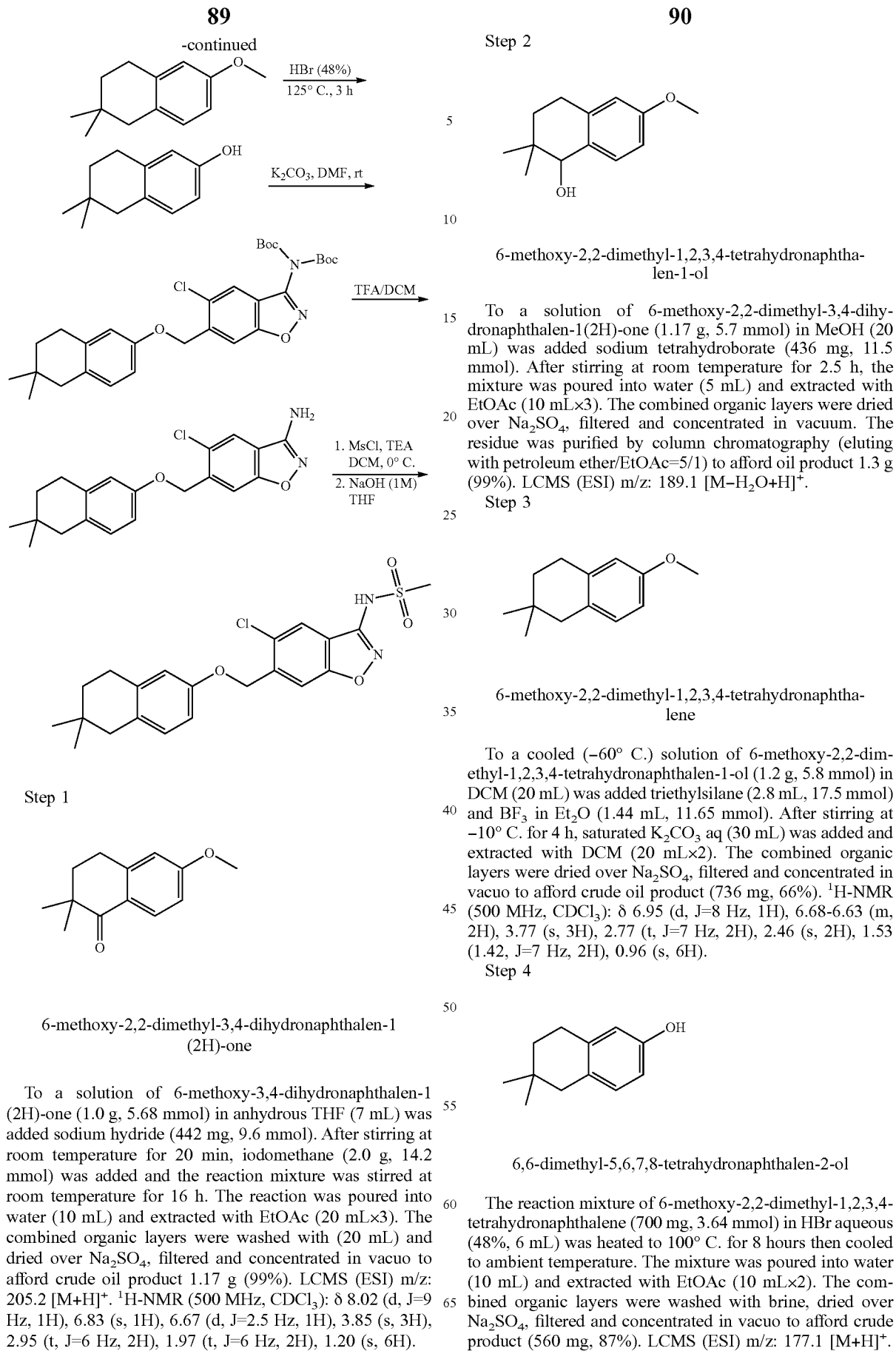

Step 1

6-methoxy-2,2-dimethyl-3,4-dihydronaphthalen-1 (2H)-one

To a solution of 6-methoxy-3,4-dihydronaphthalen-1 (2H)-one (1.0 g, 5.68 mmol) in anhydrous THF (7 mL) was added sodium hydride (442 mg, 9.6 mmol). After stirring at room temperature for 20 min, iodomethane (2.0 g, 14.2 mmol) was added and the reaction mixture was stirred at room temperature for 16 h. The reaction was poured into water (10 mL) and extracted with EtOAc (20 mL×3). The combined organic layers were washed with (20 mL) and dried over $Na_2SO_4$, filtered and concentrated in vacuo to afford crude oil product 1.17 g (99%). LCMS (ESI) m/z: 205.2 [M+H]$^+$. $^1$H-NMR (500 MHz, CDCl$_3$): δ 8.02 (d, J=9 Hz, 1H), 6.83 (s, 1H), 6.67 (d, J=2.5 Hz, 1H), 3.85 (s, 3H), 2.95 (t, J=6 Hz, 2H), 1.97 (t, J=6 Hz, 2H), 1.20 (s, 6H).

Step 2

6-methoxy-2,2-dimethyl-1,2,3,4-tetrahydronaphthalen-1-ol

To a solution of 6-methoxy-2,2-dimethyl-3,4-dihydronaphthalen-1(2H)-one (1.17 g, 5.7 mmol) in MeOH (20 mL) was added sodium tetrahydroborate (436 mg, 11.5 mmol). After stirring at room temperature for 2.5 h, the mixture was poured into water (5 mL) and extracted with EtOAc (10 mL×3). The combined organic layers were dried over $Na_2SO_4$, filtered and concentrated in vacuum. The residue was purified by column chromatography (eluting with petroleum ether/EtOAc=5/1) to afford oil product 1.3 g (99%). LCMS (ESI) m/z: 189.1 [M–H$_2$O+H]$^+$.

Step 3

6-methoxy-2,2-dimethyl-1,2,3,4-tetrahydronaphthalene

To a cooled (–60° C.) solution of 6-methoxy-2,2-dimethyl-1,2,3,4-tetrahydronaphthalen-1-ol (1.2 g, 5.8 mmol) in DCM (20 mL) was added triethylsilane (2.8 mL, 17.5 mmol) and BF$_3$ in Et$_2$O (1.44 mL, 11.65 mmol). After stirring at –10° C. for 4 h, saturated K$_2$CO$_3$ aq (30 mL) was added and extracted with DCM (20 mL×2). The combined organic layers were dried over Na$_2$SO$_4$, filtered and concentrated in vacuo to afford crude oil product (736 mg, 66%). $^1$H-NMR (500 MHz, CDCl$_3$): δ 6.95 (d, J=8 Hz, 1H), 6.68-6.63 (m, 2H), 3.77 (s, 3H), 2.77 (t, J=7 Hz, 2H), 2.46 (s, 2H), 1.53 (1.42, J=7 Hz, 2H), 0.96 (s, 6H).

Step 4

6,6-dimethyl-5,6,7,8-tetrahydronaphthalen-2-ol

The reaction mixture of 6-methoxy-2,2-dimethyl-1,2,3,4-tetrahydronaphthalene (700 mg, 3.64 mmol) in HBr aqueous (48%, 6 mL) was heated to 100° C. for 8 hours then cooled to ambient temperature. The mixture was poured into water (10 mL) and extracted with EtOAc (10 mL×2). The combined organic layers were washed with brine, dried over Na$_2$SO$_4$, filtered and concentrated in vacuo to afford crude product (560 mg, 87%). LCMS (ESI) m/z: 177.1 [M+H]$^+$.

Step 5

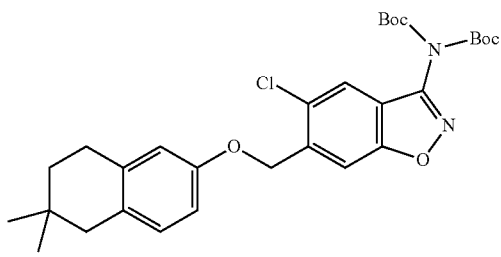 [SMILES: CC1(C)CCc2cc(OCc3cc4onc(N(C(=O)OC(C)(C)C)C(=O)OC(C)(C)C)c4cc3Cl)ccc2C1]

tert-butyl N-[(tert-butoxy)carbonyl]-N-(5-chloro-6-{[(6,6-dimethyl-7,8-dihydro-5H-naphthalen-2yl)-oxy]methyl}-1,2-benzoxazol-3-yl)carbamate To a solution of tert-butyl N-[6-(bromomethyl)-5-chloro-1,2-benzoxazol-3-yl]-N-[(tert-butoxy)carbonyl]carbamate (131 mg, 0.28 mmol) in DMF (1 mL) was added 6,6-dimethyl-5,6,7,8-tetrahydronaphthalen-2-ol (50 mg, 0.28 mmol) and potassium carbonate (116 mg, 0.84 mmol). After stirring at 30° C. for 4 h, the mixture was poured into water (5 mL) and EtOAc (3 mL). The organic layer was dried over $Na_2SO_4$, filtered and concentrated in vacuo to afford crude product (50 mg, 32%). LCMS (ESI) m/z: 402 [M-156+H]$^+$.

Step 6

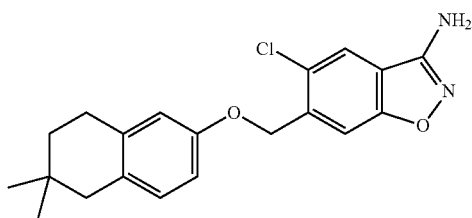 [SMILES: CC1(C)CCc2cc(OCc3cc4onc(N)c4cc3Cl)ccc2C1]

5-chloro-6-((6,6-dimethyl-5,6,7,8-tetrahydronaphthalen-2-yloxy)methyl)benzo[d]isoxazol-3-amine To a solution of tert-butyl N-[(tert-butoxy)carbonyl]-N-(5-chloro-6-{[(6,6-dimethyl-7,8-dihydro-5H-naphthalen-2yl)oxy]methyl}-1,2-benzoxazol-3-yl)carbamate (crude) in DCM (1 mL) was added trifluoroacetic acid (0.5 mL). After stirring at room temperature for 1 h, the reaction mixture was concentrated and the crude product was dissolved in EtOAc (5 mL). The organic layer was washed with aqueous sodium bicarbonate (5 mL), brine (5 mL), dried over anhydrous $Na_2SO_4$, filtered and concentrated to afford crude solid product (30 mg, 93%). LCMS (ESI): m/z: 357 [M+H]$^+$.

Step 7

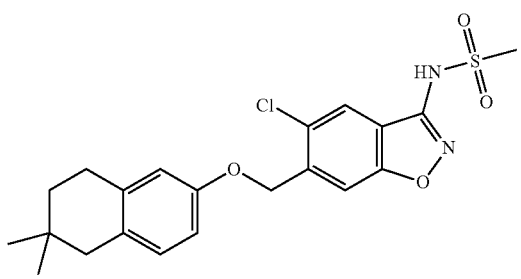

N-(5-chloro-6-((6,6-dimethyl-5,6,7,8-tetrahydronaphthalen-2-yloxy)methyl)benzo[d]-isoxazol-3-yl)methanesulfonamide Methanesulfonyl chloride (19 mg, 0.17 mmol) was added dropwise to a solution of 5-chloro-6-((6,6-dimethyl-5,6,7,8-tetrahydronaphthalen-2-yloxy)methyl)benzo[d]isoxazol-3-amine (30 mg, 0.084 mmol, crude) and triethylamine (25 mg, 0.25 mmol) in DCM (1 mL) at 0° C. After stirring at room temperature for 2 h, the solvent was removed under vacuo and the residue was dissolved in THF (2 mL) and NaOH (1 M, 1.0 mL). The mixture was stirred at room temperature for 2 h then HCl (1M) was added to adjust pH to 6. The reaction mixture was diluted with ethyl acetate (10 mL), washed with water (3 mL), brine (3 mL), dried over $Na_2SO_4$, filtered and concentrated. The residue was purified by reverse phase combiflash (20%-50% $CH_3CN/H_2O$ in 0.1% $NH_4HCO_3$) to get the target compound (10 mg, 27%) as a white solid. LCMS (ESI) Method A: RT=6.34 min, m/z: 435.0 [M+H]$^+$; $^1$H-NMR (500 MHz, MeOD-d$_4$): δ 7.77 (s, 1H), 7.57 (s, 1H), 6.85 (d, J=7.5 Hz, 1H), 6.67-6.66 (m, 1H), 5.10 (s, 2H), 3.08 (s, 3H), 2.70 (t, J=7 Hz, 2H), 2.36 (s, 2H), 1.45 (t, J=6.5 Hz, 2H), 0.87 (s, 6H).

Example 21

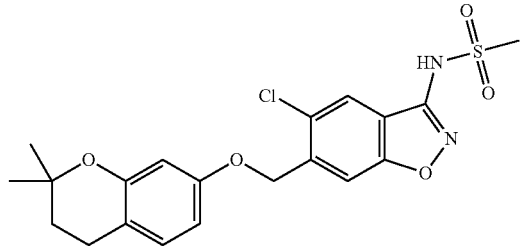

N-(5-chloro-6-((2,2-dimethylchroman-7-yloxy)methyl)benzo[d]isoxazol-3-yl)-methanesulfonamide Synthetic scheme

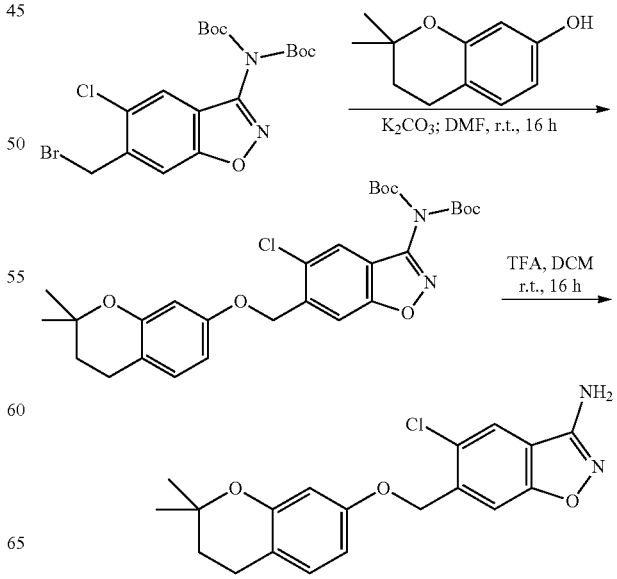

-continued

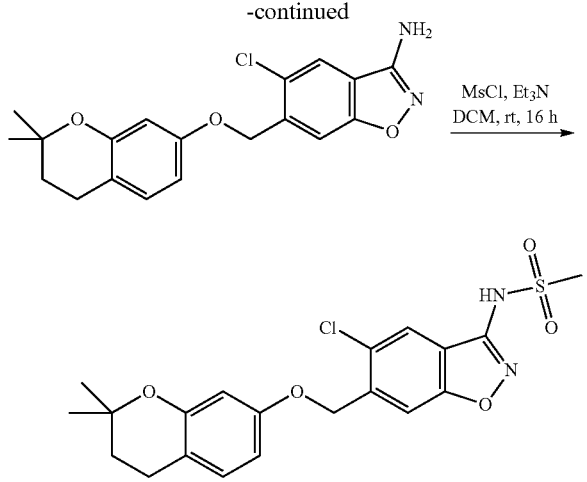

Step 1

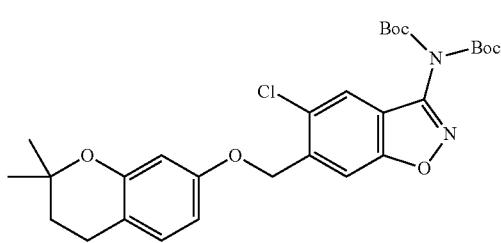 [SMILES: CC(C)(C)OC(=O)N(C(=O)OC(C)(C)C)c1noc2cc(COc3ccc4c(c3)OC(C)(C)CC4)c(Cl)cc12]

tert-butyl N-[(tert-butoxy)carbonyl]-N-(5-chloro-6-
{[(2,2-dimethyl-3,4-dihydro-2H-1-benzopyran-7-yl)
oxy]methyl}-1,2-benzoxazol-3-yl)carbamate A mixture of tert-butyl N-[6-(bromomethyl)-5-chloro-1,
2-benzoxazol-3-yl]-N-[(tert-butoxy)-carbonyl]carbamate
(230 mg, 0.498 mmol), potassium carbonate (207 mg, 1.50
mmol) and 2,2-dimethylchroman-7-ol (150 mg, 0.842
mmol) in DMF (20 mL) was stirred at room temperature for
16 h. The mixture was extracted with EtOAc (50 mL×3) and
the combined organic layers were washed with brine, dried
over Na$_2$SO$_4$, filtered and concentrated to get crude product
(450 mg). LCMS (ESI) m/z: 403.1 [M+H-100-56]$^+$.

Step 2

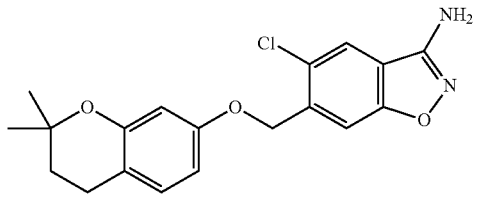 [SMILES: CC1(C)CCc2ccc(OCc3cc4onc(N)c4cc3Cl)cc2O1]

5-chloro-6-((2,2-dimethylchroman-7-yloxy)methyl)
benzo[d]isoxazol-3-amine

A mixture of N-[(tert-butoxy)carbonyl]-N-(5-chloro-6-{
[(2,2-dimethyl-3,4-dihydro-2H-1-benzopyran-7-yl)oxy]
methyl}-1,2-benzoxazol-3-yl)carbamate (450 mg, 0806
mmol) and trifluoroacetic acid (5.0 mL) in DCM (20 mL)
was stirred at room temperature for 16 h. Saturated Na$_2$CO$_3$
(150 mL) was added to adjust pH to 9-10 and the mixture
was extracted with EtOAc (150 mL×5). The combined
organic layers were washed with brine, dried over Na$_2$SO$_4$,
filtered, concentrated and purified by reverse phase column
flash (56%-62% CH$_3$CN/H$_2$O in 0.5% NH$_4$HCO$_3$) to give
5-chloro-6-((2,2-dimethylchroman-7-yloxy)methyl)benzo
[d]isoxazol-3-amine (150 mg, 80%) as a white solid. LCMS
(ESI) m/z: 359.0 [M+H]$^+$.

Step 3

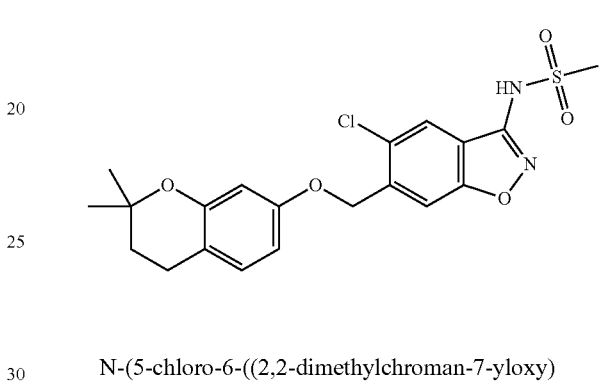

N-(5-chloro-6-((2,2-dimethylchroman-7-yloxy)
methyl)benzo[d]isoxazol-3-yl)-methanesulfonamide A mixture of 5-chloro-6-((2,2-dimethylchroman-7-yloxy)
methyl)benzo[d]isoxazol-3-amine (50 mg, 0.14 mmol) and
methanesulfonyl chloride (2.2 g, 19 mmol) in DCM (15 mL)
was stirred at room temperature for 3 h. The mixture was
extracted with EtOAc (50 mL×3) and the combined organic
layers were washed with brine, dried over Na$_2$SO$_4$, filtered,
concentrated and purified by reverse phase column flash
(36%-40% CH$_3$CN/H$_2$O in 0.5% NH$_4$HCO$_3$) to give N-(5-
chloro-6-((2,2-dimethylchroman-7-yloxy)methyl)benzo[d]
isoxazol-3-yl)methanesulfonamide (38.6 mg, 63%) as a yel-
low solid. LCMS (ESI) Method A: RT=5.58 min m/z: 437.1
[M+H]$^+$. $^1$H-NMR (500 MHz, MeOH-d$_4$): δ 7.83 (s, 1H),
7.56 (s, 1H), 6.99 (d, J=8.0 Hz, 1H), 6.55-6.52 (m, 1H), 6.39
(d, J=2.5 Hz, 1H), 5.19 (s, 2H), 3.10 (s, 3H), 2.75-2.73 (m,
2H), 1.82-1.79 (m, 2H), 1.32 (s, 6H).

Example 22

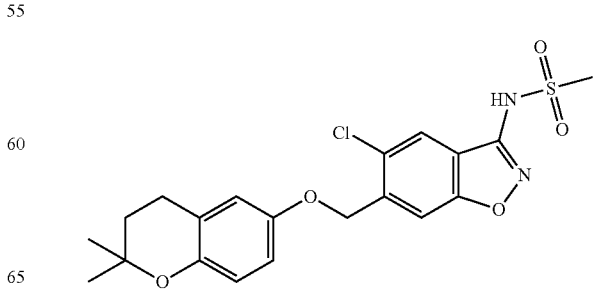

N-(5-chloro-6-((2,2-dimethylchroman-6-yloxy)methyl)benzo[d]isoxazol-3-yl)-methanesulfonamide Synthetic scheme

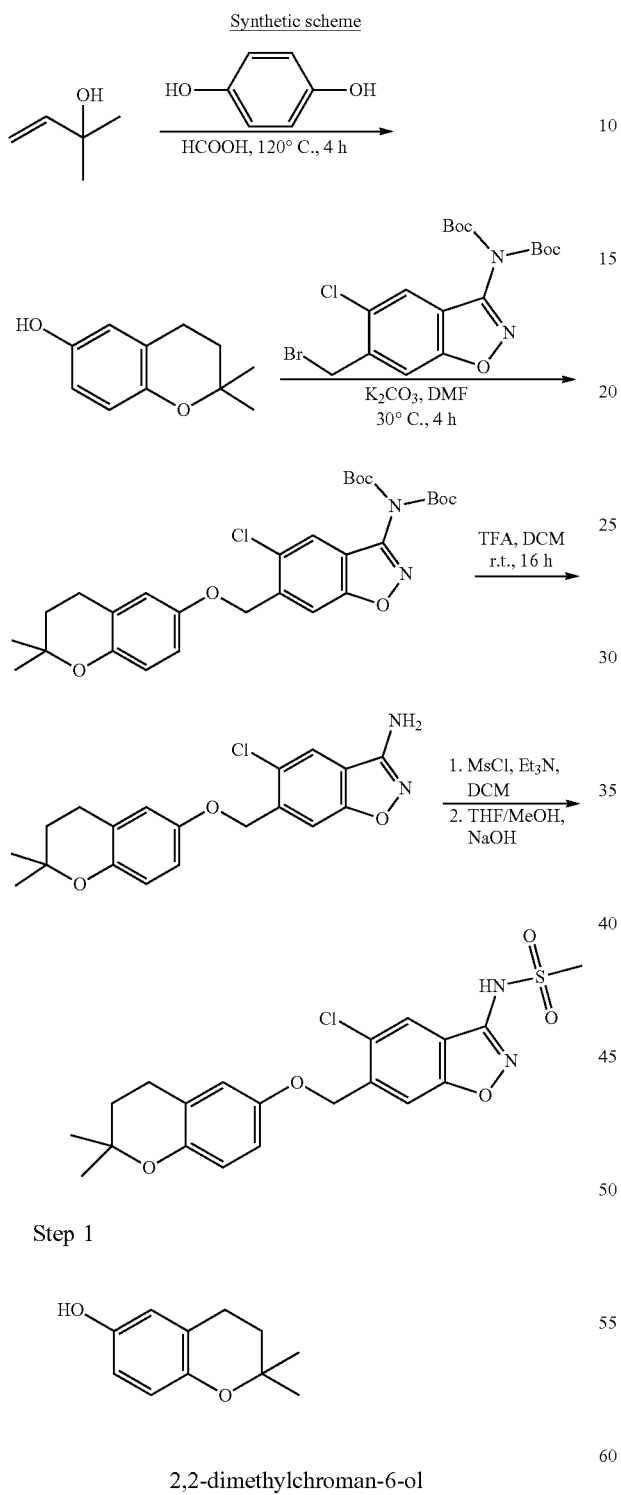

Step 1

2,2-dimethylchroman-6-ol

A mixture of 2-methylbut-3-en-2-ol (2.00 g, 23.2 mmol), hydroquinone (5.00 g, 45.4 mmol) and formic acid (100 mL) was stirred at 120° C. for 4 h. The solvent was removed and saturated aq NaHCO₃ was added to adjust pH to 8-9. The mixture was extracted with EtOAc (150 mL×3) and the combined organic layers were washed with brine, dried over Na₂SO₄, filtered, concentrated and purified by silica gel column (eluting with petroleum ether/EtOAc, from 35/1 to 25/1) to afford 2,2-dimethylchroman-6-ol as off-white solid (1.30 g, 31%). LCMS (ESI) m/z: 177.0 [M−H]⁻.

Step 2

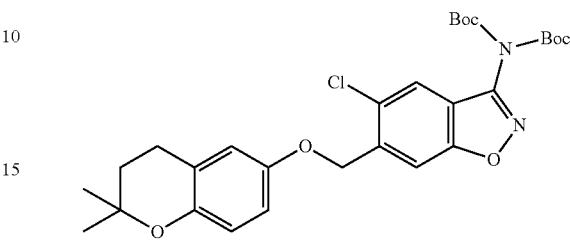

tert-butyl N-[(tert-butoxy)carbonyl]-N-(5-chloro-6-{[(2,2-dimethyl-3,4-dihydro-1-benzopyran-6-yl)-oxy]methyl}-1,2-benzoxazol-3-yl)carbamate A mixture of tert-butyl N-[6-(bromomethyl)-5-chloro-1,2-benzoxazol-3-yl]-N-[(tert-butoxy)-carbonyl]carbamate (200 mg, 0.433 mmol), K₂CO₃ (180 mg, 1.30 mmol) and 2,2-dimethylchroman-6-ol (93.0 mg, 0.522 mmol) in DMF (20 mL) was stirred at 30° C. for 4 h. The mixture was extracted with EtOAc (50 mL×3) and the combined organic layers were washed with brine, dried over Na₂SO₄, filtered and concentrated to give crude product without further purification (450 mg, crude). LCMS (ESI) m/z: 402.9 [M+H-156]⁺.

Step 3

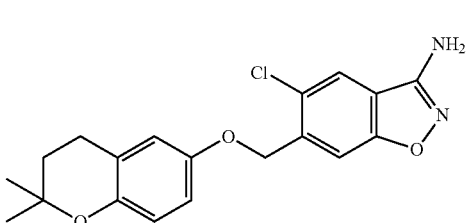

5-chloro-6-((2,2-dimethylchroman-6-yloxy)methyl)benzo[d]isoxazol-3-amine

A mixture of tert-butyl N-[(tert-butoxy)carbonyl]-N-(5-chloro-6-{[(2,2-dimethyl-3,4-dihydro-1-benzopyran-6-yl)oxy]methyl}-1,2-benzoxazol-3-yl)carbamate (450 mg, 0806 mmol) and TFA (10 mL) in DCM (20 mL) was stirred at room temperature for 16 h. Saturated aq Na₂CO₃ (150 mL) was added to adjust pH to 9-10 and the mixture was extracted with EtOAc (150 mL×5). The combined organic layers were washed with brine, dried over Na₂SO₄, filtered, concentrated and purified by reverse phase column flash (52-56% CH₃CN/H₂O in 0.5% NH₄HCO₃) to give target product (90 mg, 58%, two step) as an off-white solid. LCMS (ESI) m/z: 358.9 [M+H]⁺.

Step 4

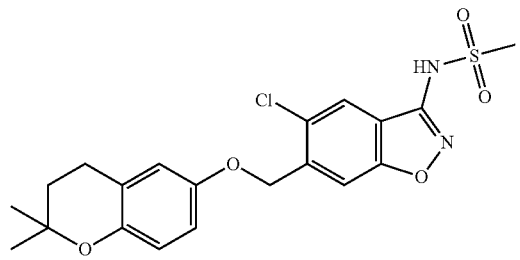

N-(5-chloro-6-((2,2-dimethylchroman-6-yloxy)methyl)benzo[d]isoxazol-3-yl)-methanesulfonamide A mixture of 5-chloro-6-((2,2-dimethylchroman-6-yloxy)methyl)benzo[d]isoxazol-3-amine (45 mg, 0.13 mmol), TEA (5.0 mL) and methanesulfonyl chloride (2.0 g, 17 mmol) in DCM (15 mL) was stirred at room temperature for 3 h. Saturated aq NaHCO$_3$ (150 mL) was added and the mixture was extracted with EtOAc (50 mL×3). The combined organic layers were washed with brine, dried over Na$_2$SO$_4$, filtered and concentrated. The crude product was dissolved in THF/MeOH (20/10 mL) and NaOH (1.0N, 2.0 mL) then stirred at room temperature for 16 h. At the end of reaction, HCl (2.0 M, 20 mL) was added and extracted with EtOAc (50 mL×3), the combined organic layers were washed with brine, dried over Na$_2$SO$_4$, filtered, concentrated and purified by reverse phase column flash (35-42% CH$_3$CN/H$_2$O in 0.5% formic acid) to give the target product (21.0 mg, 38% for two step) as a white solid. LCMS (ESI) Method A: RT=5.42 min, m/z: 437.0 [M+H]$^+$. $^1$H-NMR (500 MHz, MeOH-d$_4$): δ 7.90 (s, 1H), 7.70 (s, 1H), 6.81-6.78 (m, 2H), 6.67 (d, J=8.5 Hz, 1H), 5.19 (s, 2H), 3.21 (s, 3H), 2.81-2.78 (m, 2H), 1.82-1.79 (m, 2H), 1.31 (s, 6H).

Example 23

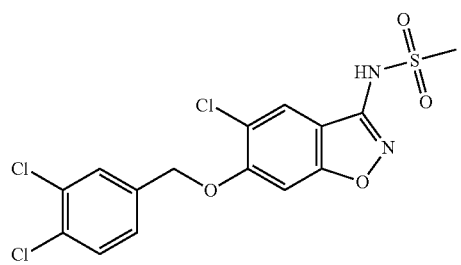 [SMILES: CS(=O)(=O)Nc1noc2cc(OCc3ccc(Cl)c(Cl)c3)c(Cl)cc12]

N-(5-chloro-6-(3,4-dichlorobenzyloxy)benzo[d]isoxazol-3-yl)methanesulfonamide

Synthetic scheme

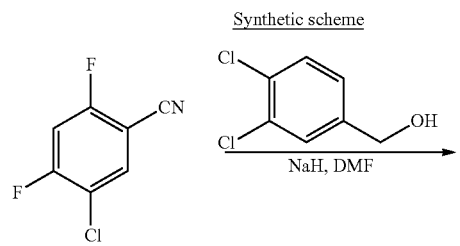

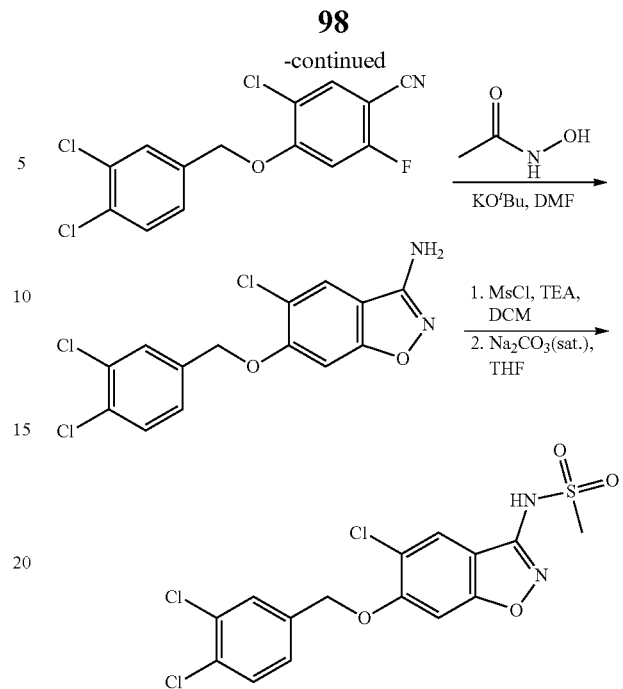

Step 1

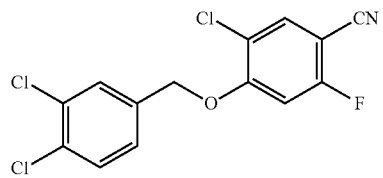

5-chloro-4-(3,4-dichlorobenzyloxy)-2-fluorobenzonitrile

To a solution of (3,4-dichlorophenyl)methanol (350 mg, 1.98 mmol) in DMF (3 mL) was added sodium hydride (60%, 80 mg, 4.00 mmol) at 0° C. After stirring at 0° C. for 30 minutes, 5-chloro-2,4-difluorobenzonitrile (345 mg, 1.99 mmol) was added in portions. The reaction mixture was stirred at room temperature for 6 h, quenched by saturated NH$_4$Cl (10 mL) and extracted with ethyl acetate (5 mL×3). The combined organic layers were washed with brine, dried over MgSO$_4$, filtered and concentrated in vacuo to afford 5-chloro-4-(3,4-dichloro-benzyloxy)-2-fluorobenzonitrile as a yellow solid. The residue was used in the next step without further purification. LCMS (ESI) m/z: 329.9 [M−H]$^-$.

Step 2

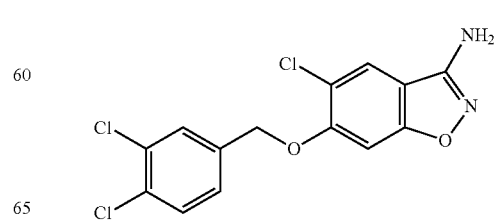

5-chloro-6-(3,4-dichlorobenzyloxy)benzo[d]isoxazol-3-amine

To a mixture of N-hydroxyacetamide (35 mg, 0.45 mmol) in dry DMF (2 mL) was added potassium tert-butoxide (50 mg, 0.45 mmol). After stirring at room temperature for 30 min, 5-chloro-4-(3,4-dichlorobenzyloxy)-2-fluorobenzonitrile (50 mg, 0.15 mmol) was added. The mixture was stirred at room temperature for 16 h, quenched by water (5 mL) and extracted with ethyl acetate (5 mL×3). The combined organic layers were dried over MgSO$_4$, filtered, concentrated and purified by reverse phase combiflash (20%-60% MeCN/H$_2$O in 0.1% NH$_4$HCO$_3$) to give 5-chloro-6-(3,4-dichlorobenzyloxy)benzo[d]isoxazol-3-amine (27 mg, 51%) as a white solid. LCMS (ESI) m/z: 342.9 [M−H]$^-$.

Step 3

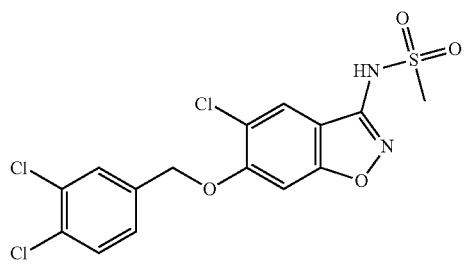 [SMILES: CS(=O)(=O)Nc1noc2cc(OCc3ccc(Cl)c(Cl)c3)c(Cl)cc12]

N-(5-chloro-6-(3,4-dichlorobenzyloxy)benzo[d]isoxazol-3-yl)methanesulfonamide

Methanesulfonyl chloride (8 mg, 0.07 mmol) was added dropwise to a solution of 5-chloro-6-(3,4-dichlorobenzyloxy)benzo[d]isoxazol-3-amine (20 mg, 0.06 mmol) and triethylamine (15 mg, 0.14 mmol) in DCM (1 mL) at 0° C. After stirring at room temperature for 2 h, the solvent was removed in vacuuo and the residue was dissolved in THF (1 mL) and NaOH (1 M, 0.5 mL). After stirring at room temperature for 2 h, HCl (1M) was added to adjust pH to 6; the reaction mixture was diluted with ethyl acetate (15 mL), washed with water (3 mL), brine (3 mL), dried over Na$_2$SO$_4$, filtered and concentrated. The residue was purified by reverse phase combiflash (20%-50% MeCN/H$_2$O in 0.1% NH$_4$HCO$_3$) to afford the target compound (17 mg, 68%) as a white solid. LCMS (ESI) Method A: RT=5.42 min, m/z: 420.9 [M−H]$^-$. $^1$H-NMR (500 MHz, MeOD-d$_4$): δ 7.81 (s, 1H), 7.73 (d, J=2.0 Hz, 1H), 7.59 (d, J=8.0 Hz, 1H), 7.48 (dd, J=8.0, 2.0 Hz, 1H), 7.22 (s, 1H), 5.25 (s, 2H), 3.13 (s, 3H).

Example 24

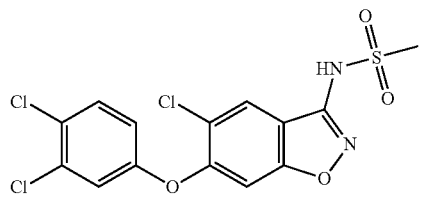 [SMILES: CS(=O)(=O)Nc1noc2cc(Oc3ccc(Cl)c(Cl)c3)c(Cl)cc12]

N-(5-chloro-6-(3,4-dichlorophenoxy)benzo[d]isoxazol-3-yl)methanesulfonamide

Synthetic scheme

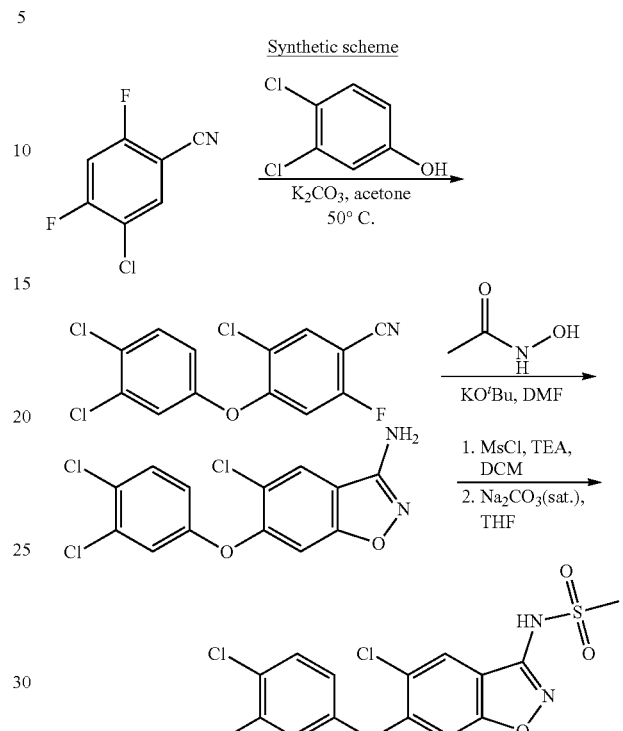

Step 1

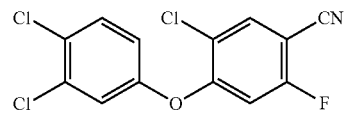 [SMILES: N#Cc1cc(Cl)c(Oc2ccc(Cl)c(Cl)c2)cc1F]

5-chloro-4-(3,4-dichlorophenoxy)-2-fluorobenzonitrile

A mixture of 5-chloro-2,4-difluorobenzonitrile (345 mg, 1.99 mmol), 3,4-dichlorophenol (326 mg, 2.00 mmol) and potassium carbonate (552 mg, 4.00 mmol) in acetone (10 mL) was stirred at 50° C. for 3 h. The reaction mixture was diluted with ethyl acetate, washed with water, brine, dried over MgSO$_4$, filtered and concentrated in vacuo to afford 5-chloro-4-(3,4-dichlorophenoxy)-2-fluorobenzonitrile as a yellow solid. The residue was used for next step without further purification. LCMS (ESI) m/z: 315.8 [M−H]$^-$.

Step 2

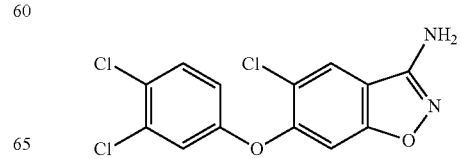

101

5-chloro-6-(3,4-dichlorophenoxy)benzo[d]isoxazol-3-amine

To a mixture of N-hydroxyacetamide (45 mg, 0.56 mmol) in dry DMF (2 mL) was added potassium tert-butoxide (62 mg, 0.56 mmol). After stirring at room temperature for 30 min, 5-chloro-4-(3,4-dichlorophenoxy)-2-fluorobenzonitrile (60 mg, 0.19 mmol) was added. The mixture was stirred at room temperature for 16 h, quenched by water (5 mL) and extracted with ethyl acetate (5 mL×3). The combined organic layers were dried over MgSO₄, filtered and concentrated. The residue was purified by reverse phase combiflash (20%-60% MeCN/H₂O in 0.1% NH₄HCO₃) to afford 5-chloro-6-(3,4-dichlorophenoxy)benzo[d]isoxazol-3-amine (37 mg, 59%) as a white solid. LCMS (ESI) m/z: 329.0 [M–H]⁻.

Step 3

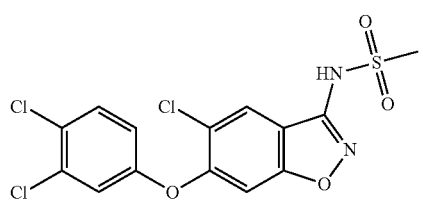

N-(5-chloro-6-(3,4-dichlorophenoxy)benzo[d]isoxazol-3-yl)methanesulfonamide

Methanesulfonyl chloride (12 mg, 0.10 mmol) was added dropwise to a solution of 5-chloro-6-(3,4-dichlorophenoxy)benzo[d]isoxazol-3-amine (33 mg, 0.10 mmol) and triethylamine (22 mg, 0.20 mmol) in DCM (1 mL) at 0° C. After stirring at room temperature for 2 h, the solvent was removed in vacuo and the residue was dissolved in THF (1 mL) and NaOH (1 M, 0.5 mL). After stirring at room temperature for 2 h, HCl (1M) was added to adjust pH to 6; the reaction mixture was diluted with ethyl acetate (15 mL), washed with water (3 mL) then brine (3 mL), dried over Na₂SO₄, filtered and concentrated. The residue was purified by reverse phase combiflash (20%-50% MeCN/H₂O in 0.1% NH₄HCO₃) to give the target compound (24 mg, 60%) as a white solid. LCMS (ESI) Method A: RT=5.40 min, m/z: 406.9 [M–H]⁻. ¹H-NMR (500 MHz, MeOD-d₄): δ 7.92 (s, 1H), 7.49 (d, J=8.5 Hz, 1H), 7.18-7.16 (m, 2H), 6.91 (dd, J=9.0, 2.0 Hz, 1H), 3.15 (s, 3H).

Example 25

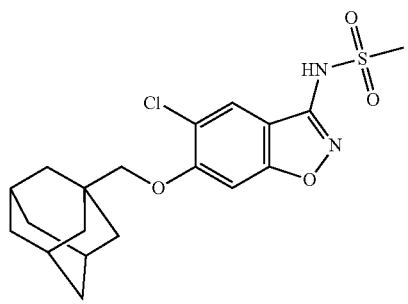 [SMILES: CS(=O)(=O)Nc1noc2cc(OCC34CC5CC(CC(C5)C3)C4)c(Cl)cc12]

102

N-[6-(adamantan-1-ylmethoxy)-5-chloro-1,2-benzoxazol-3-yl]methanesulfonamide

Synthetic scheme

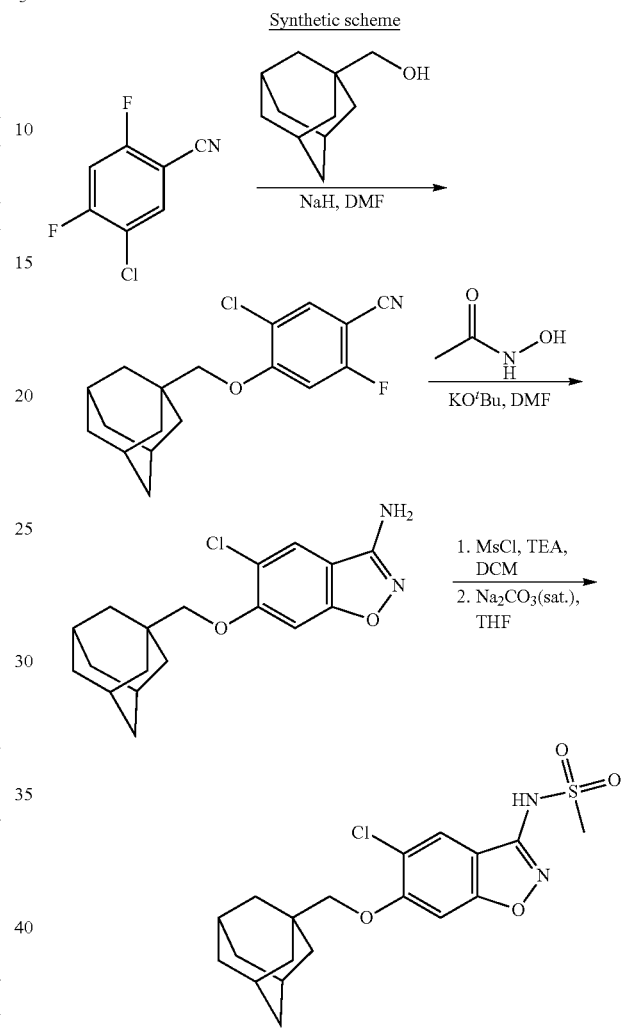

Step 1

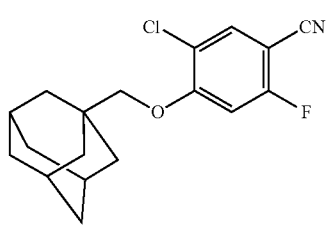 [SMILES: N#Cc1cc(Cl)c(OCC23CC4CC(CC(C4)C2)C3)cc1F]

4-(adamantan-1-ylmethoxy)-5-chloro-2-fluorobenzonitrile

To a solution of adamantan-1-ylmethanol (192 mg, 1.16 mmol) in DMF (3 mL) was added sodium hydride (60%, 70 mg, 2.32 mmol) at 0° C. After stirring at 0° C. for 30 minutes, a solution of 5-chloro-2,4-difluorobenzonitrile (200 mg, 1.16 mmol) in DMF (1 mL) was added slowly. The reaction mixture was stirred at room temperature for 6 h, quenched by saturated NH₄Cl (10 mL), and extracted with ethyl acetate (5 mL×3). The combined organic layers were washed with brine, dried over MgSO₄, filtered and concentrated in vacuo to afford 4-(adamantan-1-ylmethoxy)-5-chloro-2-fluorobenzonitrile as a yellow solid. The residue was used in the next step without further purification. LCMS (ESI) m/z: 318.0 [M−H]⁻.

Step 2

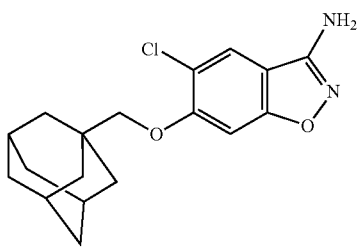 [SMILES: Nc1noc2cc(OCC34CC5CC(CC(C5)C3)C4)c(Cl)cc12]

6-(adamantan-1-ylmethoxy)-5-chloro-1,2-benzoxazol-3-amine

To a mixture of N-hydroxyacetamide (36 mg, 0.48 mmol) in dry DMF (2 mL) was added potassium tert-butoxide (54 mg, 0.48 mmol). After stirring at room temperature for 30 min, 4-(adamantan-1-ylmethoxy)-5-chloro-2-fluorobenzonitrile (50 mg, 0.16 mmol) was added and stirred at room temperature for another 16 h. The reaction mixture was quenched by water (5 mL) and extracted with ethyl acetate (5 mL×3). The combined organic layers were dried over MgSO₄, filtered and concentrated. The residue was purified by reverse phase combiflash (20%-60% MeCN/H₂O in 0.1% NH₄HCO₃) to afford 6-(adamantan-1-ylmethoxy)-5-chloro-1,2-benzoxazol-3-amine (21 mg, 40%) as a white solid. LCMS (ESI) m/z: 331.0 [M−H]⁻.

Step 3

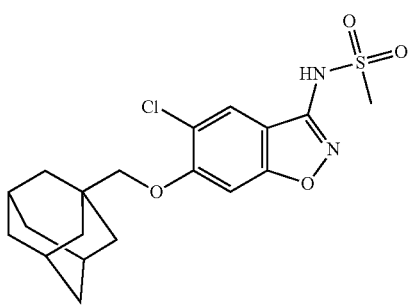 [SMILES: CS(=O)(=O)Nc1noc2cc(OCC34CC5CC(CC(C5)C3)C4)c(Cl)cc12]

N-[6-(adamantan-1-ylmethoxy)-5-chloro-1,2-benzoxazol-3-yl]methanesulfonamide

Methanesulfonyl chloride (8 mg, 0.07 mmol) was added dropwise to a solution of 5-chloro-6-(3,4-dichlorobenzyloxy)benzo[d]isoxazol-3-amine (21 mg, 0.06 mmol) and triethylamine (15 mg, 0.14 mmol) in DCM (1 mL) at 0° C. After stirring at room temperature for 2 h, the solvent was removed in vacuo and the residue was dissolved in THF (1 mL) and NaOH (1 M, 0.5 mL). The mixture was stirred at room temperature for another 2 h, HCl (1M) was added to adjust pH to 6; the reaction mixture was diluted with ethyl acetate (15 mL), washed with water (3 mL) and brine (3 mL), dried over Na₂SO₄, filtered and concentrated. The residue was purified by reverse phase combiflash (20%-50% MeCN/H₂O in 0.1% NH₄HCO₃) to afford the target compound (17 mg, 72%) as a white solid. LCMS (ESI) Method A: RT=5.97 min, m/z: 410.9 [M+H]⁺. ¹H-NMR (500 MHz, MeOD-d₄): δ 7.80 (s, 1H), 7.13 (s, 1H), 3.68 (s, 2H), 3.20 (s, 3H), 2.06 (br s, 3H), 1.86-1.77 (m, 12H).

Example 26

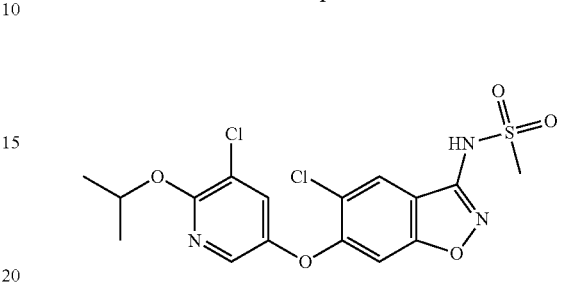

N-(5-chloro-6-(5-chloro-6-isopropoxypyridin-3-yloxy)benzo[d]isoxazol-3-yl)-methanesulfonamide Synthetic scheme

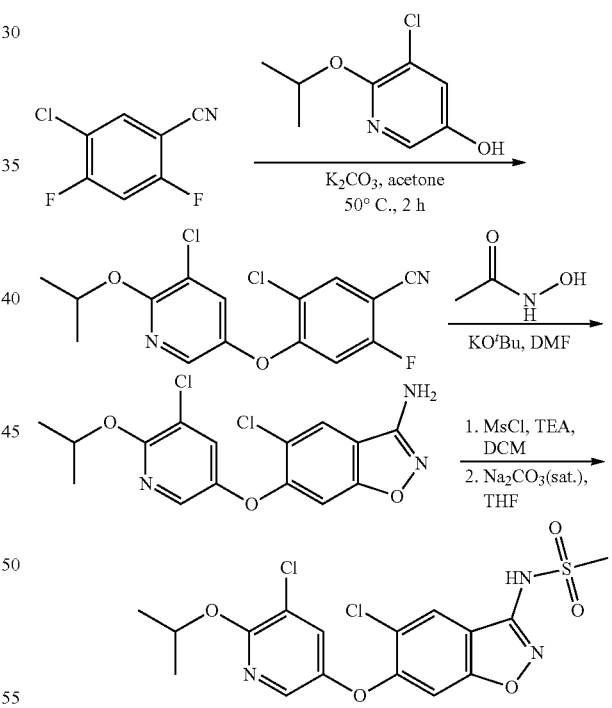

Step 1

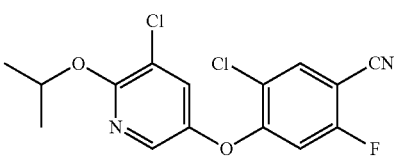 [SMILES: CC(C)Oc1ncc(Oc2cc(F)c(C#N)cc2Cl)cc1Cl]

5-chloro-4-(5-chloro-6-isopropoxypyridin-3-yloxy)-2-fluorobenzonitrile

A mixture of 5-chloro-2,4-difluorobenzonitrile (52 mg, 0.30 mmol), 5-chloro-6-isopropoxy-pyridin-3-ol (56 mg, 0.30 mmol) and potassium carbonate (125 mg, 0.90 mmol) in acetone (10 mL) was stirred at 50° C. for 2 h. The mixture was filtered and concentrated in vacuo. The resulting residue was purified by silica gel column chromatography (eluting with petroleum ether/ethyl acetate, from 20/1 to 5/1) to give 5-chloro-4-(5-chloro-6-isopropoxypyridin-3-yloxy)-2-fluorobenzonitrile (75 mg, 75%) as a white solid. LCMS (ESI) m/z: 341.0 [M+H]$^+$.

Step 2

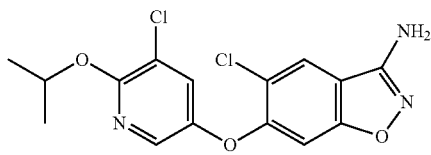 [SMILES: CC(C)Oc1ncc(Oc2cc3onc(N)c3cc2Cl)cc1Cl]

5-chloro-6-(5-chloro-6-isopropoxypyridin-3-yloxy)benzo[d]isoxazol-3-amine

To a solution of N-hydroxyacetamide (50 mg, 0.66 mmol) in DMF (4 mL) was added potassium tert-butanolate (74 mg, 0.66 mmol). The resulting white suspension was stirred at room temperature for 30 min. Then 5-chloro-4-(5-chloro-6-isopropoxypyridin-3-yloxy)-2-fluoro-benzonitrile (75 mg, 0.22 mmol) was added and the mixture was stirred at 50° C. for 16 h. After cooling to room temperature, water (100 mL) was added and extracted with EtOAc (30 mL×3). The combined organic layers were washed with brine (100 mL), dried over anhydrous sodium sulfate, filtered and concentrated to give 5-chloro-6-(5-chloro-6-isopropoxypyridin-3-yloxy)-benzo[d]isoxazol-3-amine (80 mg, crude) as a solid which was used in the next step without further purification. LCMS (ESI) m/z: 354.0 [M+H]$^+$.

Step 3

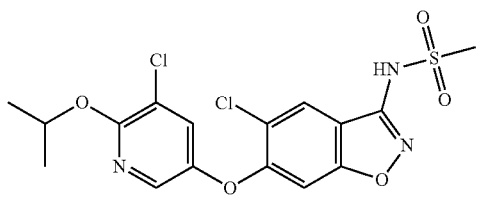 [SMILES: CC(C)Oc1ncc(Oc2cc3onc(NS(C)(=O)=O)c3cc2Cl)cc1Cl]

N-(5-chloro-6-(5-chloro-6-isopropoxypyridin-3-yloxy)benzo[d]isoxazol-3-yl) methanesulfonamide To a solution of 5-chloro-6-(5-chloro-6-isopropoxypyridin-3-yloxy)benzo[d]isoxazol-3-amine (80 mg, 0.23 mmol) in DCM (6 mL) was added methanesulfonyl chloride (40 mg, 0.35 mmol) and triethylamine (70 mg, 0.70 mmol). After stirring at room temperature for 1 h, the solvent was removed in vacuo and the crude product was dissolved in THF (4 mL) then the saturated aqueous Na$_2$CO$_3$ (4 mL) was added and the mixture was stirred at room temperature for 1 h. The mixture was extracted with EtOAc (20 mL×3). The combined organic layers were concentrated and purified by reverse-phase prep-HPLC to afford the target compound (15 mg, 16% for two steps) as white solid. (LCMS (ESI) Method A: RT=5.53 min, m/z: 432.0 [M+H]$^+$. $^1$H-NMR (500 MHz, DMSO-d$_6$): δ 8.02 (d, J=3 Hz, 1H), 7.87 (d, J=2.5 Hz, 1H), 7.14 (s, 1H), 7.10 (s, 1H), 5.28-5.25 (m, 1H), 2.88 (s, 3H), 1.34 (d, J=6 Hz, 6H).

Example 27

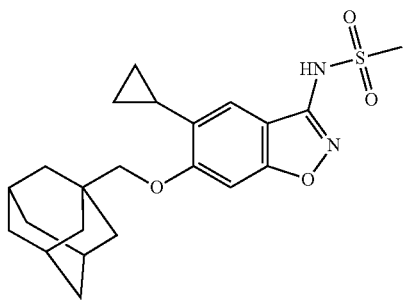 [SMILES: CS(=O)(=O)Nc1noc2cc(OCC34CC5CC(CC(C5)C3)C4)c(C3CC3)cc12]

N-[6-(adamantan-1-ylmethoxy)-5-cyclopropyl-1,2-benzoxazol-3-yl]methanesulfonamide Synthetic scheme

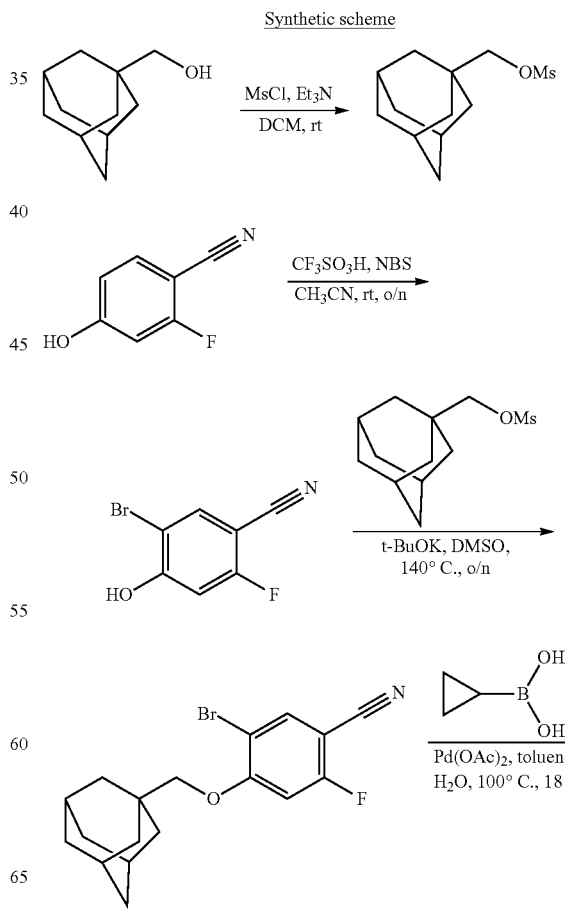

107
-continued

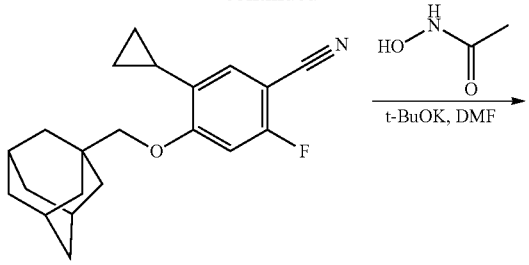

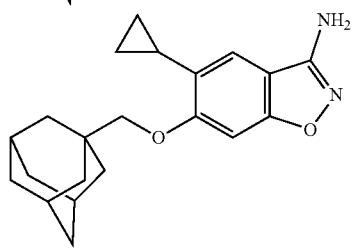

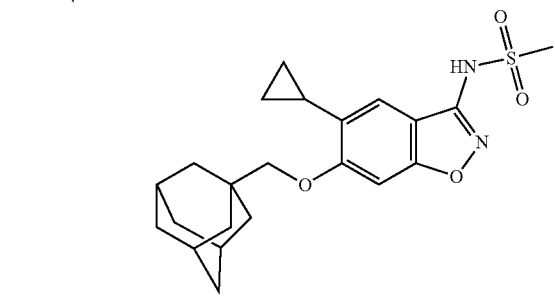

Step 1

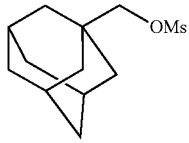 [SMILES: CS(=O)(=O)OCC12CC3CC(CC(C3)C1)C2]

adamantan-1-ylmethyl methanesulfonate

To a solution of adamantan-1-ylmethanol (1.0 g, 6.1 mmol) in DCM (20 mL), methanesulfonyl chloride (1.0 g, 9.0 mmol) and triethylamine (1.8 g, 18 mmol) were added. After stirring at room temperature over night, the reaction mixture was washed with aqueous sodium bicarbonate (10 mL) and brine (10 mL), dried over anhydrous sodium sulfate, filter and concentrated to give adamantan-1-ylmethyl methanesulfonate (1.4 g, 96%) as a white solid. $^1$H-NMR (500 MHz, CDCl$_3$): δ 3.78 (s, 2H), 3.00 (s, 3H), 2.02 (s, 3H), 1.75-1.64 (m, 6H), 1.58-1.57 (m, 6H).

Step 2

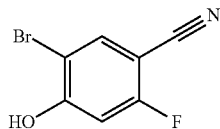

108

5-bromo-2-fluoro-4-hydroxybenzonitrile

To a solution of 2-fluoro-4-hydroxybenzonitrile (1.0 g, 7.3 mmol) in acetonitrile (20 mL) at −30° C. was added trifluoromethanesulfonic acid (1.2 g, 8.0 mmol) dropwise. The solution was stirred at −30° C. for 10 min then N-bromosuccinimide (1.8 g, 10.2 mmol) was added. After stirring at ambient temperature for 18 h, the reaction was quenched by saturated aqueous sodium hydrogen carbonate and extracted with ethyl acetate (20 mL×3). The combined organic layers were washed with brine (20 mL), dried over anhydrous sodium sulfate, filtered and concentrated in vacuo. The resulting crude residue was purified by SGC (eluting with petroleum ether/EtOAc=10/1) to give 5-bromo-2-fluoro-4-hydroxybenzonitrile (600 mg, 38%) as a white solid. LCMS (ESI) m/z: 214.1 [M−H]$^+$. $^1$H-NMR (500 MHz, CDCl$_3$): δ 7.75 (d, J=6.5 Hz, 1H), 6.90 (d, J=10.0 Hz, 1H), 6.25 (s, 1H).

Step 3

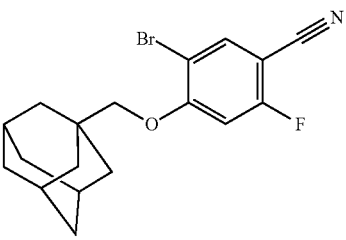 [SMILES: N#Cc1cc(Br)c(OCC23CC4CC(CC(C4)C2)C3)cc1F]

4-(adamantan-1-ylmethoxy)-5-bromo-2-fluorobenzonitrile

A mixture of 5-bromo-2-fluoro-4-hydroxybenzonitrile (1.3 g, 6.0 mmol), adamantan-1-ylmethyl methanesulfonate (0.98 g, 4.0 mmol) and potassium tert-butanolate (0.67 g, 6.0 mmol) in DMSO (20 mL) was stirred at 140° C. in a sealed tube for 12 h. The mixture was cooled to room temperature and diluted with water (30 mL) followed by extraction with ethyl acetate (30 mL×3). The organic layers were washed with brine (30 mL), dried over anhydrous sodium sulfate, filtered and concentrated. The crude product was purified by SGC (eluting with petroleum ether/EtOAc=10/1) to afford 4-(adamantan-1-ylmethoxy)-5-bromo-2-fluorobenzonitrile (410 mg, 19%) as a white solid. $^1$H-NMR (500 MHz, CDCl$_3$): δ 7.75 (d, J=7.0 Hz, 1H), 6.69 (d, J=10.5 Hz, 1H), 3.58 (s, 2H), 2.05 (s, 3H), 1.80-1.77 (m, 3H), 1.72-1.69 (m, 9H).

Step 4

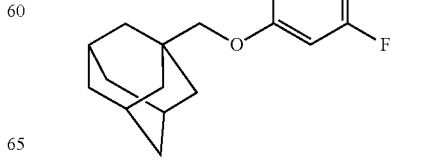

4-(adamantan-1-ylmethoxy)-5-cyclopropyl-2-fluorobenzonitrile

To a solution of 4-(adamantan-1-ylmethoxy)-5-bromo-2-fluorobenzonitrile (270 mg, 0.74 mmol), cyclopropylboronic acid (96 mg, 1.1 mmol), potassium phosphate (628 mg, 3.0 mmol) and tricyclohexylphosphine tetrafluoroborate (28 mg, 0.074 mmol) in toluene (4 mL) and water (0.2 mL) under a nitrogen atmosphere was added palladium acetate (8 mg, 0.037 mmol). The reaction mixture was heated to 100° C. for 18 h then cooled to ambient temperature. Water (10 mL) was added and the mixture was extracted with ethyl acetate (10 mL×3), the combined organics were washed with brine (10 mL), dried over anhydrous sodium sulfate, filtered and concentrated in vacuo. The residue was purified by SGC (eluting with petroleum ether/EtOAc=10/1) to afford 4-(adamantan-1-ylmethoxy)-5-cyclopropyl-2-fluorobenzonitrile (110 mg, 46%) as a white solid. $^1$H-NMR (500 MHz, CDCl$_3$): δ 7.06 (d, J=7.5 Hz, 1H), 6.59 (d, J=11.5 Hz, 1H), 3.53 (s, 2H), 2.04 (s, 3H), 1.80-1.77 (m, 3H), 1.71-1.68 (m, 9H), 1.25-1.24 (m, 1H), 0.96-0.94 (m, 2H), 0.60-0.59 (m, 2H).

Step 5

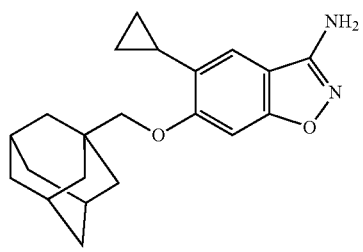 [SMILES: Nc1noc2cc(OCC34CC5CC(CC(C5)C3)C4)c(C3CC3)cc12]

6-(adamantan-1-ylmethoxy)-5-cyclopropyl-1,2-benzoxazol-3-amine

Potassium tert-butanolate (73 mg, 0.65 mmol) was added to a solution of N-hydroxyacetamide (48 mg, 0.65 mmol) in DMF (2 mL). The resulting white suspension was stirred at room temperature for 30 min then 4-(adamantan-1-ylmethoxy)-5-cyclopropyl-2-fluorobenzonitrile (70 mg, 0.22 mmol) was added and the mixture was stirred at 50° C. for 12 h. After cooling to room temperature, water (10 mL) was added and the mixture was extracted with EtOAc (10 mL×3). The combined organic layers were washed with brine (10 mL), dried over anhydrous sodium sulfate, filtered and concentrated. The residue was purified by CombiFlash (0-80% CH$_3$CN/H$_2$O in 0.1% NH$_4$HCO$_3$) to give 6-(adamantan-1-ylmethoxy)-5-cyclopropyl-1,2-benzoxazol-3-amine (40 mg, 54%) as a white solid. LCMS (ESI) m/z: 339.7 [M+H]$^+$.

Step 6

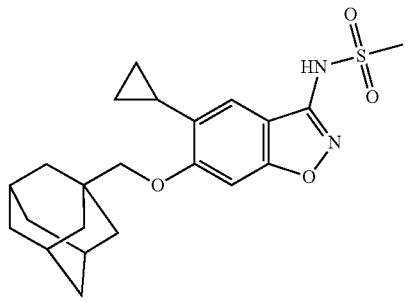 [SMILES: CS(=O)(=O)Nc1noc2cc(OCC34CC5CC(CC(C5)C3)C4)c(C3CC3)cc12]

N-[6-(adamantan-1-ylmethoxy)-5-cyclopropyl-1,2-benzoxazol-3-yl]methanesulfonamide To a solution of 6-(adamantan-1-ylmethoxy)-5-cyclopropyl-1,2-benzoxazol-3-amine (40 mg, 0.12 mmol) in DCM (2 mL) was added methanesulfonyl chloride (20 mg, 0.18 mmol) and triethylamine (36 mg, 0.36 mmol). After stirring at room temperature for 2 h, the solvent was removed in vacuo and the crude product was dissolved in THF/CH$_3$OH (2 mL/0.5 mL). Aqueous sodium hydroxide (0.5 mL, 1.0 M) was added, the reaction was stirred at 25° C. overnight. The mixture was acidified with HCl and the solid was purified by CombiFlash (0-45% CH$_3$CN/H$_2$O in 0.1% NH$_4$HCO$_3$) to afford N-[6-(adamantan-1-ylmethoxy)-5-cyclopropyl-1,2-benzoxazol-3-yl]methanesulfonamide (20 mg, 40%) as a white solid. LCMS (ESI) Method A: RT=6.27 min, m/z: 417.7 [M+H]$^+$. $^1$H-NMR (500 MHz, DMSO-d$_6$): δ 11.26 (s, 1H), 7.43 (s, 1H), 7.14 (s, 1H), 3.66 (s, 2H), 3.27 (s, 3H), 2.12-2.08 (m, 1H), 2.00 (s, 3H), 1.75-1.66 (m, 12H), 0.96-0.92 (m, 2H), 0.58-0.55 (m, 2H).

Example 28

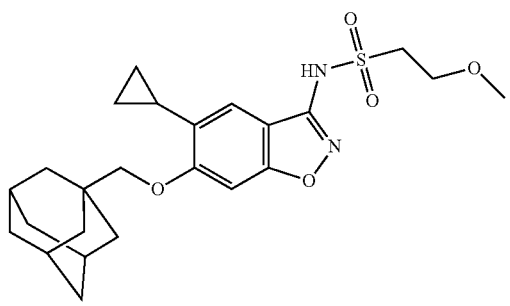 [SMILES: COCCS(=O)(=O)Nc1noc2cc(OCC34CC5CC(CC(C5)C3)C4)c(C3CC3)cc12]

N-[6-(adamantan-1-ylmethoxy)-5-cyclopropyl-1,2-benzoxazol-3-yl]-2-methoxyethane-1-sulfonamide The synthetic procedure was the same as Example 25. LCMS (ESI) Method A: RT=6.35 min, m/z: 461.1 [M+H]$^+$. $^1$H-NMR (500 MHz, DMSO-d$_6$): δ 11.25 (s, 1H), 7.42 (s, 1H), 7.11 (s, 1H), 3.70-3.66 (m, 4H), 3.65 (s, 2H), 3.16 (s, 3H), 2.11-2.08 (m, 1H), 2.00 (s, 3H), 1.74-1.66 (m, 12H), 0.95-0.93 (m, 2H), 0.57-0.55 (m, 2H).

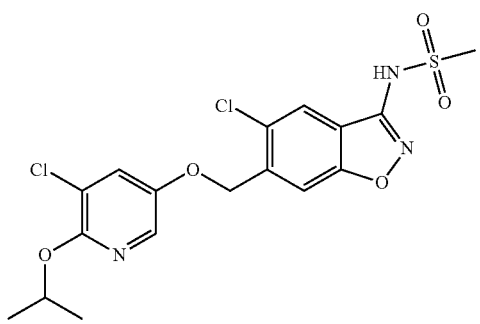 [SMILES: CC(C)Oc1ncc(OCc2cc3onc(NS(C)(=O)=O)c3cc2Cl)cc1Cl]

Example 29

N-(5-chloro-6-((5-chloro-6-isopropoxypyridin-3-yloxy)methyl)benzo[d]isoxazol-3-yl)-methanesulfonamide

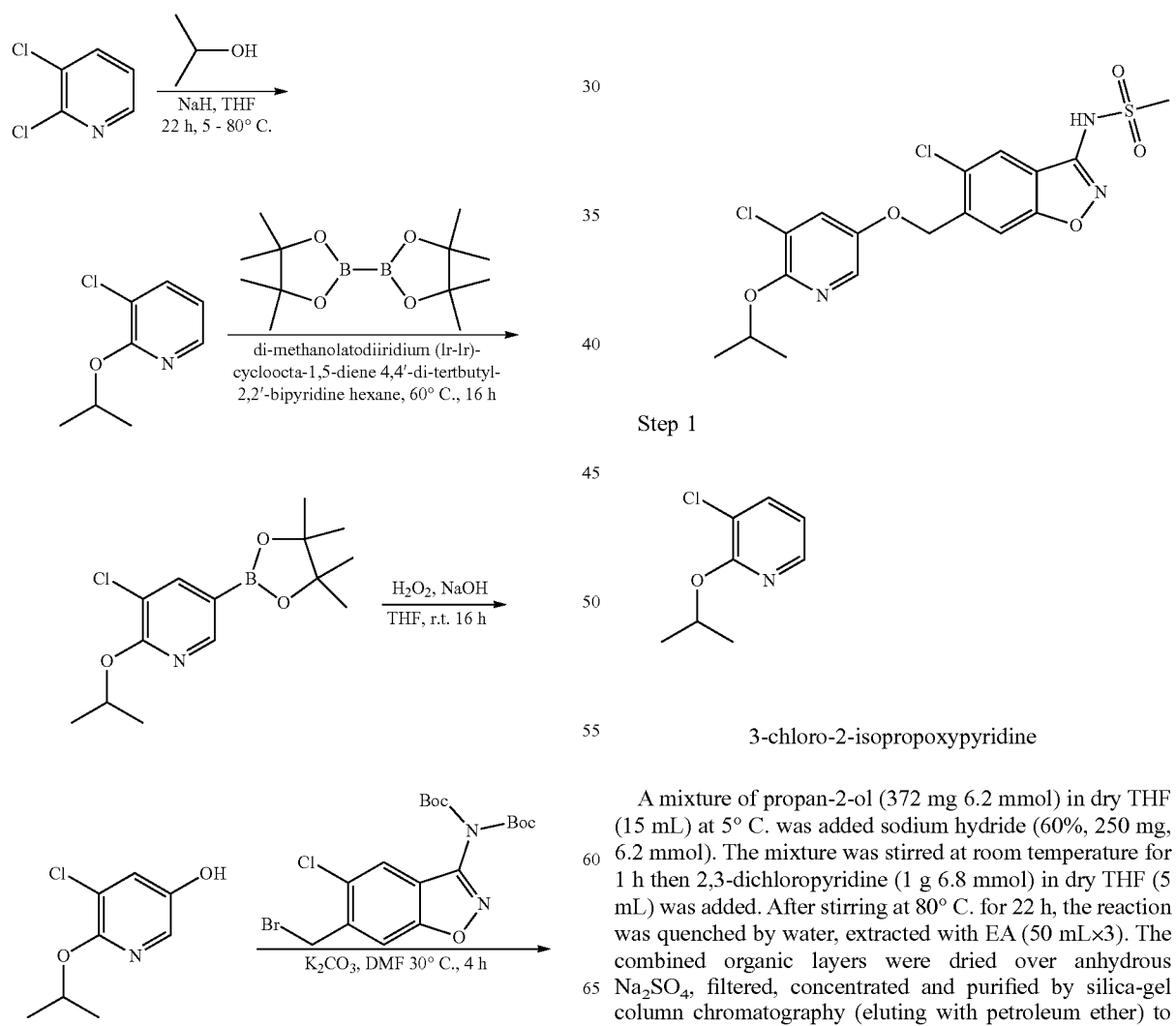

Step 1

3-chloro-2-isopropoxypyridine

A mixture of propan-2-ol (372 mg 6.2 mmol) in dry THF (15 mL) at 5° C. was added sodium hydride (60%, 250 mg, 6.2 mmol). The mixture was stirred at room temperature for 1 h then 2,3-dichloropyridine (1 g 6.8 mmol) in dry THF (5 mL) was added. After stirring at 80° C. for 22 h, the reaction was quenched by water, extracted with EA (50 mL×3). The combined organic layers were dried over anhydrous Na$_2$SO$_4$, filtered, concentrated and purified by silica-gel column chromatography (eluting with petroleum ether) to give 3-chloro-2-isopropoxypyridine (400 mg, 35%).

Step 2

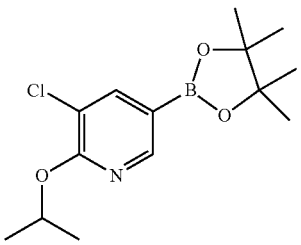 [SMILES: CC(C)Oc1ncc(B2OC(C)(C)C(C)(C)O2)cc1Cl]

3-chloro-2-isopropoxy-5-(4,4,5,5-tetramethyl-1,3,2-dioxaborolan-2-yl)pyridine

A mixture of 3-chloro-2-isopropoxypyridine (400 mg, 2.35 mmol), 4,4,4',4',5,5,5',5'-octamethyl-2,2'-bi(1,3,2-dioxaborolane) (716 mg, 2.82 mmol), di-methanolatodi-iridium(Ir—Ir)-cycloocta-1,5-diene (31 mg, 0.047 mmol) and 4,4'-di-tertbutyl-2,2'-bipyridine (90 mg, 0.33 mmol) in hexane (10 mL) was stirred at 60° C. for 16 h. The reaction was quenched by methanol (2 mL) and the resulting mixture was concentrated to give 3-chloro-2-isopropoxy-5-(4,4,5,5-tetramethyl-1,3,2-dioxaborolan-2-yl)pyridine (500 mg, crude) as a solid which was used in the next step without further purification. LCMS (ESI) in/z: 298.1 [M+H]+.

Step 3

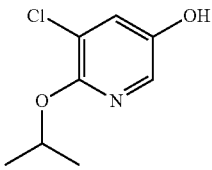

5-chloro-6-isopropoxypyridin-3-ol

A solution of 3-chloro-2-isopropoxy-5-(4,4,5,5-tetramethyl-1,3,2-dioxaborolan-2-yl)pyridine (500 mg, crude), aqueous NaOH (20 mL, 2%), THF (20 mL) and hydrogen peroxide (4 mL, 30%) was stirred at room temperature for 16 h. The mixture was extracted with EtOAc and the combined organic layers were dried over anhydrous Na₂SO₄, filtered, concentrated and purified by silica-gel column chromatography (eluting with petroleum ether/ethyl acetate, from 10/1 to 1/1) to give 5-chloro-6-isopropoxypyridin-3-ol (140 mg, 32% for two steps) as a white solid. LCMS (ESI) m/z: 188.1 [M+H]+.

Step 4

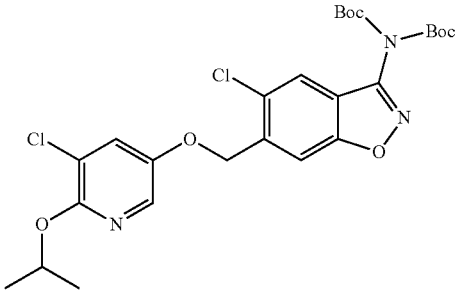 [SMILES: CC(C)Oc1ncc(OCc2cc3onc(N(C(=O)OC(C)(C)C)C(=O)OC(C)(C)C)c3cc2Cl)cc1Cl]

tert-butyl N-[(tert-butoxy)carbonyl]-N-(5-chloro-6-{[(5-chloro-6-isopropoxypyridin-3-yl)oxy]methyl}-1,2-benzoxazol-3-yl)carbamate A mixture of 5-chloro-6-isopropoxypyridin-3-ol (100 mg, 0.53 mmol), tert-butyl N-[6-(bromomethyl)-5-chloro-1,2-benzoxazol-3-yl]-N-[(tert-butoxy)carbonyl]carbamate (243 mg, 0.53 mmol) and potassium carbonate (220 mg, 1.6 mmol) in DMF (8 mL) was stirred at 30° C. for 4 h. The mixture was filtered and concentrated in vacuo. The resulting residue was purified by SGC (eluting with petroleum ether/ethyl acetate, from 20/1 to 3/1) to give tert-butyl N-[(tert-butoxy)carbonyl]-N-(5-chloro-6-{[(5-chloro-6-isopropoxypyridin-3-yl)oxy]methyl}-1,2-benzoxaz ol-3-yl)carbamate (180 mg, yield: 60%) as a white solid. LCMS (ESI) m/z: 567.9 [M+H]+.

Step 5

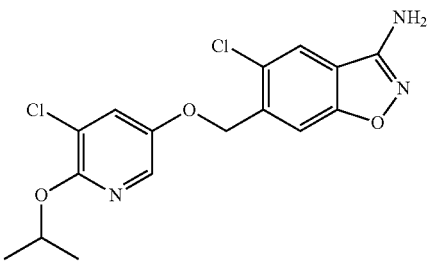 [SMILES: CC(C)Oc1ncc(OCc2cc3onc(N)c3cc2Cl)cc1Cl]

5-chloro-6-((5-chloro-6-isopropoxypyridin-3-yloxy)methyl)benzo[d]isoxazol-3-amine A solution of tert-butyl N-[(tert-butoxy)carbonyl]-N-(5-chloro-6-{[(5-chloro-6-isopropoxypyridin-3-yl)oxy]methyl}-1,2-benzoxazol-3-yl)carbamate (180 mg, 0.32 mmol) in trifluoroacetic acid (6.0 mL) and DCM (6.0 mL) was stirred at room temperature for 1 h. The reaction was quenched by saturated aqueous NaHCO₃ and extracted with DCM (20 mL×3). The combined organic layers were dried over Na₂SO₄, filtered and concentrated to give 5-chloro-6-((5-chloro-6-isopropoxypyridin-3-yloxy)methyl)benzo[d]isoxazol-3-amine (200 mg, crude) as a solid which was used in the next step without further purification. LCMS (ESI) m/z: 368.0 [M+H]+.

Step 6

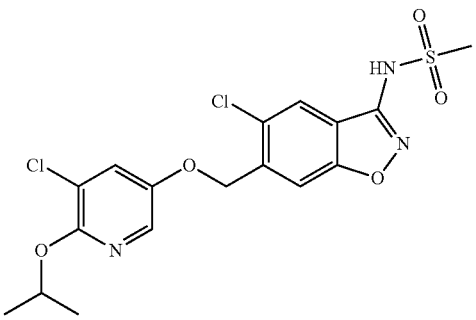 [SMILES: CC(C)Oc1ncc(OCc2cc3onc(NS(C)(=O)=O)c3cc2Cl)cc1Cl]

N-(5-chloro-6-((5-chloro-6-isopropoxypyridin-3-yloxy)methyl)benzo[d]isoxazol-3-yl)-methanesulfonamide To a solution of 5-chloro-6-((5-chloro-6-isopropoxypyridin-3-yloxy)methyl)benzo-[d]isoxazol-3-amine (140 mg, crude) in DCM (8 mL) was added methanesulfonyl chloride (65 mg, 0.57 mmol) and triethylamine (120 mg, 1.2 mmol). After stirring at room temperature for 1 h, the solvent was removed in vacuo and the crude product was dissolved in THF/CH₃OH (4 mL/1 mL). Aqueous sodium hydroxide (2 mL, 1.0 M) was added; the reaction mixture was stirred at room temperature for 1 h then extracted with EtOAc (20 mL×3). The combined organic layers were concentrated and purified by reverse-phase prep-HPLC to afford N-(5-chloro-6-((5-chloro-6-isopropoxypyridin-3-yloxy)methyl)-benzo[d]isoxazol-3-yl)methanesulfonamide (80 mg, 84% for two steps) as white solid. (LCMS (ESI) Method A: RT=5.54 min, m/z: 446.0 [M+H]$^+$. $^1$H-NMR (500 MHz, CDCl₃): δ 7.93 (s, 1H), 7.81-7.77 (m, 2H), 7.42 (s, 1H), 5.25-5.20 (m, 3H), 3.31 (s, 3H), 1.39 (d, J=6 Hz, 6H).

Example 30

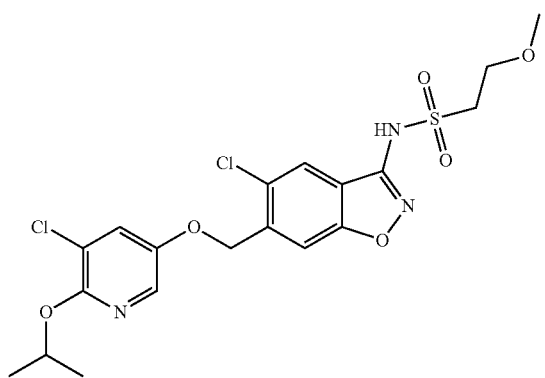 [SMILES: COCCS(=O)(=O)Nc1noc2cc(COc3cnc(OC(C)C)c(Cl)c3)c(Cl)cc12]

N-(5-chloro-6-((5-chloro-6-isopropoxypyridin-3-yloxy)methyl)benzo[d]isoxazol-3-yl)-2-methoxy-ethanesulfonamide The synthetic procedure was the same as Example 29. LCMS (ESI) Method A: RT=5.58 min, m/z: 489.8 [M+H]$^+$. $^1$H-NMR (500 MHz, CDCl₃): δ 7.80 (s, 1H), 7.76 (d, J=2.5 Hz, 1H), 7.55 (s, 1H), 7.36 (d, J=2.5 Hz, 1H), 5.25-5.22 (m, 1H), 5.09 (s, 2H), 3.85-3.84 (m, 2H), 3.57-3.56 (m, 2H), 3.36 (s, 3H), 1.37 (d, J=6.5 Hz, 6H).

Example 31

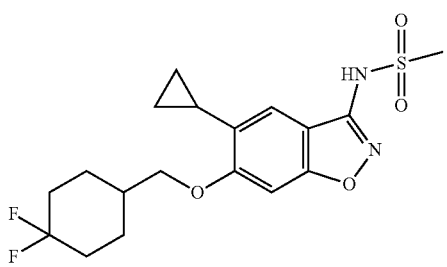 [SMILES: CS(=O)(=O)Nc1noc2cc(OCC3CCC(F)(F)CC3)c(C3CC3)cc12]

N-(5-cyclopropyl-6-((4,4-difluorocyclohexyl)methoxy)benzo[d]isoxazol-3-yl)-methanesulfonamide Synthetic scheme

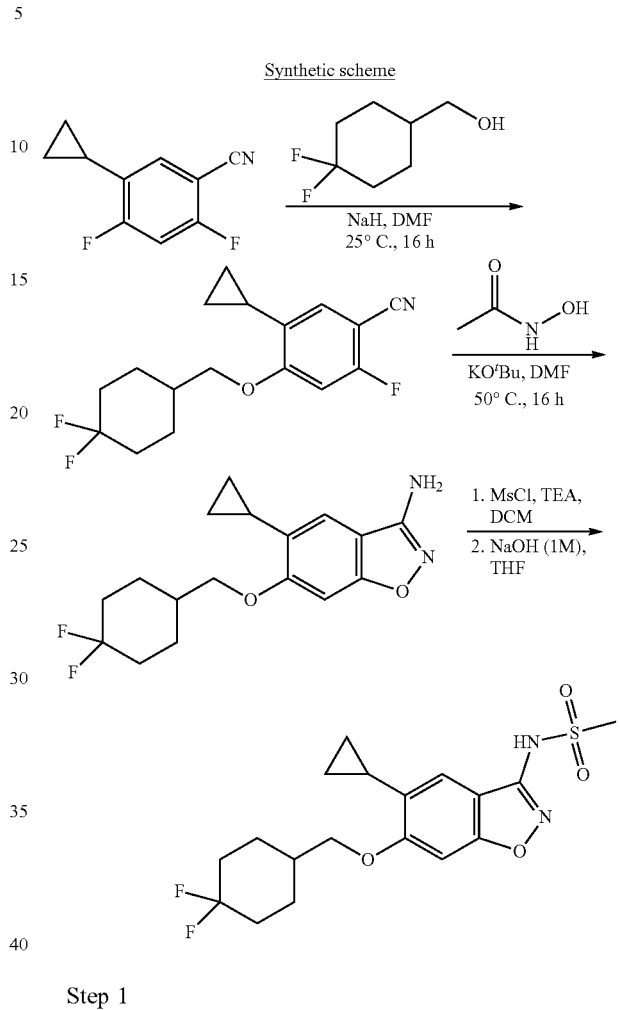

Step 1

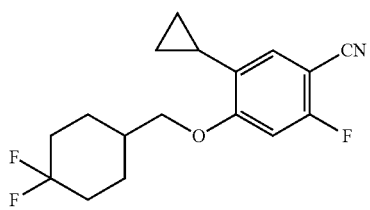 [SMILES: N#Cc1cc(C2CC2)c(OCC2CCC(F)(F)CC2)cc1F]

5-cyclopropyl-4-((4,4-difluorocyclohexyl)methoxy)-2-fluorobenzonitrile

To a solution of (4,4-difluorocyclohexyl)methanol (126 mg, 0.84 mmol) in DMF (4 mL), sodium hydride (60%) (38 mg, 0.95 mmol) was added and the reaction mixture was stirred at room temperature for 1 h. A solution of 5-cyclopropyl-2,4-difluorobenzonitrile (100 mg, 0.56 mmol) in DMF (1 mL) was added and the mixture was stirred at 25° C. overnight. The mixture was diluted with water (10 mL) and extracted with EtOAc (10 mL×3). The combined organic layers were washed with brine (10 mL), dried over Na₂SO₄, filtered and concentrated. The residue was purified by SGC (eluting with petroleum ether/EtOAc=10/1) to afford 5-cyclopropyl-4-((4,4-difluorocyclohexyl)methoxy)-2-fluorobenzonitrile (70 mg, 41% yield) as an oil.

Step 2

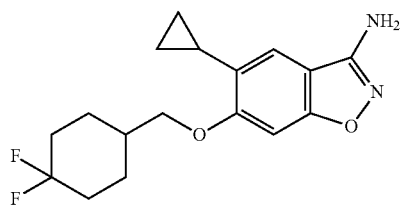 [SMILES: Nc1noc2cc(OCC3CCC(F)(F)CC3)c(C3CC3)cc12]

5-cyclopropyl-6-((4,4-difluorocyclohexyl)methoxy)benzo[d]isoxazol-3-amine

Potassium tert-butanolate (76 mg, 0.68 mmol) was added to a solution of N-hydroxyacetamide (51 mg, 0.68 mmol) in DMF (3 mL). The resulting white suspension was stirred at room temperature for 30 min then 5-cyclopropyl-4-((4,4-difluorocyclohexyl)methoxy)-2-fluorobenzonitrile (70 mg, 0.23 mmol) was added and the mixture was stirred at 50° C. for 12 h. After cooling to room temperature, water (100 mL) was added and the mixture was extracted with EtOAc (100 mL×3). The combined organic layers were washed with brine (100 mL), dried over anhydrous sodium sulfate, filtered and concentrated. The residue was purified by CombiFlash (0-70% CH$_3$CN/H$_2$O in 0.1% NH$_4$HCO$_3$) to afford 5-cyclopropyl-6-((4,4-difluoro-cyclohexyl)-methoxy)benzo[d]isoxazol-3-amine (40 mg, 54%) as a white solid. LCMS (ESI): m/z: 323.1 [M+H]$^+$.

Step 3

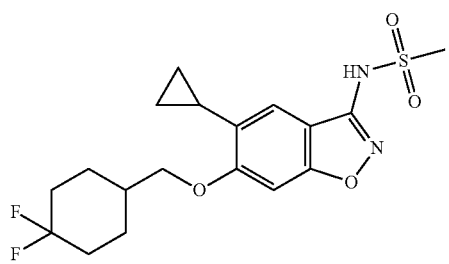 [SMILES: CS(=O)(=O)Nc1noc2cc(OCC3CCC(F)(F)CC3)c(C3CC3)cc12]

N-(5-cyclopropyl-6-((4,4-difluorocyclohexyl)methoxy)benzo[d]isoxazol-3-yl)-methanesulfonamide To a solution of 5-cyclopropyl-6-((4,4-difluorocyclohexyl)methoxy)benzo[d]isoxazol-3-amine (40 mg, 0.12 mmol) in DCM (2 mL) was added methanesulfonyl chloride (28 mg, 0.25 mmol) and triethylamine (38 mg, 0.37 mmol). After stirring at room temperature for 2 h, the solvent was removed in vacuo and the crude product was dissolved in THF/CH$_3$OH (2 mL/0.5 mL). Aqueous sodium hydroxide (0.5 mL, 1.0 M) was added and the reaction was stirred at 25° C. overnight. Acidified with HCl and filtered to get a solid. The solid was purified by CombiFlash (0-45% CH$_3$CN/H$_2$O in 0.1% NH$_4$HCO$_3$) to afford N-(5-cyclopropyl-6-((4,4-difluorocyclohexyl)-methoxy)benzo[d]isoxazol-3-yl)methanesulfonamide (28 mg, 56%) as a white solid. LCMS (ESI) Method A: RT=4.96 min, m/z: 401.0 [M+H]$^+$. $^1$H-NMR (500 MHz, MeOD-d$_4$): δ 7.23 (s, 1H), 6.88 (s, 1H), 3.87 (d, J=6.0 Hz, 2H), 3.09 (s, 3H), 2.04-1.90 (m, 6H), 1.82-1.69 (m, 2H), 1.49-1.42 (m, 2H), 0.84-0.80 (m, 2H), 0.53-0.50 (m, 2H).

Example 32

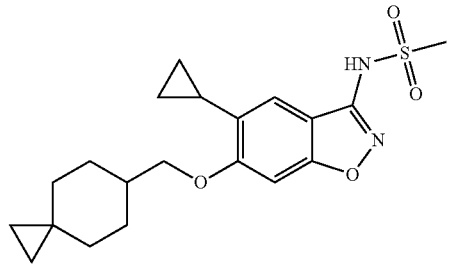 [SMILES: CS(=O)(=O)Nc1noc2cc(OCC3CCC4(CC3)CC4)c(C3CC3)cc12]

N-(5-cyclopropyl-6-{spiro[2.5]octan-6-ylmethoxy}-1,2-benzoxazol-3-yl)-methanesulfonamide The synthetic procedure was the same as Example 31. LCMS (ESI) Method A: RT=5.95 min, m/z: 391.1 [M+H]$^+$. $^1$H-NMR (500 MHz, MeOD-d$_4$): δ 7.10 (s, 1H), 6.75 (s, 1H), 3.72 (d, J=5.5 Hz, 2H), 2.98 (s, 3H), 1.91-1.57 (m, 6H), 1.20-1.16 (m, 2H), 0.77-0.67 (m, 4H), 0.41-0.38 (m, 2H), 0.09-0.01 (m, 4H).

Example 33

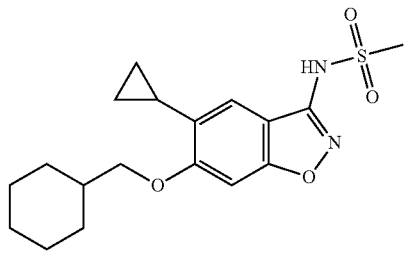 [SMILES: CS(=O)(=O)Nc1noc2cc(OCC3CCCCC3)c(C3CC3)cc12]

N-(6-(cyclohexylmethoxy)-5-cyclopropylbenzo[d]isoxazol-3-yl)methanesulfonamide

Synthetic scheme

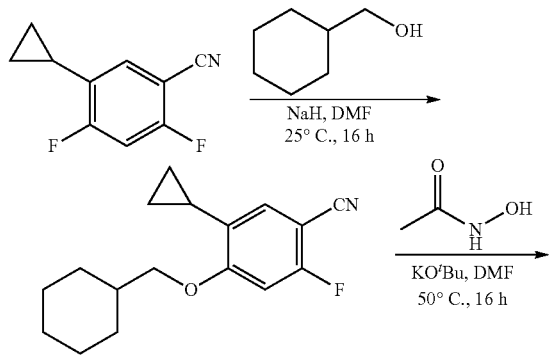

119

-continued

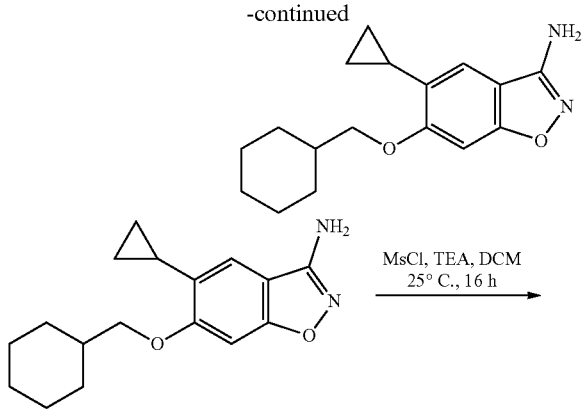

Step 1

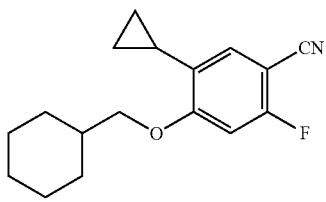 [SMILES: N#Cc1cc(C2CC2)c(OCC2CCCCC2)cc1F]

4-(cyclohexylmethoxy)-5-cyclopropyl-2-fluorobenzonitrile

A mixture of cyclohexylmethanol (64 mg, 0.56 mmol) in DMF (10 mL) and sodium hydride (60%, 25 mg, 0.63 mmol) was stirred at 0° C. for 30 min, then 5-cyclopropyl-2,4-difluorobenzonitrile (100 mg, 0.558 mmol) in DMF (10 mL) was added. After stirring at 25° C. for 16 h, EtOAc (150 mL) and saturated NaHCO₃ (50 mL) was added. The organic layer was washed with saturated NaHCO₃ (50 mL×3) and the combined organic layers were washed with brine (50 mL×2), dried over Na₂SO₄, filtered and concentrated to get crude product as a pale yellow oil without further purification (150 mg, crude).

Step 2

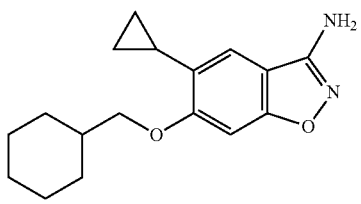 [SMILES: Nc1noc2cc(OCC3CCCCC3)c(C3CC3)cc12]

120

6-(cyclohexylmethoxy)-5-cyclopropylbenzo[d]isoxazol-3-amine

A mixture of N-hydroxyacetamide (124 mg, 1.65 mmol) and potassium tert-butanolate (159 mg, 1.65 mmol) in DMF (20 mL) was stirred at 5° C. for 30 min then a solution of 4-(cyclohexylmethoxy)-5-cyclopropyl-2-fluorobenzonitrile (150 mg, 0.549 mmol) in DMF (10 mL) was added. After stirring at 50° C. for 16 h, EtOAc (150 mL) and water (50 mL) were added and the organic layer was washed with water (50 mL×3). The combined organic layers were washed with brine (50 mL×2), dried over Na₂SO₄, filtered and concentrated. The residue was purified by reverse phase column flash (58-61% CH₃CN/H₂O in 0.1% NH₄HCO₃) to afford 6-(cyclohexylmethoxy)-5-cyclopropylbenzo[d]isoxazol-3-amine (50 mg, 31% for two steps). LCMS (ESI) m/z: 287.1 [M+H]⁺.

Step 3

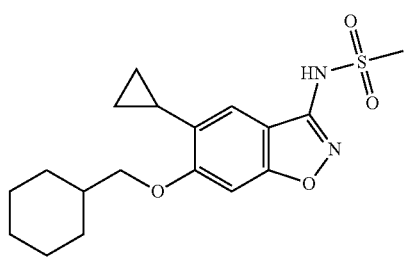

N-(6-(cyclohexylmethoxy)-5-cyclopropylbenzo[d]isoxazol-3-yl)methanesulfonamide

A mixture of 6-(cyclohexylmethoxy)-5-cyclopropylbenzo[d]isoxazol-3-amine (50 mg, 0.17 mmol), triethylamine (200 mg, 1.98 mmol) and methanesulfonyl chloride (0.1 mL, 1.30 mmol) in DCM (15 mL) was stirred at 25° C. for 16 h. The reaction was quenched by saturated NaHCO₃ (100 mL) then extracted with EtOAc (50 mL×3). The combined organic layers were washed with saturated NaHCO₃ and brine, dried over Na₂SO₄, filtered, concentrated and purified by reverse phase column flash (60-63% CH₃CN/H₂O in 0.1% NH₄HCO₃) to give N-(6-(cyclohexylmethoxy)-5-cyclopropylbenzo[d]isoxazol-3-yl)methanesulfonamide (21.0 mg, 38%) as an off-white solid. LCMS (ESI) m/z: 365.1 [M+H]⁺. ¹H-NMR (500 MHz, MeOH-4): δ 7.36 (s, 1H), 7.04 (s, 1H), 3.92 (d, J=6.0 Hz, 2H), 3.30 (s, 3H), 2.16-2.13 (m, 1H), 1.97-1.89 (m, 3H), 1.84-1.82 (m, 2H), 1.77-1.74 (m, 1H), 1.42-1.35 (m, 2H), 1.32-1.19 (m, 3H), 0.98-0.94 (m, 2H), 0.66-0.63 (m, 2H).

Example 34

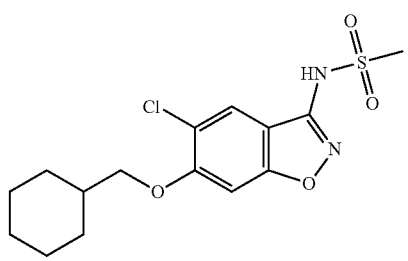 [SMILES: CS(=O)(=O)Nc1noc2cc(OCC3CCCCC3)c(Cl)cc12]

N-(5-chloro-6-(cyclohexylmethoxy)benzo[d]isoxazol-3-yl)methanesulfonamide

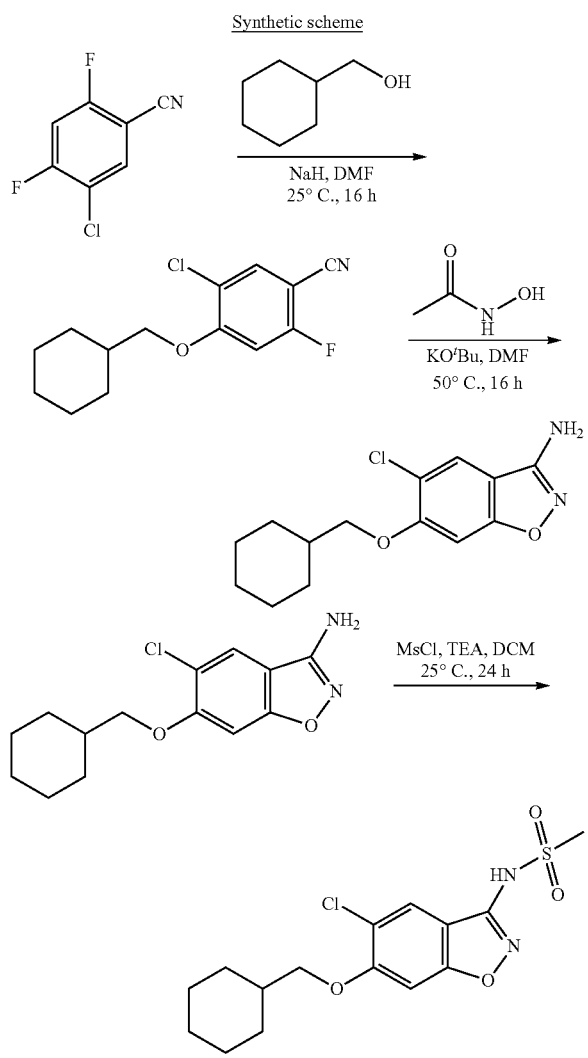

Step 1

5-chloro-4-(cyclohexylmethoxy)-2-fluorobenzonitrile

A mixture of cyclohexylmethanol (197 mg, 1.73 mmol) and sodium hydride (60%, 76 mg, 1.9 mmol) in DMF (10 mL) was stirred at 0° C. for 30 min, then 5-chloro-2,4-difluorobenzonitrile (300 mg, 1.73 mmol) in DMF (10 mL) was added. After stirring at 25° C. for 16 h, EtOAc (150 mL) and saturated NaHCO₃ (50 mL) was added. The aqueous phase was extracted with EtOAc (50 mL×3) and the combined organic layers were washed with brine (50 mL×2), dried over Na₂SO₄, filtered and concentrated to give crude product as a pale yellow oil without further purification (500 mg, crude).

Step 2

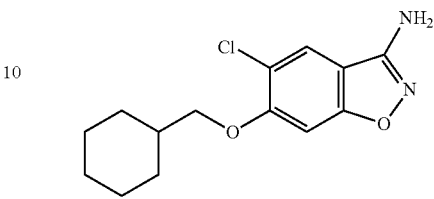

5-chloro-6-(cyclohexylmethoxy)benzo[d]isoxazol-3-amine

A mixture of N-hydroxyacetamide (421 mg, 5.61 mmol) and potassium tert-butanolate (538 mg, 5.60 mmol) in DMF (20 mL) was stirred at 5° C. for 30 min then 5-chloro-4-(cyclohexylmethoxy)-2-fluorobenzonitrile (500 mg, 1.87 mmol) in DMF (10 mL) was added. After stirring at 50° C. for 16 h, EtOAc (150 mL) and water (50 mL) was added. The aqueous phase was extracted with EtOAc (50 mL×3) and the combined organic layers were washed with brine (50 mL×2), dried over Na₂SO₄, filtered and concentrated. The crude product was purified by reverse phase column flash (52-58% CH₃CN/H₂O in 0.1% NH₄HCO₃) to afford 5-chloro-6-(cyclohexylmethoxy)benzo[d]isoxazol-3-amine (145 mg, 30%, two step). LCMS (ESI) m/z: 281.0 [M+H]⁺. ¹H-NMR (500 MHz, DMSO-d6): δ 7.89 (s, 1H), 7.23 (s, 1H), 6.37 (s, 2H), 3.92 (d, J=6.0 Hz, 2H), 1.85-1.77 (m, 3H), 1.74-1.71 (m, 2H), 1.67-1.65 (m, 1H), 1.30-1.23 (m, 2H), 1.20-1.14 (m, 1H), 1.12-1.05 (m, 2H).

Step 3

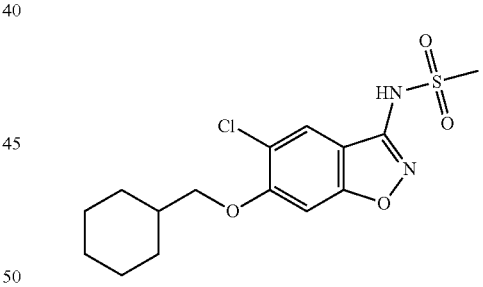

N-(5-chloro-6-(cyclohexylmethoxy)benzo[d]isoxazol-3-yl)methanesulfonamide

A mixture of 5-chloro-6-(cyclohexylmethoxy)benzo[d]isoxazol-3-amine (50 mg, 0.18 mmol), triethylamine (200 mg, 1.98 mmol) and methanesulfonyl chloride (0.1 mL, 1.30 mmol) in DCM (15 mL) was stirred at 25° C. for 24 h. The reaction was quenched by aqueous saturated NaHCO₃ (100 mL) and the mixture was extracted with EtOAc (50 mL×3). The combined organic layers were washed with saturated NaHCO₃ and brine, dried over Na₂SO₄, filtered and concentrated. The residue was purified by reverse phase column flash (56-60% CH₃CN/H₂O in 0.1% NH₄HCO₃) to give N-(5-chloro-6-(cyclohexylmethoxy)benzo[d]isoxazol-3-yl)methanesulfonamide (21.0 mg, 38%) as an off-white solid.

LCMS (ESI) Method A: RT=5.41 min, m/z: 359.0 [M+H]⁺.
¹H-NMR (400 MHz, MeOH-d₄): δ 7.83 (s, 1H), 7.20 (s, 1H), 3.94 (d, J=5.6 Hz, 2H), 3.28 (s, 3H), 1.95-1.73 (m, 6H), 1.42-1.14 (m, 5H).

Example 35

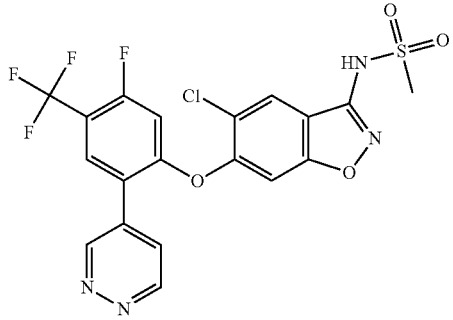 [SMILES: CS(=O)(=O)Nc1noc2cc(Oc3cc(F)c(C(F)(F)F)cc3-c3ccnnc3)c(Cl)cc12]

N-(5-chloro-6-(5-fluoro-2-(pyridazin-4-yl)-4-(trifluoromethyl)phenoxy)benzo[d]-isoxazol-3-yl)methanesulfonamide Synthetic scheme

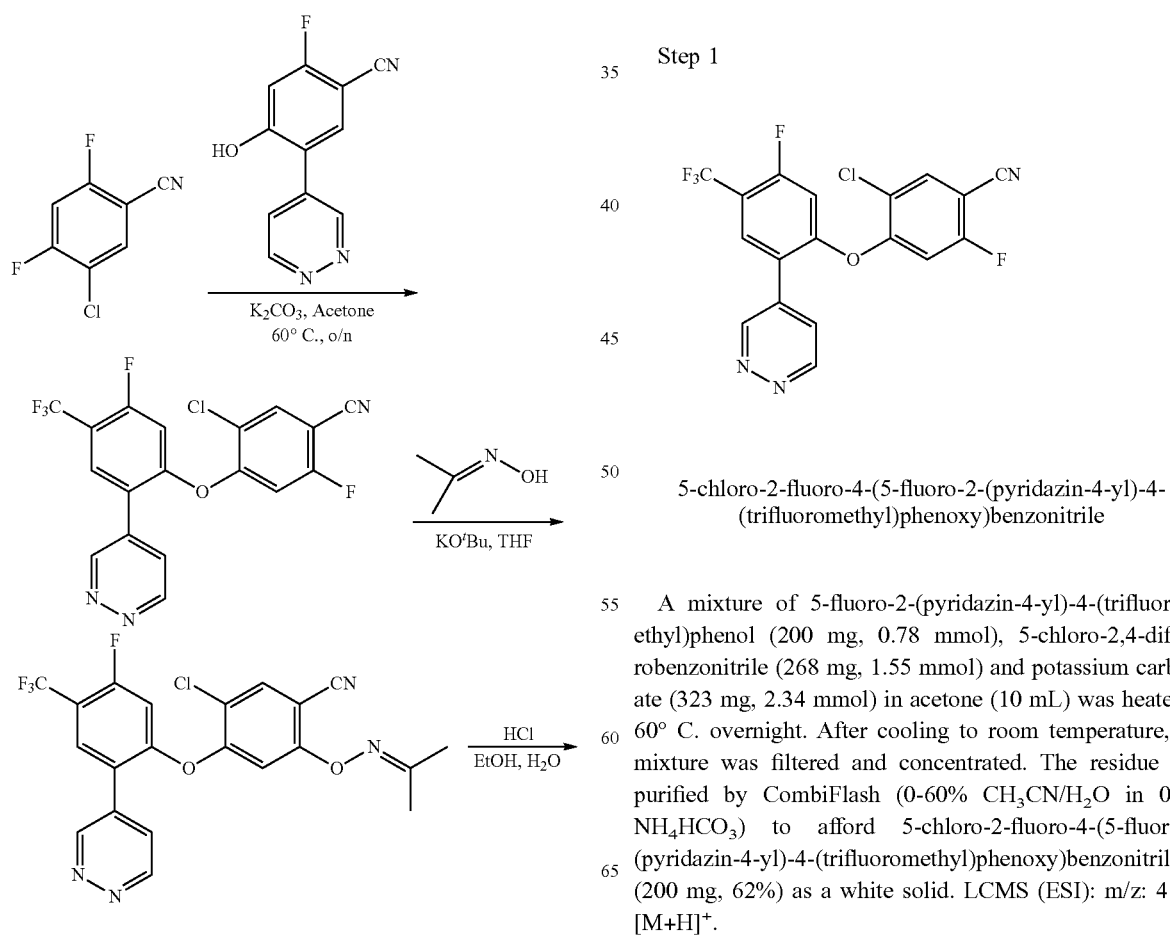

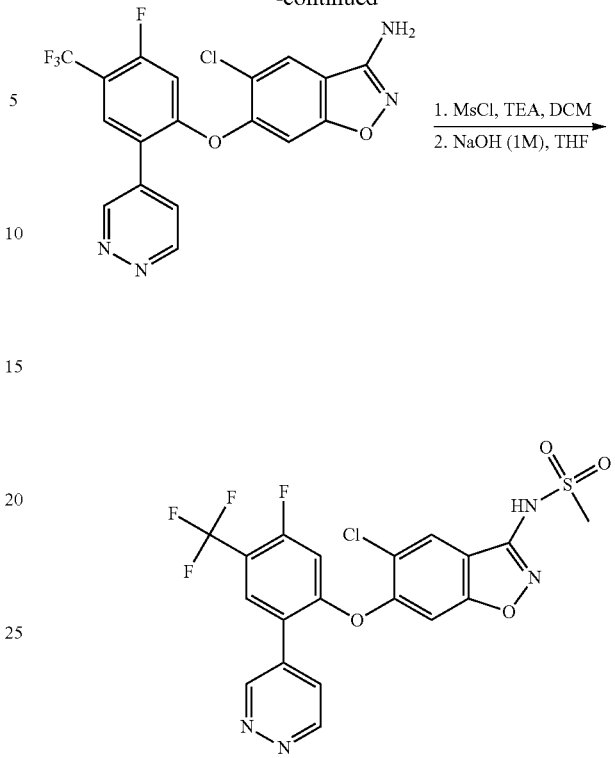

Step 1

5-chloro-2-fluoro-4-(5-fluoro-2-(pyridazin-4-yl)-4-(trifluoromethyl)phenoxy)benzonitrile A mixture of 5-fluoro-2-(pyridazin-4-yl)-4-(trifluoromethyl)phenol (200 mg, 0.78 mmol), 5-chloro-2,4-difluorobenzonitrile (268 mg, 1.55 mmol) and potassium carbonate (323 mg, 2.34 mmol) in acetone (10 mL) was heated at 60° C. overnight. After cooling to room temperature, the mixture was filtered and concentrated. The residue was purified by CombiFlash (0-60% CH₃CN/H₂O in 0.1% NH₄HCO₃) to afford 5-chloro-2-fluoro-4-(5-fluoro-2-(pyridazin-4-yl)-4-(trifluoromethyl)phenoxy)benzonitrile (200 mg, 62%) as a white solid. LCMS (ESI): m/z: 411.9 [M+H]⁺.

Step 2

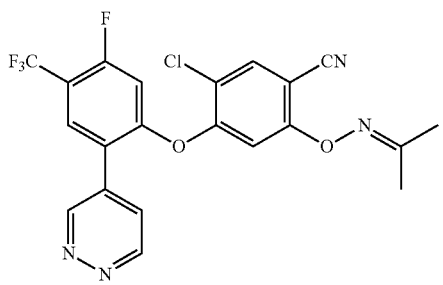 [SMILES: CC(C)=NOc1cc(Oc2cc(F)c(C(F)(F)F)cc2-c2ccnnc2)c(Cl)cc1C#N]

5-chloro-4-(5-fluoro-2-(pyridazin-4-yl)-4-(trifluoromethyl)phenoxy)-2-(propan-2-ylideneaminooxy)benzonitrile To a solution of potassium tert-butanolate (9.0 mg, 0.080 mmol) in THF (1 mL) was added acetone oxime (6.0 g, 0.080 mmol) in one portion. After stirring at room temperature for 20 min, 5-chloro-2-fluoro-4-(5-fluoro-2-(pyridazin-4-yl)-4-(trifluoromethyl)phenoxy)benzonitrile (30 mg, 0.073 mmol) was added slowly and the mixture was stirred at 60° C. overnight. The reaction was quenched by water (1 mL) then partitioned between saturated NaHCO₃ solution (5 mL) and ethyl acetate (20 mL). The organic layer was washed with water (5 mL×3) and concentrated to give 5-chloro-4-(5-fluoro-2-(pyridazin-4-yl)-4-(trifluoromethyl)phenoxy)-2-(propan-2-ylideneaminooxy)benzonitrile (30 mg, crude) as a solid which was used in the next step without further purification. LCMS (ESI) m/z: 465.0 [M+H]⁺.

Step 3

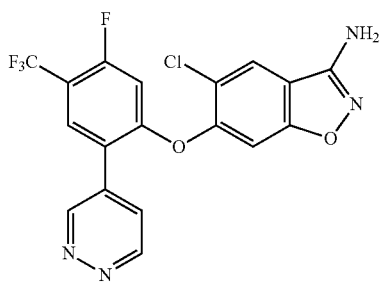 [SMILES: Nc1noc2cc(Oc3cc(F)c(C(F)(F)F)cc3-c3ccnnc3)c(Cl)cc12]

5-chloro-6-(5-fluoro-2-(pyridazin-4-yl)-4-(trifluoromethyl)phenoxy)benzo[d]isoxazol-3-amine The crude 5-chloro-4-(5-fluoro-2-(pyridazin-4-yl)-4-(trifluoromethyl)phenoxy)-2-(propan-2-ylideneaminooxy)benzonitrile (30 mg, 0.064 mmol) was treated with a mixture of EtOH (1 mL), H₂O (0.7 mL) and HCl (12 N, 0.3 mL) then heated to reflux for 2 h. After cooling to room temperature, the reaction mixture was basified with solid sodium carbonate and NaOH (1N). The mixture was extracted with ethyl acetate (5 mL×3) and the combined organic layers were washed with brine (10 mL), dried over anhydrous sodium sulfate, filtered and concentrated. The residue was purified by CombiFlash (0-60% CH₃CN/H₂O in 0.1% NH₄HCO₃) to afford 5-chloro-6-(5-fluoro-2-(pyridazin-4-yl)-4-(trifluoromethyl)phenoxy)benzo[d]isoxazol-3-amine (20 mg, 74%) as a white solid. LCMS (ESI): m/z: 424.9 [M+H]⁺.

Step 4

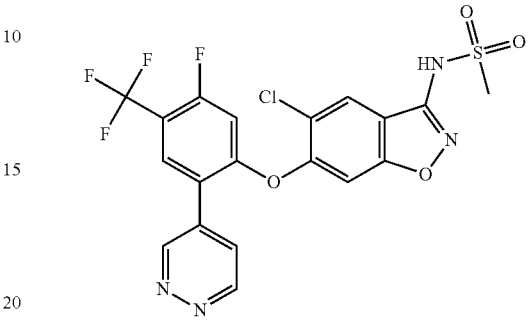

N-(5-chloro-6-(5-fluoro-2-(pyridazin-4-yl)-4-(trifluoromethyl)phenoxy)benzo[d]-isoxazol-3-yl)methanesulfonamide To a solution of 5-chloro-6-(5-fluoro-2-(pyridazin-4-yl)-4-(trifluoromethyl)phenoxy)-benzo[d]isoxazol-3-amine (20 mg, 0.047 mmol) in DCM (2 mL) was added methanesulfonyl chloride (8 mg, 0.07 mmol) and triethylamine (14 mg, 0.14 mmol). After stirring at room temperature for 2 h, the solvent was removed in vacuo and the crude product was dissolved in THF/CH₃OH (2 mL/0.5 mL) then aqueous sodium hydroxide (0.5 mL, 1.0 M) was added. After stirring at 25° C. overnight, the mixture was acidified with HCl and extracted with EtOAc (10 mL×3). The combined organic layers were washed with brine (10 mL), dried over anhydrous sodium sulfate, filtered and concentrated. The residue was purified by CombiFlash (0-55% CH₃CN/H₂O in 0.1% formic acid) to afford N-(5-chloro-6-(5-fluoro-2-(pyridazin-4-yl)-4-(trifluoromethyl)-phenoxy)benzo[d]isoxazol-3-yl)methanesulfonamide (4 mg, 17%) as a dark yellow solid. LCMS (ESI) Method A: RT=4.72 min, m/z: 503.0 [M+H]⁺. ¹H-NMR (500 MHz, DMSO-d₆): δ 9.61 (s, 1H), 9.38 (d, J=2.0 Hz, 1H), 8.13 (d, J=7.5 Hz, 1H), 8.06 (s, 1H), 7.86 (s, 1H), 7.65 (s, 1H), 7.14 (d, J=11.0 Hz, 1H), 2.97 (s, 3H).

Example 36

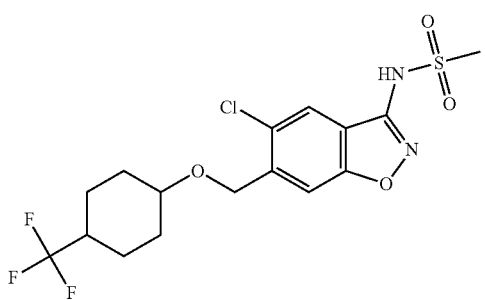 [SMILES: CS(=O)(=O)Nc1noc2cc(COC3CCC(C(F)(F)F)CC3)c(Cl)cc12]

N-(5-chloro-6-((4-(trifluoromethyl)cyclohexyloxy)methyl)benzo[d]isoxazol-3-yl)-methanesulfonamide Synthetic scheme

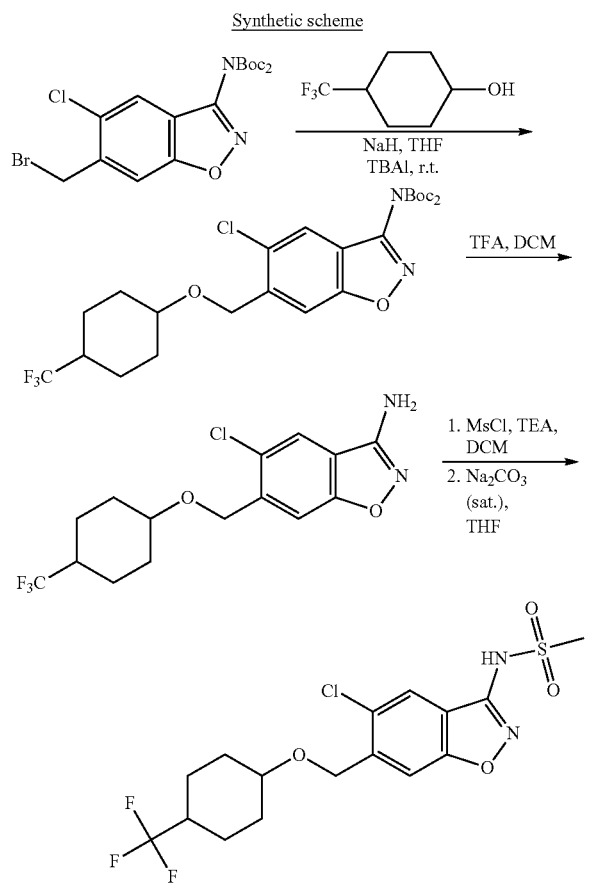

Step 1

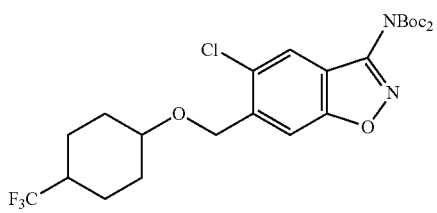

tert-butyl N-[(tert-butoxy)carbonyl]-N-[5-chloro-6-({[4-(trifluoromethyl)-cyclohexyl]oxy}methyl)-1,2-benzoxazol-3-yl]carbamate To a solution of 4-(trifluoromethyl)cyclohexanol (37 mg, 0.22 mmol) in dry THF (1 mL) was added sodium hydride (60%, 10 mg, 0.24 mmol) at 0° C. After stirring at 0° C. for 1 h, the resulting mixture was added slowly to a mixture of tert-butyl N-[6-(bromomethyl)-5-chloro-1,2-benzoxazol-3-yl]-N-[(tert-butoxy)carbonyl]carbamate (100 mg, 0.22 mmol) and tetrabutylammonium iodide (1 mg) in dry THF (0.5 mL). The reaction mixture was stirred at room temperature for 16 h, quenched by saturated NH₄Cl (5 mL) and extracted with ethyl acetate (5 mL×3). The combined organic layers were washed with brine, dried over MgSO₄, filtered and concentrated in vacuo. The residue was purified by SGC (eluting with petroleum ether/EtOAc=50/1) to afford the target compound as a pale yellow solid (66 mg, 55%). LCMS (ESI) m/z: 448.0 [M-100]⁺.

Step 2

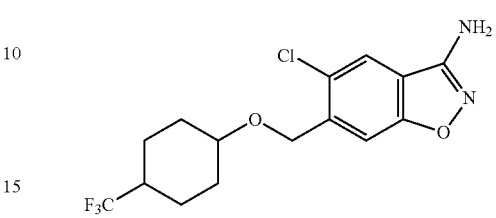

5-chloro-6-((4-(trifluoromethyl)cyclohexyloxy)methyl)benzo[d]isoxazol-3-amine

To a solution of N-[(tert-butoxy)carbonyl]-N-[5-chloro-6-({[4-(trifluoromethyl)-cyclohexyl]oxy}methyl)-1,2-benzoxazol-3-yl]carbamate (66 mg, 0.12 mmol) in DCM (1 mL) was added trifluoroacetic acid (0.2 mL). After stirring at room temperature for 2 h, the solvent was removed in vacuo and the residue was used for next step without further purification. LCMS (ESI) m/z: 347.0 [M−H]⁻.

Step 3

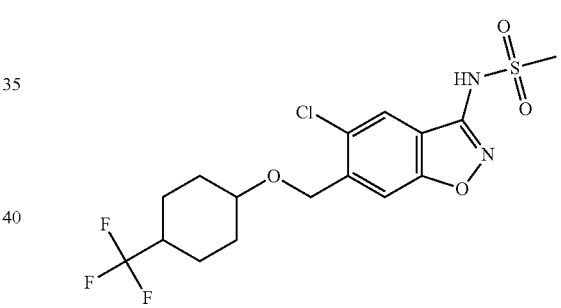

N-(5-chloro-6-((4-(trifluoromethyl)cyclohexyloxy)methyl)benzo[d]isoxazol-3-yl)methanesulfonamide Methanesulfonyl chloride (8 mg, 0.07 mmol) was added dropwise to a solution of 5-chloro-6-((4-(trifluoromethyl)cyclohexyloxy)methyl)benzo[d]isoxazol-3-amine (20 mg, 0.06 mmol) and triethylamine (15 mg, 0.14 mmol) in DCM (1 mL) at 0° C. After stirring at room temperature for 2 h, the solvent was removed in vacuo and the residue was dissolved in THF (1 mL) and NaOH (1 M, 0.5 mL). The resulting mixture was stirred at room temperature for 2 h then HCl (1M) was added to adjust pH to 6; the reaction mixture was diluted with ethyl acetate (15 mL), washed with water (3 mL) and brine (3 mL), dried over Na₂SO₄, filtered and concentrated. The residue was purified by reverse phase combiflash (20%-50% MeCN/H₂O in 0.1% NH₄HCO₃) to afford the target compound (17 mg, 65%) as a white solid. LCMS (ESI) Method A: RT=5.19 min, m/z: 426.9 [M+H]⁺. ¹H-NMR (500 MHz, MeOD-d₄): δ 7.88-7.87 (m, 1H), 7.72-7.70 (m, 1H), 4.77-4.71 (m, 2H), 3.85-3.50 (m, 1H), 3.26 (s, 3H), 2.30-1.41 (m, 9H).

Example 37

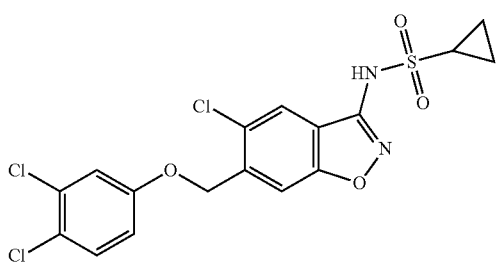 [SMILES: O=S(=O)(Nc1noc2cc(COc3ccc(Cl)c(Cl)c3)c(Cl)cc12)C1CC1]

N-(5-chloro-6-((3,4-dichlorophenoxy)methyl)benzo[d]isoxazol-3-yl)cyclopropane-sulfonamide To a mixture of 5-chloro-6-((3,4-dichlorophenoxy)methyl)benzo[d]isoxazol-3-amine (15 mg, 0.044 mmol) in dry THF at −78° C. was added LiHMDS (0.05 mL, 1M). After stirring at −78° C. for 10 min, cyclopropanesulfonyl chloride (12 mg, 0.088 mmol) was added and the mixture was stirred for additional 3 h at room temperature. The reaction was quenched by water (2 mL), filtered and purified by reverse phase Combiflash (30%-50% MeCN/H$_2$O in 0.1% NH$_4$HCO$_3$) to afford the target compound (3.3 mg, 17%) as a white solid. LCMS (ESI) Method A: RT=5.58 min, m/z: 448.9 [M+H]$^+$. $^1$H-NMR (500 MHz, CDCl$_3$): δ 7.76 (s, 1H), 7.48 (s, 1H), 7.34 (d, J=9.0 Hz, 1H), 7.15 (d, J=2.5 Hz, 1H), 6.93-6.90 (m, 1H), 5.15 (s, 2H), 1.20 (m, 1H), 1.03-1.02 (m, 2H), 0.80-0.78 (m, 2H).

Example 38

Electrophysiological Assay (In Vitro Assay)

Patch voltage clamp electrophysiology allows for the direct measurement and quantification of block of voltage-gated sodium channels (Nav's), and allows the determination of the time- and voltage-dependence of block which has been interpreted as differential binding to the resting, open, and inactivated states of the sodium channel (Hille, B., Journal of General Physiology (1977), 69: 497-515).

The following patch voltage clamp electrophysiology studies were performed on representative compounds of the invention using human embryonic kidney cells (HEK), permanently transfected with an expression vector containing the full-length cDNA coding for the desired human sodium channel α-subunit, grown in culture media containing 10% FBS, 1% PSG, and 0.5 mg/mL G418 at 37° C. with 5% CO2. HEK cells used for the electrophysiology (EP) recordings had a passage number of less than 40 for all studies and were used within three days from the time of plating. NaV1.7 and NaV1.5 cDNAs (NM_002977 and AC137587; SCN5A, respectively) were stably expressed in HEK-293 cells. The β1 subunit was coexpressed in both the NaV1.7 and NaV1.5 cell lines.

Sodium currents were measured using the patch clamp technique in the whole-cell configuration using either a PatchXpress automated voltage clamp or manually using an Axopatch 200B (Axon Instruments) or Model 2400 (A-M systems) amplifier. The manual voltage clamp protocol was as follows: Borosilicate glass micropipettes were fire-polished to a tip diameter yielding a resistance of 2-4 Mohms in the working solutions. The pipette was filled with a solution comprised of 5 mM NaCl, 10 mM CsCl, 120 mM CsF, 0.1 mM CaCl2, 2 mM MgCl2, 10 mM HEPES, 10 mM EGTA; and adjusted to pH 7.2 with CsOH. The external solution had the following composition: 140 mM NaCl, 5 mM KCl, 2 mM CaCl2, 1 mM MgCl2, 10 mM HEPES; and adjusted to pH 7.4 with NaOH. In some studies, the external sodium was reduced by equimolar replacement with choline. Osmolarity in the CsF internal and NaCl external solutions was adjusted to 300 mOsm/kg and 310 mOsm/kg with glucose, respectively. All recordings were performed at ambient temperature in a bath chamber with a volume of 150 μL. Control sodium currents were measured in 0.5% DMSO. Controls and representative compounds of the invention were applied to the recording chamber through a 4-pinch or 8-pinch valve bath perfusion system manufactured by ALA Scientific Instruments.

Currents were recorded at 40 kHz sampling frequency, filtered at 5 Hz, and stored using a Digidata-1322A analogue/digital interface with the pClamp software (Axon Instruments). Series resistance compensation was applied (60-80%). Cells were rejected if currents showed inadequate voltage control (as judged by the IV relationship during stepwise activation). All statistics in this study are given as mean±SD.

The membrane potential was maintained at a voltage where inactivation of the channel is complete (which was −60 mV for both NaV1.7 and NaV1.5). The voltage is then stepped back to a very negative (Vhold=150 mV) voltage for 20 ms and then a test pulse is applied to quantify the compound block. The 20 ms brief repolarization was long enough for compound-free channels to completely recover from fast inactivation, but the compound-bound channels recovered more slowly such that negligible recovery could occur during this interval. The percent decrease in sodium current following wash-on of compound was taken as the percent block of sodium channels.

Compounds of the invention, when tested in this model, demonstrated affinities for the inactivated state of NaV1.7 and NaV1.5 as set forth below in Table 1.

TABLE 1

| No | Structure | Name | EP_PX 293 hNav1.7 (IC50) |
|---|---|---|---|
| 1 | 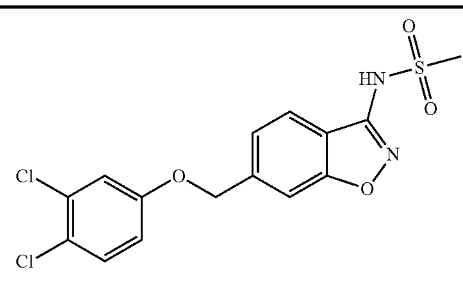 | N-[6-[(3,4-dichlorophenoxy)methyl]-1,2-benzoxazol-3-yl]methanesulfonamide | |

TABLE 1-continued

| No | Structure | Name | EP_PX 293 hNav1.7 (IC50) |
|---|---|---|---|
| 2 | 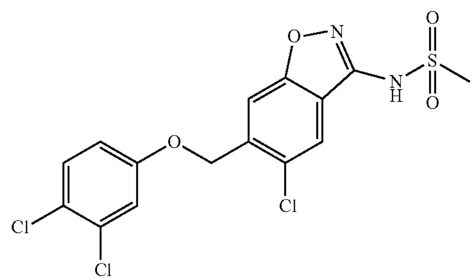 [SMILES: CS(=O)(=O)Nc1noc2cc(COc3ccc(Cl)c(Cl)c3)c(Cl)cc12] | N-[5-chloro-6-[(3,4-dichlorophenoxy)methyl]-1,2-benzoxazol-3-yl]methanesulfonamide | 0.0056 |
| 3 | 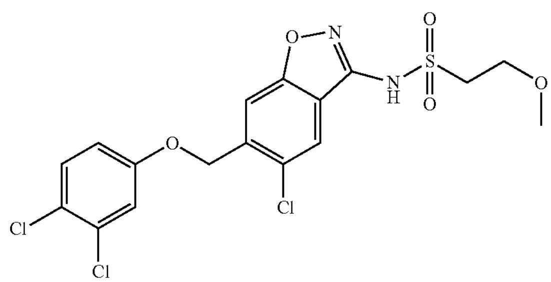 [SMILES: COCCS(=O)(=O)Nc1noc2cc(COc3ccc(Cl)c(Cl)c3)c(Cl)cc12] | N-[5-chloro-6-[(3,4-dichlorophenoxy)methyl]-1,2-benzoxazol-3-yl]-2-methoxy-ethanesulfonamide | |
| 4 | 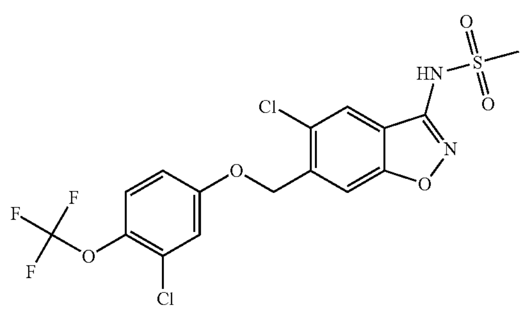 [SMILES: CS(=O)(=O)Nc1noc2cc(COc3ccc(OC(F)(F)F)c(Cl)c3)c(Cl)cc12] | N-[5-chloro-6-[[3-chloro-4-(trifluoromethoxy)phenoxy]methyl]-1,2-benzoxazol-3-yl]methanesulfonamide | |
| 5 | 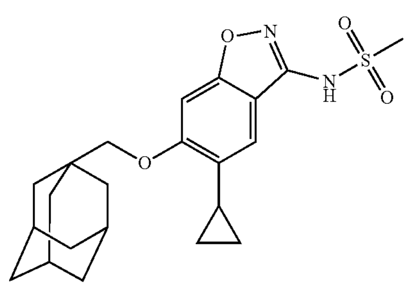 [SMILES: CS(=O)(=O)Nc1noc2cc(OCC34CC5CC(CC(C5)C3)C4)c(C3CC3)cc12] | N-[6-(1-adamantylmethoxy)-5-cyclopropyl-1,2-benzoxazol-3-yl]methanesulfonamide | 0.0010 |
| 6 | 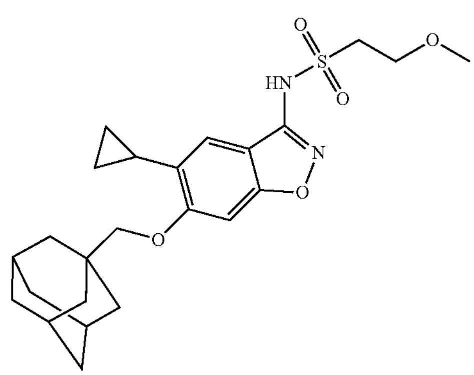 [SMILES: COCCS(=O)(=O)Nc1noc2cc(OCC34CC5CC(CC(C5)C3)C4)c(C3CC3)cc12] | N-[6-(1-adamantylmethoxy)-5-cyclopropyl-1,2-benzoxazol-3-yl]-2-methoxy-ethanesulfonamide | |

TABLE 1-continued

| No | Structure | Name | EP_PX 293 hNav1.7 (IC50) |
|---|---|---|---|
| 7 | 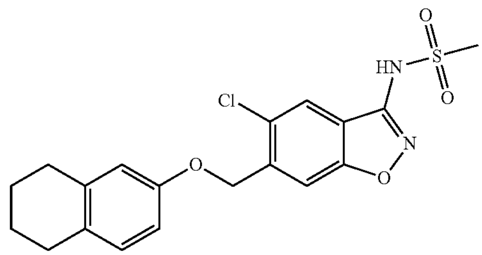 [SMILES: CS(=O)(=O)Nc1noc2cc(COc3ccc4c(c3)CCCC4)c(Cl)cc12] | N-[5-chloro-6-(tetralin-6-yloxymethyl)-1,2-benzoxazol-3-yl]methanesulfonamide | |
| 8 | 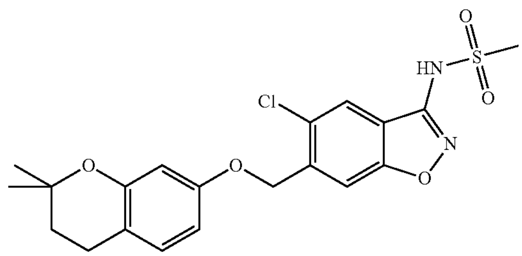 | N-[5-chloro-6-[(2,2-dimethylchroman-7-yl)oxymethyl]-1,2-benzoxazol-3-yl]methanesulfonamide | |
| 9 | 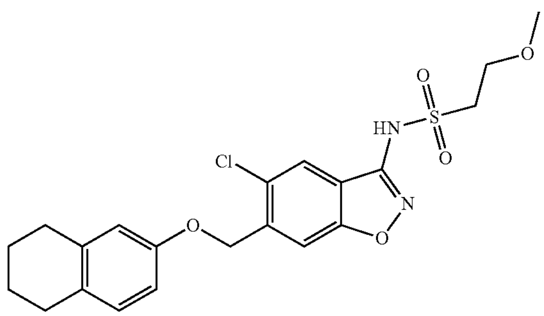 [SMILES: COCCS(=O)(=O)Nc1noc2cc(COc3ccc4c(c3)CCCC4)c(Cl)cc12] | N-[5-chloro-6-(tetralin-6-yloxymethyl)-1,2-benzoxazol-3-yl]-2-methoxy-ethanesulfonamide | |
| 10 | 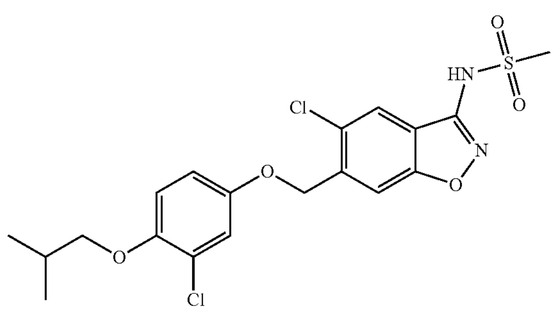 [SMILES: CC(C)COc1ccc(OCc2cc3onc(NS(C)(=O)=O)c3cc2Cl)cc1Cl] | N-[5-chloro-6-[(3-chloro-4-isobutoxy-phenoxy)methyl]-1,2-benzoxazol-3-yl]methanesulfonamide | 0.086 |
| 11 | 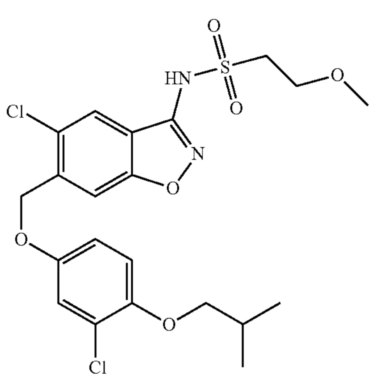 [SMILES: COCCS(=O)(=O)Nc1noc2cc(COc3ccc(OCC(C)C)c(Cl)c3)c(Cl)cc12] | N-[5-chloro-6-[(3-chloro-4-isobutoxy-phenoxy)methyl]-1,2-benzoxazol-3-yl]-2-methoxy-ethanesulfonamide | 0.002 |

TABLE 1-continued

| No | Structure | Name | EP_PX 293 hNav1.7 (IC50) |
|---|---|---|---|
| 12 | 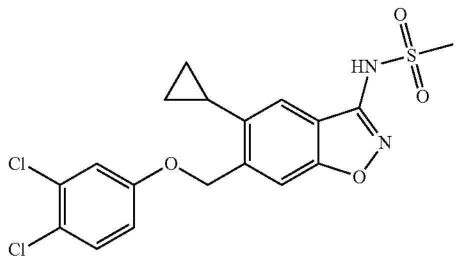 [SMILES: CS(=O)(=O)Nc1noc2cc(COc3ccc(Cl)c(Cl)c3)c(C3CC3)cc12] | N-[5-cyclopropyl-6-[(3,4-dichlorophenxy)methyl]-1,2-benzoxazol-3-yl]methanesulfonamide | |
| 13 | 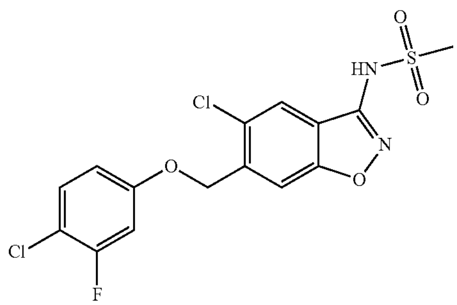 [SMILES: CS(=O)(=O)Nc1noc2cc(COc3ccc(Cl)c(F)c3)c(Cl)cc12] | N-[5-chloro-6-[(4-chloro-3-fluoro-phenoxy)methyl]-1,2-benzoxazol-3-yl]methanesulfonamide | |
| 14 | 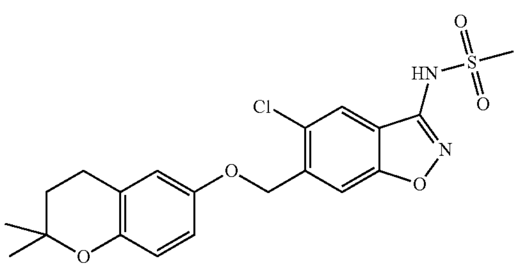 | N-[5-chloro-6-[(2,2-dimethylchroman-6-yl)oxymethyl]-1,2-benzoxazol-3-yl]methanesulfonamide | |
| 15 | 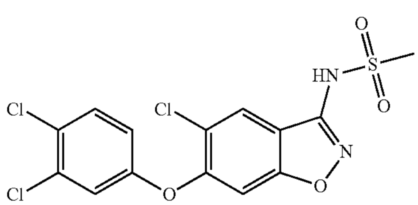 [SMILES: CS(=O)(=O)Nc1noc2cc(Oc3ccc(Cl)c(Cl)c3)c(Cl)cc12] | N-[5-chloro-6-(3,4-dichlorophenoxy)-1,2-benzoxazol-3-yl]methanesulfonamide | |
| 16 | 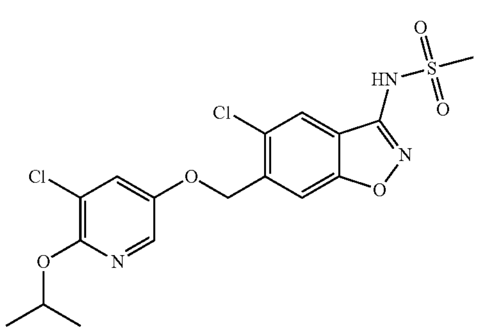 [SMILES: CC(C)Oc1ncc(OCc2cc3onc(NS(C)(=O)=O)c3cc2Cl)cc1Cl] | N-[5-chloro-6-[(5-chloro-6-isopropoxy-3-pyridyl)oxymethyl]-1,2-benzoxazol-3-yl]methanesulfonamide | 0.013 |

TABLE 1-continued

| No | Structure | Name | EP_PX 293 hNav1.7 (IC50) |
|---|---|---|---|
| 17 | 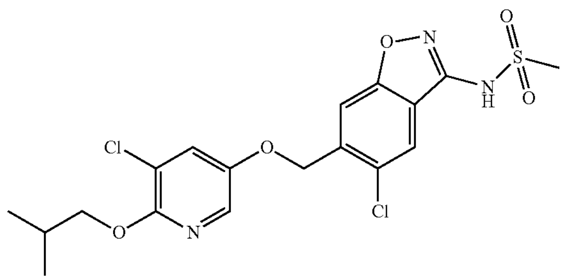 [SMILES: CC(C)COc1ncc(OCc2cc3onc(NS(C)(=O)=O)c3cc2Cl)cc1Cl] | N-[5-chloro-6-[(5-chloro-6-isobutoxy-3-pyridyl)oxymethyl]-1,2-benzoxazol-3-yl]methanesulfonamide | |
| 18 | 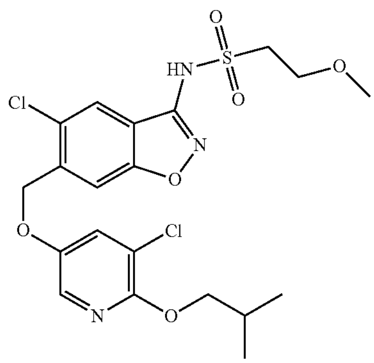 [SMILES: COCCS(=O)(=O)Nc1noc2cc(COc3cnc(OCC(C)C)c(Cl)c3)c(Cl)cc12] | N-[5-chloro-6-[(5-chloro-6-isobutoxy-3-pyridyl)oxymethyl]-1,2-benzoxazol-3-yl]-2-methoxyethanesulfonamide | |
| 19 | 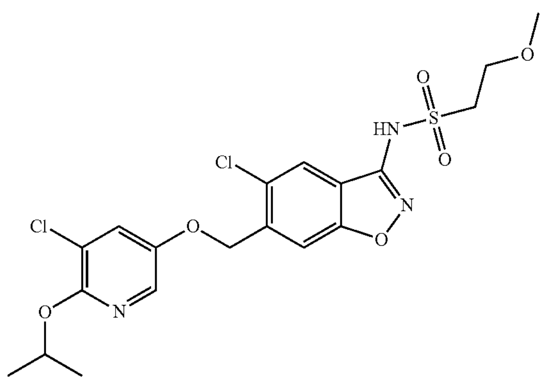 [SMILES: COCCS(=O)(=O)Nc1noc2cc(COc3cnc(OC(C)C)c(Cl)c3)c(Cl)cc12] | N-[5-chloro-6-[(5-chloro-6-isopropoxy-3-pyridyl)oxymethyl]-1,2-benzoxazol-3-yl]-2-methoxyethanesulfonamide | |
| 20 | 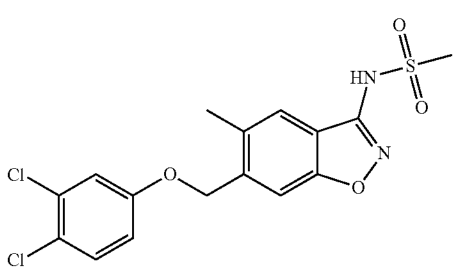 [SMILES: Cc1cc2c(NS(C)(=O)=O)noc2cc1COc1ccc(Cl)c(Cl)c1] | N-[6-[(3,4-dichlorophenoxy)methyl]-5-methyl-1,2-benzoxazol-3-yl]methanesulfonamide | |
| 21 | 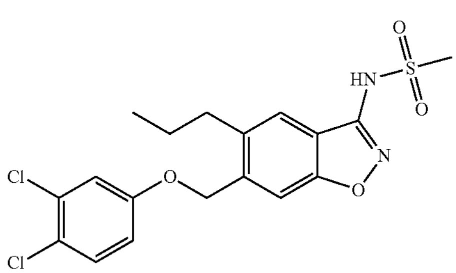 [SMILES: CCCc1cc2c(NS(C)(=O)=O)noc2cc1COc1ccc(Cl)c(Cl)c1] | N-[6-[(3,4-dichlorophenoxy)methyl]-5-propyl-1,2-benzoxazol-3-yl]methanesulfonamide | |

| No | Structure | Name | EP_PX 293 hNav1.7 (IC50) |
|---|---|---|---|
| 22 | 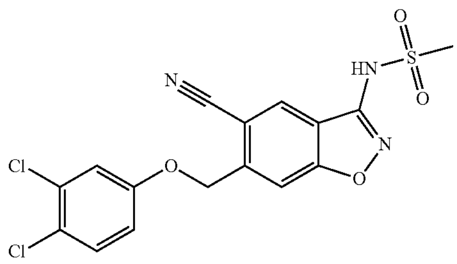 [SMILES: CS(=O)(=O)Nc1noc2cc(COc3ccc(Cl)c(Cl)c3)c(C#N)cc12] | N-[5-cyano-6-[(3,4-dichlorophenoxy)methyl]-1,2-benzoxazol-3-yl]methanesulfonamide | |
| 23 | 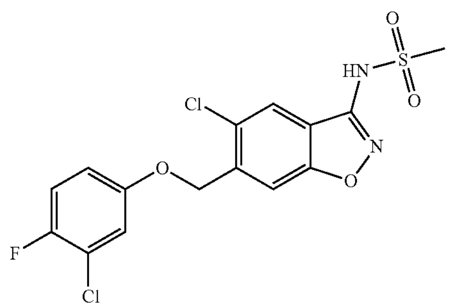 [SMILES: CS(=O)(=O)Nc1noc2cc(COc3ccc(F)c(Cl)c3)c(Cl)cc12] | N-[5-chloro-6-[(3-chloro-4-fluoro-phenoxy)methyl]-1,2-benzoxazol-3-yl]methanesulfonamide | |
| 24 | 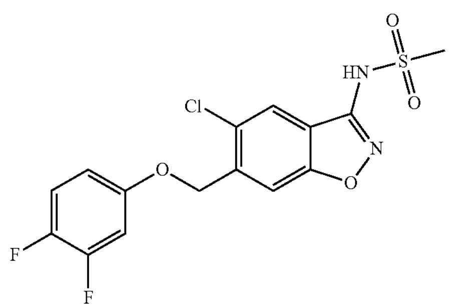 [SMILES: CS(=O)(=O)Nc1noc2cc(COc3ccc(F)c(F)c3)c(Cl)cc12] | N-[5-chloro-6-[(3,4-difluorophenoxy)methyl]-1,2-benzoxazol-3-yl]methanesulfonamide | |
| 25 | 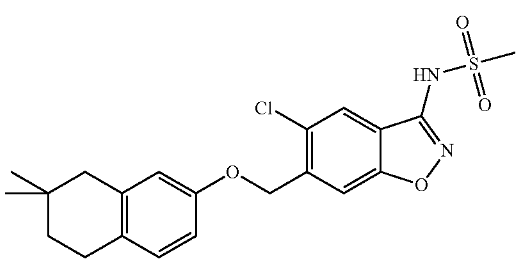 | N-[5-chloro-6-[(3,3-dimethyltetralin-6-yl)oxymethyl]-1,2-benzoxazol-3-yl]methanesulfonamide | 0.014 |
| 26 | 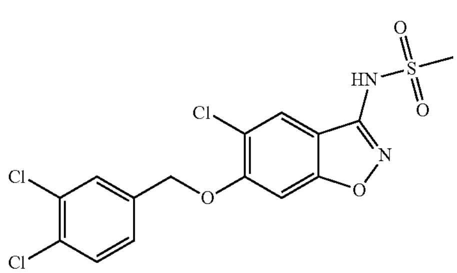 [SMILES: CS(=O)(=O)Nc1noc2cc(OCc3ccc(Cl)c(Cl)c3)c(Cl)cc12] | N-[5-chloro-6-[(3,4-dichlorophenyl)methoxy]-1,2-benzoxazol-3-yl]methanesulfonamide | 0.074 |

| No | Structure | Name | EP_PX 293 hNav1.7 (IC50) |
|---|---|---|---|
| 27 | 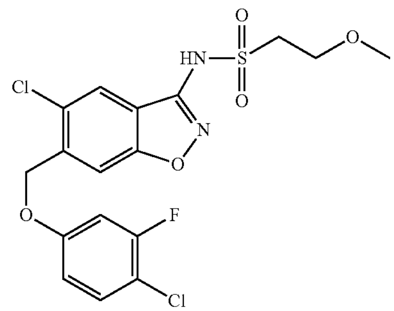 [SMILES: COCCS(=O)(=O)Nc1noc2cc(COc3ccc(Cl)c(F)c3)c(Cl)cc12] | N-[5-chloro-6-[(4-chloro-3-fluoro-phenoxy)methyl]-1,2-benzoxazol-3-yl]-2-methoxy-ethanesulfonamide | |
| 28 | 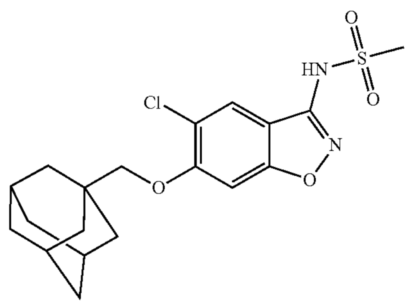 [SMILES: CS(=O)(=O)Nc1noc2cc(OCC34CC5CC(CC(C5)C3)C4)c(Cl)cc12] | N-[6-(1-adamantylmethoxy)-5-chloro-1,2-benzoxazol-3-yl]methanesulfonamide | |
| 29 | 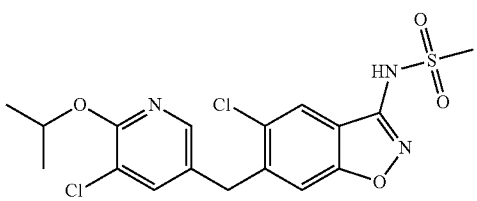 [SMILES: CC(C)Oc1ncc(Cc2cc3onc(NS(C)(=O)=O)c3cc2Cl)cc1Cl] | N-[5-chloro-6-[(5-chloro-6-isopropoxy-3-pyridyl)oxy]-1,2-benzoxazol-3-yl]methanesulfonamide | |
| 30 | 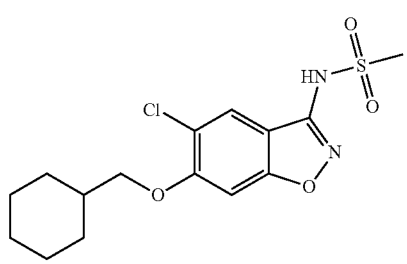 [SMILES: CS(=O)(=O)Nc1noc2cc(OCC3CCCCC3)c(Cl)cc12] | N-[5-chloro-6-(cyclohexylmethoxy)-1,2-benzoxazol-3-yl]methanesulfonamide | |
| 31 | 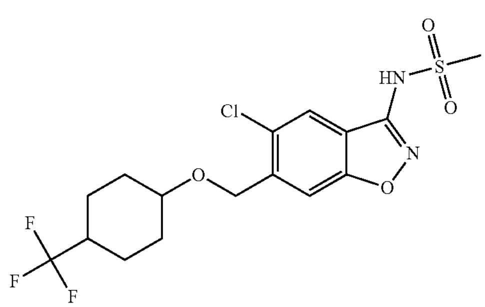 [SMILES: CS(=O)(=O)Nc1noc2cc(COC3CCC(C(F)(F)F)CC3)c(Cl)cc12] | N-[5-chloro-6-[[4-(trifluoromethyl)cyclohexoxy]methyl]-1,2-benzoxazol-3-yl]methanesulfonamide | |

TABLE 1-continued

| No | Structure | Name | EP_PX 293 hNav1.7 (IC50) |
|---|---|---|---|
| 32 | 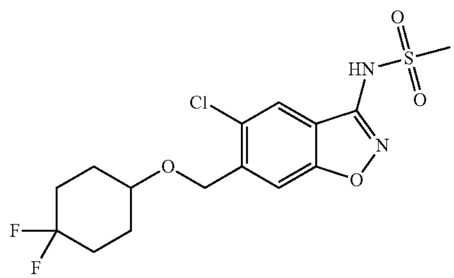 [SMILES: CS(=O)(=O)Nc1noc2cc(COC3CCC(F)(F)CC3)c(Cl)cc12] | N-[5-chloro-6-[(4,4-difluorocyclohexoxy)methyl]-1,2-bentoxazol-3-yl]methanesulfonamide | |
| 33 | 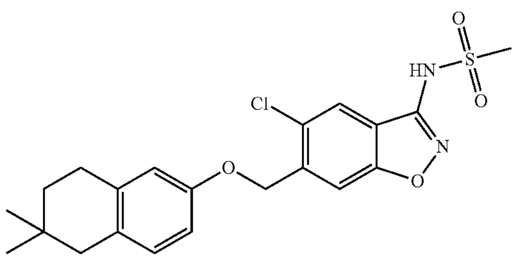 | N-[5-chloro-6-[(2,2-dimethyltetralin-6-yl)oxymethyl]-1,2-benzoxazol-3-yl]methanesulfonamide | 0.01 |
| 34 | 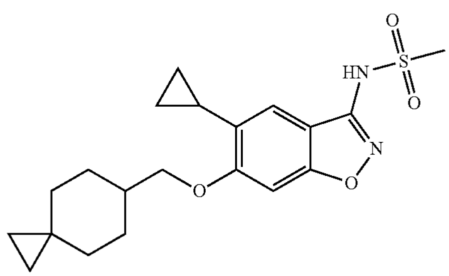 [SMILES: CS(=O)(=O)Nc1noc2cc(OCC3CCC4(CC3)CC4)c(C3CC3)cc12] | N-[5-cyclopropyl-6-(spiro[2.5]octan-6-ylmethoxy)-1,2-benzoxazol-3-yl]methanesulfonamide | |
| 35 | 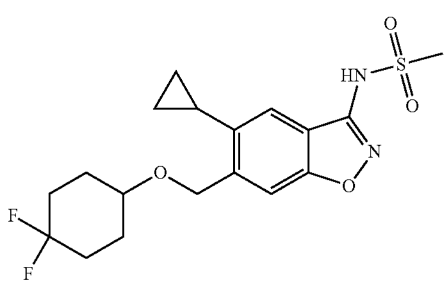 [SMILES: CS(=O)(=O)Nc1noc2cc(COC3CCC(F)(F)CC3)c(C3CC3)cc12] | N-[5-cyclopropyl-6-[(4,4-difluorocyclohexyl)methoxy]-1,2-benzoxazol-3-yl]methanesulfonamide | |
| 36 | 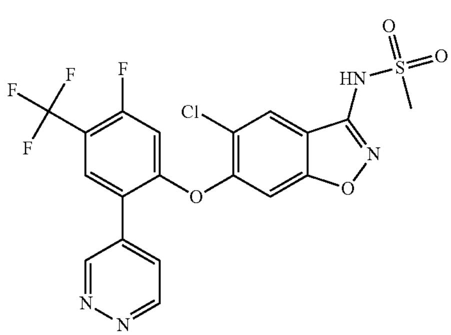 [SMILES: CS(=O)(=O)Nc1noc2cc(Oc3cc(F)c(C(F)(F)F)cc3-c3ccnnc3)c(Cl)cc12] | N-[5-chloro-6-[5-fluoro-2-pyridazin-4-yl-4-(trifluoromethyl)phenoxy]-1,2-benzoxazol-3-yl]methanesulfonamide | |

TABLE 1-continued

| No | Structure | Name | EP_PX 293 hNav1.7 (IC50) |
|---|---|---|---|
| 37 | 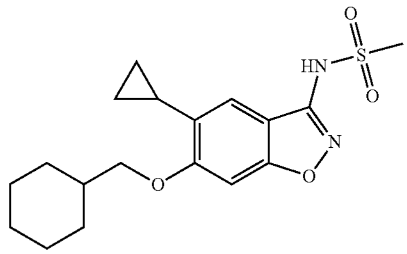 [SMILES: CS(=O)(=O)Nc1noc2cc(OCC3CCCCC3)c(C3CC3)cc12] | N-[6-(cyclohexylmethoxy)-5-cyclopropyl-1,2-benzoxazol-3-yl]methanesulfonamide | |
| 38 | 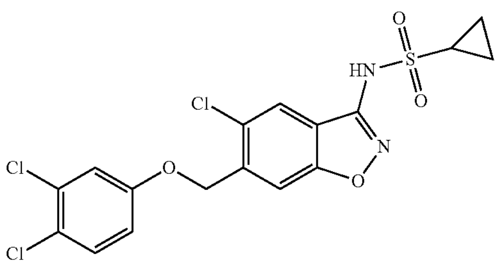 [SMILES: O=S(=O)(Nc1noc2cc(COc3ccc(Cl)c(Cl)c3)c(Cl)cc12)C1CC1] | N-[5-chloro-6-[(3,4-dichlorophenoxy)methyl]-1,2-benzoxazol-3-yl]cyclopropanesulfonamide | 0.003 |

Example 39

Analgesia Induced by Sodium Channel Blockers

Heat Induced Tail Flick Latency Test

In this test, the analgesia effect produced by administering a compound of the invention can be observed through heat-induced tail-flick in mice. The test includes a heat source consisting of a projector lamp with a light beam focused and directed to a point on the tail of a mouse being tested. The tail-flick latencies, which are assessed prior to drug treatment, and in response to a noxious heat stimulus, i.e., the response time from applying radiant heat on the dorsal surface of the tail to the occurrence of tail flick, are measured and recorded at 40, 80, 120, and 160 minutes.

For the first part of this study, 65 animals undergo assessment of baseline tail flick latency once a day over two consecutive days. These animals are then randomly assigned to one of the 11 different treatment groups including a vehicle control, a morphine control, and 9 compounds at 30 mg/Kg are administered intramuscularly. Following dose administration, the animals are closely monitored for signs of toxicity including tremor or seizure, hyperactivity, shallow, rapid or depressed breathing and failure to groom. The optimal incubation time for each compound is determined via regression analysis. The analgesic activity of the test compounds is expressed as a percentage of the maximum possible effect (% MPE) and is calculated using the following formula:

$$\% \; MPE \frac{\text{Postdrug latency} - \text{Predrug latency}}{\text{Cut-off time (10 s)} - \text{Predrug latency}} \times 100\%$$

where:

Postdrug latency=the latency time for each individual animal taken before the tail is removed (flicked) from the heat source after receiving drug.

Predrug latency=the latency time for each individual animal taken before the tail is flicked from the heat source prior to receiving drug.

Cut-off time (10 s)=is the maximum exposure to the heat source.

Acute Pain (Formalin Test)

The formalin test is used as an animal model of acute pain. In the formalin test, animals are briefly habituated to the plexiglass test chamber on the day prior to experimental day for 20 minutes. On the test day, animals are randomly injected with the test articles. At 30 minutes after drug administration, 50 µL of 10% formalin is injected subcutaneously into the plantar surface of the left hind paw of the rats. Video data acquisition begins immediately after formalin administration, for duration of 90 minutes.

The images are captured using the Actimetrix Limelight software which stores files under the *.llii extension, and then converts it into the MPEG-4 coding. The videos are then analyzed using behaviour analysis software "The Observer 5.1", (Version 5.0, Noldus Information Technology, Wageningen, The Netherlands). The video analysis is conducted by watching the animal behaviour and scoring each according to type, and defining the length of the behaviour (Dubuisson and Dennis, 1977). Scored behaviours include: (1) normal behaviour, (2) putting no weight on the paw, (3) raising the paw, (4) licking/biting or scratching the paw. Elevation, favoring, or excessive licking, biting and scratching of the injected paw indicate a pain response. Analgesic response or protection from compounds is indicated if both paws are resting on the floor with no obvious favoring, excessive licking, biting or scratching of the injected paw.

Analysis of the formalin test data is done according to two factors: (1) Percent Maximal Potential Inhibitory Effect (% MPIE) and (2) pain score. The % MPIEs is calculated by a series of steps, where the first is to sum the length of non-normal behaviours (behaviours 1, 2, 3) of each animal. A single value for the vehicle group is obtained by averaging all scores within the vehicle treatment group. The following calculation yields the MPIE value for each animal:

MPIE (%)=100−[(treatment sum/average vehicle value)×100%]

The pain score is calculated from a weighted scale as described above. The duration of the behaviour is multiplied by the weight (rating of the severity of the response), and divided by the total length of observation to determine a pain rating for each animal. The calculation is represented by the following formula:

$$\text{Pain rating} = [0(T0) + 1(T1) + 2(T2) + 3(T3)]/(T0 + T1 + T2 + T3)$$

CFA Induced Chronic Inflammatory Pain

In this test, tactile allodynia is assessed with calibrated von Frey filaments. Following a full week of acclimatization to the vivarium facility, 150 μL of the "Complete Freund's Adjuvant" (CFA) emulsion (CFA suspended in an oil/saline (1:1) emulsion at a concentration of 0.5 mg/mL) is injected subcutaneously into the plantar surface of the left hind paw of rats under light isoflurane anaesthesia. Animals are allowed to recover from the anaesthesia and the baseline thermal and mechanical nociceptive thresholds of all animals are assessed one week after the administration of CFA. All animals are habituated to the experimental equipment for 20 minutes on the day prior to the start of the experiment. The test and control articles are administrated to the animals, and the nociceptive thresholds measured at defined time points after drug administration to determine the analgesic responses to each of the six available treatments. The time points used are previously determined to show the highest analgesic effect for each test compound.

Thermal nociceptive thresholds of the animals are assessed using the Hargreaves test Animals are placed in a Plexiglas enclosure set on top of an elevated glass platform with heating units. The glass platform is thermostatically controlled at a temperature of approximately 30° C. for all test trials Animals are allowed to accommodate for 20 minutes following placement into the enclosure until all exploration behaviour ceases. The Model 226 Plantar/Tail Stimulator Analgesia Meter (IITC, Woodland Hills, Calif.) is used to apply a radiant heat beam from underneath the glass platform to the plantar surface of the hind paws. During all test trials, the idle intensity and active intensity of the heat source are set at 1 and 45 respectively, and a cut off time of 20 seconds is employed to prevent tissue damage.

The response thresholds of animals to tactile stimuli are measured using the Model 2290 Electrovonfrey anesthesiometer (IITC Life Science, Woodland Hills, Calif.) following the Hargreaves test. Animals are placed in an elevated Plexiglas enclosure set on a mire mesh surface. After 10 minutes of accommodation, pre-calibrated Von Frey hairs are applied perpendicularly to the plantar surface of both paws of the animals in an ascending order starting from the 0.1 g hair, with sufficient force to cause slight buckling of the hair against the paw. Testing continues until the hair with the lowest force to induce a rapid flicking of the paw is determined or when the cut off force of approximately 20 g is reached. This cut off force is used because it represent approximately 10% of the animals' body weight and it serves to prevent raising of the entire limb due to the use of stiffer hairs, which would change the nature of the stimulus.

Postoperative Models of Nociception

In this model, the hypealgesia caused by an intra-planar incision in the paw is measured by applying increased tactile stimuli to the paw until the animal withdraws its paw from the applied stimuli. While animals are anaesthetized under 3.5% isofluorane, which is delivered via a nose cone, a 1 cm longitudinal incision is made using a number 10 scalpel blade in the plantar aspect of the left hind paw through the skin and fascia, starting 0.5 cm from the proximal edge of the heel and extending towards the toes. Following the incision, the skin is apposed using 2, 3-0 sterilized silk sutures. The injured site is covered with Polysporin and Betadine. Animals are returned to their home cage for overnight recovery.

The withdrawal thresholds of animals to tactile stimuli for both operated (ipsilateral) and unoperated (contralateral) paws can be measured using the Model 2290 Electrovonfrey anesthesiometer (IITC Life Science, Woodland Hills, Calif.). Animals are placed in an elevated Plexiglas enclosure set on a mire mesh surface. After at least 10 minutes of acclimatization, pre-calibrated Von Frey hairs are applied perpendicularly to the plantar surface of both paws of the animals in an ascending order starting from the 10 g hair, with sufficient force to cause slight buckling of the hair against the paw. Testing continues until the hair with the lowest force to induce a rapid flicking of the paw is determined or when the cut off force of approximately 20 g is reached. This cut off force is used because it represent approximately 10% of the animals' body weight and it serves to prevent raising of the entire limb due to the use of stiffer hairs, which would change the nature of the stimulus.

Neuropathic Pain Model; Chronic Constriction Injury

Briefly, an approximately 3 cm incision is made through the skin and the fascia at the mid thigh level of the animals' left hind leg using a no. 10 scalpel blade. The left sciatic nerve is exposed via blunt dissection through the biceps femoris with care to minimize haemorrhagia. Four loose ligatures are tied along the sciatic nerve using 4-0 non-degradable sterilized silk sutures at intervals of 1 to 2 mm apart. The tension of the loose ligatures is tight enough to induce slight constriction of the sciatic nerve when viewed under a dissection microscope at a magnification of 4 fold. In the sham-operated animal, the left sciatic nerve is exposed without further manipulation. Antibacterial ointment is applied directly into the wound, and the muscle is closed using sterilized sutures. Betadine is applied onto the muscle and its surroundings, followed by skin closure with surgical clips.

The response thresholds of animals to tactile stimuli are measured using the Model 2290 Electrovonfrey anesthesiometer (IITC Life Science, Woodland Hills, Calif.). Animals are placed in an elevated Plexiglas enclosure set on a mire mesh surface. After 10 minutes of accommodation, pre-calibrated Von Frey hairs are applied perpendicularly to the plantar surface of both paws of the animals in an ascending order starting from the 0.1 g hair, with sufficient force to cause slight buckling of the hair against the paw. Testing continues until the hair with the lowest force to induce a rapid flicking of the paw is determined or when the cut off force of approximately 20 g is reached. This cut off force is used because it represents approximately 10% of the animals' body weight and it serves to prevent raising of the entire limb due to the use of stiffer hairs, which would change the nature of the stimulus.

Thermal nociceptive thresholds of the animals are assessed using the Hargreaves test. Following the measurement of tactile thresholds, animals are placed in a Plexiglass enclosure set on top of an elevated glass platform with heating units. The glass platform is thermostatically controlled at a temperature of approximately 24 to 26° C. for all test trials. Animals are allowed to accommodate for 10 minutes following placement into the enclosure until all exploration behaviour ceases. The Model 226 Plantar/Tail Stimulator Analgesia Meter (IITC, Woodland Hills, Calif.) is used to apply a radiant heat beam from underneath the glass platform to the plantar surface of the hind paws. During all test trials, the idle intensity and active intensity of the heat source are set at 1 and 55 respectively, and a cut off time of 20 seconds is used to prevent tissue damage.

Neuropathic Pain Model: Spinal Nerve Ligation

The spinal nerve ligation (SNL) neuropathic pain model is used as an animal (i.e. rat) model of neuropathic pain. In the SNL test, the lumbar roots of spinal nerves L5 and L6 are tightly ligated to cause nerve injury, which results in the development of mechanical hyperalgesia, mechanical allodynia and thermal hypersensitivity. The surgery is performed two weeks before the test day in order for the pain state to fully develop in the animals. Several spinal nerve ligation variations are used to characterize the analgesic properties of a compound of the invention.

Ligation of the L5 spinal nerve;
Ligation of the L5 and L6 spinal nerves;
Ligation and transection of the L5 spinal nerve;
Ligation and transection of the L5 and L6 spinal nerves; or
Mild irritation of the L4 spinal nerve in combination with any one of the above (1)-(4).

While the animals are anaesthetized under 3.5% isofluorane delivered via a nose cone, an approximately 2.5 cm longitudinal incision is made using a number 10 scalpel blade in the skin just lateral to the dorsal midline, using the level of the posterior iliac crests as the midpoint of the incision. Following the incision, the isoflourane is readjusted to maintenance levels (1.5%-2.5%). At mid-sacral region, an incision is made with the scalpel blade, sliding the blade along the side of the vertebral column (in the saggital plane) until the blade hits the sacrum. Scissors tips are introduced through the incision and the muscle and ligaments are removed from the spine to expose 2-3 cm of the vertebral column. The muscle and fascia are cleared from the spinal vertebra in order to locate the point where the nerve exits from the vertebra. A small glass hook is placed medial to the spinal nerves and the spinal nerves are gently elevated from the surrounding tissues. Once the spinal nerves have been isolated, a small length of non-degradable 6-0 sterilized silk thread is wound twice around the ball at the tip of the glass hook and passed back under the nerve. The spinal nerves are then firmly ligated by tying a knot, ensuring that the nerve bulges on both sides of the ligature. The procedure may be repeated as needed. In some animals, the L4 spinal nerve may be lightly rubbed (up to 20 times) with the small glass hook to maximize the development of neuropathic pain. Antibacterial ointment is applied directly into the incision, and the muscle is closed using sterilized sutures. Betadine is applied onto the muscle and its surroundings, followed by skin closure with surgical staples or sterile non-absorbable monofilament 5-0 nylon sutures.

The analgesic effect produced by topical administration of a compound of the invention to the animals can then be observed by measuring the paw withdrawal threshold of animals to mechanical tactile stimuli. These may be measured using either the mechanical allodynia procedure or the mechanical hyperalgesia procedure as described below. After establishment of the appropriate baseline measurements by either method, topical formulation of a compound of the invention is applied on the ipsilateral ankle and foot. The animals are then placed in plastic tunnels for 15 minutes to prevent them from licking the treated area and removing the compound. Animals are placed in the acrylic enclosure for 15 minutes before testing the ipsilateral paw by either of the methods described below, and the responses are recorded at 0.5, 1.0 and 2.0 hour post treatment.

A. Mechanical Allodynia Method

The pain threshold of animals to mechanical alloydnia for both operated and control animals can be measured approximately 14 days post-surgery using manual calibrated von Frey filaments as follows. Animals are placed in an elevated plexiglass enclosure set on a mire mesh surface. Animals are allowed to acclimate for 20-30 minutes. Pre-calibrated Von Frey hairs are applied perpendicularly to the plantar surface of the ipsilateral paw of the animals starting from the 2.0 g hair, with sufficient force to cause slight buckling of the hair against the paw to establish the baseline measurements. Stimuli are presented in a consecutive manner, either in an ascending or descending order until the first change in response is noted, after which four additional responses are recorded for a total of six responses. The six responses measured in grams are entered into a formula as described by Chaplan, S. R. et al., J. Neurosci. Methods, 1994 July; 53(1):55-63, and a 50% withdrawal threshold is calculated. This constitutes the mechanical allodynia value.

B. Mechanical Hyperalgesia Method

The response thresholds of animals to tactile stimuli were measured using the Model 2290 Electrovonfrey anesthesiometer (IITC Life Science, Woodland Hills, Calif.) Animals were placed in an elevated Plexiglas enclosure set on a wire mesh surface. After 15 minutes of accommodation in this enclosure, a von Frey hair was applied perpendicularly to the plantar surface of the ipsilateral hind paws of the animals, with sufficient force, measured in grams, to elicit a crisp response of the paw. The response indicated a withdrawal from the painful stimulus and constituted the efficacy endpoint. The data were expressed as percent change from baseline threshold measured in grams.

Example 40

In Vivo Assay for Treatment of Pruritis

The compounds of the invention can be evaluated for their activity as antipruritic agents by in vivo test using rodent models. One established model for peripherally elicited pruritus is through the injection of serotonin into the rostral back area (neck) in hairless rats. Prior to serotonin injections (e.g., 2 mg/mL, 50 µL), a dose of a compound of the present invention can be applied systemically through oral, intravenous or intraperitoneal routes or topically to a circular area fixed diameter (e.g. 18 mm) Following dosing, the serotonin injections are given in the area of the topical dosing. After serotonin injection the animal behaviour is monitored by video recording for 20 min-1.5 h, and the number of scratches in this time compared to vehicle treated animals. Thus, application of a compound of the current invention could suppress serotonin-induced scratching in rats.

All of the U.S. patents, U.S. patent application publications, U.S. patent applications, foreign patents, foreign patent applications and non patent publications referred to in this specification (including PCT/CN2013/072689) are incorporated herein by reference in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

We claim:
1. A compound of Formula I:

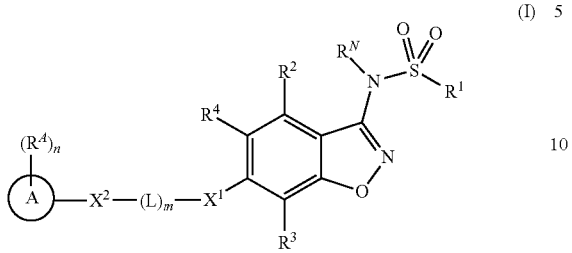

or a pharmaceutically acceptable salt thereof, wherein:
$R^1$ is $C_{1-8}$ alkyl, $C_{1-8}$ haloalkyl, $C_{1-8}$ alkoxy, $C_{3-12}$ carbocycle, C-linked $C_{2-11}$ heterocycle or $-NR^{1A}R^{1B}$, wherein $R^{1A}$ and $R^{1B}$ are each independently selected from the group consisting of hydrogen, $C_{1-8}$ alkyl, $C_{1-8}$ alkoxy, (6-10 membered aryl)-$(X^{R1})_{0-1}$—, and 5-10 membered heteroaryl)-$(X^{R1})_{0-1}$—, and wherein $R^{1A}$ and $R^{1B}$ are optionally combined to form a 3 to 8 membered heterocyclic ring optionally comprising 1 additional heteroatoms selected from N, O and S as ring vertex and optionally fused thereto is a benzene or pyridine ring; $X^{R1}$ is selected from the group consisting of $C_{1-4}$ alkylene, $C_{1-4}$ heteroalkylene, $C_{2-4}$ alkenylene, and $C_{2-4}$ alkynylene; and wherein the aliphatic and aromatic portions of $R^1$ are optionally substituted with from 1 to 5 $R^{R1}$ substituents selected from the group consisting of $C_{1-8}$ alkyl, $C_{1-8}$ haloalkyl, oxo (=O), F, Cl, Br, I, —OH, —CN, —NO$_2$, $-(X^{1R})_{0-1}-NR^{R1a}R^{R1b}$, $-(X^{1R})_{0-1}OR^{R1a}$, $-(X^{1R})_{0-1}SR^{R1a}$, $-(X^{1R})_{0-1}N(R^{R1a})C(=O)OR^{R1c}$, $-(X^{1R})_{0-1}OC(=O)N(R^{R1a})(R^{R1b})$, $-(X^{1R})_{0-1}N(R^{R1a})C(=O)N(R^{R1a})(R^{R1b})$, $-(X^{1R})_{0-1}C(=O)N(R^{R1a})(R^{R1b})$, $-(X^{1R})_{0-1}N(R^{R1a})C(=O)R^{R1b}$, $-(X^{1R})_{0-1}C(=O)OR^{R1a}$, $-(X^{1R})_{0-1}OC(=O)R^{R1a}$, $-(X^{1R})_{0-1}P(=O)(OR^{R1a})(R^{R1b})$, $-(X^{1R})_{0-1}S(O)_{1-2}R^{R1c}$, $-(X^{1R})_{0-1}S(O)_{1-2}N(R^{R1a})(R^{R1b})$, $-(X^{1R})_{0-1}N(R^{R1a})S(O)_{1-2}N(R^{R1a})(R^{R1b})$ and $-(X^{1R})_{0-1}N(R^{R1a})S(O)_{1-2}(R^{R1c})$, wherein $X^{1R}$ is selected from the group consisting of $C_{1-4}$ alkylene, $C_{1-4}$ heteroalkylene, $C_{2-4}$ alkenylene and $C_{2-4}$ alkynylene; wherein $R^{R1a}$ and $R^{R1b}$ are independently selected from the group consisting of hydrogen, $C_{1-8}$ alkyl, $C_{1-8}$ haloalkyl, $C_{3-8}$ carbocycle, phenyl, benzyl, $C_{5-6}$ heteroaryl and $C_{2-7}$ heterocycle; $R^{R1c}$ is selected from the group consisting of $C_{1-8}$ alkyl, $C_{1-8}$ haloalkyl, $C_{3-8}$ carbocycle, phenyl, benzyl, $C_{5-6}$ heteroaryl and $C_{2-7}$ heterocycle;
$R^N$ is hydrogen, $C_{1-4}$ alkyl or $C_{1-4}$ haloalkyl;
$R^2$ and $R^3$ are each independently selected from the group consisting of H, F, Cl, Br, I, —CN, $C_{1-8}$ alkyl, $C_{1-8}$ haloalkyl and $C_{1-8}$ alkoxy;
$R^4$ is selected from the group consisting of H, F, Cl, Br, I, —CN, $C_{1-8}$ alkyl, $C_{1-8}$ haloalkyl, $C_{1-8}$ alkoxy, $C_{3-8}$ carbocycle, $C_{2-7}$ heterocycle, phenyl and 5-6 membered heteroaryl comprising 1 to 3 heteroatoms selected from N, O and S, wherein said 5-6 membered heteroaryl is further optionally substituted with from 1 to 3 $R^5$ substituents selected from F, Cl, Br, I, —CN, $C_{1-4}$ alkyl, $C_{1-4}$ haloalkyl and $C_{1-4}$ alkoxy;
L is a linker selected from the group consisting of $C_{1-4}$ alkylene, $C_{2-4}$ alkenylene, $C_{2-4}$ alkynylene, and $C_{1-4}$ heteroalkylene, wherein L is optionally substituted with from 1 to 3 $R^L$ substituents selected from the group consisting of =O, $C_{1-4}$ alkyl, $C_{1-4}$ haloalkyl and $C_{1-4}$ acyl;

the subscript m represents the integer 0 or 1;
$X^1$ and $X^2$ are each independently selected from the group consisting of absent, —O—, —S(O)—, —S(O)$_2$— and —N($R^X$)— wherein $R^x$ is H, $C_{1-8}$ alkyl, $C_{1-8}$ acyl or —S(O)$_2$($C_{1-8}$ alkyl), and wherein if the subscript m is 0 then one of $X^1$ or $X^2$ is absent;

the subscript n is an integer from 0 to 5;

A is selected from the group consisting of hydrogen, $C_3$-$C_{20}$carbocycle, $C_3$-$C_{20}$heterocycle, aryl, and heteroaryl, wherein if A is hydrogen then the subscript n is 0; and $R^A$ is selected from the group consisting of $C_{1-8}$ alkyl, $C_{1-8}$ haloalkyl, F, Cl, Br, I, —OH, —CN, —NO$_2$, carbocycle, heterocycle, heteroaryl, $-(X^{RA})_{0-1}NR^{A1}R^{A2}$, $-(X^{RA})_{0-1}OR^{A1}$, $-(X^{RA})_{0-1}SR^{A1}$, $-(X^{RA})_{0-1}N(R^{A1})C(=O)OR^{A3}$, $-(X^{RA})_{0-1}OC(=O)N(R^{A1})(R^{A2})$, $-(X^{RA})_{0-1}N(R^{A1})C(=O)N(R^{A1})(R^{A2})$, $-(X^{RA})_{0-1}C(=O)N(R^{A1})(R^{A2})$, $-(X^{RA})_{0-1}N(X^{RA})C(=O)R^{A2}$, $-(X^{RA})_{0-1}C(=O)OR^{A1}$, $-(X^{RA})_{0-1}OC(=O)R^{A1}$, $-P(=O)(OR^{A1})(OR^{A2})$, $-(X^{RA})_{0-1}S(O)_{1-2}R^{A3}$, $-(X^{RA})_{0-1}S(O)_{1-2}N(R^{A1})(R^{A2})$, $-(X^{RA})_{0-1}N(R^{A1})S(O)_{1-2}N(R^{A1})(R^{A2})$ and $-(X^{RA})_{0-1}N(R^{A1})S(O)_{1-2}(R^{A3})$, wherein $X^{RA}$ is selected from the group consisting of $C_{1-4}$ alkylene, $C_{1-4}$ heteroalkylene, $C_{2-4}$ alkenylene and $C_{2-4}$ alkynylene; wherein $R^{A1}$ and $R^{A2}$ are independently selected from the group consisting of hydrogen, $C_{1-8}$alkyl, $C_{1-8}$haloalkyl, $C_{3-8}$ carbocycle, tetrahydronaphthalene, phenyl, benzyl, $C_{5-6}$ heteroaryl and $C_{2-7}$ heterocycle; $R^{A3}$ is selected from the group consisting of $C_{1-8}$ alkyl, $C_{1-8}$ haloalkyl, $C_{3-8}$ carbocycle, tetrahydronaphthalene, phenyl, benzyl, $C_{5-6}$ heteroaryl and $C_{2-7}$ heterocycle; and wherein the aliphatic and aromatic portions of a $R^A$ substituent is optionally substituted with from 1 to 5 $R^{RA}$ substituents selected from, F, Cl, Br, I, —NH$_2$, —OH, —CN, —NO$_2$, =O, $C_{1-4}$ alkyl, $C_{1-4}$ haloalkyl, $C_{1-4}$ alkoxy, $C_{1-4}$ (halo)alkyl-C(=O)—, $C_{1-4}$ (halo)alkyl-S(O)$_{0-2}$—, $C_{1-4}$ (halo)alkyl-C(=O)N(H)—, $C_{1-4}$ (halo)alkyl-N(H)—C(=O)—, ((halo)alkyl)$_2$N—C(=O)—, $C_{1-4}$ (halo)alkyl-OC(=O)N(H)—, $C_{1-4}$ (halo)alkyl-OC(=O)N(H)—, (halo)alkyl-N(H)—C(=O)O—, ((halo)alkyl)$_2$N—C(=O)O—, $C_{1-4}$ alkylamino, $C_{1-4}$ dialkylamino, $C_{3-6}$ carbocycle, $C_{3-6}$cycloalkoxy, $C_{2-5}$ heterocycloalkoxy and tetrahydronaphthalene.

2. The compound of claim 1, wherein the compound has the formula

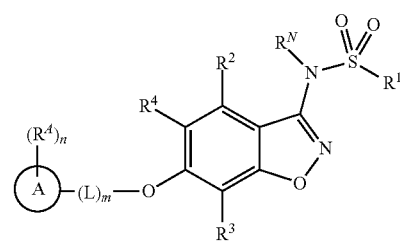

153

-continued

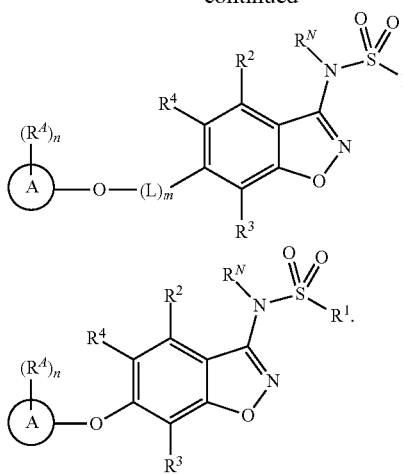

3. The compound of claim 1 wherein $R^4$ is F, Cl, Br, I, —CN, $C_{1-8}$alkyl, $C_{1-8}$ haloalkyl, $C_{1-8}$ alkoxy, or $C_{3-8}$ carbocycle.

4. The compound of claim 1 wherein $R^4$ is Cl or $C_{3-8}$ cyclopropyl.

5. The compound of claim 1 wherein $R^1$ is $C_{1-8}$ alkyl or $C_{3-12}$ carbocycle, wherein the aliphatic portions of $R^1$ are optionally substituted with from 1 to 5 $R^{R1}$ substituents.

6. The compound of claim 5 wherein $R^1$ is methyl, cyclopropyl, or 2-methoxyethyl.

7. The compound of claim 1 wherein $R^1$ is selected from the group consisting of: —NH(CH$_3$), —N(CH$_3$)$_2$,

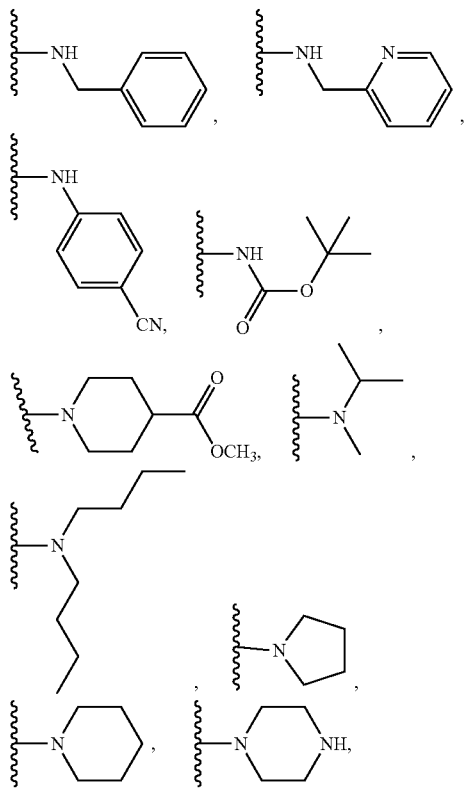

154

-continued

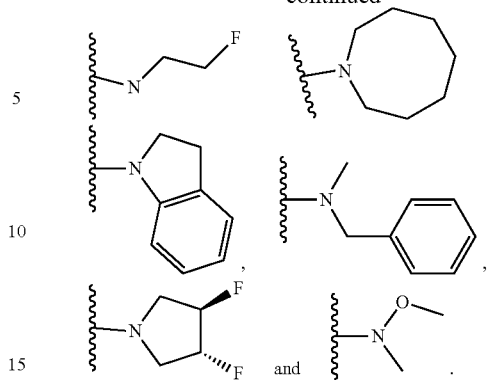

8. The compound of claim 1 wherein $X^1$ is —O— or —N(H)—; $X^2$ is absent; the subscript m is 1; and -(L)- is an optionally substituted group selected from the group consisting of $C_{1-4}$ alkylene, $C_{2-4}$ alkenylene or $C_{2-4}$ alkynylene.

9. The compound of claim 1 wherein A is an optionally substituted ring selected from the group consisting of cyclopropane, cyclobutane, cyclopentane, cyclohexane, cycloheptane, adamantane, bicyclo[2.1.1]hexane, bicyclo[2.2.2]octane, bicyclo[2.2.1]heptane, bicyclo[3.1.1]heptane, bicyclo[3.2.1]octane, bicyclo[4.1.1]octane, bicyclo[3.3.1]nonane and 1,2,3,4-tetrahydro-1,4-methanonaphthalene, 1,2,3,4-tetrahydroisoquinoline, cubane, spiro[2,5]octane, tetrahydronaphthalene and chromane.

10. The compound of claim 9, wherein ring A is an optionally substituted ring selected from the group consisting of cyclopropane, cyclobutane, cyclopentane, cyclohexane, adamantane, cubane, bicyclo[2.2.2]octane, bicyclo[3.1.1]heptane, bicyclo[2.2.1]heptane, spiro[2,5]octane, tetrahydronaphthalene and chromane.

11. The compound of claim 1 wherein ring A is selected from the group consisting of

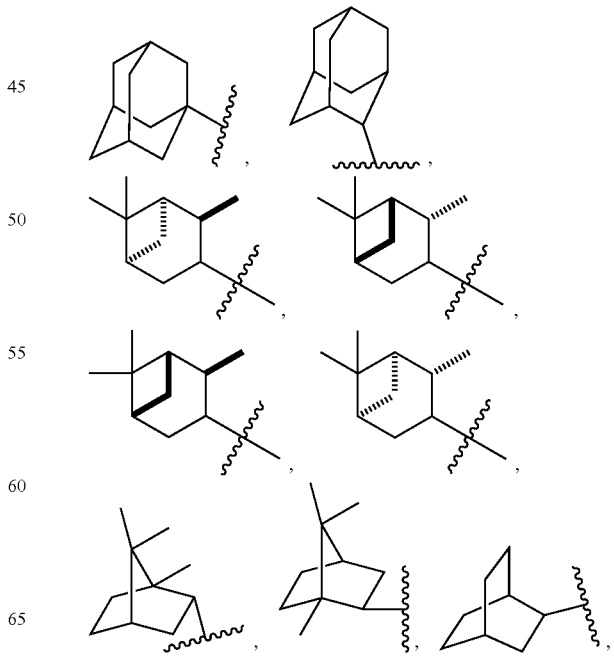

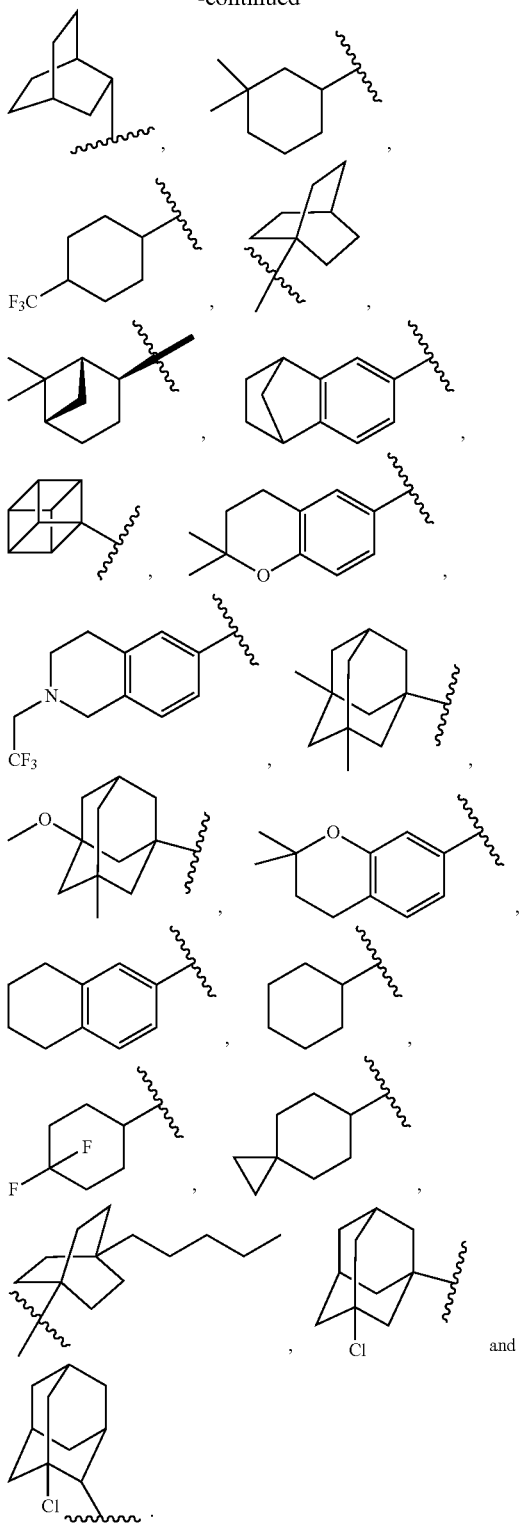

12. The compound of claim 1 wherein ring A is an optionally substituted ring selected from the group consisting of azetidine, pyrrolidine, piperidine, homopiperidine, (1R,5S)-8-azabicyclo[3.2.1]octane, 3-oxa-9-azabicyclo[3.3.1]nonane, (1s,4s)-7-azabicyclo[2.2.1]heptane, (1R, 4S)-5-azabicyclo-[2.1.1]hexane, 7-(trifluoromethyl)-1,2,3,4-tetrahydropyrrolo[1,2-a]pyrazine and quinuclidine.

13. The compound of claim 1 wherein A is selected from the group consisting of

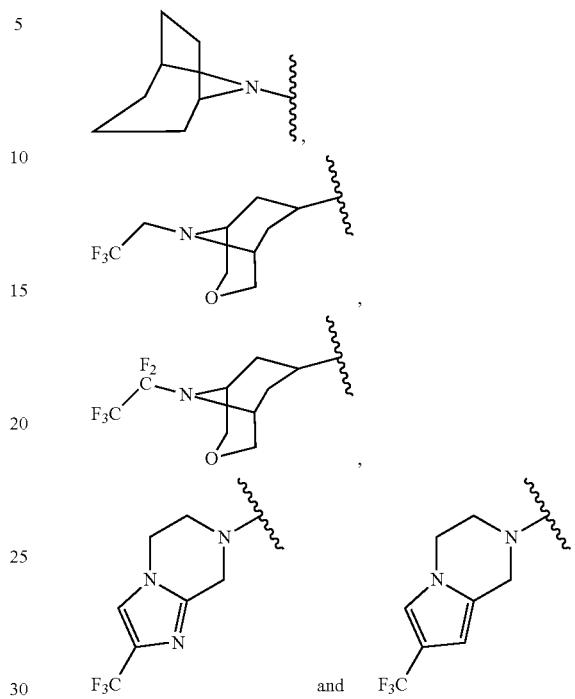

14. The compound of claim 1 wherein $R^A$ is selected from the group consisting of $C_{1-4}$ alkyl, $C_{1-4}$ haloalkyl, $C_{3-5}$ carbocycle, $C_{2-4}$ heterocycle, F, Cl, Br, I, —OH, —NH$_2$, —CN, —NO$_2$, $C_{1-4}$ alkoxy, —C(=O)—N($R^{A1}$)($R^{A2}$) and —N($R^{A1}$)($R^{A2}$).

15. The compound of claim 14, wherein $R^A$ is methyl, trifluromethyl, difluoromethyl, monofluoromethyl, ethyl, pentafluoroethyl, cyclopropyl, —F, Cl, —OH, —NH$_2$ or —CN.

16. The compound of claim 1 wherein A is selected from the group consisting of benzene, pyridine, pyrimidine, pyrazine, pyridazine, benzothiazole, indole, quinoline, isoquinoline, quinazoline, benzoxazole, benzimidazole, pyrrolopyridine, dihydrobenzofuran, dihydroindene, and indoline.

17. The compound of claim 16 wherein $R^A$ is selected from the group consisting of $C_{1-4}$ alkyl, $C_{1-4}$ haloalkyl, $C_{3-5}$ carbocycle, 3-5 membered heterocycle, $C_{1-4}$ haloalkoxy, F, Cl, Br, I, —OH, —NH$_2$, —CN, —NO$_2$, $C_{1-4}$ alkoxy, —(X$^{RA}$)$_{0-1}$OR$^{A1}$, —C(=O)—N($R^{A1}$)($R^{A2}$) and —N($R^{A1}$)($R^{A2}$), wherein the aliphatic portions of a $R^A$ are optionally substituted with from 1 to 5 $R^{RA}$ substitutents selected from, F, Cl, Br, and I.

18. The compound of claim 16 wherein $R^A$ is methyl, trifluromethyl, difluoromethyl, monofluoromethyl, ethyl, pentafluoroethyl, cyclopropyl, n-propoxy, isopropoxy, sec-butyloxy, n-butyloxy, tert-butyloxy, —F, Cl, —OH, —NH$_2$ or —CN.

19. The compound of claim 1 wherein

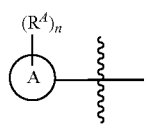

is selected from:
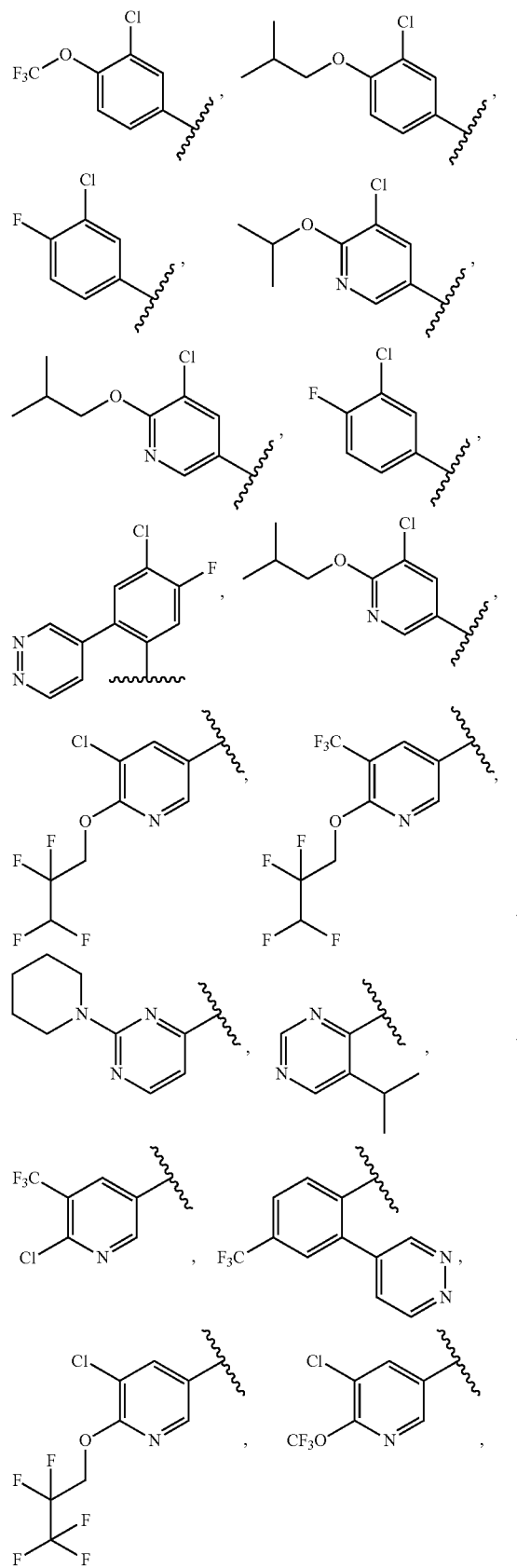
-continued
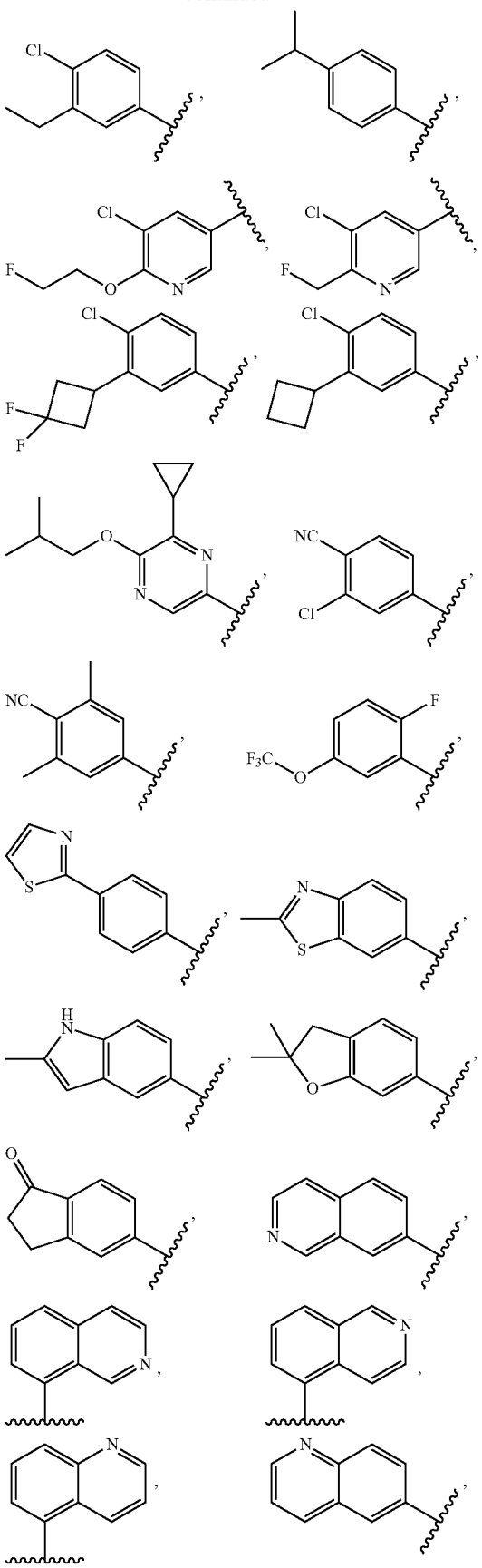

-continued
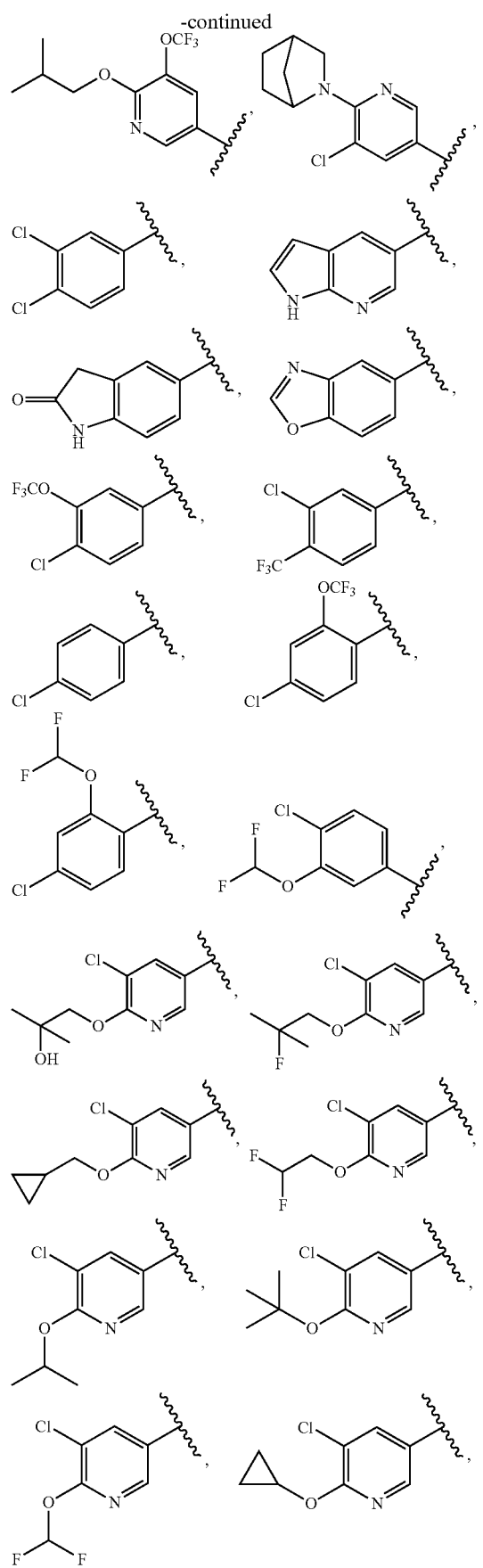
-continued
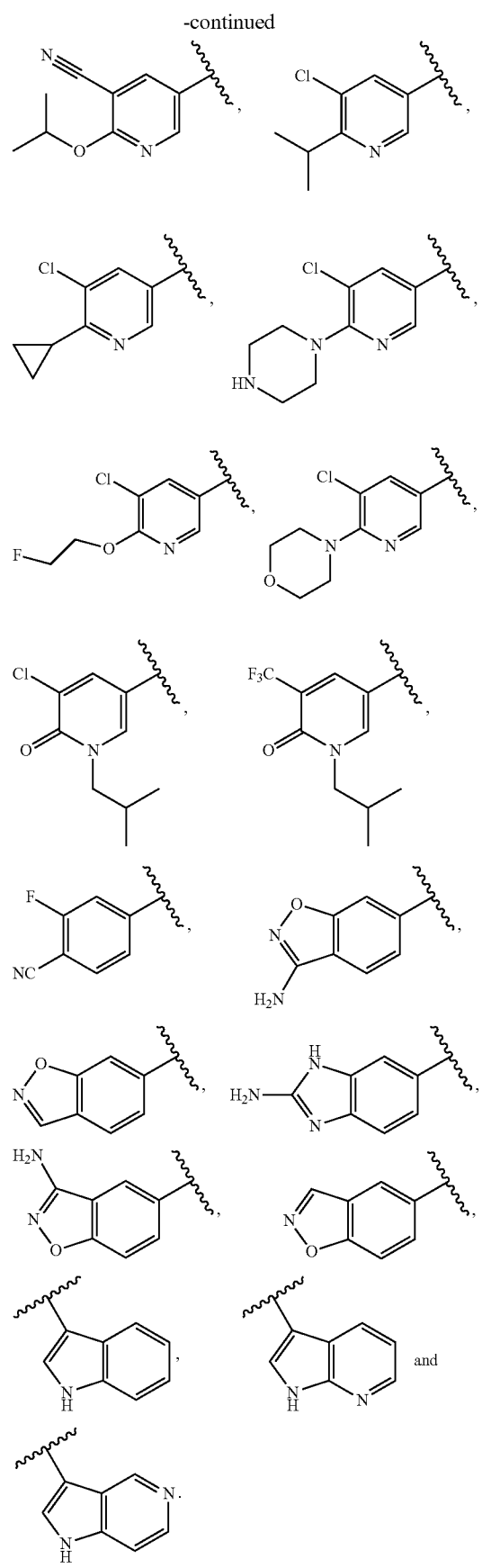

20. The compound of claim 1 wherein
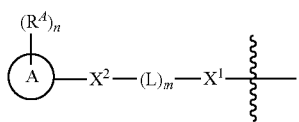
is selected from:
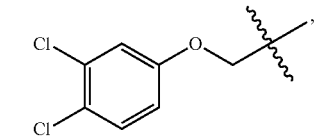,
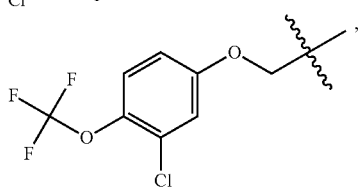,
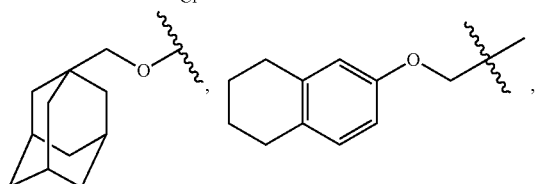,
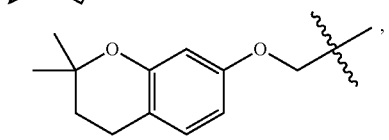,
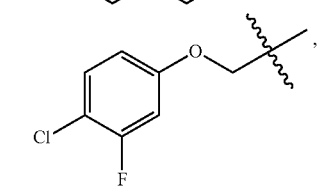,
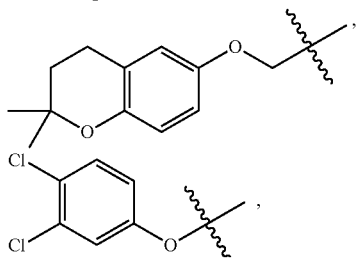,
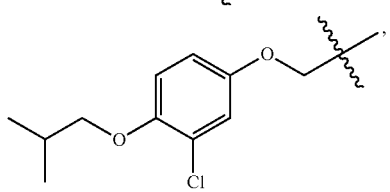,
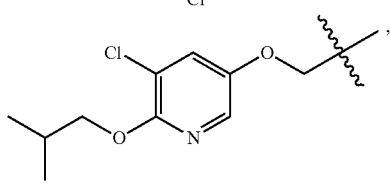,
-continued
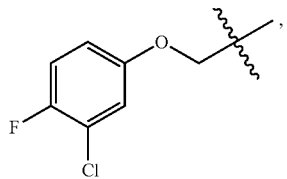,
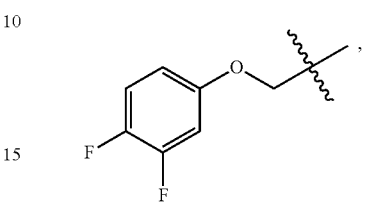,
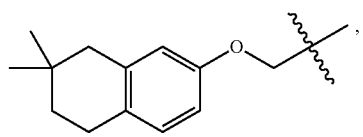,
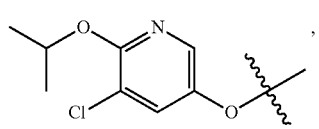,
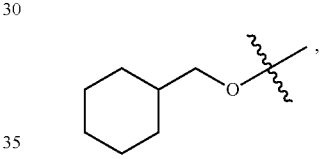,
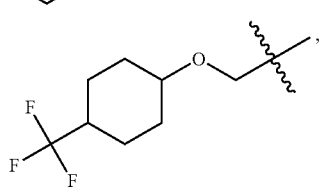,
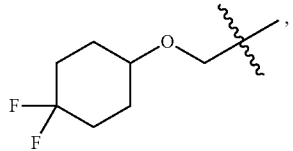,
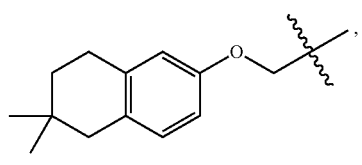,
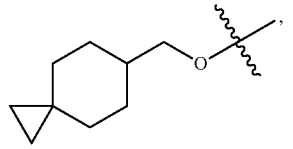,
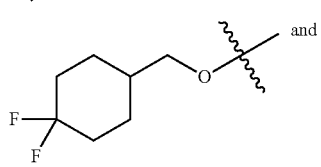 and -continued
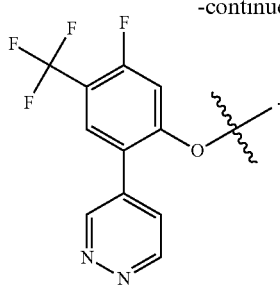
21. The compound of claim 1, selected from the group consisting of:
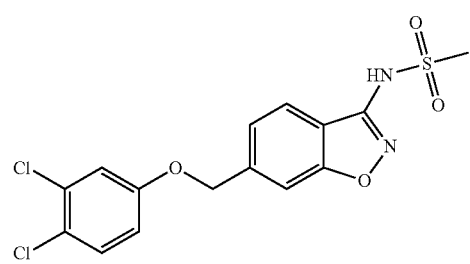
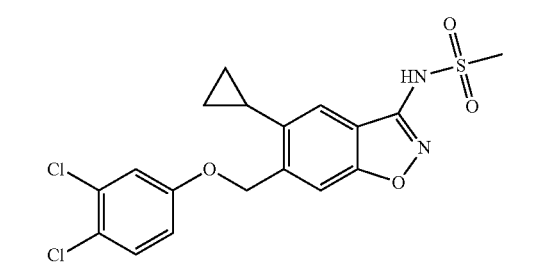
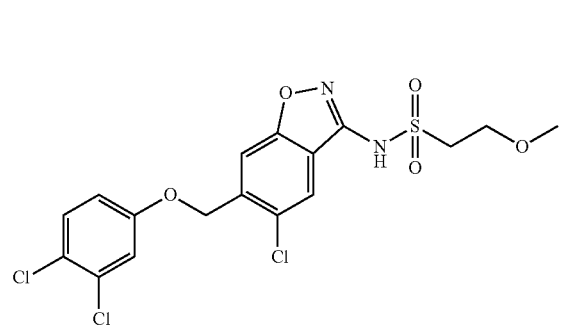
-continued
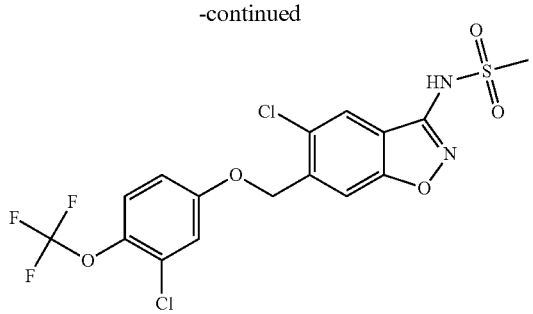
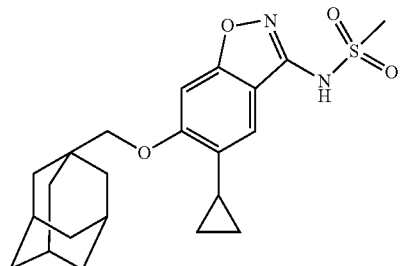
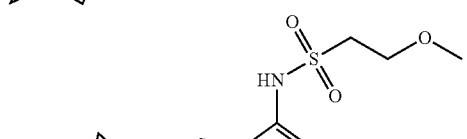
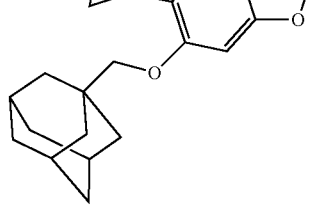
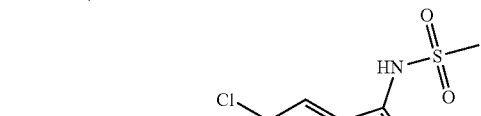
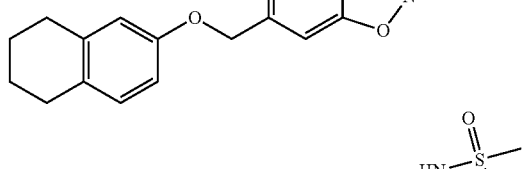
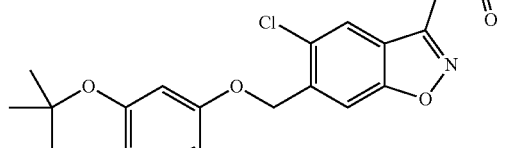
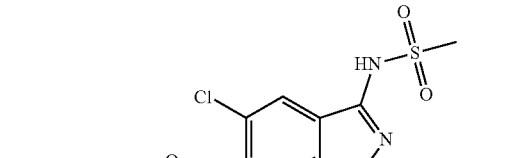
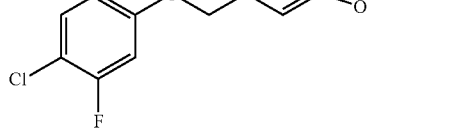

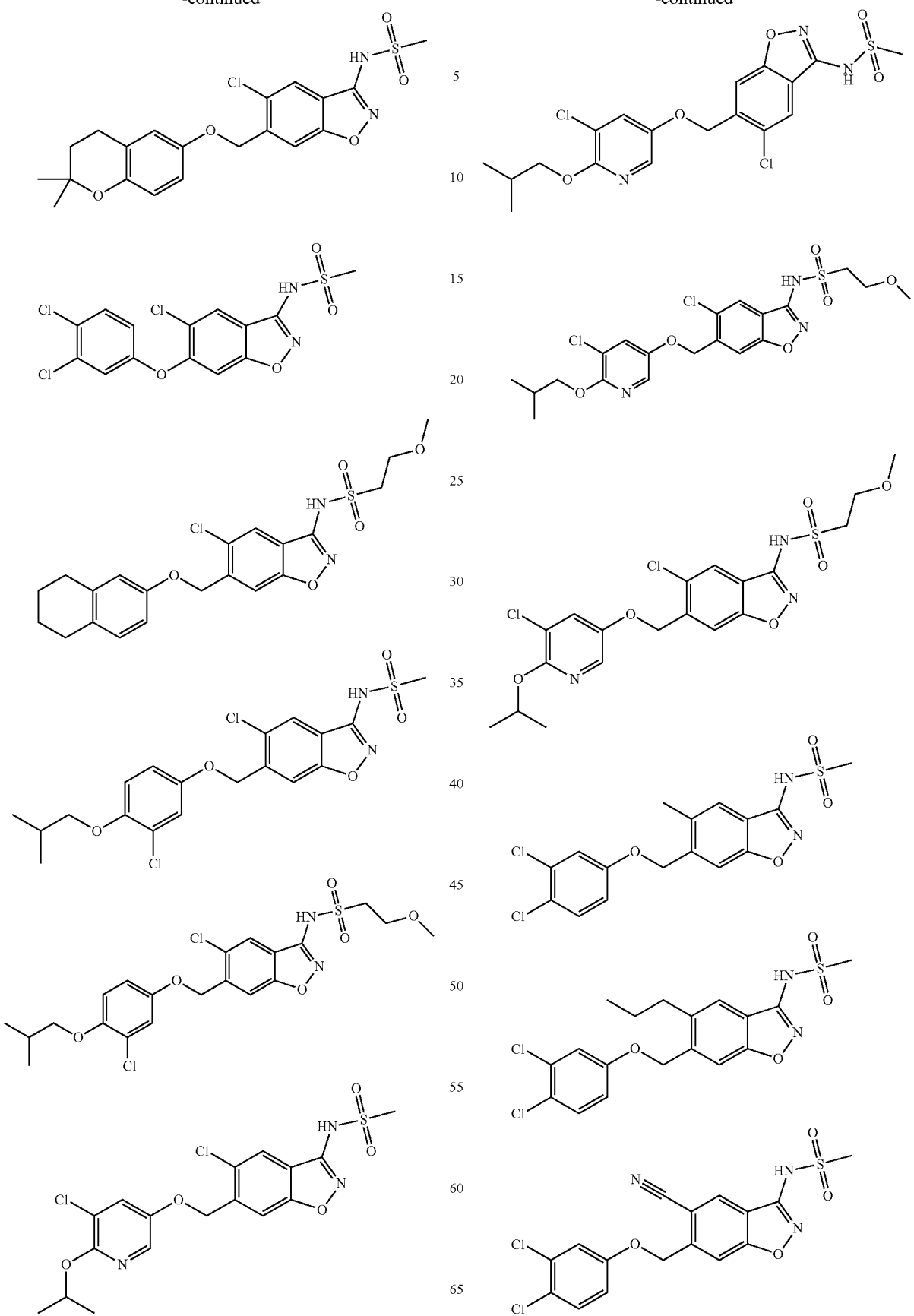

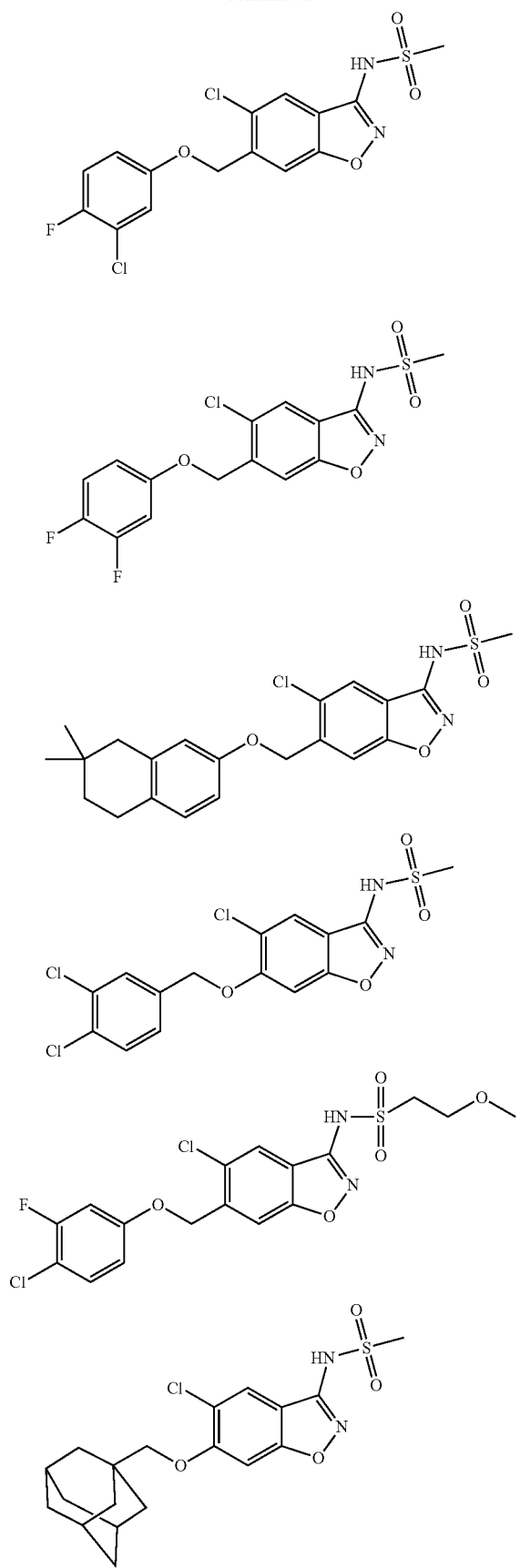
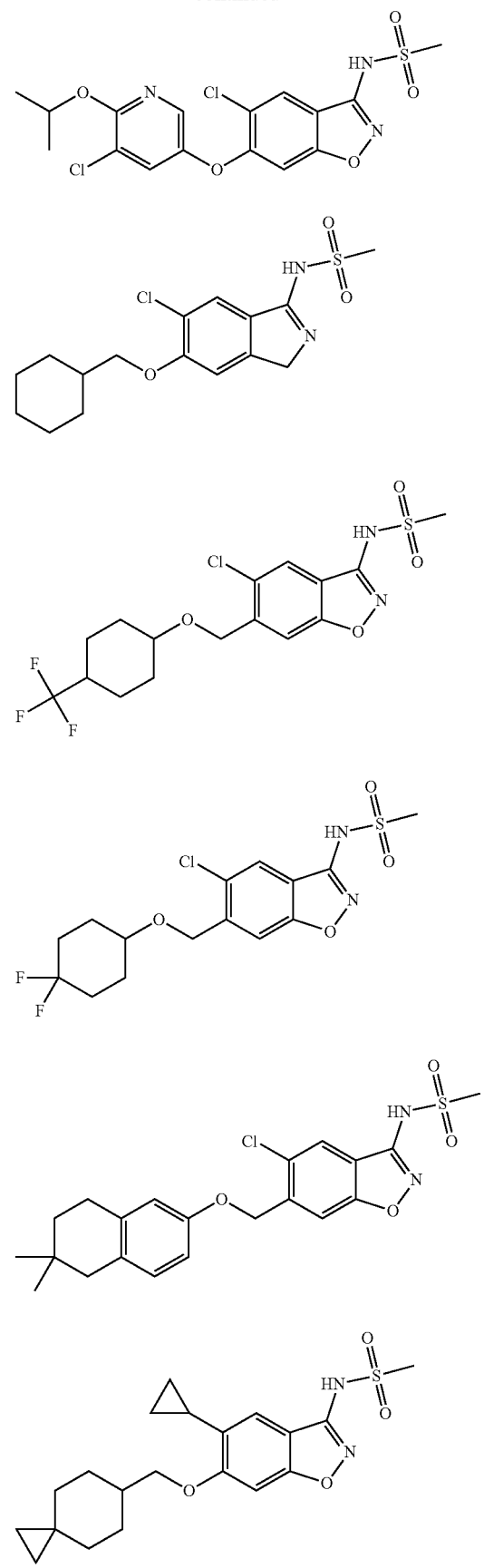

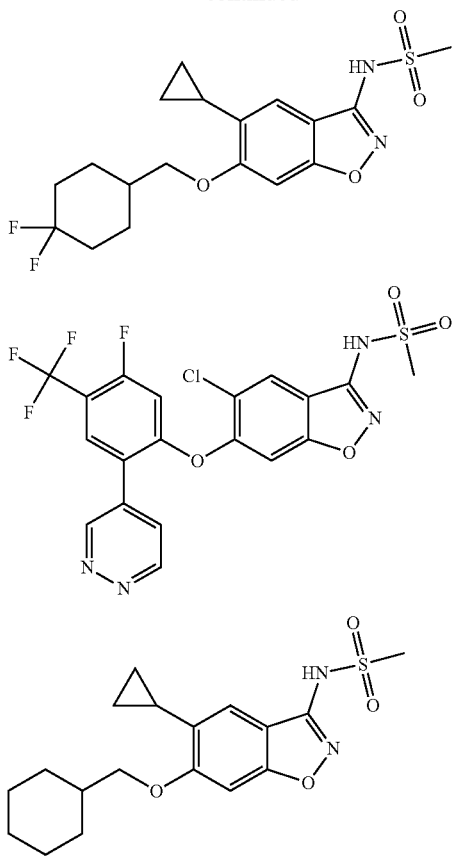

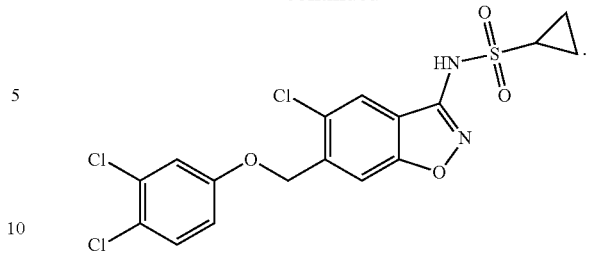

and

22. A pharmaceutical composition comprising a compound of Formula I as described in claim 1, or a pharmaceutically acceptable salt thereof, and a pharmaceutically acceptable excipient.

23. A method of treating a sodium channel-mediated disease or condition in a mammal selected from the group consisting of pain, depression, cardiovascular diseases, respiratory diseases, and psychiatric diseases, and combinations thereof, wherein the method comprises administering to the mammal in need thereof a therapeutically effective amount of a compound of Formula I as described in claim 1, or a pharmaceutically acceptable salt thereof.

24. The method of claim 23, wherein said disease or condition is selected from the group consisting of neuropathic pain, inflammatory pain, visceral pain, cancer pain, chemotherapy pain, trauma pain, surgical pain, post-surgical pain, childbirth pain, labor pain, neurogenic bladder, ulcerative colitis, chronic pain, persistent pain, peripherally mediated pain, centrally mediated pain, chronic headache, migraine headache, sinus headache, tension headache, phantom limb pain, dental pain, peripheral nerve injury or a combination thereof.

* * * * *

UNITED STATES PATENT AND TRADEMARK OFFICE
CERTIFICATE OF CORRECTION

PATENT NO.        : 9,493,429 B2
APPLICATION NO.   : 14/772726
DATED             : November 15, 2016
INVENTOR(S)       : Chien-An Chen et al.

It is certified that error appears in the above-identified patent and that said Letters Patent is hereby corrected as shown below:

In the Claims

Column 151, Line 21, Claim 1, please delete "5-10" and insert -- (5-10 --;

Column 151, Line 34, Claim 1, please delete "-$(X^{1R})_{0-1}$--$NR^{R1a}R^{R1b}$," and insert -- -$(X^{1R})_{0-1}NR^{R1a}R^{R1b}$, --;

Column 152, Line 24, Claim 1, please delete "-$(X^{RA})_{0-1}N(X^{RA})C(=O)R^{A2}$," and insert -- -$(X^{RA})_{0-1}N(R^{A1})C(=O)R^{A2}$, --;

Column 155, Line 65, Claim 12, please delete "(1 s, 4s)" and insert -- (1s, 4s) --;

Column 155, Line 66, Claim 12, please delete "5-azabicyclo- [2.1.1]hexane" and insert -- 5-azabicyclo[2.1.1]hexane --;

Column 168, Lines 10-20, Claim 21, please delete the following compound

" 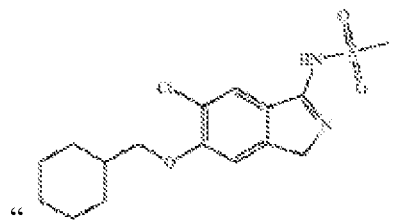 " and insert the following -- 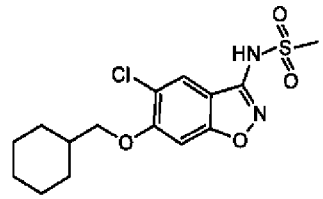 --, therefor.

Signed and Sealed this
Seventh Day of November, 2017

Joseph Matal
*Performing the Functions and Duties of the
Under Secretary of Commerce for Intellectual Property and
Director of the United States Patent and Trademark Office*